(12) United States Patent
Parthasaradhi Reddy et al.

(10) Patent No.: US 11,034,718 B2
(45) Date of Patent: Jun. 15, 2021

(54) C-3 NOVEL TRITERPENONE WITH C-17 REVERSE AMIDE DERIVATIVES AS HIV INHIBITORS

(71) Applicant: HETERO LABS LIMITED, Telangana (IN)

(72) Inventors: Bandi Parthasaradhi Reddy, Hyderabad (IN); Gazula Levi David Krupadanam, Hyderabad (IN); Adulla Panduranga Reddy, Hyderabad (IN); Kasireddy Bhaskar Reddy, Hyderabad (IN); Lanka VL Subrahmanyam, Hyderabad (IN); Kura Rathnakar Reddy, Hyderabad (IN)

(73) Assignee: HETERO LABS LIMITED, Hyderabad (IN)

( * ) Notice: Subject to any disclaimer, the term of this patent is extended or adjusted under 35 U.S.C. 154(b) by 0 days.

(21) Appl. No.: 16/688,400

(22) Filed: Nov. 19, 2019

(65) Prior Publication Data
US 2020/0087342 A1    Mar. 19, 2020

Related U.S. Application Data

(62) Division of application No. 15/549,678, filed as application No. PCT/IB2016/000811 on Feb. 9, 2016, now Pat. No. 10,533,035.

(30) Foreign Application Priority Data

Feb. 9, 2015   (IN) .............................. 623/CHE/2015

(51) Int. Cl.
C07J 63/00   (2006.01)
A61P 31/18   (2006.01)

(52) U.S. Cl.
CPC .............. *C07J 63/008* (2013.01); *A61P 31/18* (2018.01)

(58) Field of Classification Search
CPC ................................ C07J 63/008; A61P 31/18
See application file for complete search history.

(56) References Cited

U.S. PATENT DOCUMENTS

| | | | |
|---|---|---|---|
| 4,598,095 A | 7/1986 | Nishimura et al. |
| 5,679,828 A | 10/1997 | Lee et al. |
| 6,451,851 B1 | 9/2002 | Sumegi |
| 6,670,345 B1 | 10/2003 | Ramadoss et al. |
| 7,923,573 B2 | 4/2011 | Tamaki et al. |
| 8,802,727 B2 | 8/2014 | Partharadhi Reddy et al. |
| 9,067,966 B2 | 6/2015 | Parthasaradhi Reddy et al. |
| 9,637,516 B2 | 5/2017 | Parthasaradhi Reddy et al. |
| 9,868,758 B2 | 1/2018 | Bandi et al. |
| 2002/0068757 A1 | 6/2002 | Lin et al. |
| 2004/0204389 A1 | 10/2004 | Chen et al. |
| 2006/0194774 A1 | 8/2006 | Selzer et al. |
| 2006/0205697 A1 | 9/2006 | Robinson et al. |
| 2008/0207573 A1 | 8/2008 | Yager et al. |
| 2008/0214516 A1 | 9/2008 | Selzer et al. |
| 2009/0023698 A1 | 1/2009 | Krasutsky et al. |
| 2011/0015196 A1 | 1/2011 | Parthasaradhi Reddy et al. |
| 2011/0077228 A1 | 3/2011 | Moinet et al. |
| 2011/0152229 A1 | 6/2011 | Chen et al. |
| 2011/0218204 A1 | 9/2011 | Parthasaradhi Reddy et al. |
| 2014/0221328 A1 | 8/2014 | Parthasaradhi Reddy et al. |
| 2015/0119373 A1 | 4/2015 | Reddy et al. |
| 2015/0337004 A1 | 11/2015 | Reddy et al. |
| 2017/0008921 A1 | 1/2017 | Reddy et al. |
| 2017/0129916 A1 | 5/2017 | Parthasaradhi Reddy et al. |
| 2017/0129917 A1 | 5/2017 | Bandi et al. |
| 2018/0215780 A1 | 8/2018 | Parthasaradhi Reddy et al. |
| 2018/0237472 A1 | 8/2018 | Bandi et al. |

FOREIGN PATENT DOCUMENTS

| | | |
|---|---|---|
| CA | 2223513 A1 | 12/1996 |
| CA | 2767642 C | 1/2011 |
| CN | 1861627 A | 11/2006 |
| CN | 101287744 A | 10/2008 |
| EP | 1218402 B1 | 5/2004 |
| WO | 9502071 A1 | 1/1995 |

(Continued)

OTHER PUBLICATIONS

Aguilera et al., "Stereodivergent synthesis of the first bis(cyclobutane) γ-dipeptides and mixed γ-oligomers", Tetrahedron: Asymmetry 19, 2008, pp. 302-308.

(Continued)

*Primary Examiner* — Sahar Javanmard
(74) *Attorney, Agent, or Firm* — Cantor Colburn LLP

(57) ABSTRACT

The invention relates to C-3 novel triterpenone with C-17 reverse amide derivatives, related compounds, and pharmaceutical compositions useful for the therapeutic treatment of viral diseases and particularly HIV mediated diseases.

Formula (1)

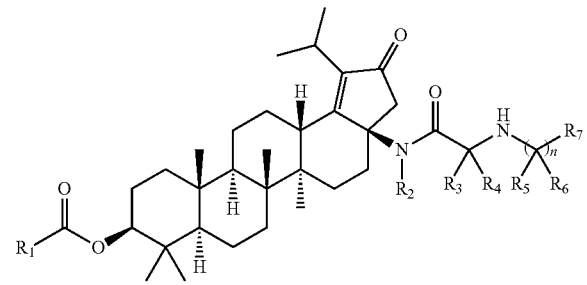

10 Claims, No Drawings

(56) References Cited

FOREIGN PATENT DOCUMENTS

| WO | 199502071 A1 | 1/1995 |
|---|---|---|
| WO | 9858675 | 12/1998 |
| WO | 0046235 A1 | 8/2000 |
| WO | 0107646 A2 | 2/2001 |
| WO | 0165957 A2 | 9/2001 |
| WO | 02091858 A1 | 11/2002 |
| WO | 03037908 A1 | 5/2003 |
| WO | 2003037908 A1 | 5/2003 |
| WO | 2005090380 A1 | 9/2005 |
| WO | 2006053255 A2 | 5/2006 |
| WO | 2006105356 A2 | 10/2006 |
| WO | 2007002411 A1 | 1/2007 |
| WO | 2007141383 A1 | 12/2007 |
| WO | 2007141389 A1 | 12/2007 |
| WO | 2007141390 A1 | 12/2007 |
| WO | 2007141391 A1 | 12/2007 |
| WO | 2007141392 A2 | 12/2007 |
| WO | 2008057420 A2 | 5/2008 |
| WO | 2008091532 A1 | 7/2008 |
| WO | 2008127364 A2 | 10/2008 |
| WO | 2009082818 A1 | 7/2009 |
| WO | 2009082819 A1 | 7/2009 |
| WO | 2009100532 A1 | 8/2009 |
| WO | 2010132334 A1 | 11/2010 |
| WO | 2011007230 A2 | 1/2011 |
| WO | 2011100308 A1 | 8/2011 |
| WO | 2011153315 A1 | 12/2011 |
| WO | 2011153319 A1 | 12/2011 |
| WO | 2012095705 A1 | 7/2012 |
| WO | 2013001144 A1 | 1/2013 |
| WO | 2013020245 A1 | 2/2013 |
| WO | 2013090664 A1 | 6/2013 |
| WO | 2013090683 A1 | 6/2013 |
| WO | 2013091144 A1 | 6/2013 |
| WO | 2013117137 A1 | 8/2013 |
| WO | 2013160810 A2 | 10/2013 |
| WO | 2014093941 A1 | 6/2014 |
| WO | 2014105926 A1 | 7/2014 |
| WO | 2015198263 A2 | 12/2015 |
| WO | 2016178092 A2 | 11/2016 |
| WO | 2017017630 A1 | 2/2017 |
| WO | 2017021922 A1 | 2/2017 |
| WO | 2017064628 A1 | 4/2017 |
| WO | 2017115329 A1 | 7/2017 |
| WO | 2017149518 A1 | 9/2017 |
| WO | 2018025247 A1 | 2/2018 |
| WO | 2018029602 A1 | 2/2018 |
| WO | 2018029604 A1 | 2/2018 |
| WO | 2018029610 A1 | 2/2018 |
| WO | 2018064628 A2 | 4/2018 |
| WO | 2018069857 A1 | 4/2018 |

OTHER PUBLICATIONS

Averett, D. "Anti-HIV compound assessment by two novel high capacity assays", Journal of Virological Methods, 1989, vol. 23, pp. 263-276.

Cecilia et al., "Neutralization Profiles of Primary Human Immunodeficiency Virus Type 1 Isolates in the Context of Coreceptor Usage", Journal of Virology, Sep. 1998, vol. 72, No. 9, pp. 6988-6996.

Clark et al., "Synthesis and antiviral activity of 2'-deoxy-2'-fluoro-2'-C-methyl purine nucleosides as inhibitors of hepatitis C virus RNA replication", Bioorganic & Medicinal Chemistry Letters 16 2006, pp. 1712-1715.

Cole, S.P.C., "Rapid chemosensitivity testing of human lung tumor cells using the MTT assay", Cancer Chemotherapy and Pharmacology, 1986, 17, pp. 259-263.

Connor et al., "Characterization of the Functional Properties of env Genes from Long-Term Survivors of Human Immunodeficiency Virus Type 1 Infection", Journal of Virology, 1996, vol. 70, No. 8, pp. 5306-5311.

Dang et al. "Betulinic Acid Derivatives as Human Immunodeficiency Virus Type 2 (HIV-2) Inhibitors" J. Med. Chem., 2009, 52 (23), pp. 7887-7891.

Fedyuk N.V. et al., Problems of Virology 1992, (3) 135, Abstract Only, 1 page.

Flekhter et al, "Synthesis and Antiinflammatory Activity of New Acylated Betulin Derivatives", Pharmaceutical Chemistry Journal, 2002, vol. 36, No. 9, pp. 488-491.

Flekhter et al. "Synthesis and Antiinflammatory Activity of New Acylated Betulin Derivatives," Pharmaceutical Chemistry Journal 2002, vol. 36, Issue 9, pp. 29-32.

Fujioka et al. "Anti-AIDS Agents, 11. Betulinic Acid and Platanic Acid as anti-HIV Principles from Syzigium Claviflorum, and the Anti-HIV Activity of Structurally Related Triterpenoids", Journal of Natural Products, 1994, vol. 57, No. 2, pp. 243-247.

Gerrish et al., "Triterpene based compounds with potent anti-maturation activity against HIV-1," Bioorganic & Medicinal Chemistry Letters, 2008, vol. 18, Issue 24, pp. 6377-6380.

Harrington et al., "Direct detection of infectious HIV_1 in blood using a centrifugation-indicator cell assay", Journal of Virological Methods, 2000, vol. 88, pp. 111-115.

International Preliminary Report on Patentability for International Application No. PCT/IB2016/000811, International Filing Date Feb. 9, 2016, dated Aug. 15, 2017, 7 pages.

International Search Report for International Application No. PCT/IB2015/054784, International Filing Date Jun. 25, 2015, dated Dec. 15, 2015, 4 pages.

International Search Report for International Application No. PCT/IB2016/000811. International Filing Date Feb. 9, 2016, dated Dec. 2, 2016, 5 pages.

International Search Report, International Application No. PCT/IB25015/054864; International Filing Date: Jun. 29, 2015; dated Oct. 16, 2015; 4 Pages.

International Search Report; International Application No. PCT/IB2016/051424; International Filing Date Mar. 12, 2016; dated Aug. 29, 2016; 4 pages.

International Search Report; International Application No. PCT/US2013/077751; International Filing Date Dec. 26, 2013; dated Mar. 18, 2014; 6 pages.

Jeong H-J et al: "Preparation of amino acid conjugates of betulinic acid with activity against human melanoma", Bioorganic & Medicinal Chemistry Letters, Pergamon, Amsterdam, NL, vol. 9, No. 8, Apr. 19, 1999, pp. 1201-1204.

Kashiwada et al., "Betulinic Acid and Dihydrobetulinic Acid Derivatives as Potent Anti-HIV Agents", J. Med. Chem. 1996, 39, pp. 1016-1017.

Koyanagi et al., "Selective Cytotoxicity of AIDS Virus Infection Towards HTLV-I-Transformed Cell Lines", Int. J. Cancer, 1985, vol. 36, pp. 445-451.

Li et al., "PA-457: A potent HIV inhibitor that disrupts core condensation by targeting a late step in Gag processing", Proc. Natl. Acad. Sci. 2003, pp. 13555-13560.

Martin, David E.; "Bevirimat: a novel maturation inhibitor for the treatment of HIV-1 infection"; Antiviral Chemistry & Chemotherapy, 19: 107-113. 2008.

Meek et al., "Inhibition of HIV-1 protease in infected T-lymphocytes by synthetic peptide analogues", Nature, 1990, vol. 343, pp. 90-92.

Mimoto et al., "Structure-Activity Relationship of Small-Sized HIV Protease Inhibitors Containing Allophenylnorstatine", J. Med. Chem., 1999, vol. 42, No. 10, pp. 1789-1802.

Mitsuya et al., "Inhibition of the in vitro infectivity and cytopathic effect of human T-lymphotrophic virus type III/lymphadenopathy-associated virus (HTLV-III/LAV) by 2',3'-dideoxynucleosides", Proc. Natl. Acad. Sci. USA, 1986, vol. 83, pp. 1911-1915.

Moglioni et al., "Divergent Routes to Chiral Cyclobutane Synthons from (-)-a-Pinene and Their Use in the Steroselective Synthesis of Dehydro Amino Acids", J. Org. Chem. 2000, 65, pp. 3934-3940.

Mosmann, T., Rapid Colorimetric Assay for Cellular Growth and Survival: Application to Proliferation and Cytotoxicity Assays. Journal of Immunological Methods, 65 (1983) 55-63.

(56) References Cited

OTHER PUBLICATIONS

Nair et al., "A Facile and Efficient Synthesis of 3,3-Dimethyl Isopropylidene Proline From (+)-3-Carene", J. Org. Chem., 2010, vol. 75, No. 4, pp. 1285-1288.
Pau et al., Antiretroviral Therapy, Infect. Dis. Clin. N. Am., 2014, 28, 371-402.
Popik et al., "Human Immunodeficiency Virus Type 1 Uses Lipid Raft-Colocalized CD4 and Chemokine Receptors for Productive Entry into CD4+ T Cells", J. of Virology, 2002, pp. 4709-4722.
Qian et al., "Anti-AIDS Agents 90. Novel C-28 Modified Bevirimat Analogues as Potent HIV Maturation Inhibitors," Journal of Medicinal Chemistry, 2012, vol. 55, Issue 18, pp. 8128-8136.
Qian Keduo et al: "Anti-AIDS agents 81. Design, synthesis, and structure-activity relationship study of betulinic acid and moronic acid derivatives as potent HIV maturation inhibitors.", Journal of Medicinal Chemistry Apr. 22, 2010, vol. 53, No. 8, pages.
Quian et al., "Anti-AIDS Agents. 78. Synthesis, Metabolic Stability Assessment, and Antiviral Evaluation," Journal of Medicinal Chemistry, 2009, vol. 52, Issue 10, pp. 3248-3258.
Ravi et al, "HIV-1 long terminal repeat promoter regulated dual reporter: Potential use in screening of transcription modulators", Analytical Biochemistry, 2007, vol. 360, pp. 315-317.
Roda Rani et al., "A conserved molecular action of native and recombinant Epap-1 in inhibition of HIV-1 gp120 mediated viral entry", Archives of Biochemistry and Biophysics, 2006, vol. 456, pp. 79-92.
Roos et al., "LuSIV Cells: A Reporter Cell Line for the Detection and Quantation of a Single Cycle of HIV and SIV Replication", Virology, 2000, vol. 273, pp. 307-315.
Silverman, "The Organic Chemistry of Drug Design and Drug Action," Academic Press; 1992, pp. 352-355.
Taiwo et al., "Unmet therapeutic needs in the new era of combination antiretroviral therapy for HIV-1", J. antimicrob Chemother 2010; 65: 1100-1107.
Tyle, P., "Iontophoretic Devices for Drug Delivery", Pharmaceutical Research, vol. 3, No. 6, 1986, 318-326.
Uckun et al., "TXU (Anti-CD7)-Pokeweed Antiviral Protein as a Potent Inhibitor of Human Immunodeficiency Virus", Antimicrobial Agents and Chemotherapy, Feb. 1998, vol. 42, No. 2, pp. 383-388.
Weislow et al., New Soluble-Formazan Assay for HIV-1 Cytopathic Effects: Application to High-Flux Screening of Synthetic and Natural Products for AIDS-Antiviral Activity, J. Natl. Cancer Inst., 1989, 81, pp. 577-586.
Written Opinion for International Application No. PCT/2015/054784, International Filing Date Jun. 25, 2015, dated Dec. 15, 2015, 8 pages.
Written Opinion for International Application No. PCT/IB2016/000811, International Filing Date Feb. 9, 2016, dated Dec. 2, 2016, 6 pages.
Written Opinion for International Application No. PCT/IB2016/051424, International Filing Date Mar. 12, 2016, dated Aug. 29, 2016, 7 pages.
Written Opinion of the International Searching Authority; International Application No. PCT/US2013/077751; International Filing Date Dec. 26, 2013; dated Mar. 18, 2014; 12 pages.
Written Opinion, International Application No. PCT/IB25015/054864; International Filing Date: Jun. 29, 2015; dated Oct. 16, 2015; 5 Pages.
Zhou et al., "Inhibition of HIV-1 Maturation via Drug Association with the Viral Gag Protein in Immature HIV-1 Particles", J. of Bio. Chem. vol. 280, No. 51, pp. 42149-42155, 2005.

Zhu, et al., "Synthesis and Anti-HIV Activity Oleanolic Acid Derivatives", Bioorganic & Medicinal Chemistry Letters, 2001, vol. 11, pp. 3115-3118.
Aguado et al., "Enantidivergent synthesis of cyclobutyl-(Z)-a,β-dehydro-a-amino acid derivatives from (-)-cis-pinononic acid", Tetrahedron: Asymmetry 14, 2003, pp. 217-223.
Antimonova et al., "Synthesis of Betulonic Acid Amindes", Chemistry of Natural Compounds, 2008, vol. 44, No. 3, pp. 327-333.
Balzarini et al., "9-(2phosphonylmethoxyethyl)adenine (PMEA) effectively inhibits retrovirus replication in vitro and simian immunodeficiency virus infection in rhesus monkeys", AIDS, 1991, 5:21-28.
Barre-Sinoussi et al., "Isolation of a T-Lymphotropic Retrovirus from a Patient at Risk for Acquired Immune Deficiency Syndrome (AIDS)", Science, 1983, vol. 220, pp. 868-871.
Broder et al., "A Pathogenic Retrovirus (HTLV-III) Linked to AIDS", The New England Journal of Medicine, 1984, vol. 311, No. 20, pp. 1292-1297.
Daluge et al., "5-Chloro-2',3'-Dideoxy-3'-Fluorouridine (935U83), a Selective Anti-Human Immonudeficiency Virus Agent with an Improved Metabolic and Toxicological Profile", Antimicrobial Agents and Chemotherapy, 1994, vol. 38, No. 7, pp. 1590-1603.
Erice et al., "Anti-Human Immunodeficiency Virus Type 1 Activity of an Anti-CD4 Immunoconjugate Containing Pokeweed Antiviral Protein", Antimicrobial Agents and Chemotherapy, Apr. 1993, vol. 37, No. 4, pp. 835-838.
Greene, T. W. and P. G. M. Wuts, "Protective Groups in Organic Synthesis", 3rd edition, John Wiley & Sons, Inc., New York, 1999.
Hashimoto, F., et al., "Anti-AIDS Agents—XXVIL. Synthesis and Anti-HIV Activity of Betulinic Acid and Dihydrobetulinic Acid Derivatives", Bioorganic & Medicinal Chemistry, 1997, vol. 5, No. 12, pp. 2133-2143.
International Search Report and Written Opinion for International Application No. PCT/IB2010001677, International Application Filing Date Jul. 5, 2010, dated Apr. 12, 2011, 23 pages.
International Search Report and Written Opinion for International Application No. PCT/IB2011/054183, International Filing Date Sep. 22, 2011, dated Mar. 16, 2012, 14 pages.
International Search Report for International Application No. PCT/IB2013/053120, International Filing Date Apr. 19, 2013, dated Oct. 4, 2013, 7 pages.
International Search Report; International Application No. PCT/IB2011/054183; Date of Mailing of the International Search Report dated Mar. 16, 2012; 3 pages.
Kanamoto et al., "Anti-Human Immunodeficiency Virus Activity of YK-FH312 (a Betulinic Acid Derivative), a Novel Compound Blocking Viral Maturation", Antimicrobial Agents and Chemotherapy, 2001, pp. 1225-1230.
Sakalian et al., "3-O-(3',3'-Dimethysuccinyl) Betulinic Acid Inhibits Maturation of the Human Immunodeficiency Virus Type 1 Gag Precursor Assemble In Vitro", J. of Virology, 2006, pp. 5716-5722.
Schwartz et al., "A Rapid Calorimetric Test for the Study of Anti-HIV Agents", AIDS Research and Human Retroviruses, 1988, vol. 4, No. 6, pp. 441-448.
Sun, I., et al., "Anti-AIDS Agents, 34. Synthesis and Structure-Activity Relationships of Betulin Derivatives as Anti-HIV Agents", J. Med. Chem. 1998, vol. 41, pp. 4648-4657.
Written Opinion for International Application No. PCT/IB2013/053120, International Application Filing Date Apr. 19, 2013, dated Oct. 4, 2013, 5 pages.
Zhou et al., "Small-Molecule Inhibition of Human Immunodeficiency Virus Type 1 Replication by Specific Targeting of the Final Step of Virion Maturation", J. of Virology, 2004, pp. 922-929.

C-3 NOVEL TRITERPENONE WITH C-17 REVERSE AMIDE DERIVATIVES AS HIV INHIBITORS

CROSS-REFERENCE TO RELATED APPLICATIONS

This application is a divisional of U.S. patent application Ser. No. 15/549,678 filed 9 Aug. 2017, which is a U.S. National Stage Application of International Application Serial No. PCT/IB2016/000811 filed on 9 Feb. 2016, each of which is hereby incorporated by reference in its entirety. This application claims the benefit of Indian provisional application no 623/CHE/2015 filed on 9 Feb. 2015 which is hereby incorporated by reference in its entirety.

FIELD OF THE INVENTION

The present invention relates to C-3 novel triterpenone with C-17 reverse amide derivatives and related compounds, compositions useful for therapeutic treatment of viral diseases and particularly HIV mediated diseases.

BACKGROUND OF THE INVENTION

The Human Immunodeficiency Virus (HIV) has now been established as the causative agent of the Acquired Immunodeficiency Syndrome (AIDS) for over 20 years (Science 1983, 220,868-871; N.Eng.J.Med. 1984, 311, 1292-1297). AIDS is characterized by the destruction of the immune system, particularly of CD4+T-cells. HIV is a retrovirus, and the HIV life cycle encompasses several crucial steps, starting from the attachment of the virus to the host cell membrane and finishing with the release of progeny virons from the cell.

The natural compound betulinic acid, isolated from Syzygium clavifolium and several other plant species was found to possess anti-HIV activity. Chemical modifications were undertaken by several research groups in an attempt to identify potent anti-HIV agents by making semi-synthetic analogs of betulinic acid, leading to the discovery of bevirimat as a compound with a novel mechanism of action (J. Nat. Prod. 199457(2):243-7; J. Med. Chem. 1996, 39(5), 1016). Further studies shown that bevirimat acts by disrupting Gag processing (Proc. Natl. Acad. Sci. USA 2003, 100(23):13555-60; Antimicrob. Agents. Chemother. 2001, 45(4), 1225-30; J. Virol. 2004, 78(2): 922-9; J. Biol. Chem. 2005, 280(51):42149-55; J. Virol. 2006, 80(12): 5716-22) and to be a first-in-class maturation inhibitor with a potent activity against HIV-1. Bevirimat went up to phase 2 clinical trials, in clinic despite optimal plasma concentrations, not all patients given bevirimat have a robust viral load reduction. It was reported that non-respondant patients had more frequent base line Gag polymorphisms near the capsid SP-1 cleavage site than responders. (HIV gag polymorphism determines treatment response to bevirimat. XVII international HIV drug resistance work shop Jun. 10-14, 2008, Sitges, Spain).

Encouraged by these developments, medicinal chemists started exploring betulinic acid derivatives and related compounds intensively for their therapeutic activities. For example, WO 2014/093941 describes pharmaceutical compositions of betulin derivatives; WO 2009/082819 describes preparation of 17-amino lupane derivatives as anti-HIV agents; WO 2013/117137 describes lupane triterpenoids derivatives and pharmaceutical use thereof; WO 2013/020245 describes carbonyl derivatives of betulin; WO 2009/082818 describes preparation of C21-keto lupane derivatives for the treatment of HIV infections; WO 2011/100308 describes preparation of betulin derivatives for treatment of HIV-1; WO 2013/090664 describes preparation of betulin derivatives for the treatment of HIV; WO 2013/091144 describes preparation of propenoate derivatives of betulin useful for the treatment of HIV; WO 2013/090683 describes preparation of betulin propenoate derivatives for the treatment of HIV.

Given the fact of the world wide epidemic level of AIDS, there is a strong continued need for new effective drugs for treatment of HIV infected patients, disease conditions and/or disorders mediated by HIV by discovering new compounds with novel structures and/or mechanism of action(s).

SUMMARY OF THE INVENTION

The present invention relates to the compounds of the formula (1)

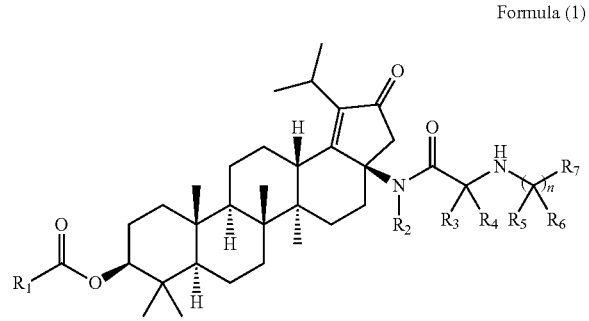

Formula (1)

wherein, $R_1$ can be substituted or unsubstituted $C_1$-$C_6$ alkyl,

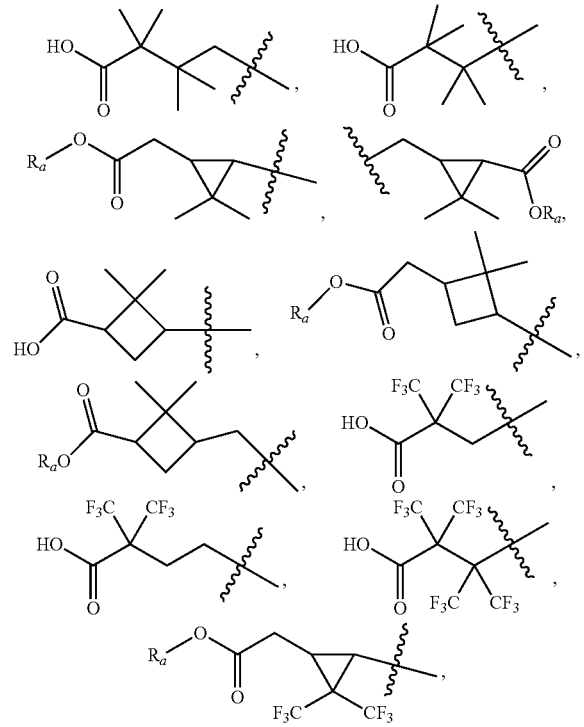

-continued

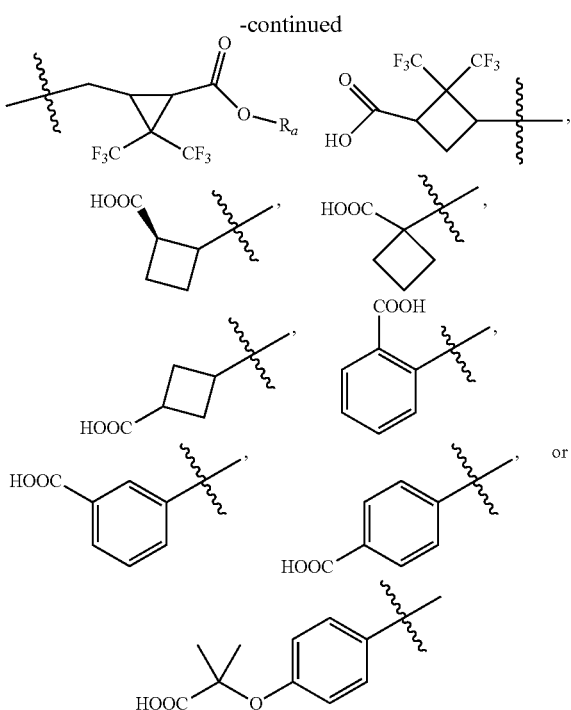

(wherein $R_a$ can be hydrogen, substituted or unsubstituted $C_1$-$C_6$ alkyl, or substituted or unsubstituted $C_3$-$C_8$ cycloalkyl);

$R_2$ can be hydrogen, substituted or unsubstituted $C_1$-$C_6$ alkyl, substituted or unsubstituted $C_2$-$C_6$ alkoxylalkoxy or substituted or unsubstituted $C_1$-$C_6$ amino alkyl;

$R_3$ and $R_4$ can be independently selected from substituted or unsubstituted $C_1$-$C_6$ alkyl, substituted or unsubstituted amine, substituted or unsubstituted $C_3$-$C_8$ cycloalkyl, substituted or unsubstituted heterocyclyl or substituted or unsubstituted heteroaryl or $R_3$ and $R_4$ can be taken together with the carbon atom to which they are attached to form substituted or unsubstituted $C_3$-$C_8$ cycloalkyl, epoxide, oxetane or azetidine;

$R_5$ and $R_6$ can be independently selected from hydrogen, substituted or unsubstituted $C_1$-$C_6$ alkyl and $R_5$ and $R_6$ can be taken together with the carbon atom to which they are attached to form substituted or unsubstituted $C_3$-$C_8$ cycloalkyl or $R_5$ and $R_6$ can be together represent oxo;

$R_7$ can be hydrogen, substituted or unsubstituted $C_1$-$C_6$ alkyl, substituted or unsubstituted $C_1$-$C_6$ alkoxy, substituted or unsubstituted amino, substituted or unsubstituted $C_1$-$C_6$ amino alkyl, substituted or unsubstituted $C_3$-$C_8$ cycloalkyl, substituted or unsubstituted $C_6$-$C_{12}$ aryl, substituted or unsubstituted heterocyclyl, substituted or unsubstituted heteroaryl, or $S(O)_2R_b$; wherein the substituents can be independently selected from one or more $R_m$;

$R_m$ can be halo, $C_1$-$C_6$ alkyl, haloalkyl, amino, —C(O)OR$_c$, substituted or unsubstituted heterocyclyl, substituted or unsubstituted heterocyclylalkyl, substituted or unsubstituted heteroaryl or —S(O)$_2R_b$;

$R_b$ and $R_c$ can be independently selected from substituted or unsubstituted $C_1$-$C_6$ alkyl or substituted or unsubstituted $C_6$-$C_{12}$ aryl;

'n' can be an integer selected from 0, for 2;

pharmaceutically acceptable salts, pharmaceutically acceptable solvates, pharmaceutically acceptable hydrates, tautomers, stereoisomers, ester prodrugs, or combination thereof.

It should be understood that the formula (1) structurally encompasses all stereoisomers, including enantiomers, diastereomers, racemates, and combinations thereof which may be contemplated from the chemical structure of the genus described herein.

It should be understood that the formula (1) structurally encompasses all tautomers.

Also contemplated are prodrugs of the compounds of the formula (1), including ester prodrugs.

According to one embodiment, there is provided a compound of formula (1), wherein $R_1$ is

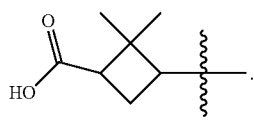 [SMILES: *C1CC(C(=O)O)C1(C)C]

According to another embodiment, there is provided a compound of formula (1), wherein $R_2$ is hydrogen.

According to yet another embodiment there is provided a compound of formula (1), wherein $R_3$ and $R_4$ are methyl.

According to yet another embodiment there is provided a compound of formula (1), wherein $R_3$ and $R_4$ together with the carbon atom to which they are attached to form substituted or unsubstituted $C_{3-6}$ cycloalkyl.

According to yet another embodiment there is provided a compound of formula (1), wherein the above said $C_{3-6}$ cycloalkyl is cyclopropyl, cyclobutyl, cyclopentyl, cyclohexyl.

According to yet another embodiment there is provided a compound of formula (1), wherein $R_5$ and $R_6$ are hydrogen.

According to yet another embodiment there is provided a compound of formula (1), wherein $R_5$ and $R_6$ are methyl.

According to yet another embodiment there is provided a compound of formula (1), wherein $R_5$ and $R_6$ together with the carbon atom to which they are attached form $C_{3-6}$ cycloalkyl.

According to yet another embodiment there is provided a compound of formula (1), wherein the above said $C_{3-6}$ cycloalkyl is cyclopropyl and cyclopentyl.

According to yet another embodiment there is provided a compound of formula (1), wherein $R_5$ and $R_6$ together represent oxo.

According to yet another embodiment, there is provided a compound of formula (1), wherein $R_7$ is substituted phenyl; wherein the substituents are chloro, methyl, fluoro, trifluoromethyl, morpholine, methylsulfonyl, 4-Methyl-1H-imidazole, oxazole, 1,3,4-Oxadiazole, thiomorpholine 1,1-dioxide or 4-methylthiomorpholine 1,1-dioxide.

According to yet another embodiment there is provided a compound of formula (1), wherein $R_7$ is substituted pyridine; wherein the substituents are methyl, amino, morpholine or chloro.

According to yet another embodiment there is provided a compound of formula (1), wherein $R_7$ is pyrrolidine.

According to yet another embodiment, there is provided a compound of formula (1), wherein $R_7$ is pyrrolidine which is substituted with —C(O)OR$_c$; wherein R$_c$ is tertiary butyl.

According to yet another embodiment there is provided a compound of formula (1), wherein $R_7$ is pyrazine.

According to yet another embodiment there is provided a compound of formula (1), wherein $R_7$ is pyrazine which is substituted with methyl.

According to yet another embodiment there is provided a compound of formula (1), wherein $R_7$ is furan which is substituted with methyl.

According to yet another embodiment there is provided a compound of formula (1), wherein $R_7$ is piperazine which is substituted with ethyl.

According to yet another embodiment there is provided a compound of formula (1), wherein $R_7$ is quinoline.

According to yet another embodiment there is provided a compound of formula (1), wherein $R_7$ is piperidine.

According to yet another embodiment, there is provided a compound of formula (1), wherein $R_7$ is thiomorpholine 1,1-dioxide.

According to yet another embodiment there is provided a compound of formula (1), wherein $R_7$ is 1H-benzo[d]imidazole.

According to yet another embodiment, there is provided a compound of formula (1), wherein $R_7$ is 1H-benzo[d]imidazole which is substituted with methyl pyridine.

According to yet another embodiment there is provided a compound of formula (1), wherein $R_7$ is 1H-benzo[d]imidazole which is substituted with pyrazine.

According to yet another embodiment there is provided a compound of formula (1), wherein $R_7$ is thiazole which is substituted with methyl or amino.

According to yet another embodiment there is provided a compound of formula (1), wherein $R_7$ is imidazole which is substituted with methyl.

According to yet another embodiment there is provided a compound of formula (1), wherein $R_7$ is pyrazole which is substituted with isopropyl.

According to yet another embodiment there is provided a compound of formula (1), wherein $R_7$ is isoxazole which is substituted with methyl.

According to yet another embodiment, there is provided a compound of formula (1), wherein $R_7$ is 1,3,4-Oxadiazole which is substituted with methyl.

According to yet another embodiment there is provided a compound of formula (1), wherein $R_7$ is pyrimidine.

According to yet another embodiment there is provided a compound of formula (1), wherein $R_7$ is pyrazolo[1,5-a]pyrimidine.

According to yet another embodiment, there is provided a compound of formula (1), wherein $R_7$ is —S(O)$_2$R$_b$; wherein R$_b$ is methyl or 4-chloro phenyl.

According to yet another embodiment, there is provided a compound of formula (1), wherein $R_7$ is N,N-dimethyl amino.

According to yet another embodiment there is provided a compound of formula (1), wherein $R_7$ is tertiary butyl.

According to yet another embodiment there is provided a compound of formula (1), wherein $R_7$ is tertiary butoxy.

According to yet another embodiment there is provided a compound of formula (1), wherein $R_7$ is cyclohexyl.

According to yet another embodiment, there is provided a compound of formula (1), wherein 'n' is 0.

According to yet another embodiment there is provided a compound of formula (1), wherein 'n' is 1.

According to yet another embodiment there is provided a compound of formula (1), wherein 'n' is 2.

Accordingly, one other aspect of the present invention provides compounds of formula (1A)

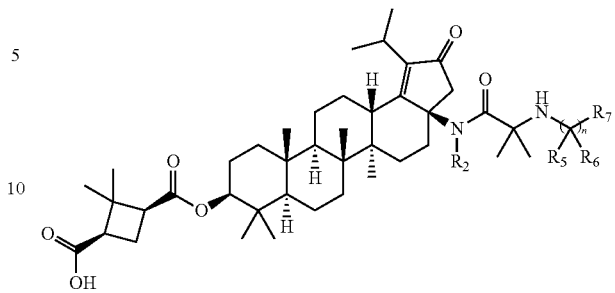

Formula (1A)

wherein, $R_2$, $R_5$, $R_6$, $R_7$ and 'n' are same as defined in formula (1);

pharmaceutically acceptable salts, pharmaceutically acceptable solvates, pharmaceutically acceptable hydrates, tautomers, stereoisomers, ester prodrugs, or combination thereof.

It should be understood that the formula (1A) structurally encompasses all stereoisomers, including enantiomers, diastereomers, racemates, and combinations thereof which may be contemplated from the chemical structure of the genus described herein.

It should be understood that the formula (1A) structurally encompasses all tautomers.

Also contemplated are prodrugs of the compounds of the formula (1A), including ester prodrugs.

According to one embodiment, there is provided a compound of formula (1A), wherein $R_2$ is hydrogen.

According to one embodiment, there is provided a compound of formula (1A), wherein $R_5$ and $R_6$ are hydrogen.

According to one embodiment, there is provided a compound of formula (1A), wherein $R_5$ and $R_6$ are methyl.

According to one embodiment, there is provided a compound of formula (1A), wherein $R_5$ and $R_6$ together represent oxo.

According to one embodiment, there is provided a compound of formula (1A), wherein $R_5$ and $R_6$ together with the carbon atom to which they are attached to form $C_{3-6}$ cycloalkyl.

According to one embodiment, there is provided a compound of formula (1A), wherein the above said $C_{3-6}$ cycloalkyl is cyclopropyl, cyclopentyl or cyclohexyl.

According to yet another embodiment, there is provided a compound of formula (1A), wherein $R_7$ is substituted phenyl; wherein the substituents are chloro, methyl, fluoro, trifluoromethyl, morpholine, methylsulfonyl, 4-Methyl-1H-imidazole, oxazole, 1,3,4-Oxadiazole, thiomorpholine 1,1-dioxide or 4-methylthiomorpholine 1,1-dioxide.

According to yet another embodiment there is provided a compound of formula (1A), wherein $R_7$ is substituted pyridine, wherein the substituents are methyl, amino, morpholine or chloro.

According to yet another embodiment there is provided a compound of formula (1A), wherein $R_7$ is pyrrolidine.

According to yet another embodiment, there is provided a compound of formula (1A), wherein $R_7$ is pyrrolidine which is substituted with —C(O)OR$_c$; wherein R$_c$ is tertiary butyl.

According to yet another embodiment there is provided a compound of formula (1A), wherein $R_7$ is pyrazine.

According to yet another embodiment there is provided a compound of formula (1A), wherein $R_7$ is pyrazine which is substituted with methyl.

According to yet another embodiment there is provided a compound of formula (1A), wherein $R_7$ is furan which is substituted with methyl.

According to yet another embodiment there is provided a compound of formula (1A), wherein $R_7$ is piperazine which is substituted with ethyl.

According to yet another embodiment there is provided a compound of formula (1A), wherein $R_7$ is quinoline.

According to yet another embodiment there is provided a compound of formula (1A), wherein $R_7$ is piperidine.

According to yet another embodiment, there is provided a compound of formula (1A), wherein $R_7$ is thiomorpholine 1,1-dioxide.

According to yet another embodiment there is provided a compound of formula (1A), wherein $R_7$ is 1H-benzo[d] imidazole.

According to yet another embodiment there is provided a compound of formula (1A), wherein $R_7$ is 1H-benzo[d] imidazole which is substituted with methyl pyridine or pyrazine.

According to yet another embodiment there is provided a compound of formula (1A), wherein $R_7$ is thiazole which is substituted with methyl or amino.

According to yet another embodiment there is provided a compound of formula (1A), wherein $R_7$ is imidazole which is substituted with methyl.

According to yet another embodiment there is provided a compound of formula (1A), wherein $R_7$ is pyrazole which is substituted with isopropyl.

According to yet another embodiment there is provided a compound of formula (1A), wherein $R_7$ is isoxazole which is substituted with methyl.

According to yet another embodiment, there is provided a compound of formula (1A), wherein $R_7$ is 1,3,4-oxadiazole which is substituted with methyl.

According to yet another embodiment there is provided a compound of formula (1A), wherein $R_7$ is pyrimidine.

According to yet another embodiment, there is provided a compound of formula (1A), wherein $R_7$ is pyrazolo[1,5-a]pyrimidine.

According to yet another embodiment there is provided a compound of formula (1A), wherein $R_7$ is —S(O)$_2$R$_b$; wherein R$_b$ is methyl or 4-chloro phenyl.

According to yet another embodiment there is provided a compound of formula (1A), wherein $R_7$ is N,N-dimethyl amino.

According to yet another embodiment there is provided a compound of formula (1A), wherein $R_7$ is tertiary butyl.

According to yet another embodiment there is provided a compound of formula (1A), wherein $R_7$ is tertiary butoxy.

According to yet another embodiment there is provided a compound of formula (1A), wherein $R_7$ is cyclohexyl.

According to yet another embodiment there is provided a compound of formula (1A), wherein 'n' is 0.

According to yet another embodiment there is provided a compound of formula (1A), wherein 'n' is 1.

According to yet another embodiment there is provided a compound of formula (1A), wherein 'n' is 2.

Accordingly, one other aspect of the present invention provides compounds of formula (1B)

Formula (1B)

wherein, $R_2$, $R_5$, $R_6$, $R_7$ and 'n' are same as defined in formula (1);

X can be selected from —O—, —CH$_2$O—, —CH$_2$N—, or (—CH$_2$—)$_m$;

'm' can be an integer selected from 1, 2, 3 or 4;

pharmaceutically acceptable salts, pharmaceutically acceptable solvates, pharmaceutically acceptable hydrates, tautomers, stereoisomers, ester prodrugs, or combination thereof.

It should be understood that the formula (1B) structurally encompasses all stereoisomers, including enantiomers, diastereomers, racemates, and combinations thereof which may be contemplated from the chemical structure of the genus described herein.

It should be understood that the formula (1B) structurally encompasses all tautomers.

Also contemplated are prodrugs of the compounds of the formula (1B), including ester prodrugs.

According to one embodiment, there is provided a compound of formula (1B), wherein $R_2$ is hydrogen.

According to one embodiment, there is provided a compound of formula (1B), wherein X is —CH$_2$—.

According to one embodiment, there is provided a compound of formula (1B), wherein $R_5$ and $R_6$ together represent oxo.

According to another embodiment, there is provided a compound of formula (1B), wherein $R_7$ is phenyl which is substituted with chloro, methyl or fluoro.

According to another embodiment, there is provided a compound of formula (1B), wherein $R_7$ is pyridyl which is substituted with methyl or morpholine.

According to another embodiment, there is provided a compound of formula (1B), wherein $R_7$ is pyrimidine.

According to another embodiment, there is provided a compound of formula (1B), wherein 'n' is 1.

According to another embodiment, there is provided a compound of formula (1B), wherein 'm' is 1.

According to another embodiment, there is provided a compound of formula (1B), wherein 'm' is 2.

According to another embodiment, there is provided a compound of formula (1B), wherein 'm' is 3.

According to another embodiment, there is provided a compound of formula (1B), wherein 'm' is 4.

Below are the representative compounds, which are illustrative in nature only and are not intended to limit to the scope of the invention (Nomenclature has been generated from ChemBioDraw Ultra 13.0 version):

(1R,3S)-3-(((((3aR,5aR,5bR,7aR,9S,11aR,11bR,13aS)-3a-(2-(4-chlorobenzamido)-2-methylpropanamido)-1-isopropyl-5a,5b,8,8,11a-pentamethyl-2-oxo-3,3a,4,5,5a,5b, 6,7,7a,8, 9,10,11,11a,11b,12,13,13a-octadecahydro-2H- cyclopenta[a]chrysen-9-yl)oxy)carbonyl)-2,2-dimethylcyclobutane-1-carboxylic acid (Compound 1), (1R,3S)-3-((((3aR,5aR,5bR,7aR,9S,11aR,11bR,13aS)-3a-(2-(1-(4-chlorophenyl) cyclopropane-1-carboxamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a] chrysen-9-yl) oxy)carbonyl)-2,2-dimethylcyclobutane-1-carboxylic acid (Compound 2), (1R,3S)-3-((((3aR,5aR,5bR,7aR,9S,11aR,11bR,13aS)-3a-(2-benzamido-2-methyl propanamido)-1-isopropyl-5a,5b,8,8,11a-pentamethyl-2-oxo-3,3a,4,5,5a,5b,6,7,7a,8,9,10,11, 11a,11b,12,13,13a-octadecahydro-2H-cyclopenta[a]chrysen-9-yl)oxy)carbonyl)-2,2-dimethyl cyclobutane-1-carboxylic acid (Compound 3), (1R,3S)-3-((((3aR,5aR,5bR,7aR,9S,11aR,11bR,13aS)-3a-(2-(3,4-dichlorobenzamido)-2-methylpropanamido)-1-isopropyl-5a,5b,8,8,11a-pentamethyl-2-oxo-3,3a,4,5,5a,5b,6,7,7a, 8,9,10,11,11a,11b,12,13,13a-octadecahydro-2H-cyclopenta[a]chrysen-9-yl)oxy)carbonyl)-2,2-dimethylcyclobutane-1-carboxylic acid (Compound 4), (1R,3S)-3-((((3aR,5aR,5bR,7aR,9S,11aR,11bR,13aS)-1-isopropyl-5a,5b,8,8,11a-pentamethyl-3a-(2-methyl-2-(pyrazine-2-carboxamido)propanamido)-2-oxo-3,3a,4,5,5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Compound 5), (1R,3S)-3-((((3aR,5aR,5bR,7aR,9S,11aR,11bR,13aS)-3a-(2-(6-aminonicotinamido)-2-methylpropanamido)-1-isopropyl-5a,5b,8,8,11a-pentamethyl-2-oxo-3,3a,4,5,5a,5b, 6,7,7a, 8,9,10,11,11a,11b,12,13,13a-octadecahydro-2H-cyclopenta[a]chrysen-9-yl)oxy)carbonyl)-2,2-dimethylcyclobutane-1-carboxylic acid (Compound 6), (1R,3S)-3-((((3aR,5aR,5bR,7aR,9S,11aR,11bR,13aS)-1-isopropyl-5a,5b,8,8,11a-pentamethyl-3a-(2-methyl-2-(5-methylpyrazine-2-carboxamido)propanamido)-2-oxo-3,3a, 4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Compound 7), (1R,3S)-3-((((3aR,5aR,5bR,7aR,9S,11aR,11bR,13aS)-3a-(2-((S)-1-(tert-butoxy carbonyl)pyrrolidine-2-carboxamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Compound 8), (1R,3S)-3-((((3aR,5aR,5bR,7aR,9S,11aR,11bR,13aS)-3a-(2-(2-(4-ethylpiperazin-1-yl)acetamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid (Compound 9), (1R,3S)-3-((((3aR,5aR,5bR,7aR,9S,11aR,11bR,13aS)-1-isopropyl-5a,5b,8,8,11a-pentamethyl-3a-(2-methyl-2-(2-(piperidin-1-yl)acetamido)propanamido)-2-oxo-3,3a,4,5,5a, 5b,6,7,7a,8,9,10,11,11a,11b,12,13,13a-octadecahydro-2H-cyclopenta[a]chrysen-9-yl)oxy carbonyl)-2,2-dimethylcyclobutane-1-carboxylic acid (Compound 10), (1R,3S)-3-((((3aR,5aR,5bR,7aR,9S,11aR,11bR,13aS)-3a-(2-(2-amino-2-methyl propanamido)-2-methylpropanamido)-1-isopropyl-5a,5b,8,8,11a-pentamethyl-2-oxo-3,3a,4,5, 5a,5b,6,7,7a,8,9,10,11,11a,11b,12,13,13a-octalecahydro-2H-cyclopenta[a]chrysen-9-yl)oxy carbonyl)-2,2-dimethylcyclobutane-1-carboxylic acid hydrochloride (Compound 11), (1R,3S)-3-((((3aR,5aR,5bR,7aR,9S,11aR,11bR,13aS)-3a-(2-(1H-benzo[d]imidazole-5-carboxamido)-2-methylpropanamido)-1-isopropyl-5a,5b,8,8,11a-pentamethyl-2-oxo-3,3a,4, 5,5a,5b,6,7,7a,8,9,10,11,11a,11b,12,13,13a-octadecahydro-2H-cyclopenta[a]chrysen-9-yl) oxy) carbonyl)-2,2-dimethylcyclobutane-1-carboxylic acid (Compound 12), (1R,3S)-3-((((3aR,5aR,5bR,7aR,9S,11aR,11bR,13aS)-1-isopropyl-5a,5b,8,8,11a-pentamethyl-3a-(2-methyl-2-(2-(6-methylpyridin-3-yl)-1H-benzo[d]imidazole-5-carboxamido)propanamido)-2-oxo-3,3a,4,5,5a,5b,6,7,7a,8,9,10, 11,11a,11b,12,13,13a-octadecahydro-2H-cyclopenta[a]chrysen-9-yl)oxy)carbonyl)-2,2-dimethyl cyclobutane-1-carboxylic acid (Compound 13), (1R,3S)-3-((((3aR,5aR,5bR,7aR,9S,11aR,11bR,13aS)-3a-(2-(2,4-dimethylthiazole-5-carboxamido)-2-methylpropanamido)-1-isopropyl-5a,5b,8,8,11a-pentamethyl-2-oxo-3,3a,4, 5,5a,5b,6,7,7a,8,9,10,11,11a,11b,12,13,13a-octadecahydro-2H-cyclopenta[a]chrysen-9-yl) oxy) carbonyl)-2,2-dimethylcyclobutane-1-carboxylic acid (Compound 14), (1R,3S)-3-((((3aR,5aR,5bR,7aR,9S,11aR,11bR,13aS)-1-isopropyl-5a,5b,8,8,11a-pentamethyl-3a-(2-methyl-2-(2-(pyrazin-2-yl)-1H-benzo[d]imidazole-5-carboxamido)propan amido)-2-oxo-3,3a,4,5,5a,5b,6,7,7a,8,9,10,11, 11a,11b,12,13,13a-octadecahydro-2H-cyclo penta[a] chrysen-9-yl)oxy)carbonyl)-2,2-dimethylcyclobutane-1-carboxylic acid (Compound 15), (1R,3S)-3-((((3aR,5aR,5bR,7aR,9S,11aR,11bR,13aS)-1-isopropyl-5a,5b,8,8,11a-pentamethyl-3a-(2-methyl-2-(1-methyl-1H-imidazole-2-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 16), (1R,3S)-3-((((3aR,5aR,5bR,7aR,9S,11aR,11bR,13aS)-1-isopropyl-3a-(2-(3-isopropyl-1H-pyrazole-5-carboxamido)-2-methylpropanamido)-5a,5b,8,8,11a-pentamethyl-2-oxo-3,3a, 4,5,5a,5b,6,7,7a,8,9,10,11,11a,11b,12,13,13a-octadecahydro-2H-cyclopenta[a]chrysen-9-yl) oxy)carbonyl)-2,2-dimethylcyclobutane-1-carboxylic acid (Compound 17), (1R,3S)-3-((((3aR,5aR,5bR,7aR,9S,11aR,11bR,13aS)-1-isopropyl-5a,5b,8,8,11a-pentamethyl-3a-(2-methyl-2-(4-morpholinobenzamido)propanamido)-2-oxo-3,3a,4,5,5a, 5b, 6,7,7a,8,9,10,11,11a,11b,12,13,13a-octadecahydro-2H-cyclopenta[a]chrysen-9-yl)oxy carbonyl)-2,2-dimethylcyclobutane-1-carboxylic acid (Compound 18), (1R,3S)-3-((((3aR,5aR,5bR,7aR,9S,11aR,11bR,13aS)-3a-(2-(3,5-dimethylisoxazole-4-carboxamido)-2-methylpropanamido)-1-isopropyl-5a,5b,8,8,11a-pentamethyl-2-oxo-3,3a, 4,5,5a,5b,6,7,7a,8,9,10,11,11a,11b,12,13,13a-octadecahydro-2H-cyclopenta[a]chrysen-9-yl) oxy) carbonyl)-2,2-dimethylcyclobutane-1-carboxylic acid (Compound 19), (1R,3S)-3-((((3aR,5aR,5bR,7aR,9S,11aR,11bR,13aS)-1-isopropyl-5a,5b,8,8,11a-pentamethyl-3a-(2-methyl-2-(4-(4-methyl-1H-imidazol-1-yl)benzamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 20), (1S,3R)-3-((((3aR,5aR,5bR,7aR,9S,11aR,11bR,13aS)-3a-(2-(4-chlorobenzamido)-2-methylpropanamido)-1-isopropyl-5a,5b,8,8,11a-pentamethyl-2-oxo-3,3a,4,5,5a,5b, 6,7,7a,8, 9,10,11,11a,11b,12,13,13a-octadecahydro-2H-cyclopenta[a]chrysen-9-yl)oxy)carbonyl)-2,2-dimethylcyclobutane-1-carboxylic acid (Compound 21), (1R,3S)-3-((((3aR,5aR,5bR,7aR,9S,11aR,11bR,13aS)-3a-(2-(4-fluorobenzamido)-2-methylpropanamido)-1-isopropyl-5a,5b,8,8,11a-pentamethyl-2-oxo-3,3a,4,5,5a,5b, 6,7,7a,8, 9,10,11,11a,11b,12,13,13a-octadecahydro-2H-cyclopenta[a]chrysen-9-yl)oxy)carbonyl)-2,2-dimethylcyclobutane-1-carboxylic acid (Compound 22), (1R,3S)-3-((((3aR,5aR,5bR,7aR,9S,11aR,11bR,13aS)-1-isopropyl-5a,5b,8,8,11a-pentamethyl-3a-(2-methyl-2-(4-methylbenzamido)propanamido)-2-oxo-3,3a,4,5,5a,5b,6, 7, 7a,8,9,10,11,11a,11b,12,13,13a-octalecahydro-2H-cyclopenta[a]chrysen-9-yl)oxy)carbonyl)-2,2-dimethylcyclobutane-1-carboxylic acid (Compound 23), (1R,3S)-3-((((3aR,5aR,5bR,7aR,9S,11aR,11bR,13aS)-3a-(2-(furan-3-carboxamido)-2-methylpropanamido)-1-isopropyl-5a,5b,8,8, 11a-pentamethyl-2-oxo-3,3a,4,5,5a,5b, 6,7,7a,8, 9,10,11,11a,11b,12,13,13a-octadecahydro-2H-cyclopenta[a]chrysen-9-yl)oxy)carbonyl)-2,2-dimethylcyclobutane-1-carboxylic acid (Compound 24), (1R,3S)-3-((((3aR,5aR,5bR,7aR,9S,11aR,11bR,13aS)-1-isopropyl-5a,5b,8,8,11a-pentamethyl-3a-(2-methyl-2-(4-(trifluoromethyl)benzamido)propanamido)-2-oxo-3,3a,4, 5, 5a,5b,6,7,7a,8,9,10,11,11a,11b,12,13,13a-octalecahydro-2H-cyclopenta[a]chrysen-9-yl)oxy carbonyl)-2,2-dimethylcyclobutane-1-carboxylic acid (Compound 25), (1R,3S)-3-((((3aR,5aR,5bR,7aR,9S,11aR,11bR,13aS)-3a-(2-(furan-2-carboxamido)-2-methylpropanamido)-1-isopropyl-5a,5b,8,8,11a-pentamethyl-2-oxo-3,3a,4,5,5a,5b, 6,7,7a, 8,9,10,11,11a,11b,12,13,13a-octadecahydro-2H-cyclopenta[a]chrysen-9-yl)oxy)carbonyl)-2,2-dimethylcyclobutane-1-carboxylic acid (Compound 26), (1R,3S)-3-((((3aR,5aR,5bR,7aR,9S,11aR,11bR,13aS)-1-isopropyl-5a,5b,8,8,11a-pentamethyl-3a-(2-methyl-2-(1-phenylcyclopentane-1-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Compound 27), (1R,3S)-3-((((3aR,5aR,5bR,7aR,9S,11aR,11bR,13aS)-1-isopropyl-5a,5b,8,8,11a-pentamethyl-3a-(2-methyl-2-(quinoline-2-carboxamido)propanamido)-2-oxo-3,3a,4,5, 5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Compound 28), (1R,3S)-3-((((3aR,5aR,5bR,7aR,9S,11aR,11bR,13aS)-1-isopropyl-5a,5b,8,8,11a-pentamethyl-3a-(2-methyl-2-(3-methylpicolinamido)propanamido)-2-oxo-3,3a,4,5,5a,5b, 6,7,7a,8,9,10,11,11a,11b,12,13,13a-octadecahydro-2H-cyclopenta[a]chrysen-9-yl)oxy carbonyl)-2,2-dimethylcyclobutane-1-carboxylic acid (Compound 29), (1R,3S)-3-((((3aR,5aR,5bR,7aR,9S,11aR,11bR,13aS)-1-isopropyl-5a,5b,8,8,11a-pentamethyl-3a-(2-methyl-2-(2-methylfuran-3-carboxamido)propanamido)-2-oxo-3,3a,4, 5, 5a,5b,6,7,7a,8,9,10,11,11a,11b,12,13,13a-octalecahydro-2H-cyclopenta[a]chrysen-9-yl)oxy carbonyl)-2,2-dimethylcyclobutane-1-carboxylic acid (Compound 30), (1R,3S)-3-((((3aR,5aR,5bR,7aR,9S,11aR,11bR,13aS)-1-isopropyl-5a,5b,8,8,11a-pentamethyl-3a-(2-methyl-2-(2-morpholinonicotinamido)propanamido)-2-oxo-3,3a,4,5, 5a,5b, 6,7,7a,8,9,10,11,11a,11b,12,13,13a-octadecahydro-2H-cyclopenta[a]chrysen-9-yl)oxy carbonyl)-2,2-dimethylcyclobutane-1-carboxylic acid (Compound 31), (1R,3S)-3-((((3aR,5aR,5bR,7aR,9S,11aR,11bR,13aS)-1-isopropyl-5a,5b,8,8,11a-pentamethyl-3a-(2-methyl-2-(pyrimidine-2-carboxamido)propanamido)-2-oxo-3,3a,4, 5,5a,5b, 6,7,7a,8,9,10,11,11a,11b,12,13,13a-octadecahydro-2H-cyclopenta[a]chrysen-9-yl)oxy carbonyl)-2,2-dimethylcyclobutane-1-carboxylic acid (Compound 32), (1R,3S)-3-((((3aR,5aR,5bR,7aR,9S,11aR,11bR,13aS)-3a-(2-(2,5-dimethylfuran-3-carboxamido)-2-methylpropanamido)-1-isopropyl-5a,5b,8,8,11a-pentamethyl-2-oxo-3, 3a,4,5, 5a,5b,6,7,7a,8,9,10,11,11a,11b,12,13,13a-octalecahydro-2H-cyclopenta[a]chrysen-9-yl)oxy carbonyl)-2,2-dimethylcyclobutane-1-carboxylic acid (Compound 33), (1R,3S)-3-((((3aR,5aR,5bR,7aR,9S,11aR,11bR,13aS)-3a-(2-(2-(1,1-dioxidothio morpholino)acetamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 34), (1R,3S)-3-((((3aR,5aR,5bR,7aR,9S,11aR,11bR,13aS)-1-isopropyl-5a,5b,8,8,11a-pentamethyl-3a-(2-methyl-2-(piperidine-4-carboxamido)propanamido)-2-oxo-3,3a,4,5, 5a,5b, 6,7,7a,8,9,10,11,11a,11b,12,13,13a-octadecahydro-2H-cyclopenta[a]chrysen-9-yl)oxy carbonyl)-2,2-dimethylcyclobutane-1-carboxylic acid hydrochloride (Compound 35), (1R,3S)-3-((((3aR,5aR,5bR,7aR,9S,11aR,11bR,13aS)-3a-(2-((S)-2-amino-3-methyl butanamido)-2-methylpropanamido)-1-isopropyl-5a,5b,8,8,11a-pentamethyl-2-oxo-3,3a,4,5, 5a,5b,6,7,7a,8,9,10,11,11a,11b,12,13,13a-octalecahydro-2H-cyclopenta[a]chrysen-9-yl)oxy carbonyl)-2,2-dimethylcyclobutane-1-carboxylic acid hydrochloride (Compound 36), (1R,3S)-3-((((3aR,5aR,5bR,7aR,9S,11aR,11bR,13aS)-3a-(1-(4-chlorobenzamido) cyclopropane-1-carboxamido)-1-isopropyl-5a,5b,8,8,11a-pentamethyl-2-oxo-3,3a,4,5, 5a,5b, 6,7,7a,8,9,10,11,11a,11b,12,13,13a-octadecahydro-2H-cyclopenta[a]chrysen-9-yl)oxy carbonyl)-2,2-dimethylcyclobutane-1-carboxylic acid (Compound 37), (1R,3S)-3-((((3aR,5aR,5bR,7aR,9S,11aR,11bR,13aS)-1-isopropyl-5a,5b,8,8,11a-pentamethyl-3a-(1-(6-methylnicotinamido)cyclopropane-1-carboxamido)-2-oxo-3,3a,4, 5,5a, 5b,6,7,7a,8,9,10,11,11a,11b,12,13,13a-octadecahydro-2H-cyclopenta[a]chrysen-9-yl)oxy carbonyl)-2,2-dimethylcyclobutane-1-carboxylic acid (Compound 38), (1R,3S)-3-((((3aR,5aR,5bR,7aR,9S,11aR,11bR,13aS)-3a-(1-(4-fluorobenzamido) cyclopropane-1-carboxamido)-1-isopropyl-5a,5b,8,8,11a-pentamethyl-2-oxo-3,3a,4,5,5a, 5b, 6,7,7a,8,9,10,11,11a,11b,12,13,13a-octadecahydro-2H-cyclopenta[a]chrysen-9-yl)oxy carbonyl)-2,2-dimethylcyclobutane-1-carboxylic acid (Compound 39), (1R,3S)-3-((((3aR,5aR,5bR,7aR,9S,11aR,11bR,13aS)-1-isopropyl-5a,5b,8,8,11a-pentamethyl-3a-(1-(4-methylbenzamido)cyclopropane-1-carboxamido)-2-oxo-3,3a,4, 5,5a,5b, 6,7,7a,8,9,10,11,11a,11b,12,13,13a-octadecahydro-2H-cyclopenta[a]chrysen-9-yl)oxy carbonyl)-2,2-dimethylcyclobutane-1-carboxylic acid (Compound 40), (1S,3R)-3-((((3aR,5aR,5bR,7aR,9S,11aR,11bR,13aS)-3a-(1-(4-chlorobenzamido) cyclopropane-1-carboxamido)-

1-isopropyl-5a,5b,8,8,11a-pentamethyl-2-oxo-3,3a,4,5, 5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 41), (1R,3S)-3-(((((3aR,5aR,5bR,7aR,9S,11aR,11bR,13aS)-3a-(1-(4-chlorobenzamido) cyclobutane-1-carboxamido)-1-isopropyl-5a,5b,8,8,11a-pentamethyl-2-oxo-3,3a,4,5,5a, 5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 42), (1R,3S)-3-((((3aR,5aR,5bR,7aR,9S,11aR,11bR,13aS)-1-isopropyl-5a,5b,8,8,11a-pentamethyl-3a-(1-(6-methylnicotinamido)cyclobutane-1-carboxamido)-2-oxo-3,3a,4,5, 5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 43), (1R,3S)-3-((((3aR,5aR,5bR,7aR,9S,11aR,11bR,13aS)-1-isopropyl-5a,5b,8,8,11a-pentamethyl-2-oxo-3a-(1-(pyrimidine-2-carboxamido)cyclobutane-1-carboxamido)-3, 3a,4,5, 5a,5b,6,7,7a,8,9,10,11,11a,11b,12,13,13a-octalecahydro-2H-cyclopenta[a]chrysen-9-yl)oxy carbonyl)-2,2-dimethylcyclobutane-1-carboxylic acid (Compound 44), (1R,3S)-3-((((3aR,5aR,5bR,7aR,9S,11aR,11bR,13aS)-1-isopropyl-5a,5b,8,8,11a-pentamethyl-3a-(1-(2-morpholinonicotinamido)cyclobutane-1-carboxamido)-2-oxo-3, 3a,4,5, 5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 45), (1R,3S)-3-((((3aR,5aR,5bR,7aR,9S,11aR,11bR,13aS)-3a-(1-(4-chlorobenzamido) cyclopentane-1-carboxamido)-1-isopropyl-5a,5b,8,8,11a-pentamethyl-2-oxo-3,3a,4,5,5a, 5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 46), (1R,3S)-3-((((3aR,5aR,5bR,7aR,9S,11aR,11bR,13aS)-1-isopropyl-5a,5b,8,8,11a-pentamethyl-3a-(1-(6-methylnicotinamido)cyclopentane-1-carboxamido)-2-oxo-3,3a,4, 5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 47), (1R,3S)-3-((((3aR,5aR,5bR,7aR,9S,11aR,11bR,13aS)-3a-(1-(4-chlorobenzamido) cyclohexane-1-carboxamido)-1-isopropyl-5a,5b,8,8,11a-pentamethyl-2-oxo-3,3a,4,5,5a, 5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 48), (1R,3S)-3-((((3aR,5aR,5bR,7aR,9S,11aR,11bR,13aS)-1-isopropyl-5a,5b,8,8,11a-pentamethyl-3a-(1-(6-methylnicotinamido)cyclohexane-1-carboxamido)-2-oxo-3,3a,4,5, 5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 49), (1R,3S)-3-((((3aR,5aR,5bR,7aR,9S,11aR,11bR,13aS)-1-isopropyl-5a,5b,8,8,11a-pentamethyl-3a-(1-(4-methylbenzamido)cyclohexane-1-carboxamido)-2-oxo-3,3a,4,5, 5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 50), (1R,3S)-3-((((3aR,5aR,5bR,7aR,9S,11aR,11bR,13aS)-1-isopropyl-5a,5b,8,8,11a-pentamethyl-3a-(2-methyl-2-(4-(methylsulfonyl)benzamido)propanamido)-2-oxo-3,3a,4, 5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 51), (1R,3S)-3-((((3aR,5aR,5bR,7aR,9S,11aR,11bR,13aS)-1-isopropyl-5a,5b,8,8,11a-pentamethyl-3a-(2-methyl-2-((S)-piperidine-3-carboxamido)propanamido)-2-oxo-3, 3a,4,5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid hydrochloride (Compound 52), (1R,3S)-3-((((3aR,5aR,5bR,7aR,9S,11aR,11bR,13aS)-3a-(2-(2-(4-chlorophenyl) acetamido)-2-methylpropanamido)-1-isopropyl-5a,5b,8,8,11a-pentamethyl-2-oxo-3, 3a,4,5, 5a,5b,6,7,7a,8,9,10,11,11a,11b,12,13,13a-octalecahydro-2H-cyclopenta[a]chrysen-9-yl)oxy) carbonyl)-2,2-dimethylcyclobutane-1-carboxylic acid (Compound 53), (1R,3S)-3-((((3aR,5aR,5bR,7aR,9S,11aR,11bR,13aS)-1-isopropyl-5a,5b,8,8,11a-pentamethyl-3a-(2-methyl-2-(pyrazolo[1,5-a]pyrimidine-3-carboxamido)propanamido)-2-oxo-3,3a,4,5,5a,5b,6,7,7a,8,9,10,11,11a,11b,12, 13,13a-octadecahydro-2H-cyclopenta[a]chrysen-9-yl) oxy)carbonyl)-2,2-dimethylcyclobutane-1-carboxylic acid (Compound 54), (1R,3S)-3-((((3aR,5aR,5bR,7aR,9S,11aR,11bR,13aS)-3a-(2-(2-aminothiazole-4-carboxamido)-2-methylpropanamido)-1-isopropyl-5a,5b,8,8,11a-pentamethyl-2-oxo-3, 3a,4,5, 5a,5b,6,7,7a,8,9,10,11,11a,11b,12,13,13a-octalecahydro-2H-cyclopenta[a]chrysen-9-yl)oxy) carbonyl)-2,2-dimethylcyclobutane-1-carboxylic acid (Compound 55), (1R,3S)-3-((((3aR,5aR,5bR,7aR,9S,11aR,11bR,13aS)-1-isopropyl-5a,5b,8,8,11a-pentamethyl-3a-(2-methyl-2-(4-(5-methyl-1,3,4-oxadiazol-2-yl)benzamido)propanamido)-2-oxo-3,3a,4,5,5a,5b,6,7,7a,8,9,10,11,11a,11b,12, 13,13a-octadecahydro-2H-cyclopenta[a]chrysen-9-yl) oxy)carbonyl)-2,2-dimethylcyclobutane-1-carboxylic acid (Compound 56), (1R,3S)-3-((((3aR,5aR,5bR,7aR,9S,11aR,11bR,13aS)-3a-(2-(4-(1,1-dioxidothio morpholino)benzamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 57), (1R,3S)-3-((((3aR,5aR,5bR,7aR,9S,11aR,11bR,13aS)-3a-(2-(4-((1,1-dioxidothio morpholino)methyl)benzamido)-2-methylpropanamido)-1-isopropyl-5a,5b,8,8,11a-penta methyl-2-oxo-3,3a,4,5,5a,5b,6,7,7a,8,9,10,11,11a,11b,12, 13,13a-octadecahydro-2H-cyclo penta[a]chrysen-9-yl) oxy)carbonyl)-2,2-dimethyl cyclobutane-1-carboxylic acid (Compound 58), (1R,3S)-3-((((3aR,5aR,5bR,7aR,9S,11aR,11bR,13aS)-3a-(2-(2-(dimethylamino) acetamido)-2-methylpropanamido)-1-isopropyl-5a, 5b,8, 8,11a-pentamethyl-2-oxo-3, 3a,4,5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 59), (1R,3S)-3-((((3aR,5aR,5bR,7aR,9S,11aR,11bR,13aS)-1-isopropyl-5a,5b,8,8,11a-pentamethyl-3a-(2-methyl-2-(6-methylpicolinamido)propanamido)-2-oxo-3,3a,4,5,5a,5b, 6,7,7a,8,9,10,11,11a,11b,12,13,13a-octadecahydro-2H-cyclopenta[a]chrysen-9-yl)oxy) carbonyl)-2,2-dimethyl-cyclobutane-1-carboxylic acid (Compound 60), (1R,3S)-3-((((3aR,5aR,5bR,7aR,9S,11aR,11bR,13aS)-1-isopropyl-5a,5b,8,8,11a-pentamethyl-3a-(2-methyl-2-(6-methylnicotinamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethyl-cyclobutane-1-carboxylic acid (Compound 61), (1R,3S)-3-((((3aR,5aR,5bR,7aR,9S,11aR,11bR,13aS)-1-isopropyl-5a,5b,8,8,11a-pentamethyl-3a-(2-methyl-2-pivalamidopropanamido)-2-oxo-3,3a,4,5,5a,5b,6, 7,7a,8,9,10,11, 11a,11b,12,13,13a-octadecahydro-2H-cyclopenta[a]chrysen-9-yl)oxy)carbonyl)-2,2-dimethyl cyclobutane-1-carboxylic acid (Compound 62), sodium (1R,3S)-3-((((3aR,5aR,5bR,7aR,9S,11aR,11bR,13aS)-1-isopropyl-5a,5b,8,8, 11a-pentamethyl-3a-(2-methyl-2-(methylsulfonamido)propanamido)-2-oxo-3,3a, 4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylate (Compound 63), (1R,3S)-3-((((3aR,5aR,5bR,7aR,9S,11aR,11bR,13aS)-3a-(2-((ethoxy)carbonyl)amino)-2-methylpropanamido)-1-isopropyl-5a,5b,8,8,11a-pentamethyl-2-oxo-3,3a,4,5,5a,5b,6,7,7a, 8,9,10,11,11a,11b,12,13,13a-octadecahydro-2H-cyclopenta[a]chrysen-9-yl)oxy)carbonyl)-2,2-dimethylcyclobutane-1-carboxylic acid (Compound 64), (1R,3S)-3-((((3aR,5aR,5bR,7aR,9S,11aR,11bR,13aS)-3a-(2-((4-chlorophenyl) sulfonamido)-2-methylpropanamido)-1-isopropyl-5a,5b,8,8,11a-pentamethyl-2-oxo-3,3a,4,5, 5a,5b,6,7,7a,8,9,10,11,11a,11b,12,13,13a-octalecahydro-2H-cyclopenta[a]chrysen-9-yl)oxy) carbonyl)-2,2-dimethylcyclobutane-1-carboxylic acid (Compound 65), (1R,3S)-3-((((3aR,5aR,5bR,7aR,9S,11aR,11bR,13aS)-3a-(2-(cyclohexanecarbox amido)-2-methylpropanamido)-1-isopropyl-5a,5b,8,8,11a-pentamethyl-2-oxo-3,3a,4,5,5a, 5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Compound 66), (1R,3S)-3-((((3aR,5aR,5bR,7aR,9S,11aR,11bR,13aS)-1-isopropyl-5a,5b,8,8,11a-pentamethyl-3a-(2-methyl-2-((pyridin-2-ylmethyl)amino)propanamido)-2-oxo-3,3a,4, 5,5a, 5b,6,7,7a,8,9,10,11,11a,11b,12,13,13a-octadecahydro-2H-cyclopenta[a]chrysen-9-yl)oxy carbonyl)-2,2-dimethylcyclobutane-1-carboxylic acid (Compound 67), (1R,3S)-3-((((3aR,5aR,5bR,7aR,9S,11aR,11bR,13aS)-3a-(2-((4-chlorobenzypamino)-2-methylpropanamido)-1-isopropyl-5a,5b,8,8,11a-pentamethyl-2-oxo-3,3a,4,5,5a, 5b,6,7,7a, 8,9,10,11,11a,11b,12,13,13a-octadecahydro-2H-cyclopenta[a]chrysen-9-yl)oxy)carbonyl)-2,2-dimethylcyclobutane-1-carboxylic acid (Compound 68), (1R,3S)-3-((((3aR,5aR,5bR,7aR,9S,11aR,11bR,13aS)-3a-(2-(((1-(4-chlorophenyl) cyclopropyl)methyl)amino)-2-methylpropanamido)-1-isopropyl-5a,5b,8,8,11a-pentamethyl-2-oxo-3,3a,4,5,5a,5b,6,7,7a,8,9,10,11,11a,11b,12, 13,13a-octadecahydro-2H-cyclopenta[a]chrysen-9-yl)oxy)carbonyl)-2,2-dimethylcyclobutane-1-carboxylic acid (Compound 69), (1R,3S)-3-((((3aR,5aR,5bR,7aR,9S,11aR,11bR,13aS)-3a-(2-(5-chloropicolinamido)-2-methylpropanamido)-1-isopropyl-5a,5b,8,8,11a-pentamethyl-2-oxo-3,3a,4,5,5a,5b, 6,7,7a, 8,9,10,11,11a,11b,12,13,13a-octadecahydro-2H-cyclopenta[a]chrysen-9-yl)oxy)carbonyl)-2,2-dimethylcyclobutane-1-carboxylic acid (Compound 70), (1R,3S)-3-((((3aR,5aR,5bR,7aR,9S,11aR,11bR,13aS)-1-isopropyl-5a,5b,8,8,11a-pentamethyl-3a-(2-methyl-2-(3-(6-methylpyridin-3-yl)ureido)propanamido)-2-oxo-3,3a, 4,5, 5a,5b,6,7,7a,8,9,10,11,11a,11b,12,13,13a-octalecahydro-2H-cyclopenta[a]chrysen-9-yl)oxy) carbonyl)-2,2-dimethylcyclobutane-1-carboxylic acid (Compound 71), (1R,3S)-3-((((3aR,5aR,5bR,7aR,9S,11aR,11bR,13aS)-1-isopropyl-5a,5b,8,8,11a-pentamethyl-3a-(2-methyl-2-(3-(6-methylpyridin-2-yl)ureido)propanamido)-2-oxo-3,3a, 4,5, 5a,5b,6,7,7a,8,9,10,11,11a,11b,12,13,13a-octalecahydro-2H-cyclopenta[a]chrysen-9-yl)oxy) carbonyl)-2,2-dimethylcyclobutane-1-carboxylic acid (Compound 72), (1R,3S)-3-((((3aR,5aR,5bR,7aR,9S,11aR,11bR,13aS)-3a-(2-((2-(dimethylamino) ethyl)amino)-2-methylpropanamido)-1-isopropyl-5a,5b,8,8,11a-pentamethyl-2-oxo-3, 3a,4,5, 5a,5b,6,7,7a,8,9,10,11,11a,11b,12,13,13a-octalecahydro-2H-cyclopenta[a]chrysen-9-yl)oxy) carbonyl)-2,2-dimethylcyclobutane-1-carboxylic acid (Compound 73), (1R,3S)-3-((((3aR,5aR,5bR,7aR,9S,11aR,11bR,13aS)-3a-(2-amino-2-methylpropan amido)-1-isopropyl-5a,5b,8,8, 11a-pentamethyl-2-oxo-3,3a,4,5,5a,5b,6,7,7a,8,9,10,11, 11a, 11b,12,13,13a-octadecahydro-2H-cyclopenta[a]chrysen-9-yl)oxy)carbonyl)-2,2-dimethyl cyclobutane-1-carboxylic acid hydrochloride (Compound 74), (1R,3S)-3-((((3aR,5aR,5bR,7aR,9S,11aR,11bR,13aS)-3a-(2-((tert-butoxy)carbonyl) amino)-2-methylpropanamido)-1-isopropyl-5a,5b,8,8,11a-pentamethyl-2-oxo-3, 3a,4,5,5a,5b, 6,7,7a,8,9,10,11,11a,11b,12,13,13a-octadecahydro-2H-cyclopenta[a]chrysen-9-yl)oxy carbonyl)-2,2-dimethylcyclobutane-1-carboxylic acid (Compound 75), (1R,3S)-3-((((3aR,5aR,5bR,7aR,9S,11aR,11bR,13aS)-1-isopropyl-5a,5b,8,8,11a-pentamethyl-3a-(2-methyl-2-((S)-pyrrolidine-2-carboxamido)propanamido)-2-oxo-3, 3a,4,5, 5a,5b,6,7,7a,8,9,10,11,11a,11b,12,13,13a-octalecahydro-2H-cyclopenta[a]chrysen-9-yl)oxy) carbonyl)-2,2-dimethylcyclobutane-1-carboxylic acid hydrochloride (Compound 76), or pharmaceutically acceptable salts, solvates, including hydrates and prodrugs of compounds are also contemplated.

The present invention also provides a pharmaceutical composition that includes at least one compound as described herein and at least one pharmaceutically acceptable excipient (such as a pharmaceutically acceptable carrier or diluent). Specifically, the pharmaceutical composition comprises a therapeutically effective amount of at least one compound described herein. The compound(s) present in the composition may be associated with a pharmaceutically acceptable excipient (such as a carrier or a diluent) or may be diluted by a carrier, or enclosed within a carrier which may be in the form of a capsule, sachet, or other container.

The compounds and pharmaceutical compositions described herein are useful in the treatment of diseases, conditions and/or disorders mediated by viral infections.

The present invention further provides a method of treating a disease, condition and/or disorder mediated by viral infections in a subject in need thereof by administering to the subject one or more compounds described herein in a therapeutically effective amount to treat that infection, specifically in the form of a pharmaceutical composition.

Also provided herein are processes for preparing compounds described herein.

The invention provides a method for preventing; ameliorating or treating a HIV mediated disease, disorder or syndrome in a subject in need thereof comprising administering to the subject a therapeutically effective amount of a compound of the invention. The invention further provides a method, wherein the HIV mediated disease, disorder or syndrome is like AIDS, AIDS related complex, or a syndrome characterized by symptoms such as persistent generalized lymphadenopathy, fever and weight loss, or a retroviral infection genetically related to AIDS.

Anti HIV inhibitory potential of the compounds of present invention may be demonstrated by any one or more methodologies known in the art, such as by using the assays described in Mossman T, December 1983, *Journal of immunological methods*, 65 (1-2), 55-63 and *SPC Cole, cancer chemotherapy and Pharmacology*, 1986, 17, 259-263.

DETAILED DESCRIPTION OF THE INVENTION

The present invention provides C-3 novel triterpenone with C-17 reverse amide derivatives and related compounds, which may be used as antiviral particularly as anti-HIV compounds and processes for the synthesis of these compounds. Pharmaceutically acceptable salts, pharmaceutically acceptable solvates, enantiomers, diastereomers of the derivatives, together with pharmaceutically acceptable carriers, excipients or diluents, which can be used for the treatment of diseases, condition and/or disorders mediated by viral infections, are also provided.

The Following Definitions Apply to the Terms as Used Herein

The terms "halogen" or "halo" includes fluorine, chlorine, bromine, or iodine.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "alkoxy" refers to a straight or branched hydrocarbon chain with oxygen radical consisting carbon and hydrogen atoms, containing saturation or unsaturation, having from one to eight carbon atoms, and which is attached through oxygen atom to the rest of the molecule by a single bond, e.g., methyloxy, ethyloxy, n-propyloxy, 1-methylethyloxy (isopropyloxy), n-butyloxy, n-pentyloxy, and 1,1-dimethylethyloxy (t-butyloxy).

The term "alkoxylalkoxy" refers to a straight or branched hydrocarbon chain with oxygen radical consisting carbon atom, hydrogen atom and alkoxy groups, containing saturation or unsaturation, having from one to eight carbon atoms, and which is attached through oxygen atom to the rest of the molecule by a single bond, e.g., 2-(methyloxy) ethyloxy, 2-(ethyloxy)ethyloxy, 2-(n-propyloxy)ethyloxy, and 3-(isopropylo xy)butyloxy.

The term "amine" refers to an organic compounds and functional groups that contain a basic nitrogen atom with a lone pair. Amines are derivatives of ammonia, wherein one or more hydrogen atoms have been replaced by a substituent such as an alkyl or aryl group these may respectively be called alkylamines and arylamines; amines in which both types of substituent are attached to one nitrogen atom may be called alkylarylamines. Important amines include amino acids, trimethylamine, and aniline.

The term "amino acid" refers to a straight or branched hydrocarbon chain containing an amine group, a carboxylic acid group, and a side-chain that is specific to each amino acid and which is attached through the nitrogen atom of the amine group to the rest of the molecule by a single bond, e.g., alanine, valine, isoleucine, leucine, phenylalanine, or tyrosine.

The term "amino alkyl" refers to any amino derivative of an alkyl radical more specifically dimethylamino.

The term "cycloalkyl" denotes a non-aromatic mono or multicyclic ring system of from 3 to about 12 carbon atoms, such as cyclopropyl, cyclobutyl, cyclopentyl, and cyclohexyl. Examples of multicyclic cycloalkyl groups include, but are not limited to, perhydronapththyl, adamantyl and norbornyl groups, bridged cyclic groups and spirobicyclic groups, e.g., spiro (4,4) non-2-yl.

The term "aryl" refers to an aromatic radical having from 6 to 14 carbon atoms such as phenyl, naphthyl, tetrahydronapthyl, indanyl, and biphenyl.

The term "haloalkyl" refers to alkyl group (as defined above) is substituted with one or more halogens. A monohaloalkyl radical, for example, may have a chlorine, bromine, iodine or fluorine atom. Dihalo and polyhaloalkyl radicals may have two or more of the same or different halogen atoms. Examples of haloalkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluoro chloromethyl, dichloro fluoromethyl, difluoroethyl, difluoropropyl and the like.

The terms "heterocyclyl" and "heterocyclic ring" refer to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, tetrazoyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl and 1,4-Thiazine-1,1-dione. The heterocyclic ring radical may be attached to the main structure at any heteroatom or carbon atom that results in the creation of a stable structure.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure.

The term "heteroaryl" refers to an aromatic heterocyclic ring radical. Examples of such heteroaryl include, but are not limited to pyridyl, pyrazinyl, furanyl, quinolinyl, tetrazoyl, triazolyl, 1,3-Diaza-1H-indenyl, thiazolyl, imidazolyl, pyrazolyl, isoxazolyl, pyrazolo[1,5-a]pyrimidinyl, 1,3,4-Oxadiazolyl, thiazolidinyl, isothiazolyl, quinuclidinyl, isothiazolidinyl, indolyl, isoindolyl, indolinyl and isoindolinyl.

The heteroaryl ring radical may be attached to the main structure at any heteroatom or carbon atom that results in the creation of a stable structure.

"Substituted" refers to 1-3 substituents on the same position or on different positions with the same groups or different groups. Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, haloalkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, s substituted or unsubstituted amino, substituted or unsubstituted heteroaryl, substituted or unsubstituted heterocyclylalkyl ring, substituted or substituted or unsubstituted heterocyclic ring. The substituents in the aforementioned "substituted" groups cannot be further substituted. For example, when the substituent on "substituted alkyl" is "substituted aryl", the substituent on "substituted aryl" cannot be "substituted alkenyl".

The term "prodrug" denotes a derivative of a compound, which derivative, when administered to warm-blooded animals, e.g. humans, is converted into the compound (drug). The enzymatic and/or chemical hydrolytic cleavage of the compounds of the present invention occurs in such a manner that the proven drug form (parent carboxylic acid drug) is released, and the moiety or moieties split off remain nontoxic or are metabolized so that nontoxic metabolic products are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "treating" or "treatment" of a state, disease, disorder or condition includes:

(1) preventing or delaying the appearance of clinical symptoms of the state, disease, disorder or condition developing in a subject that may be afflicted with or predisposed to the state, disease, disorder or condition but does not yet experience or display clinical or subclinical symptoms of the state, disease, disorder or condition;

(2) inhibiting the state, disease, disorder or condition, i.e., arresting or reducing the development of the state, disease, disorder or condition or at least one clinical or subclinical symptom thereof; or (3) relieving the state, disease, disorder or condition, i.e., causing regression of the state, disease, disorder or condition or at least one of its clinical or subclinical symptoms.

The benefit to a subject receiving treatment is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disease, disorder or condition, is sufficient to effect such treatment. The "therapeutically effective amount" will vary depending on the compound, the state, disease, disorder or condition and its severity and the age, weight, physical condition and responsiveness of the subject receiving treatment.

The compounds of the present invention may form salts. Non-limiting examples of pharmaceutically acceptable salts forming part of this invention include salts derived from inorganic bases salts of organic bases salts of chiral bases, salts of natural amino acids and salts of non-natural amino acids. Certain compounds of the present invention are capable of existing in stereo isomeric forms (e.g., diastereomers, enantiomers, racemates, and combinations thereof). With respect to the overall compounds described by the Formula (1), the present invention extends to these stereo isomeric forms and to mixtures thereof. To the extent prior art teaches synthesis or separation of particular stereoisomers, the different stereo isomeric forms of the present invention may be separated from one another by the methods known in the art, or a given isomer may be obtained by stereospecific or asymmetric synthesis. Tautomeric forms and mixtures of compounds described herein are also contemplated.

Pharmaceutically acceptable solvates includes hydrates and other solvents of crystallization (such as alcohols). The compounds of the present invention may form solvates with low molecular weight solvents by methods known in the art.

Pharmaceutical Compositions

The pharmaceutical compositions provided in the present invention include at least one compound described herein and at least one pharmaceutically acceptable excipient (such as a pharmaceutically acceptable carrier or diluent). Specifically, the contemplated pharmaceutical compositions include a compound(s) described herein in an amount sufficient to treat viral infection in a subject.

The subjects contemplated include, for example, a living cell and a mammal, including human. The compound of the present invention may be associated with a pharmaceutically acceptable excipient (such as a carrier or a diluent) or be diluted by a carrier, or enclosed within a carrier which can be in the form of a capsule, sachet, or other container.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters, and polyoxyethylene.

The carrier or diluent may include a sustained release material, such as, for example, glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick-, sustained-, or delayed-release of the active ingredient after administration to the subject by employing procedures known in the art.

The pharmaceutical compositions described herein may be prepared, e.g., as described in *Remington: The Science* and Practice of Pharmacy, 20th Ed., 2003 (Lippincott Williams & Wilkins). For example, the active compound can be mixed with a carrier, or diluted by a carrier, or enclosed within a carrier, which may be in the form of an ampule, capsule, or sachet. When the carrier serves as a diluent, it may be a solid, semi-solid, or liquid material that acts as a vehicle, excipient, or medium for the active compound.

The pharmaceutical compositions may be in conventional forms, for example, capsules, tablets, solutions, suspensions, injectables or products for topical application. Further, the pharmaceutical composition of the present invention may be formulated so as to provide desired release profile.

The route of administration may be any route which effectively transports the active compound to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is specifically suitable.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Exemplary carriers for tablets, dragees, or capsules include lactose, cornstarch, and/or potato starch. A syrup or elixir can be used in cases where a sweetened vehicle can be employed.

A typical tablet that may be prepared by conventional tableting techniques.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, specifically aqueous solutions with the active compound dissolved in polyhydroxylated castor oil.

Methods of Screening

Antiviral HIV activity and cytotoxicity of compounds present invention can be measured in parallel by following the methods published in the literature.

The cytotoxic effect of compounds can be analyzed by measuring the proliferation of cells using the 3-(4,5-Dimethylthiazol-2-yl)-2,5-diphenyl tetrazlium bromide (MTT) staining. Cells ($5 \times 10^3$ cells/well) will be incubated in in 96 well plates in the presence or absence of compounds. At the end of treatment, 20 µl of MTT (5 mg/ml in PBS) will be added to each well and incubated for an additional 4 hours at 37° C. The purpleblue MTT formazan precipitate will be dissolved in a triplex reagent containing 10% SDS, 5% isobutanol and 10 mmol/lit HCl. The activity of mitochondria, reflecting cellular growth and viability, will be evaluated by measuring the optical density at 570 nm on micro titer plate.

Action of compounds on replication of HIV in Sup-Tl cells can be determined by the method published by Roda Rani et al., 2006 (Archives of Biochemistry and Biophysics, Volume 456, Issue 1, 1 Dec. 2006, Pages 79-92).

Briefly, $1 \times 10^6$ Sup-Tl cells with 100% cell viability will be seeded in RPMI 1640, 0.1% FBS four 12 well plates. Increasing concentrations of Epap-1 peptides will be added to the cells and will be infected with $HIV1_{93\ IN\ 101}$ each at final concentration of virus equivalent to 2 ng of p24 per ml. The infected cells will be incubated at 37° C. and 5% $CO_2$ incubator for 2 hours. After 2 hours the cells will be pelleted at 350 g for 10 minutes, supernatant will be discarded and cell will be held with RPMI 1640 containing 10% FBS. The cells will be resuspended in the same medium with increasing concentrations of Epap-1 peptides and will be incubated for 96 hours. The cells will be supplemented with peptides at every 24 hours. The supernatants will be collected after 96 hours and analyzed using P24 antigen capture assay kit (SAIC Fredrick). The infection in the absence of Epap-1 will be considered to be 0% inhibition Azidothymidine (AZT) will be taken as positive control.

Action of compound on virus entry and quantification of virus entered can be done in terms of GFP expression by the following the methods published J. Virol. 72, 6988 (1998) by in Cecilia et al., and Analytical Biochemistry Volume 360, Issue 2, 15 Jan. 2007, Pages 315-317 (Dyavar S. Ravi and Debashis Mitra).

Briefly, cells will be seeded in to wells of 24 well plates 1 day prior to the experiment. The cells will be transfected with Tat-reporter. The virus inoculum will be adjusted to 1,000-4,000 TCID 50/ml in assay medium (DMEM, 10% FCS, glutamine and antibiotics), 50 µl aliquots will be incubated with serial dilutions of compounds (50 µl) for 1 hour at 37° C. The reporter expression will be quantified at appropriate time calculated inhibitory doses referrers to the concentration of these agents in this preincubation mixture.

Other relevant references useful for screening antiviral HIV activity are: Averett, D. R.1989. Anti-HIV compound assessment by two novel high capacity assays. J. Virol. Methods 23: 263-276; Schwartz, O., et al.1998; A rapid and simple colorimeric test fror the study of anti HIV agents. AIDS Res. and Human Retroviruses, 4(6):441-447; Daluge, S. M., et al. 1994. 5-Chloro-2',3'-deoxy-3'fluorouridine (935U83), a selective anti human immunodeficiency virus agent with an improved metabolic and toxicological profile; Antimicro. Agents and Chemotherapy, 38(7):1590-1603; H. Mitsuya and S. Border, Inhibition of the in vitro infectivity and cytopathic effect of human T-lymphotropic virus type lymphadenopathy-associated virus (HLTV-III/LAV) by 2,3'-dideoxynucleosides, Proc. Natl. Acad. Sci. USA,83,1911-15 (1986); Pennington et al., Peptides 1990; Meek T. D et al., Inhibition of HIV-1 protease in infected T-limphocytes by synthetic peptide analogues, Nature, 343, p90 (1990); Weislow et al., J. Natl. Cancer Inst. 81, 577-586, 1989; T. Mimoto et al., J. Med. Chem., 42, 1789-1802, 1999; Uckun et al 1998, Antimicrobial Agents and Chemotherapy 42:383; for P24 antigen assay Erice et al., 1993, Antimicrob. Ag. Chemotherapy 37: 385-383; Koyanagi et al., Int. J. Cancer, 36, 445-451, 1985; Balzarini et al. AIDS (1991), 5, 21-28; Connor et al., Journal of virology,1996, 70, 5306-5311; Popik et al., Journal of virology, 2002, 76, 4709-4722; Harrigton et al., Journal of Virology Methods, 2000, 88, 111-115; Roos et al., Virology 2000, 273, 307-315; Fedyuk N. V. et al; Problems of Virology 1992, (3)P135; Mosmann T, December 1983, Journal of immunological methods, 65 (1-2), 55-63; SPC Cole, cancer chemotherapy and Pharmacology, 1986, 17, 259-263, Antiviral methods and protocols (Eds: D Kinchington and R. F. Schinazi) Humana Press Inc., 2000, HIV protocols (Eds: N. L. Michael and J. H. Kim) Humana Press Inc, 1999, DAIDS Virology manual from HIV laboratories, Publication NIH-97-3838, 1997, 4. HIV-1 p24 antigen capture assay, enzyme immunoassay for detection of Human immunodeficiency Virus Type 1 (HIV-1) p24 in tissue culture media—Advanced bio science laboratories, Inc kit procedure.

Methods of Treatment

The present invention provides compounds and pharmaceutical formulations thereof that are useful in the treatment of diseases, conditions and/or disorders mediated by viral infections. The connection between therapeutic effect and antiviral is illustrated. For example, PCT publication Nos. WO 01//07646, WO 01/65957, or WO 03/037908; US publication Nos. U.S. Pat. No. 4,598,095 or US 2002/0068757; EP publication Nos. EP 0989862 or EP 0724650; Bioorganic & Medicinal Chemistry Letters, 16, (6), 1712-1715, 2006; and references cited therein, all of which are incorporated herein by reference in their entirety and for the purpose stated.

The present invention further provides a method of treating a disease, condition and/or disorder mediated by viral infections in a subject in need thereof by administering to the subject a therapeutically effective amount of a compound or a pharmaceutical composition of the present invention.

Diseases, conditions, and/or disorders that are mediated by viral infections are believed to include, but are not limited to, HIV infection, HBV infection, HCV infection a retroviral infection genetically related to HIV, AIDS, inflammatory disease, respiratory disorders (including adult respiratory distress syndrome (ARDS), bronchitis, chronic bronchitis, chronic obstructive pulmonary disease, cystic fibrosis, asthma, emphysema, rhinitis and chronic sinusitis), inflammatory bowel disease (including Crohn's disease and ulcerative colitis), multiple sclerosis, rheumatoid arthritis, graft rejection (in particular but not limited to kidney and lung allografts), endometriosis, type I diabetes, renal diseases, chronic pancreatitis, inflammatory lung conditions, chronic heart failure and bacterial infections (in particular but not limited to tuberculosis).

The compounds of the present invention can obtain more advantageous effects than additive effects in the prevention or treatment of the above diseases when using suitably in combination with the available drugs. Also, the administration dose can be decreased in comparison with administration of either drug alone, or adverse effects of co administrated drugs other than antiviral can be avoided or declined.

Methods of Preparation

The compounds described herein may be prepared by techniques known in the art. In addition, the compounds described herein may be prepared by following the reaction sequence as depicted in Scheme 1. Further, in the following schemes, where specific bases, acids, reagents, solvents, coupling agents, etc., are mentioned, it is understood that other bases, acids, reagents, solvents, coupling agents etc., known in the art may also be used and are therefore included within the present invention. Variations in reaction conditions, for example, temperature and/or duration of the reaction, which may be used as known in the art, are also within the scope of the present invention. All the stereoisomers of the compounds in these schemes, unless otherwise specified, are also encompassed within the scope of this invention.

Compounds of the present invention can be synthesized from naturally occurring Betulinic acid or betulin. Key intermediates required for synthesizing analogues are either commercially available, or can be prepared by the methods published in the literature. For example, the key intermediates in the present invention were prepared by modifying the procedures published in Journal of organic chemistry 2010, 75, 1285-1288; Journal of organic chemistry 2000, 65, 3934-3940; Tetrahedron: asymmetry 2008, 19, 302-308; or Tetrahedron: asymmetry 2003, 14, 217-223.

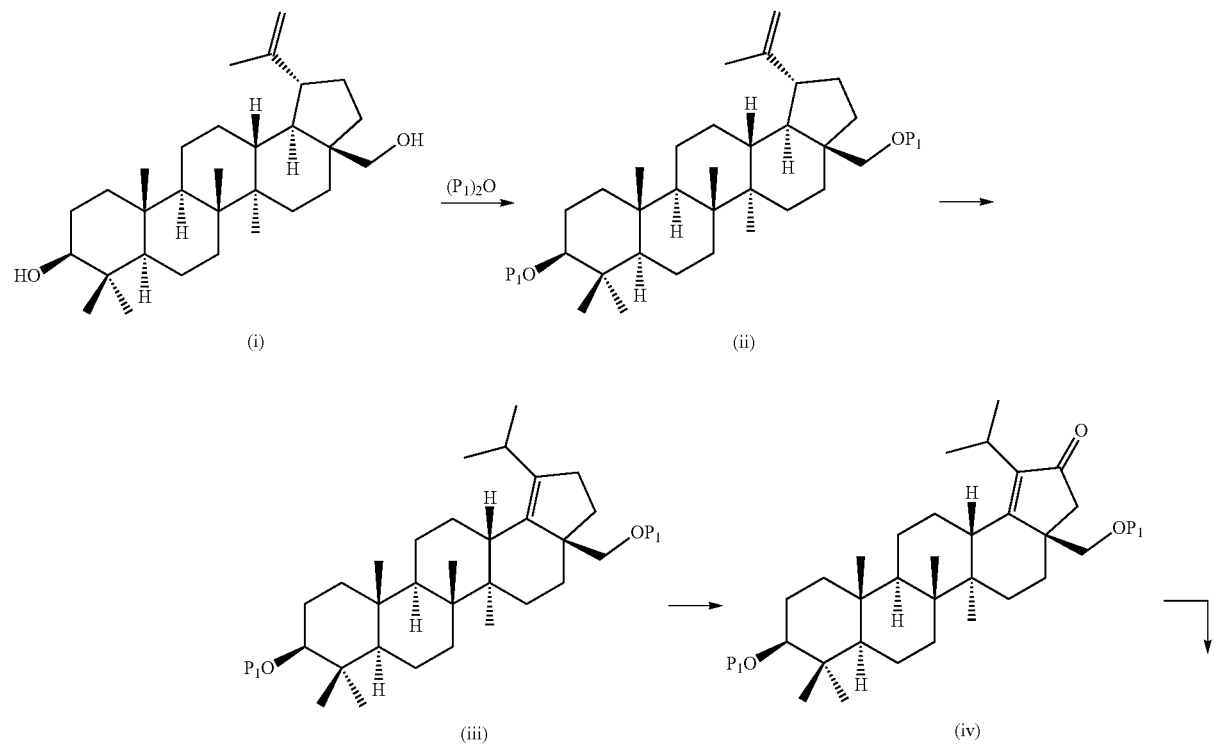

Scheme-1

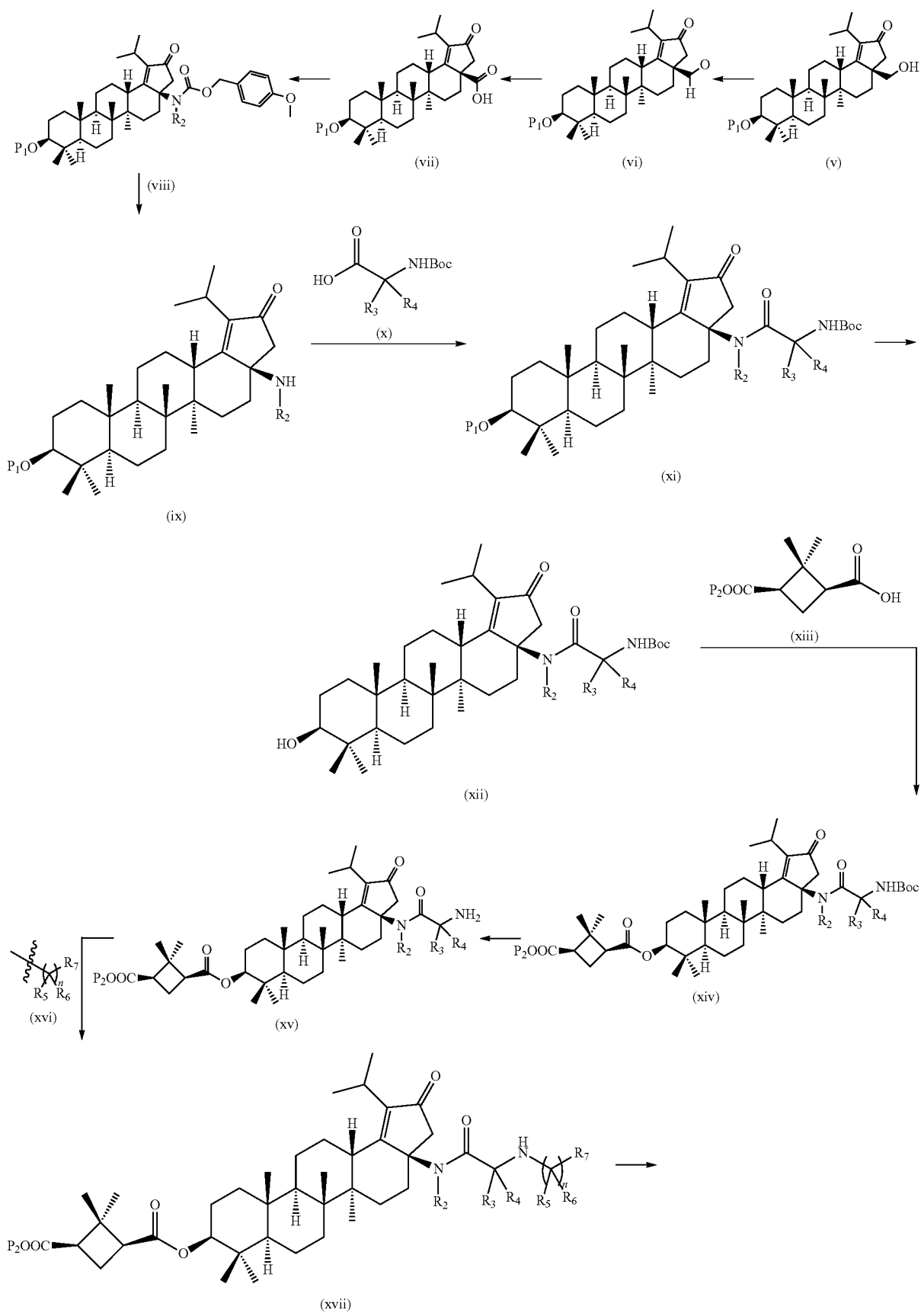

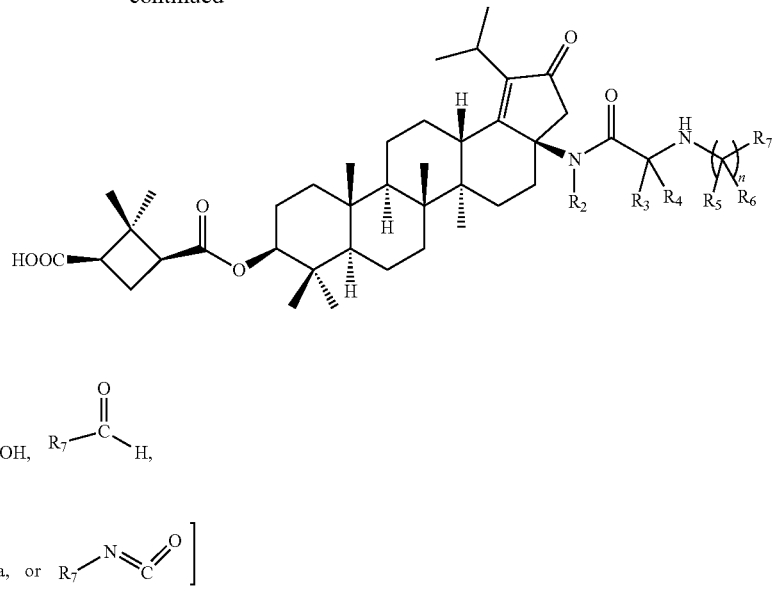

(Formula 1)

wherein Formula 1, $R_7 \underset{R_6 \ R_5}{\overset{R_4 \ R_3}{\diagdown}}{}_n\diagup$ is $R_7-\overset{O}{\underset{\|}{C}}-OH$, $R_7-\overset{O}{\underset{\|}{C}}-H$, $R_7-\overset{O}{\underset{\|}{C}}-Cl$, $R_7-\overset{O}{\underset{\|}{\overset{\|}{C}}}-ONa$, or $R_7-N\!=\!C\!=\!O$ The compounds of formula 1 (wherein, $R_2$, $R_3$, $R_4$, $R_5$, $R_6$ and $R_7$ are same as defined above) can be prepared as described in Scheme 1. The C-3 & C-28 di alcohol compounds of formula (i) can be reacted with a suitable acetate forming reagents such as anhydrides, acid halides, mixed anhydrides or the like in the presence of bases such as triethylamine (TEA), diisopropylethylamine (DIPEA), pyridine or the like in the solvents such as dichloromethane (DCM), chloroform ($CHCl_3$), toluene, tetrahydrofuran (THF) or the like with or without addition of catalysts such as dimethyl amino pyridine (DMAP) or the like to give the C-3 & C-28 protected alcohol compounds of formula (ii) ($P_1$ and $P_2$ are protecting groups such as acetyl, benzyl or the like). The C-3 & C-28 protected alcohol compounds of formula (ii) with terminal double bond can be migrated to the E-ring compounds of formula (iii) in the presence of hydrogen bromide (HBr) in acetic acid (AcOH), acetic acid (AcOH) and acetic anhydride ($Ac_2O$) in solvents like toluene, benzene, xylene or the like. The E-ring compounds of formula (iii) can be converted to give the Enone compounds of formula (iv) in the presence of sodium dichromate ($Na_2Cr_2O_7$), sodium acetate (NaOAc), acetic acid (AcOH), acetic anhydride ($Ac_2O$) in solvents like toluene, benzene or the like. The Enone C-28 compounds of formula (iv) can be deprotected to give the C-28 alcohol compounds of formula (v) in the presence of potassium hydroxide (KOH) or the like in the combination of solvents such as toluene:ethanol (EtOH) (1:1) or with reagents like Aluminum isopropoxide (Al(i-Pro)$_3$) in solvents like 2-propanol or the like. The C-28 alcohol compounds of formula (v) can be converted to give the C-28 aldehyde compounds of formula (vi) in the presence of pyridinium chlorochromate (PCC), pyridinium dichromate (PDC), Dessmartin periodinane (DMP) or Swern oxidation conditions in the solvents such as dichloromethane (DCM) or the like. The C-28 aldehyde compounds of formula (vi) can be converted to give the C-28 acid compounds of formula (vii) in the presence of oxidising agents such as sodium chlorite ($NaClO_2$) or the like in the presence of a scavenger such as 2-methyl-2-butene or the like in the presence of a buffer reagent such as sodiumdihydrogen phosphate ($NaH_2PO_4$) or the like in the combination of solvents such as tert-butanol (t-BuOH), tetrahydrofuran (THF) and water ($H_2O$) or the like. The C-28 alcohol compounds of formula (v) can be converted in one pot method to C-28 acid compounds of formula (vii) in the presence of oxidizing agents such as 2,2,6,6-Tetramethyl-1-piperidinyloxy, free radical, 2,2,6,6-Tetramethylpiperidine 1-oxyl (TEMPO), Sodium hypochlorite (NaOCl) and Sodium chlorite ($NaClO_2$) in the presence of buffer reagent such as sodiumdihydrogen phosphate ($NaH_2PO_4$) and the bases like $NaHCO_3$ in combination of solvents like Tetrahydrofuran (THF) and water ($H_2O$). The C-28 acid compounds of formula (vii) can be converted to the C-17 carbamate compounds of formula (viii) by using the reagents like diphenylphosphoryl azide (DPPA) or ethylchloroformate and sodium azide ($NaN_3$) in the presence of bases such as triethylamine (TEA), N,N-Diisopropylethylamine (DIPEA) in solvents such as 1,2-DCE, THF or Toluene in the presence of alcohols such as 4-methoxybenzyl alcohol (PMBOH), tert-butyl alcohol (t-BuOH) or the like. The C-17 carbamate compounds of formula (viii) can be cleaved in the presence of acid medium such as trifluoroacetic acid (TFA), HCl/1,4-dioxane or the like in the solvents such as dichloromethane (DCM) or chloroform ($CHCl_3$) or the like to give the amine compounds of formula (ix). The C-17 amine compounds of formula (ix) can be reacted with the acid compounds of formula (x) in the presence of coupling reagents such as O-(7-Azabenzotriazol-1-yl)-N,N,N',N'-tetramethyluroniumhexafluorophosphate (HATU), O-(Benzotriazol-1-yl)-N,N,N',N'-tetramethyluroniumhexafluoro phosphate (HBTU), 1-Ethyl-3-(3-dimethylaminopropyl)carbodiimide (EDCI), 1-Hydroxybenzo triazole (HOBt) or the like in the presence of bases such as triethylamine (TEA), N,N-Diisopropylethylamine (DIPEA) or the like in the solvents such as 1,2-dichloroethane (1,2-DCE), dimethylformamide (DMF) or the like to give the C-17amide compounds of formula (xi). The C-3 protected alcohol compounds of formula (xi) can be deprotected to give the C-3 alcohol compounds of formula (xii) in the presence of inorganic bases such as Lithium hydroxide (LiOH), sodium hydroxide (NaOH), potassium hydroxide (KOH) or the like in the solvents such as methanol (MeOH):tetrahydrofuran (THF):water ($H_2O$) (4:2:1) (or) 1,4-dioxane:water ($H_2O$) (4:1) or the like. The C-3 alcohol compounds of formula (xii) can be reacted with the acid compounds of formula (xiii) to give the C-3 ester compounds of formula (xiv) in different ways like (a) Acid and alcohol coupling in the presence of coupling reagents such as 2,4,6-trichlorobenzyl chloride, or the like in the presence of bases such as triethylamine (TEA), N,N-Diisopropylethylamine (DIPEA) and catalysts such as 4-dimethylaminopyridine (DMAP) in the solvents such as 1,2-dichloroethane (1,2-DCE), dichloromethane (DCM) or the like.

(b) acid alcohol coupling in the presence of coupling reagents such EDCI, HOBt in the presence of bases such as triethylamine (TEA), N,N-Diisopropylethylamine (DIPEA) and catalysts such as 4-dimethylaminopyridine (DMAP) in the solvents such as dichloromethane (DCM) and N,N-dimethylformamide (DMF) or the like.

The C-17 substituted N-protected compounds of formula (xiv) can be deprotected in the presence of deprotecting agents such as trifluoroacetic acid (TFA) or HCl/1,4-dioxane or the like in the solvents such as dichloromethane (DCM) or the like to give the C-17 substituted amine compounds of formula (xv). The C-17 substituted amine compounds of formula (xv) can be reacted with the compounds of formula (xvi) to form C-3 ester compounds of formula (xvii) in different ways like a) acid and amine coupling in the presence of coupling reagents such as O-(7-Azabenzotriazol-1-yl)-N,N,N',N'-tetra methyluroniumhexafluorophosphate (HATU), O-(Benzotriazol-1-yl)-N,N,N',N'-tetramethyl uroniumhexafluorophosphate (HBTU), 1-Ethyl-3-(3-dimethyl amino propyl)carbodiimide (EDCI), 1-Hydroxybenzotriazole (HOBt) or the like in the presence of bases such as triethylamine (TEA), N,N-Diisopropylethylamine (DIPEA) or the like in the solvents such as 1,2-dichloroethane (1,2-DCE), dimethylformamide (DMF) or the like.

b) reductive amination of amine and aldehyde in the presence of reducing agents such as sodium triacetoxyborohydride (STAB) or Sodium borohydride or sodium cyanoborohydride ($NaCNBH_3$) or the like in the solvents such as 1,2-dichloroethane (1,2-DCE), tetrahydrofuran (THF), Methanol (MeOH), Acetonitrile ($CH_3CN$) or the like.

c) acid chloride and amine coupling in the presence of bases such as triethylamine (TEA), or diisopropylethylamine (DIPEA) or the like in the solvents such as dichloromethane (DCM) or the like.

d) amine and sodium sulphite adduct coupling in the presence of reductive agents such as sodium cyano borohydride ($NaCNBH_3$) or the like in the presence of bases such as triethylamine (TEA) or the like in the solvents such as methanol (MeOH) or the like.

e) Amine and isocyanato coupling in the presence of bases such as triethylamine (TEA), diisopropylethylamine (DIPEA) or the like in the solvents such as tetrahydrofuran (THF) or the like.

The ester compounds of formula (xvii) can be hydrolysed to give the acid compounds of formula 1 in the presence of aqueous solution of inorganic bases such as Lithium hydroxide (LiOH), sodium hydroxide (NaOH) or potassium hydroxide (KOH) or the like in the combination of solvents such as tetrahydrofuran (THF):methanol (MeOH) (1:1) or the like.

The abbreviations used in the entire specification may be summarized herein below with their particular meaning: DIPEA (N,N-Diisopropylethylamine); ° C. (degree Celsius); δ (delta); ppm (parts per million); % (percentage); DMSO-$d_6$ (Deuterated DMSO); d (Doublet); dd (Doublet of doublet); EtOH (Ethanol); EtOAc (Ethyl acetate); g or gr (gram); H or $H_2$ (Hydrogen); HCl (Hydrochloric acid); h or hr. (Hours); HATU (O-(7-Azabenzotriazol-1-yl)-N,N,N',N'-tetramethyluroniumhexafluoro phosphate); Hz (Hertz); HPLC (High-performance liquid chromatography); mmol (Milli mol); M (Molar); ml (Millilitre); mg (Milli gram); m (Multiplet); mm (Millimetre); MHz (Megahertz); ESI-MS (Electron spray Ionization Mass spectra); min (Minutes); mM (Milli molar); NaOH (Sodium hydroxide); $N_2$ (Nitrogen); NMR (Nuclear magnetic resonance spectroscopy); S (Singlet); TEA (Triethyl amine); TLC (Thin Layer Chromatography); THF (Tetrahydrofuran); tert (Tertiary), TFA/$CF_3COOH$ (Trifluoro acetic acid); t (Triplet); IC (Inhibitory concentration), nM (Nano molar); pH (Pouvoir hydrogen); $(Boc)_2O$ (Di-tert-butyl dicarbonate); DCM (dichloromethane); DMF (N,N-dimethyl formamide); DMAP (4-(Dimethylamino)pyridine); eq (equivalent); Ltr or L (Liter); $CDCl_3$ (Deuterated chloroform); J (Coupling constant); JAB (Coupling constant); $NaH_2PO_4$ (Sodium dihydrogen phosphate); $Na(OAc)_3BH_3$ (Sodium triacetoxyborohydride); AcOH (Acetic acid); $NaCNBH_3$ (Sodium cyanoborohydride); ABq (AB quartet); $Cs_2CO_3$ (Cesium carbonate); CuI (Copper(I) iodide); MTBE (Methyl tert-butyl ether); HBr (Hydrogen bromide); $Ac_2O$ (Acetic anhydride); $NaHCO_3$ (Sodium bicarbonate); $Na_2SO_4$ (Sodium sulphate); 1,2-DCE (1,2-dichloroethane); HBTU (O-(Benzotriazol-1-yl)-N,N,N',N'-tetramethyluroniumhexafluoro phosphate); KOH (Potassium hydroxide); MeOH (methanol); EDCI (1-Ethyl-3-(3-dimethyl aminopropyl)carbodiimide); HOBt (1-Hydroxybenzotriazole); brs (broad singlet); DPPA (Diphenyl phosphoryl azide) and BINAP (2,2'-bis(diphenylphosphino)-1,1'-binaphthyl).

EXPERIMENTAL

The present invention is further illustrated by the following examples, which are not to be construed in any way as imposing limitations upon the scope of this disclosure, but rather are intended to be illustrative only. On the contrary, it is to be clearly understood that resort may be had to various other embodiments, modifications, and equivalents thereof which, after reading the description herein, may suggest themselves to one of ordinary skill in the art without departing from the spirit of the present invention. Thus, the skilled artisan will appreciate how the experiments and examples may be further implemented as disclosed by variously altering the following examples, substituents, reagents, or conditions.

INTERMEDIATES

Intermediate 1: Preparation of 1-((3aR,5aR,5bR, 7aR,9S,11aR,11bR,13aS)-3a-(2-amino-2-methylpropanamido)-1-isopropyl-5a,5b,8,8, 11a-pentamethyl-2-oxo-3,3a,4,5,5a,5b,6,7,7a,8,9,10,11,11a,11b,12,13, 13a-octadecahydro-2H-cyclopenta[a]chrysen-9-yl) 3-benzyl (1S,3R)-2,2-dimethylcyclobutane-1,3-dicarboxylate

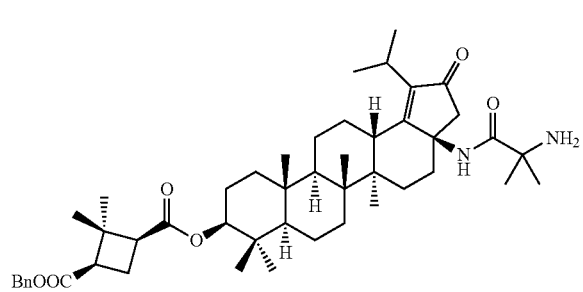

Step 1: Synthesis of ((1R,3a5,5aR,5bR,7aR,9S, 11aR,11bR,13aR,13bR)-9-acetoxy-5a,5b,8,8,11a-pentamethyl-1-(prop-1-en-2-yl)icosahydro-3aH-cyclopenta[a]chrysen-3a-yl)methyl acetate

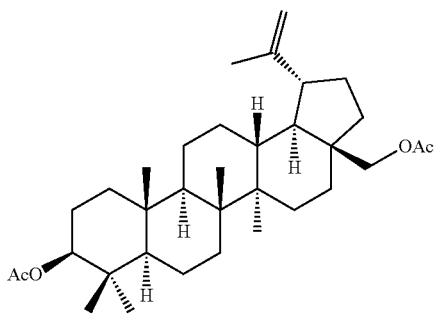

A mixture of (1R,3aS,5aR,5bR,7aR,9S,11aR,11bR,13aR, 13bR)-3a-(hydroxymethyl)-5a,5b,8,8,11a-pentamethyl-1-(prop-1-en-2-yl)icosahydro-1H-cyclopenta[a]chrysen-9-ol (400 g, 0.904 mol, 1.0 eq) and acetic anhydride (3.4 Ltr) were heated at 140° C. for about 3 hours. TLC indicated starting material was consumed and the desired product was observed. The reaction mixture was cooled to 0° C., solid was filtered, washed with water (2 Ltr) and dried under vacuum to obtain the desired product (400 g, yield: 84%) as an off-white solid. $^1$H NMR (300 MHz, CDCl$_3$): δ ppm 4.68 (d, 1H), 4.59 (s, 1H), 4.50-4.43 (m, 1H), 4.25 (d, J=11.1 Hz, 1H), 3.85 (d, J=11.1 Hz, 1H), 2.50-2.40 (m, 1H), 2.07 (s, 3H), 2.04 (s, 3H), 2.01-1.71 (m, 4H), 1.70-1.62 (m, 4H), 1.68 (s, 3H), 1.61-1.43 (m, 4H), 1.43-1.36 (m, 4H), 1.33-1.18 (m, 3H), 1.18-1.09 (m, 1H), 1.08-0.94 (m, 3H), 1.03 (s, 3H), 0.97 (s, 3H), 0.88-0.75 (m, 10H).

Step 2: Synthesis of ((3aS,5aR,5bR,7aR,9S,11aR, 11bR,13aS)-9-acetoxy-1-isopropyl-5a,5b,8,8,11a-pentamethyl-2,3,4,5,5a,5b,6,7,7a,8,9,10,11,11a,11b, 12,13,13a-octadecahydro-3aH-cyclopenta[a]chrysen-3a-yl)methyl acetate

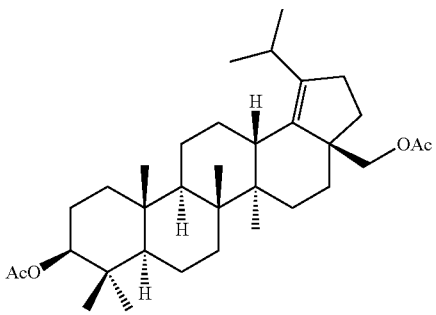

HBr in acetic acid (800 ml, 33%), was added to a suspension of ((1R,3aS,5aR,5bR,7aR,9S,11aR,11bR,13aR, 13bR)-9-acetoxy-5a,5b,8,8,11a-pentamethyl-1-(prop-1-en-2-yl) icosahydro-3aH-cyclo penta[a]chrysen-3a-yl)methyl acetate (step 1, 400 g, 0.76 mol, 1.0 eq) in toluene (800 ml), Ac$_2$O (800 ml) and acetic acid (800 ml) previously heated at 105° C. The reaction mixture was stirred and heated at this temperature for about 1.5 hours. After cooling down, sodium acetate (480 g) was added and the resulting reaction mixture was evaporated to dryness. The residue was taken up in CH$_2$Cl$_2$ (1200 ml) and the organic phase was washed with water (2×500 ml), dried over sodium sulphate, filtered and evaporated under reduced pressure. The residue was recrystallized over 95% ethanol and CH$_2$Cl$_2$ to obtain the desired product (256 g, yield: 64%) as a white solid. $^1$H NMR (300 MHz, CDCl$_3$): δ ppm 4.52-4.45 (m, 1H), 4.03 (d, J=10.8 Hz, 1H), 3.98 (d, J=10.8 Hz, 1H), 3.19-3.08 (m, 1H), 2.46-2.38 (m, 1H), 2.28-2.22 (m, 2H), 2.05 (s, 3H), 2.04 (s, 3H), 2.01-1.83 (m, 2H), 1.78-1.63 (m, 6H), 1.57-1.44 (m, 3H), 1.43-1.08 (m, 8H), 1.06 (s, 3H), 1.02-0.88 (m, 12H), 0.84 (s, 3H), 0.83 (s, 3H) and 0.78 (m, 1H).

Step 3: Synthesis of ((3aR,5aR,5bR,7aR,9S,11aR, 11bR,13aS)-9-acetoxy-1-isopropyl-5a,5b,8,8,11a-pentamethyl-2-oxo-2,3,4,5,5a,5b,6,7,7a,8,9,10,11, 11a,11b,12,13,13a-octadecahydro-3aH-cyclopenta[a] chrysen-3a-yl)methyl acetate

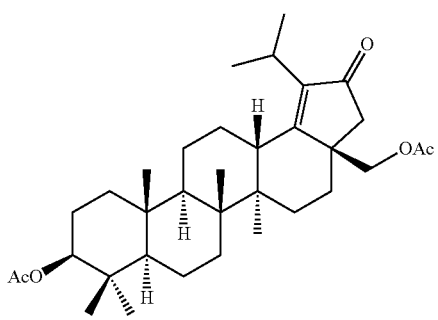

To a stirred solution of ((3aS,5aR,5bR,7aR,9S,11aR, 11bR,13aS)-9-acetoxy-1-isopropyl-5a,5b,8,8,11a-pentamethyl-2,3,4,5,5a,5b,6,7,7a,8,9,10,11,11a,11b,12,13,13a-octa decahydro-3aH-cyclopenta[a]chrysen-3a-yl)methyl acetate (step 2, 100 g, 0.190 mol, 1.0 eq) in Toluene (1280 ml) was added sodium acetate (88.96 g, 1.08 mol, 5.7 eq), sodium dichromate dihydrate (67.9 g, 0.228 mol, 1.2 eq), Ac$_2$O (414 ml) and AcOH (1700 ml) and heated at 60° C. for about 14 hours. TLC indicated starting material was consumed and the desired product was observed. After cooling down, the reaction mixture diluted with water (500 ml) and extracted with ethyl acetate (1000 ml). The organic phase was washed successively with saturated solution of sodium carbonate (1×500 ml) and brine (2×200 ml) solution. The organic layer was dried over sodium sulphate, filtered and concentrated under reduced pressure. The residue was triturated with methanol and the precipitates that formed were collected by filtration were dried under vacuum to obtain the desired product (81 g, yield: 79%) as a white solid. $^1$H NMR (300 MHz, CDCl$_3$): δ ppm 4.47 (dd, J=10.2, 6.0 Hz, 1H), 4.31 (d, J=10.8 Hz, 1H), 4.03 (d, J=10.8 Hz, 1H), 3.22-3.12 (m, 1H), 2.85 (dd, J=12.3, 3.3 Hz, 1H), 2.36 (d, J=18.6 Hz, 1H), 2.03 (s, 3H), 1.97 (s, 3H), 1.93-1.88 (m, 2H), 1.88-1.62 (m, 6H), 1.61-1.28 (m, 8H), 1.27-1.22 (m, 1H), 1.21-1.12 (m, 9H), 1.09-0.97 (m, 1H), 0.91 (s, 3H), 0.90 (s, 3H), 0.83 (s, 3H), 0.82 (s, 3H) and 0.77-0.75 (m, 1H); ESI-MS: m/z 563.4 (M+Na)$^+$.

Step 4: Synthesis of (3aR,5aR,5bR,7aR,9S,11aR, 11bR,13aS)-3a-(hydroxymethyl)-1-isopropyl-5a,5b, 8,8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl acetate

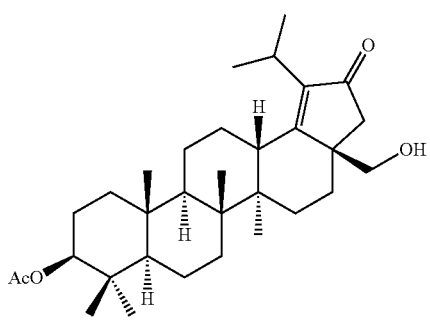

To a stirred solution of ((3aR,5aR,5bR,7aR,9S,11aR, 11bR,13aS)-9-acetoxy-1-isopropyl-5a,5b,8,8,11a-pentamethyl-2-oxo-2,3,4,5,5a,5b,6,7,7a,8,9,10,11,11a,11b,12,13, 13a-octadecahydro-3aH-cyclopenta[a]chrysen-3a-yl)methyl acetate (step 3, 70 g, 0.129 mol, 1.0 eq) in ethanol (2 L):toluene (2 L) was added potassium hydroxide (8.72 g, 0.155 mol, 1.2 eq) and stirred at room temperature for about 2 hours. TLC indicated starting material was consumed and the desired product was observed. The reaction mixture was neutralized with aqueous 1N HCl to pH adjusted to 7.0 and evaporated to dryness. The obtained residue was taken up in water (200 ml) and a small amount of acetone (20 ml). The precipitates formed were collected by filtration, washed with water and dried in vacuo to obtain the desired product (51 g, yield: 79%) as a white solid. $^1$H NMR (300 MHz, CDCl$_3$): δ ppm 4.49 (dd, J=10.5, 6.0 Hz, 1H), 3.73 (d, J=10.5 Hz, 1H), 3.67 (d, J=10.5 Hz, 1H), 3.25-3.14 (m, 1H), 2.78 (dd, J=12.3, 3.0 Hz, 1H), 2.43 (d, J=18.6 Hz, 1H), 2.05 (s, 3H), 2.02-1.65 (m, 8H), 1.60-1.25 (m, 8H), 1.24-1.17 (m, 7H), 1.13 (s, 3H), 1.12-0.97 (m, 1H), 0.94 (s, 3H), 0.92 (s, 3H), 0.86 (s, 3H), 0.85 (s, 3H), 0.80 (m, 1H); ESI-MS: m/z 521.3 (M+Na)$^+$.

Step 5: Synthesis of (3aR,5aR,5bR,7aR,9S,11aR, 11bR,13aS)-3a-formyl-1-isopropyl-5a,5b,8,8,11a-pentamethyl-2-oxo-3,3a,4,5,5a,5b,6,7,7a,8,9,10,11, 11a,11b,12,13,13a-octadecahydro-2H-cyclopenta[a]chrysen-9-yl acetate

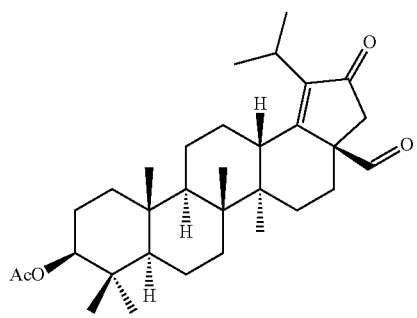

To a solution of (3aR,5aR,5bR,7aR,9S,11aR,11bR,13aS)-3a-(hydroxymethyl)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-ylacetate (step 4, 52.0 g, 0.104 mol, 1.0 eq) in CH$_2$Cl$_2$ (2 L) at room temperature was added pyridiniumchlorochromate (67.5 g, 0.313 mol, 3.0 eq) and silicagel (100-200 mesh) (67.5 g). The reaction mixture was stirred at room temperature for about 1 hour. TLC indicated starting material was consumed and the desired product was observed. The reaction mixture was diluted with water (50 ml) and extracted with CH$_2$Cl$_2$. The combined organic layers were washed with saturated sodium bicarbonate solution, dried over sodium sulphate and evaporated under reduced pressure to give a crude product, which was triturated with ethanol, solid was filtered and dried under vacuum to obtain the desired product (41.4 g, yield: 80%) as a white solid. $^1$H NMR (300 MHz, CDCl$_3$): δ ppm 9.31 (s, 1H), 4.52-4.44 (m, 1H), 3.32-3.18 (m, 1H), 2.60-2.50 (m, 1H), 2.43-2.33 (m, 2H), 2.12-2.0 (m, 2H), 2.05 (s, 3H), 2.0-1.80 (m, 2H), 1.80-1.65 (m, 3H), 1.53-1.18 (m, 15H), 1.12-1.0 (m, 2H), 1.03 (s, 3H), 0.98-0.75 (m, 12H).

Step 6: Synthesis of (3aR,5aR,5bR,7aR,9S,11aR, 11bR,13aS)-9-acetoxy-1-isopropyl-5a,5b,8,8,11a-pentamethyl-2-oxo-2,3,4,5,5a,5b,6,7,7a,8,9,10,11, 11a,11b,12,13,13a-octadecahydro-3aH-cyclopenta[a]chrysene-3a-carboxylic acid

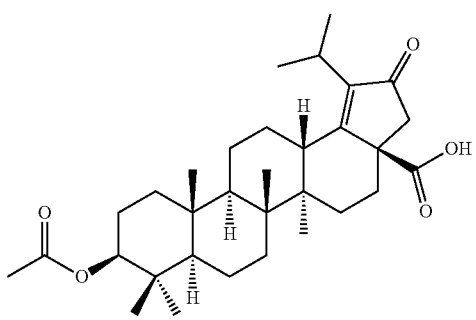

To an ice-cooled solution of (3aR,5aR,5bR,7aR,9S,11aR, 11bR,13aS)-3a-formyl-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl acetate (step 5, 33.0 g, 66.465 mmol, 1.0 eq) in t-butanol (330 ml), THF (500 ml) and 2-methyl 2-butene (60 ml) was added slowly a solution of NaClO$_2$ (71.86 g, 797.58 mmol, 12.0 eq) in 385 ml of water followed by NaH$_2$PO$_4$ (79.75 g, 664.65 mmol, 10.0 eq) in 390 ml of water (390 ml) over 15 minutes. After stirring at 0° C. for about 10 minutes, the reaction mixture was warmed to room temperature and stirred for about 1 hour. TLC indicated starting material was consumed and the desired product was observed. The reaction mixture was diluted with water (100 ml) and extracted with ethyl acetate (3×500 ml). The combined organic extracts were dried over sodium sulfate, filtered and evaporated under reduced pressure. The residue was triturated with n-hexane, solid formed was collected by filtration and dried under vacuum to obtain the desired product (33.1 g, yield: 97.3%) as a white solid. $^1$H NMR (300 MHz, CDCl$_3$): δ ppm 4.49 (dd, J=10.2, 5.7 Hz, 1H), 3.27-3.18 (m, 1H), 2.78-2.71 (m, 1H), 2.58 (d, J=18.9 Hz, 1H), 2.50-2.43 (m, 1H), 2.19 (d, J=18.6 Hz, 1H), 2.05 (s, 3H), 2.02-1.82 (m, 3H), 1.81-1.51 (m, 5H), 1.51-1.25 (m, 6H), 1.22 (d, J=1.5 Hz, 3H), 1.20 (d, J=1.5 Hz, 3H), 1.17-1.09 (m, 1H), 1.05 (s, 3H), 1.03-0.98 (m, 1H), 0.94 (s, 3H), 0.91 (s, 3H), 0.85 (s, 3H), 0.84 (s, 3H), 0.80 (m, 1H); ESI-MS: m/z 535.42 (M+Na)$^+$.

Step 7: Synthesis of (3aR,5aR,5bR,7aR,9S,11aR, 11bR,13aS)-1-isopropyl-3a-((((4-methoxy benzyl) oxy)carbonyl)amino)-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl acetate

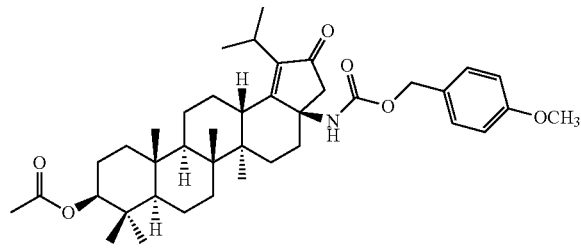

To a stirred solution of (3aR,5aR,5bR,7aR,9S,11aR,11bR, 13aS)-9-acetoxy-1-isopropyl-5a,5b,8,8,11a-pentamethyl-2-oxo-2,3,4,5,5a,5b,6,7,7a,8,9,10,11,11a,11b,12,13,13a-octadecahydro-3aH-cyclopenta[a]chrysene-3a-carboxylic acid (step 6, 33.0 g, 64.45 mmol, 1.0 eq) in 1,2-dichloroethane (500 ml) was added triethyl amine (22.43 ml, 161.13 mmol, 2.5 eq), followed by diphenylphosphonic azide (18.0 ml, 83.78 mmol, 1.3 eq). After 15 minutes stirring at room temperature, the solution was heated to reflux for about 100 minutes. After which it was converted completely to the isocyanate by TLC, p-methoxybenzyl alcohol (9.9 ml, 83.78 mmol, 1.3 eq) was added and reflux was continued for about 4 hours. TLC indicated starting material was consumed and the desired product was observed. The reaction mixture was evaporated under reduced pressure and the residue was purified by silicagel column chromatography by using 0-3% methanol in dichloromethane gradient. The fractions containing the product were combined and concentrated under reduced pressure to give the desired product (38.0 g, yield: 91.1%) as a white solid. $^1$H NMR (300 MHz, CDCl$_3$): δ ppm 7.30 (d, J=8.7 Hz, 2H), 6.87 (d, J=8.7 Hz, 2H), 4.98 (s, 2H), 4.83 (s, 1H), 4.48 (dd, J=10.5, 6.0 Hz, 1H), 3.80 (s, 3H), 3.22-3.0 (m, 1H), 2.82-2.58 (m, 2H), 2.55-2.20 (m, 2H), 2.05 (s, 3H), 1.98-1.60 (m, 7H), 1.58-1.30 (m, 7H), 1.28-1.12 (m, 8H), 1.07 (s, 3H), 0.92 (m, 6H), 0.85-0.78 (m, 7H); ESI-MS: m/z 670.51 (M+Na)$^+$.

Step 8: Synthesis of (3aR,5aR,5bR,7aR,9S,11aR, 11bR,13aS)-3a-amino-1-isopropyl-5a,5b,8,8,11a-pentamethyl-2-oxo-3,3a,4,5, 5a,5b,6,7,7a,8,9,10, 11,11a,11b,12,13,13a-octadecahydro-2H-cyclopenta [a]chrysen-9-yl acetate

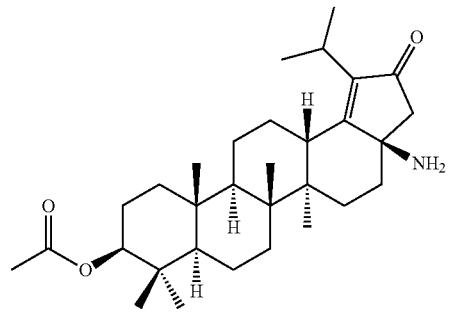

To a stirred solution of (3aR,5aR,5bR,7aR,9S,11aR,11bR, 13aS)-1-isopropyl-3a-((((4-methoxybenzyl)oxy)carbonyl) amino)-5a,5b,8,8,11a-pentamethyl-2-oxo-3,3a,4,5,5a,5b,6, 7,7a,8,9,10,11,11a,11b,12,13,13a-octadecahydro-2H-cyclopenta[a]chrysen-9-yl acetate (step 7, 38.0 g, 58.73 mmol, 1.0 eq) in DCM (320 ml) at 0° C. was added TFA (80 ml). The reaction mixture was allowed to stir at room temperature for overnight. TLC indicated starting material was consumed and the desired product was observed. The reaction mixture was evaporated under reduced pressure, water (100 ml) was added, cooled to 0° C., pH adjusted to 8.0 with saturated NaHCO$_3$ solution and extracted with DCM (3×600 ml). The combined organic extracts were dried over sodium sulfate, filtered and evaporated under reduced pressure. The residue was purified by silicagel column chromatography by using a 0-3% methanol in dichloromethane gradient. The fractions containing the product were combined and concentrated under reduced pressure to obtain the desired product (26.0 g, yield: 91.87%) as a white solid. $^1$H NMR (300 MHz, CDCl$_3$): δ ppm 4.48 (m, 1H), 3.20-3.05 (m, 1H), 2.33 (d, J=18.6 Hz, 1H), 2.23 (d, J=18.6 Hz, 1H), 2.05 (s, 3H), 1.98-1.72 (m, 4H), 1.72-1.50 (m, 7H), 1.46-1.26 (m, 5H), 1.26-1.0 (m, 11H), 0.93 (s, 3H), 0.91 (s, 3H), 0.86 (s, 3H), 0.85 (s, 3H), 0.80 (m, 1H).

Step 9: Synthesis of 2-((tert-butoxy)carbonyl)amino)-2-methylpropanoic acid

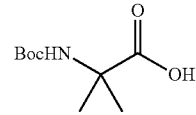

Method 1: To a stirred solution of 2-Amino-2-methylpropanoic acid (30 g, 290.92 mmol, 1.0 eq) in 1,4-dioxane (300 ml) at 0° C. was added 2N NaOH solution (300 ml) followed by (Boc)$_2$O (95.13 g, 436.38 mmol, 1.5 eq). The reaction mixture was allowed to stir at room temperature for overnight. TLC indicated starting material was consumed and the desired product was observed. The organic phase was evaporated under reduced pressure, the reaction mixture was diluted with water (50 ml), cooled to 0° C., pH adjusted to 5 with 1N HCl and then extracted with DCM (3×300 ml). The combined organic extracts were washed with water (300 ml), brine (100 ml) solution, dried over Na$_2$SO$_4$, filtered and evaporated under reduced pressure. The residue was stirred with n-hexane (300 ml) at room temperature for about 30 minutes. The obtained solid was filtered and dried under vacuum to obtain the desired product (38.0 g, yield: 64.4%) as a white solid.

Method 2: To a stirred solution of 2-carboxypropan-2-aminium chloride (15.0 g, 145.63 mmol) in 1,4-dioxane (75 mL), added 2N NaOH solution (75 mL), (Boc)$_2$O (47.62 g, 218.44 mmol) at 0° C. and stirred the reaction mixture for about 12 hours at room temperature. TLC indicated starting material was consumed and the desired product was observed. The reaction mixture was washed with EtOAc (200 mL) to remove the impurities, then aqueous part was acidified with 1N HCl (pH-2-3) and extracted with CH$_2$Cl$_2$ (2×200 mL). The combined organic extracts were washed with water, dried over Na$_2$SO$_4$, filtered and evaporated under reduced pressure. The crude residue was purified by silicagel column chromatography by using 30% EtOAc: n-Hexane as an eluent to afford the desired product (15.0 g, yield: 50.74%) as an off white solid. $^1$H NMR (300 MHz, DMSO): δ 12.18 (s, 1H), 7.05 (s, 1H), 1.36 (s, 9H), 1.29 (s, 6H); ES Mass: 226.06 [M+Na]$^+$.

Step 10: Synthesis of (3aR,5aR,5bR,7aR,9S,11aR, 11bR,13aS)-3a-(2-((tert-butoxy)carbonyl)amino)-2-methylpropanamido)-1-isopropyl-5a,5b,8,8,11a-pentamethyl-2-oxo-3,3a,4,5,5a,5b,6,7,7a,8,9,10,11, 11a,11b,12,13,13a-octadecahydro-2H-cyclopenta[a] chrysen-9-yl acetate

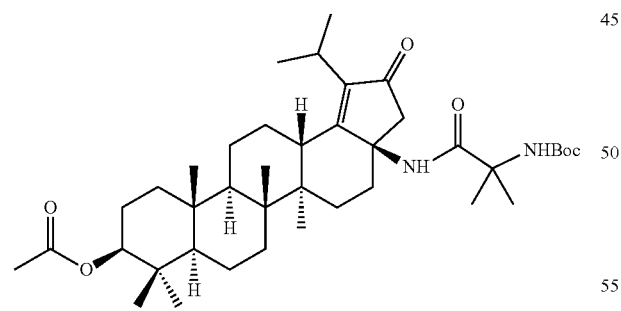

Method 1: To a stirred solution of 2-((tert-butoxy)carbonyl)amino)-2-methylpropanoic acid (step 9, 4.539 g, 22.36 mmol, 1.2 eq) in 1,2-DCE (200 ml) was added HATU (10.62 g, 27.95 mmol, 1.5 eq) followed by DIPEA (19.3 ml, 111.79 mmol, 6.0 eq). The reaction mixture was stirred at room temperature for about 30 minutes, then (3aR,5aR,5bR,7aR, 9S,11aR,11bR,13aS)-3a-amino-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl acetate (step 8, 9.0 g, 18.63 mmol, 1.0 eq) was added and stirred at same temperature for overnight. TLC indicated starting material was consumed and the desired product was observed. The reaction mixture was evaporated under reduced pressure, diluted with water (90 ml) and extracted with DCM (3×135 ml). The combined organic extracts were washed with 0.5N HCl (90 ml), water (90 ml) and brine (45 ml) solution. The organic layer was dried over Na$_2$SO$_4$, filtered and evaporated under reduced pressure. The residue was purified by silicagel column chromatography by using 0-2% methanol in dichloromethane gradient. The fractions containing the product were combined and concentrated under reduced pressure to give the desired product (11.0 g, yield: 88.7%) as an off-white solid. $^1$H NMR (300 MHz, CDCl$_3$): δ ppm 4.91 (brs, 1H), 4.49 (dd, J=10.5, 5.7 Hz, 1H), 3.20-3.08 (m, 1H), 2.86 (m, 1H), 2.68 (d, J=18.6 Hz, 1H), 2.39-2.32 (m, 1H), 2.27 (d, J=18.6 Hz, 1H), 2.05 (s, 3H), 1.98-1.86 (m, 2H), 1.84 (m, 1H), 1.81-1.52 (m, 6H), 1.49 (s, 3H), 1.47 (s, 3H), 1.42 (s, 9H), 1.39-1.34 (m, 3H), 1.29-1.19 (m, 7H), 1.18-1.13 (m, 1H), 1.17 (s, 3H), 1.10-1.01 (m, 2H), 0.92 (s, 3H), 0.91 (s, 3H), 0.856 (s, 3H), 0.85 (s, 3H), 0.80 (m, 1H); ESI-MS: m/z 691.5 (M+Na)$^+$.

Method 2: To a stirred solution of 2-((tert-butoxy)carbonyl)amino)-2-methylpropanoic acid (step 9, 7.56 g, 37.21 mmol, 1.2 eq) in DMF (150 ml) was added EDCI (9.24 g 48.3 mmol 1.5 eq) followed by DMAP (11.8 g 96.77 mmol 3eq) at 0° C. The reaction mixture was stirred at room temperature for about 30 minutes, then (3aR,5aR,5bR,7aR, 9S,11aR,11bR,13aS)-3a-amino-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl acetate (step 8, 15.0 g, 31.0 mmol, 1.0 eq) was added and stirred at room temperature for about 4 hours. TLC indicated starting material was consumed and the desired product was observed. The reaction mixture was diluted with ice water (450 ml) and white solid was obtained. The solid was filtered, dissolved in DCM, washed with water and brine solution. The organic layer was dried over Na$_2$SO$_4$, evaporated under reduced pressure to give the desired product (17.5 g, yield: 80%) as an off-white solid.

Step 11: Synthesis of tert-butyl (1-(((3aR,5aR,5bR, 7aR,9S,11aR,11bR,13aS)-9-hydroxy-1-isopropyl-5a, 5b,8,8,11a-pentamethyl-2-oxo-2,3,4,5,5a,5b,6,7,7a,8, 9,10,11,11a,11b,12,13,13a-octadecahydro-3aH-cyclopenta[a]chrysen-3a-yl)amino)-2-methyl-1-oxopropan-2-yl) carbamate

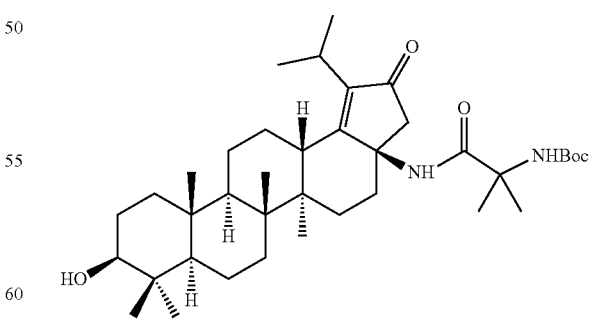

To a stirred solution of (3aR,5aR,5bR,7aR,9S,11aR,11bR, 13aS)-3a-(2-((tert-butoxy carbonyl)amino)-2-methylpropanamido)-1-isopropyl-5a,5b,8,8,11a-pentamethyl-2-oxo-3, 3a,4,5,5a,5b,6,7,7a,8,9,10,11,11a,11b,12,13,13a-octadecahydro-2H-cyclopenta[a]chrysen-9-yl acetate (step 10, 11.0 g, 16.45 mmol, 1.0 eq) in MeOH (110 ml), THF (55 ml) and water (28 ml) at 0° C. was added NaOH (6.582 g, 164.57 mmol, 10.0 eq). The mixture was removed from the ice bath and was stirred at room temperature for overnight. TLC indicated starting material was consumed and the desired product was observed. The organic phase was evaporated under reduced pressure, the reaction mixture was diluted with water (165 ml) and extracted with DCM (3×165 ml). The combined organic extracts were washed with water (110 ml), brine solution (50 ml), dried over sodium sulfate, filtered and evaporated under reduced pressure. The residue was purified by silicagel column chromatography by using 0-3% methanol in dichloromethane gradient. The fractions containing the product were combined and concentrated under reduced pressure to give the desired product (10.0 g, yield: 96.92%) as a yellow solid. $^1$H NMR (300 MHz, CDCl$_3$): δ ppm 7.0 (brs, 1H), 4.85 (brs, 1H), 3.28-3.08 (m, 2H), 2.86 (m, 1H), 2.68 (d, J=18.6 Hz, 1H), 2.38-2.31 (m, 1H), 2.27 (d, J=18.6 Hz, 1H), 1.97-1.73 (m, 4H), 1.70-1.65 (m, 3H), 1.64-1.53 (m, 3H), 1.49 (s, 3H), 1.46 (s, 3H), 1.42 (s, 9H), 1.40-1.25 (m, 5H), 1.25 (s, 3H), 1.22 (s, 3H), 1.17 (s, 3H), 1.10-1.02 (m, 1H), 0.97 (s, 3H), 0.94 (s, 3H), 0.89 (s, 3H), 0.77 (s, 3H), 0.75-0.68 (m, 1H); ESI-MS: m/z 649.5 (M+Na)$^+$.

Step 12: Synthesis of 1-benzyl 3-((3aR,5aR,5bR, 7aR,9S,11aR,11bR,13aS)-3a-(2-((tert-butoxy carbonyl)amino)-2-methylpropanamido)-1-isopropyl-5a, 5b,8,8,11a-pentamethyl-2-oxo-3,3a,4,5,5a,5b,6,7,7a, 8,9,10,11,11a,11b,12,13,13a-octadecahydro-2H-cyclopenta[a]chrysen-9-yl) (1R,3S)-2,2-dimethylcyclobutane-1,3-dicarboxylate

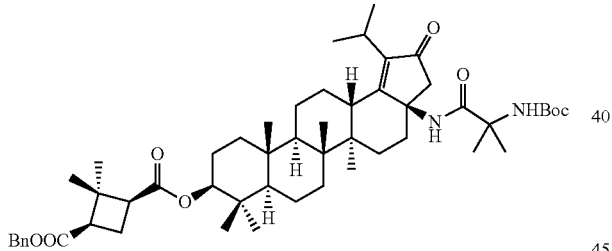

Method 1: To a stirred solution of tert-butyl (1-(((3aR, 5aR,5bR,7aR,9S,11aR,11bR,13aS)-9-hydroxy-1-isopropyl-5a,5b,8,8,11a-pentamethyl-2-oxo-2,3,4,5,5a,5b,6,7,7a,8,9,10,11,11a,11b,12,13,13a-octadecahydro-3aH-cyclopenta[a]chrysen-3a-yl)amino)-2-methyl-1-oxo propan-2-yl) carbamate (step 11, 10.0 g, 15.95 mmol, 1.0 eq) in DCM (100 ml) at 0° C. under nitrogen atmosphere was added Et$_3$N (11.12 ml, 79.75 mmol, 5.0 eq), DMAP (0.969 g, 7.975 mmol, 0.5 eq), (1S,3R)-3-((benzyloxy)carbonyl)-2,2-dimethylcyclobutane-1-carboxylic acid (prepared as described in WO 2011/007230 A2, 6.27 g, 23.92 mmol, 1.5 eq) and 2,4,6-trichlorobenzoyl chloride (4.98 ml, 31.89 mmol, 2.0 eq). The mixture was removed from the ice bath and was stirred at room temperature for overnight. TLC indicated starting material was consumed and the desired product was observed. The reaction mixture was evaporated under reduced pressure, diluted with water (100 ml) and extracted with DCM (3×100 ml). The combined organic extracts were washed with 0.5N HCl (100 ml), water (100 ml), brine solution (50 ml), dried over sodium sulfate, filtered and evaporated under reduced pressure. The residue was purified by silicagel column chromatography by using 0-10% MeOH in DCM gradient. The fractions containing the product were combined and concentrated under reduced pressure to give the desired product (10.0 g, yield: 71.9%) as an off-white solid. $^1$H NMR (300 MHz, CDCl$_3$): δ ppm 7.38-7.32 (m, 5H), 6.96 (brs, 1H), 5.15, 5.09 (ABq, J$_{AB}$=12.3 Hz, 2H), 4.84 (brs, 1H), 4.45 (dd, J=11.1, 4.5 Hz, 1H), 3.20-3.08 (m, 1H), 2.88-2.58 (m, 5H), 2.40-2.33 (m, 1H), 2.27 (d, J=18.6 Hz, 1H), 2.09-2.02 (m, 1H), 2.0-1.82 (m, 3H), 1.81-1.70 (m, 3H), 1.65-1.54 (m, 4H), 1.49 (s, 3H), 1.46 (s, 3H), 1.42 (s, 9H), 1.40-1.30 (m, 3H), 1.34 (s, 3H), 1.30-1.17 (m, 8H), 1.14 (s, 3H), 1.11-1.0 (m, 1H), 0.97 (s, 3H), 0.93 (s, 3H), 0.91 (s, 3H), 0.86 (s, 3H), 0.85 (s, 3H), 0.79 (m, 1H).

Method 2: To a stirred solution of (1S,3R)-3-((benzyloxy)carbonyl)-2,2-dimethylcyclo butane-1-carboxylic acid (prepared as described in WO 2011/007230 A2, 0.54 g, 3.89 mmol, 1.5 eq) in DMF (20 ml) at 0° C. under nitrogen atmosphere was added EDCI (0.99 g, 5.18 mmol, 2 eq), HOBT (0.52 g, 3.89 mmol, 1.5 eq), DMAP (0.15 g, 1.29 mmol, 0.5 eq), added Triethylamine (1.08 ml 7.78 mmol, 3 eq) and stirred it for about 30 minutes. Then added tert-butyl (1-(((3aR,5aR,5bR,7aR,9S,11aR,11bR,13aS)-9-hydroxy-1-isopropyl-5a,5b,8,8,11a-pentamethyl-2-oxo-2,3,4,5,5a,5b,6,7,7a,8,9,10,11,11a,11b,12,13,13a-octadecahydro-3aH-cyclopenta[a]chrysen-3a-yl)amino)-2-methyl-1-oxopropan-2-yl)carbamate (step 11, 2.0 g, 2.59 mmol, 1 eq). The reaction mixture was stirred at room temperature for about 14 hours. TLC indicated starting material was consumed and the desired product was observed. The reaction mixture was quenched with ice cold water then filtered through Buchner funnel. The solid was separated, then the solid compound was dissolved in DCM, washed with sodium bicarbonate, water, brine solution then dried over sodium sulfate and concentrated under reduced pressure to give a crude compound. The crude compound was purified by flash silica column chromatography by using 100-200 silica gel, then the product was eluted at 2% MeOH in DCM (1.5 g, yield: 65.21%) as an off-white solid.

Step 13: Synthesis of 1-((3aR,5aR,5bR,7aR,9S, 11aR,11bR,13aS)-3a-(2-amino-2-methyl propanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)3-benzyl (1S,3R)-2,2-di methylcyclobutane-1,3-dicarboxylate To a stirred solution of 1-benzyl 3-((3aR,5aR,5bR,7aR, 9S,11aR,11bR,13aS)-3a-(2-((tert-butoxy)carbonyl)amino)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 12, 10.0 g, 11.47 mmol, 1.0 eq) in DCM (80 ml) was added trifluoroacetic acid (20 ml). The reaction mixture was stirred at room temperature for about 14 hours. TLC indicated starting material was consumed and the desired product was observed. The reaction mixture was evaporated under reduced pressure, cooled to 0° C., pH adjusted to 8.0 with saturated sodium bicarbonate solution and extracted with DCM (3×100 ml). The combined organic extracts were dried over sodium sulfate, filtered and evaporated under reduced pressure. The residue was purified by silicagel column chromatography by using 0-5% methanol in dichloromethane gradient. The fractions containing the product were combined and concentrated under reduced pressure to give the desired product (8.0 g, yield: 90.4%) as an off-white solid. ¹H NMR (300 MHz, CDCl₃): δ ppm 7.99 (brs, 1H), 7.38-7.32 (m, 5H), 5.15, 5.09 (ABq, $J_{AB}$=12.3 Hz, 2H), 4.45 (dd, J=11.1, 4.5 Hz, 1H), 3.20-3.09 (m, 1H), 2.89-2.61 (m, 5H), 2.43-2.35 (m, 1H), 2.30 (d, J=18.6 Hz, 1H), 2.10-1.92 (m, 3H), 1.90-1.65 (m, 4H), 1.53-1.40 (m, 4H), 1.40-1.30 (m, 12H), 1.27-1.15 (m, 8H), 1.12 (s, 3H), 1.09-1.01 (m, 1H), 0.96 (s, 3H), 0.94 (s, 3H), 0.91 (s, 3H), 0.86 (s, 3H), 0.85 (s, 3H), 0.79 (m, 1H); ESI-MS: m/z 771.6 (M+H)⁺.

Intermediate 2: Preparation of 1-((3aR,5aR,5bR, 7aR,9S,11aR,11bR,13aS)-3a-(2-amino-2-methylpropanamido)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) 3-benzyl (1R,3S)-2,2-dimethylcyclobutane-1,3-dicarboxylate

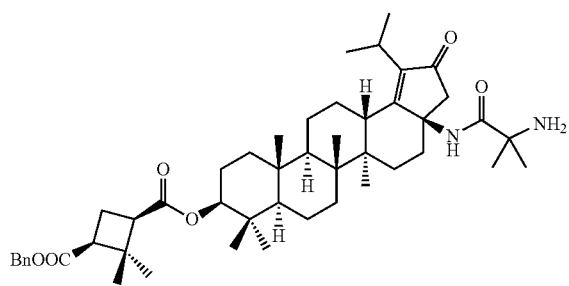

Step 1: Synthesis of (1R,3S)-3-((benzyloxy)carbonyl)-2,2-dimethylcyclobutane-1-carboxylic 2,4,6-trichlorobenzoic anhydride

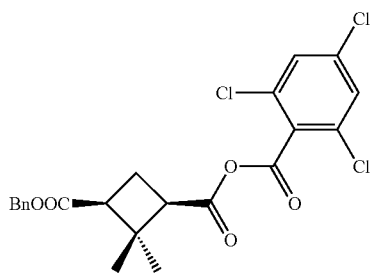

To a stirred solution of (1R,3S)-3-((benzyloxy)carbonyl)-2,2-dimethylcyclobutane-1-carboxylic acid (prepared as described in WO 2014/105926 A1, 1.0 g, 3.812 mmol, 1.0 eq) in THF (10 ml) at 0° C. under nitrogen atmosphere was added triethylamine (1.59 ml, 11.436 mmol, 3.0 eq) followed by 2,4,6-trichlorobenzoyl chloride (0.71 ml, 4.574 mmol, 1.2 eq). The reaction mixture was allowed to stir at room temperature for about 4 hours. TLC indicated starting material was consumed and the desired product was observed. The reaction mixture was evaporated under reduced pressure to obtain the desired product (1.8 g) as an oil, which is used as such for next step without further purification.

Step 2: Synthesis of 1-benzyl 3-(3aR,5aR,5bR,7aR, 9S,11aR,11bR,13aS)-3a-(2-((tert-butoxy carbonyl) amino)-2-methylpropanamido)-1-isopropyl-5a,5b,8, 8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl) (1S,3R)-2,2-dimethylcyclobutane-1,3-di carboxylate

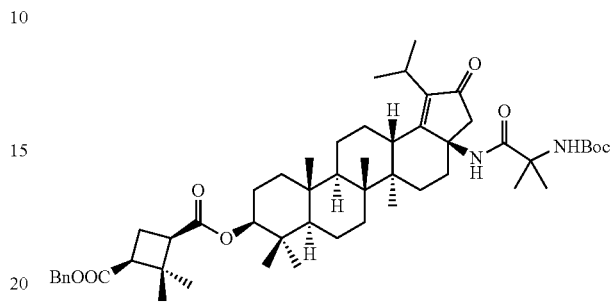

To a stirred solution of tert-butyl (1-(((3aR,5aR,5bR,7aR, 9S,11aR,11bR,13aS)-9-hydroxy-1-isopropyl-5a,5b,8,8,11a-pentamethyl-2-oxo-2,3,4,5,5a,5b,6,7,7a,8,9,10,11,11a,11b, 12,13,13a-octadecahydro-3aH-cyclopenta[a]chrysen-3a-yl) amino)-2-methyl-1-oxo propan-2-yl)carbamate (Intermediate 1-step 11, 1.5 g, 2.392 mmol, 1.0 eq) in Toluene (15 ml) at 0° C. under nitrogen atmosphere was added DMAP (0.730 g, 5.981 mmol, 2.5 eq) and (1R,3S)-3-((benzyloxy)carbonyl)-2,2-dimethylcyclobutane-1-carboxylic 2,4,6-trichloro benzoic anhydride (step 1, 1.685 g, 3.588 mmol, 1.5 eq) dissolved in toluene (15 ml). The reaction mixture was allowed to stir at room temperature for about 30 minutes and then heated to reflux for overnight. TLC indicated starting material was consumed and the desired product was observed. The reaction mixture was evaporated under reduced pressure, diluted with water (20 ml) and extracted with DCM (3×30 ml). The combined organic extracts were washed with water (20 ml), brine solution (20 ml), dried over sodium sulfate, filtered and evaporated under reduced pressure. The residue was purified by silicagel column chromatography by using 0-3% methanol in dichloromethane gradient. The fractions containing the expected product were combined and concentrated under reduced pressure to obtain the desired product (1.0 g, yield: 48.07%) as a white solid. ¹H NMR (300 MHz, CDCl₃): δ ppm 7.35 (m, 5H), 5.15, 5.10 (ABq, $J_{AB}$=12.3 Hz, 2H), 4.46 (dd, J=11.1, 4.5 Hz, 1H), 3.20-3.08 (m, 1H), 3.0-2.58 (m, 5H), 2.40-2.23 (m, 2H), 2.12-2.02 (m, 1H), 1.98-1.82 (m, 2H), 1.80-1.67 (m, 2H), 1.65-1.53 (m, 7H), 1.50 (s, 3H), 1.47 (s, 3H), 1.43 (s, 9H), 1.40-1.30 (m, 4H), 1.33 (s, 3H), 1.24 (d, J=6.9 Hz, 3H), 1.21 (d, J=6.9 Hz, 3H), 1.14 (s, 3H), 1.08-1.0 (m, 1H), 0.97-0.90 (m, 9H), 0.87-0.78 (m, 7H); ESI-MS: m/z 893.54 (M+Na)⁺.

Step 3: Synthesis of 1-((3aR,5aR,5bR,7aR,9S,11aR, 11bR,13aS)-3a-(2-amino-2-methylpropan amido)-1-isopropyl-5a,5b,8,8,11a-pentamethyl-2-oxo-3,3a,4,5, 5a,5b,6,7,7a,8,9,10,11,11a, 11b,12,13,13a-octadecahydro-2H-cyclopenta[a]chrysen-9-yl) 3-benzyl (1R,3S)-2,2-dimethyl cyclobutane-1,3-dicarboxylate To a stirred solution of 1-benzyl 3-((3aR,5aR,5bR,7aR, 9S,11aR,11bR,13aS)-3a-(2-((tert-butoxy)carbonyl)amino)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1S,3R)-2,2-dimethylcyclobutane-1,3-dicarboxylate (step 2, 1.0 g, 1.148 mmol, 1.0 eq) in DCM (8 ml) was added trifluoroacetic acid (2 ml). The reaction mixture was stirred at room temperature for overnight. TLC indicated starting material was consumed and the desired product was observed. The reaction mixture was evaporated under reduced pressure, diluted with water (10 ml), cooled to 0° C., pH adjusted to 8.0 with saturated sodium bicarbonate solution and extracted with DCM (3×50 ml). The combined organic extracts were washed with water (30 ml), dried over sodium sulfate, filtered and evaporated under reduced pressure. The residue was purified by silicagel column chromatography by using 0-5% methanol in dichloromethane gradient. The fractions containing the expected product were combined and concentrated under reduced pressure to give the desired product (0.8 g, yield: 90.3%) as a white solid.

Intermediate 3: Preparation of 1-((3aR,5aR,5bR,7aR,9S,11aR,11bR,13aS)-3a-(1-aminocyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 3-benzyl (1S,3R)-2,2-dimethylcyclobutane-1,3-dicarboxylate

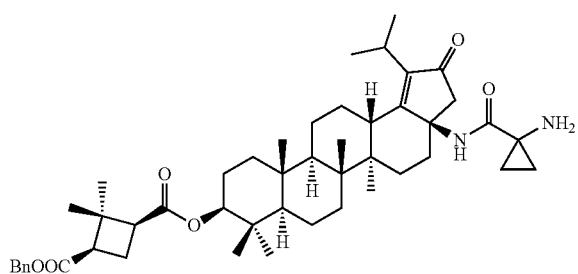

Step 1: Synthesis of 1-((tert-butoxy)carbonyl)amino)cyclopropane-1-carboxylic acid

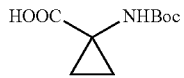

To a stirred solution of 1-aminocyclopropane-1-carboxylic acid (30 g, 149.25 mmol, 1.0 eq) in 1,4-dioxane (300 ml) at 0° C. was added 2N NaOH solution (300 ml) followed by (Boc)$_2$O (48.80 gr, 223.88 mmol, 1.5 eq). The reaction mixture was allowed to stir at room temperature for overnight. TLC indicated starting material was consumed and the desired product was observed. The organic phase was evaporated under reduced pressure, the reaction mixture was diluted with water (50 ml), cooled to 0° C., pH adjusted to 5 with 1N HCl and then extracted with DCM (3×300 ml). The combined organic extracts were washed with water (300 ml), brine (100 ml) solution, dried over Na$_2$SO$_4$, filtered and evaporated under reduced pressure. The residue was stirred with n-hexane (300 ml) at room temperature for about 30 minutes, the obtained solid was filtered and dried under vacuum to obtain the desired product (32.0 g, yield: 53.60%) as a white solid. $^1$H NMR (300 MHz, DMSO-d$_6$): δ ppm 12.26 (brs, 1H), 7.40 (s, 1H), 1.36 (s, 9H), 1.25 (d, J=12 Hz, 2H), 0.95-0.91 (d, J=12 Hz, 2H); ESI-MS: m/z 226.43 (M+Na)$^+$.

Step 2: Synthesis of (3aR,5aR,5bR,7aR,9S,11aR,11bR,13aS)-3a-(1-((tert-butoxy)carbonyl)amino)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate

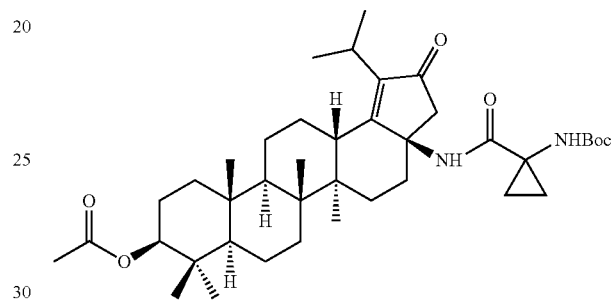

To a stirred solution of 1-((tert-butoxy)carbonyl)amino)cyclopropane-1-carboxylic acid (step 1, 12.48 g, 62.08 mmol, 1.5 eq) in DMF (150 ml) at 0° C. under nitrogen atmosphere was added EDCI (15.90 g, 82.81 mmol, 2 eq), HOBT (8.38 g, 62.11 mmol, 1.5 eq), DMAP (2.52 g, 20.70 mmol, 0.5 eq), and added Triethylamine (17.28 ml, 124.22 mmol, 3 eq) and stirred it for about 30 minutes. Then added (3aR,5aR,5bR,7aR,9S,11aR,11bR,13aS)-3a-amino-1-isopropyl-5a,5b,8,8,11a-pentamethyl-2-oxo-3,3a,4,5,5a,5b,6,7,7a,8,9,10,11,11a, 11b,12,13,13a-octadecahydro-2H-cyclopenta[a]chrysene-9-yl acetate (Intermediate 1-step 8, 20.0 g, 41.40 mmol, 1 eq) and the reaction mixture was stirred at room temperature for about 14 hours. TLC indicated starting material was consumed and the desired product was observed. The reaction mixture was quenched with ice cold water then filtered through Buchner funnel then solid was separated, then that solid compound was dissolved in DCM and washed with sodium bicarbonate, water, brine solution then dried over sodium sulfate and concentrated under reduced pressure to give a crude compound. The crude compound was purified by flash silica column chromatography (100-200 silica gel) using 1.5% MeOH in DCM as an eluent to obtain the desired product (20.0 g, yield: 72.72%) as an off pale yellow colour solid. $^1$H NMR (300 MHz, DMSO-d$_6$): δ ppm 7.37-7.20 (m, 1H), 7.02-6.81 (m, 1H), 4.41-4.36 (m, 1H), 4.06-3.99 (m, 1H), 3.74-3.47 (m, 1H), 3.23-3.10 (m, 1H), 2.97-2.89 (m, 1H), 2.80-2.73 (m, 1H), 2.38-2.27 (m, 2H), 2.20-2.14 (m, 2H), 1.90 (m, 3H), 1.86-1.49 (m, 8H), 1.39-1.34 (m, 9H), 1.28-1.17 (m, 3H), 1.15-1.09 (m, 9H), 0.99-0.94 (m, 3H), 0.89-0.87 (m, 6H), 0.83-0.80 (s, 9H); ESI-MS: m/z 689.43 (M+Na)$^+$.

Step 3: Synthesis of tert-butyl (1-(((3aR,5aR,5bR, 7aR,9S,11aR,11bR,13aS)-9-hydroxy-1-isopropyl-5a, 5b,8,8,11a-pentamethyl-2-oxo-2,3,4,5,5a,5b,6,7,7a,8, 9,10,11,11a,11b,12,13,13a-octadecahydro-3aH-cyclopenta[a]chrysen-3a-yl)carbamoyl)cyclopropyl) carbamate

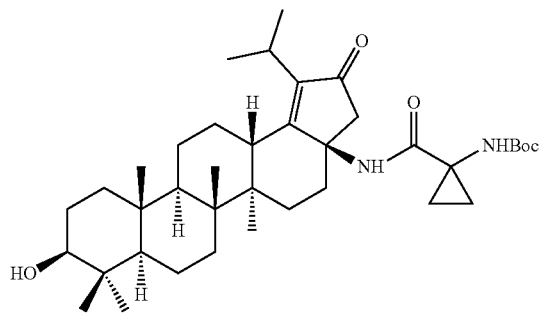

To a stirred solution of (3aR,5aR,5bR,7aR,9S,11aR,11bR, 13aS)-3a-(1-((tert-butoxy carbonyl)amino)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (step 2, 20 g, 30.03 mmol, 1.0 eq) in MeOH (200 ml), THF (100 ml) and water (50 ml) at 0° C. was added NaOH (12.01 g, 300.30 mmol, 10.0 eq). The mixture was removed from the ice bath and was stirred at room temperature for overnight. TLC indicated starting material was consumed and the desired product was observed. The organic phase was evaporated under reduced pressure, the reaction mixture was diluted with water (180 ml) and extracted with DCM (3×180 ml). The combined organic extracts were washed with water (100 ml), brine solution (50 ml), dried over sodium sulfate, filtered and evaporated under reduced pressure. The residue was purified by silicagel column chromatography by using 0-3% methanol in dichloromethane gradient. The fractions containing the product were combined and concentrated under reduced pressure to give the desired product (16.0 g, yield: 85.5%) as a white solid. $^1$H NMR (300 MHz, DMSO-$d_6$): δ ppm 8.32 (m, 1H), 7.20 (m, 1H), 4.32-4.31 (m, 1H), 3.72-3.67 (m, 1H), 3.12-2.75 (m, 3H), 2.38-2.09 (m, 4H), 1.85 (m, 4H), 1.65-1.23 (m, 19H), 1.13-1.08 (m, 10H), 0.95-0.83 (m, 13H), 0.66 (s, 3H); ESI-MS: m/z 647.43 (M+Na)$^+$.

Step 4: Synthesis of 1-benzyl 3-((3aR,5aR,5bR, 7aR,9S,11aR,11bR,13aS)-3a-(1-((tert-butoxy carbonyl)amino)cyclopropane-1-carboxamido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate

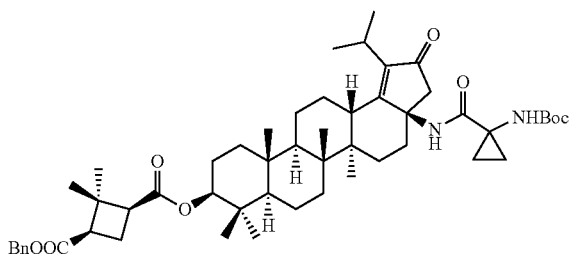

To a stirred solution of (1S,3R)-3-((benzyloxy)carbonyl)-2,2-dimethylcyclobutane-1-carboxylic acid (prepared as described in WO 2011/007230 A2, 10.07 g, 38.46 mmol, 1.5 eq) in DMF (120 ml) at 0° C. under nitrogen atmosphere was added EDCI (9.84 g, 51.28 mmol, 2 eq), HOBT (5.19 g, 38.46 mmol, 1.5 eq), DMAP (1.56 g, 12.82 mmol, 0.5 eq) and added Triethylamine (10.70 ml, 76.92 mmol, 3 eq) and stirred it for about 30 minutes. Then added tert-butyl (1-(((3aR,5aR,5bR,7aR,9S,11aR,11bR,13aS)-9-hydroxy-1-isopropyl-5a,5b,8,8,11a-pentamethyl-2-oxo-2,3,4,5,5a,5b,6, 7,7a,8,9,10,11,11a,11b,12,13,13a-octadecahydro-3aH-cyclopenta[a]chrysen-3a-yl)carbamoyl)cyclopropyl) carbamate (step 3, 16.0 g, 25.64 mmol,1 eq) and the reaction mixture was stirred at room temperature for about 14 hours. TLC indicated starting material was consumed and the desired product was observed. The reaction mixture was quenching with ice cold water then filtered through Buchner funnel then solid was separated, then that solid compound was dissolved in DCM, washed with sodium bicarbonate, water and brine solution then dried over sodium sulfate and concentrated under reduced pressure to give a crude compound. The crude compound was purified by flash silica column chromatography (100-200 silica gel) using 2% MeOH in DCM gradient. The fractions containing the product were combined and concentrated under reduced pressure to give the desired product (18.0 g, yield: 80.89%) as an off-white solid. $^1$H NMR (300 MHz, DMSO-$d_6$): δ ppm 7.36-7.34 (m, 5H), 7.32-7.20 (m, 2H), 5.14, 5.08 (ABq, $J_{AB}$=12.3 Hz, 2H), 4.35 (m, 1H), 3.74-3.69 (m, 2H), 3.12-2.84 (m, 5H), 2.38-2.14 (m, 4H), 1.96-1.90 (m, 3H), 1.73-1.1.58 (m, 8H), 1.39-1.36 (m, 14H), 1.13-1.09 (m, 14H), 0.89-0.81 (m, 16H); ESI-MS: m/z 891.32 (M+Na)$^+$.

Step 5: Synthesis of 1-((3aR,5aR,5bR,7aR,9S,11aR, 11bR,13aS)-3a-(1-aminocyclopropane-1-carboxamido)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) 3-benzyl (1S,3R)-2,2-di methylcyclobutane-1,3-dicarboxylate To a stirred solution of 1-benzyl 3-((3aR,5aR,5bR,7aR, 9S,11aR,11bR,13aS)-3a-(1-((tert-butoxy)carbonyl)amino) cyclopropane-1-carboxamido)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl) (1R,3S)-2,2-dimethylcyclobutane-1,3-dicarboxylate (step 4, 18 g, 20.73 mmol, 1.0 eq) in DCM (160 ml) was added trifluoroacetic acid (36 ml). The reaction mixture was stirred at room temperature for about 3 hours. TLC indicated starting material was consumed and the desired product was observed. The reaction mixture was slowly poured in to cold sodium bicarbonate solution, pH adjusted to 8.0 then filtered through celite pad and the filtrate was extracted with DCM (3×200 ml). The combined organic layer was washed with water (200 ml), dried over sodium sulfate, and evaporated under reduced pressure to give the desired product (13.0 g, yield: 81.76%) as an off-white solid. $^1$H NMR (300 MHz, DMSO-$d_6$): δ ppm 7.36-7.34 (m, 5H), 7.32-7.20 (m, 2H), 5.14, 5.08 (ABq, $J_{AB}$=12.3 Hz, 2H), 4.35 (m, 1H), 3.74-3.69 (m, 2H), 3.12-2.84 (m, 5H), 2.38-2.14 (m, 4H), 1.96-1.90 (m, 3H), 1.73-1.58 (m, 7H), 1.39-1.36 (m, 7H), 1.13-1.09 (m, 14H), 0.89-0.81 (m, 16H); ESI-MS: m/z 791.52 (M+Na)$^+$.

Intermediate 4: Preparation of 1-((3aR,5aR,5bR, 7aR,9S,11aR,11bR,13aS)-3a-(1-aminocyclo propane-1-carboxamido)-1-isopropyl-5a,5b,8,8,11a-pentamethyl-2-oxo-3,3a,4,5,5a,5b,6,7,7a,8,9,10,11, 11a,11b,12,13,13a-octadecahydro-2H-cyclopenta[a] chrysen-9-yl) 3-benzyl (1R,3S)-2,2-dimethylcyclobutane-1,3-dicarboxylate

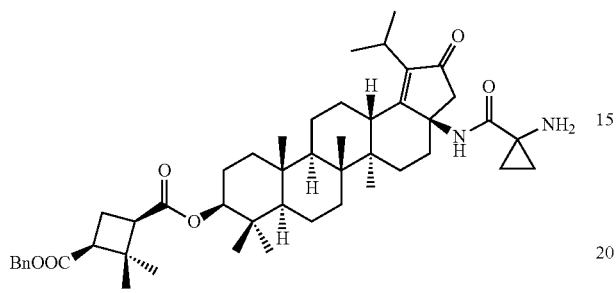

Step 1: Synthesis of 1-benzyl 3-((3aR,5aR,5bR, 7aR,9S,11aR,11bR,13aS)-3a-(1-((tert-butoxy carbonyl)amino)cyclopropane-1-carboxamido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl) (1S,3R)-2,2-dimethylcyclobutane-1,3-dicarboxylate

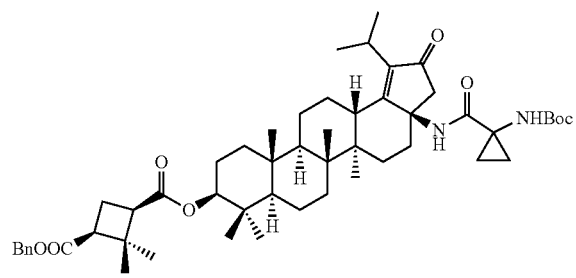

To a stirred solution of (1R,3S)-3-((benzyloxy)carbonyl)-2,2-dimethylcyclobutane-1-carboxylic acid (prepared as described in WO 2014/105926 A1, 10.11 g, 38.46 mmol, 1.5 eq) in DMF (120 ml) at 0° C. under nitrogen atmosphere was added EDCI (14.76 g, 76.92 mmol, 2 eq), HOBT (7.78 g, 57.66 mmol, 1.5 eq), DMAP (2.3 g, 19.22 mmol, 0.5 eq) and added Triethylamine (15.53 ml, 115.32 mmol, 3 eq) and stirred it for about 30 minutes. Then added tert-butyl (1-(((3aR,5aR,5bR,7aR,9S,11aR,11bR,13aS)-9-hydroxy-1-isopropyl-5a,5b,8,8,11a-pentamethyl-2-oxo-2,3,4,5,5a,5b,6, 7,7a,8,9,10,11,11a,11b,12,13,13a-octadecahydro-3aH-cyclopenta[a]chrysen-3a-yl)carbamoyl)cyclopropyl) carbamate (Intermediate 3-step 3, 16.0 g, 25.64 mmol, 1 eq). The reaction mixture was stirred at room temperature for about 14 hours. TLC indicated starting material was consumed and the desired product was observed. The reaction mixture was quenched with ice cold water then filtered through Buchner funnel then solid was separated, then that solid compound was dissolved in DCM and washed with sodium bicarbonate, water and brine solution then dried over sodium sulfate and concentrated under reduced pressure to give a crude compound. The crude compound was purified by flash silica column chromatography (100-200 silica gel) using 2% MeOH in DCM gradient. The fractions containing the product were combined and concentrated under reduced pressure to give the desired product (18.0 g, yield: 80.89%) as an off-white solid. $^1$H NMR (300 MHz, DMSO-$d_6$): δ ppm 8.32 (m, 1H), 7.20 (m, 1H), 4.32-4.31 (m, 1H), 3.72-3.67 (m, 1H), 3.12-2.75 (m, 3H), 2.38-2.09 (m, 4H), 1.85 (m, 4H), 1.65-1.23 (m, 19H), 1.13-1.08 (m, 10H), 0.95-0.83 (m, 13H), 0.66 (s, 3H); ESI-MS: m/z 647.43 (M+Na)$^+$.

Step 2: Synthesis of 1-((3aR,5aR,5bR,7aR,9S,11aR, 11bR,13aS)-3a-(1-aminocyclopropane-1-carboxamido)-1-isopropyl-5a,5b,8,8,11a-pentamethyl-2-oxo-3,3a,4,5,5a,5b,6,7,7a,8,9,10, 11,11a,11b,12,13, 13a-octadecahydro-2H-cyclopenta[a]chrysen-9-yl) 3-benzyl (1R,3S)-2,2-di methylcyclobutane-1,3-dicarboxylate To a stirred solution of 1-benzyl 3-((3aR,5aR,5bR,7aR, 9S,11aR,11bR,13aS)-3a-(1-((tert-butoxy)carbonyl)amino) cyclopropane-1-carboxamido)-1-isopropyl-5a,5b,8,8,11a-penta methyl-2-oxo-3,3a,4,5,5a,5b,6,7,7a,8,9,10,11,11a, 11b,12,13,13a-octadecahydro-2H-cyclo penta[a]chrysen-9-yl) (1S,3R)-2,2-dimethylcyclobutane-1,3-dicarboxylate (step 1, 18 g, 20.73 mmol, 1.0 eq) in DCM (160 ml) was added trifluoroacetic acid (36 ml). The reaction mixture was stirred at room temperature for about 3 hours. TLC indicated starting material was consumed and the desired product was observed. The reaction mixture was slowly poured in to cold sodium bicarbonate solution, pH adjusted to 8.0 then filtered through celite pad, the filtrate was extracted with DCM (3×200 ml). The combined organic layer was washed with water (200 ml), dried over sodium sulfate, and evaporated under reduced pressure give the desired product (13.0 g, yield: 81.76%) as an off-white solid. $^1$H NMR (300 MHz, DMSO-$d_6$): δ ppm 7.36-7.34 (m, 5H), 7.32-7.20 (m, 2H), 5.14, 5.08 (ABq, $J_{AB}$=12.3 Hz, 2H), 4.35 (m, 1H), 3.74-3.69 (m, 2H), 3.12-2.84 (m, 5H), 2.38-2.14 (m, 4H), 1.96-1.90 (m, 3H), 1.73-1.58 (m, 7H), 1.39-1.36 (m, 7H), 1.13-1.09 (m, 14H), 0.89-0.81 (m, 16H); ESI-MS: m/z 791.52 (M+Na)$^+$.

Intermediate 5: Preparation of 1-((3aR,5aR,5bR, 7aR,9S,11aR,11bR,13aS)-3a-(1-aminocyclo butane-1-carboxamido)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl) 3-benzyl (1S,3R)-2,2-dimethylcyclobutane-1, 3-dicarboxylate

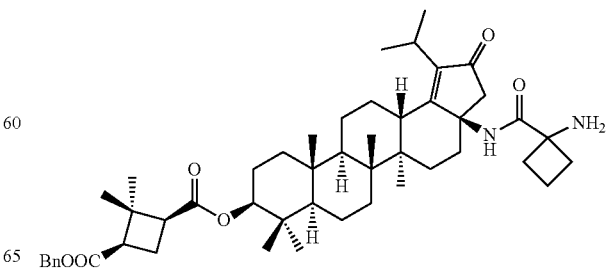

Step 1: Synthesis of 1-((tert-butoxy)carbonyl) amino)cyclobutane-1-carboxylic acid

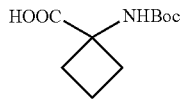

To a stirred solution of 1-aminocyclobutane-1-carboxylic acid (30 g, 139.53 mmol, 1.0 eq) in 1,4-dioxane (300 ml) at 0° C. was added 2N NaOH solution (300 ml) followed by (Boc)$_2$O (45.62 g, 209.30 mmol, 1.5 eq). The reaction mixture was allowed to stir at room temperature for overnight. TLC indicated starting material was consumed and the desired product was observed. The organic phase was evaporated under reduced pressure, the reaction mixture was diluted with water (50 ml), cooled to 0° C., pH adjusted to 5 with 1N HCl and then extracted with DCM (3×300 ml). The combined organic extracts were washed with water (300 ml), brine (100 ml) solution, dried over Na$_2$SO$_4$, filtered and evaporated under reduced pressure. The residue was stirred with n-hexane (300 ml) at room temperature for about 30 minutes, the obtained solid was filtered and dried under vacuum to give the desired product (35.0 g, yield: 62.41%) as a white solid. $^1$H NMR (300 MHz, DMSO-d$_6$): δ ppm 12.19 (brs, 1H), 7.70-7.16 (m, 1H), 2.45-2.36 (m, 2H), 2.12-2.03 (m, 2H), 1.86-1.78 (m, 2H), 1.36 (brs, 9H); ESI-MS: m/z 238.13 (M+Na)$^+$.

Step 2: Synthesis of (3aR,5aR,5bR,7aR,9S,11aR,11bR,13aS)-3a-(1-((tert-butoxy)carbonyl)amino)cyclobutane-1-carboxamido)-1-isopropyl-5a,5b,8,8,11a-pentamethyl-2-oxo-3,3a,4,5, 5a,5b,6,7,7a,8,9,10,11,11a,11b,12,13,13a-octadecahydro-2H-cyclopenta[a]chrysen-9-yl acetate

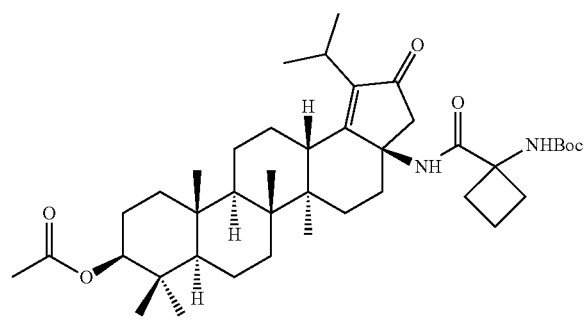

To a stirred solution of 1-((tert-butoxy)carbonyl)amino) cyclobutane-1-carboxylic acid (step 1, 13.35 g, 62.11 mmol, 1.5 eq) in DMF (160 ml) at 0° C. under nitrogen atmosphere was added EDCI (15.90 g, 82.81 mmol, 2 eq), HOBT (8.38 g, 62.11 mmol, 1.5 eq), DMAP (2.52 g, 20.70 mmol, 0.5 eq), and added Triethylamine (17.28 ml 124.22 mmol, 3 eq) and stirred it for about 30 minutes. Then added (3aR,5aR,5bR, 7aR,9S,11aR,11bR,13aS)-3a-amino-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl acetate (Intermediate 1-step 8, 20.0 g, 41.40 mmol, 1 eq) and the reaction mixture was stirred at room temperature for about 14 hours. TLC indicated starting material was consumed and the desired product was observed. The reaction mixture was quenched with ice cold water then filtered through Buchner funnel then solid was separated, then that solid compound was dissolved in DCM and washed with sodium bicarbonate, water and brine solution then dried over sodium sulfate and concentrated under reduced pressure to give a crude compound. The crude compound was purified by flash silica column chromatography (100-200 silica gel) using 2% MeOH in DCM gradient. The fractions containing the product were combined and concentrated under reduced pressure to give the desired product (22.0 g, yield: 78.15%) as an off-pale yellow solid. $^1$H NMR (300 MHz, DMSO-d$_6$): δ ppm 7.37-7.20 (m, 1H), 7.02-6.81 (m, 1H), 4.40-4.35 (m, 1H), 4.06-3.98 (m, 1H), 3.73-3.49 (m, 1H), 3.25-3.14 (m, 1H), 2.97-2.90 (m, 1H), 2.82-2.74 (m, 1H), 2.45-2.36 (m, 2H), 2.31-2.26 (m, 2H), 2.16-2.10 (m, 2H), 1.92 (m, 3H), 1.86-1.43 (m, 8H), 1.38-1.33 (m, 9H), 1.27-1.18 (m, 3H), 1.15-1.11 (m, 9H), 0.99-0.95 (m, 3H), 0.90-0.86 (m, 6H), 0.84-0.81 (s, 9H); ESI-MS: m/z 703.43 (M+Na)$^+$.

Step 3: Synthesis of tert-butyl (1-(((3aR,5aR,5bR,7aR,9S,11aR,11bR,13aS)-9-hydroxy-1-isopropyl-5a,5b,8,8,11a-pentamethyl-2-oxo-2,3,4,5,5a,5b,6,7,7a,8,9,10,11,11a,11b,12,13,13a-octadecahydro-3aH-cyclopenta[a]chrysen-3a-yl)carbamoyl)cyclobutyl) carbamate

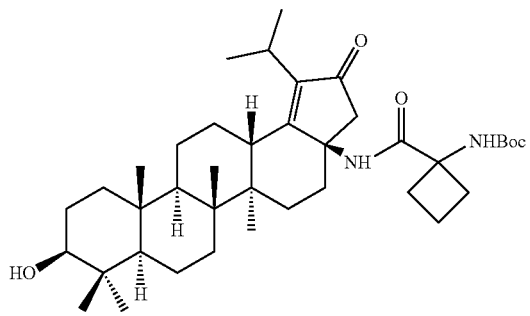

To a stirred solution of (3aR,5aR,5bR,7aR,9S,11aR,11bR, 13aS)-3a-(1-((tert-butoxy carbonyl)amino)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (step 2, 22 g, 32.35 mmol, 1.0 eq) in MeOH (180 ml), THF (90 ml) and water (50 ml) at 0° C. was added NaOH (12.94 g, 323.52 mmol, 10.0 eq). The mixture was removed from the ice bath and was stirred at room temperature for overnight. TLC indicated starting material was consumed and the desired product was observed. The organic phase was evaporated under reduced pressure, the reaction mixture was diluted with water (180 ml) and extracted with DCM (3×180 ml). The combined organic extracts were washed with water (100 ml), brine solution (50 ml), dried over sodium sulfate, filtered and evaporated under reduced pressure. The residue was purified by silicagel column chromatography by using 0-3% methanol in dichloromethane gradient. The fractions containing the product were combined and concentrated under reduced pressure to give the desired product (18 g, yield: 87.20%) as a white solid. $^1$H NMR (300 MHz, DMSO-d$_6$): δ ppm 8.35 (m, 1H), 7.22 (m, 1H), 4.34-4.30 (m, 1H), 3.75-3.68 (m, 1H), 3.14-2.77 (m, 3H), 2.52-2.43 (m, 2H), 2.40-2.11 (m, 4H), 1.89 (m, 4H), 1.69-1.33 (m, 19H), 1.15-1.11 (m, 10H), 0.99-0.85 (m, 13H), 0.68 (s, 3H); ESI-MS: m/z 661.42 (M+Na)$^+$.

Step 4: Synthesis of 1-benzyl 3-((3aR,5aR,5bR, 7aR,9S,11aR,11bR,13aS)-3a-(1-((tert-butoxy carbonyl)amino)cyclobutane-1-carboxamido)-1-isopropyl-5a,5b,8,8,11a-pentamethyl-2-oxo-3,3a,4,5,5a,5b,6,7, 7a,8,9,10,11,11a,11b,12,13,13a-octadecahydro-2H-cyclopenta[a]chrysen-9-yl) (1R,3S)-2,2-dimethylcyclobutane-1,3-dicarboxylate

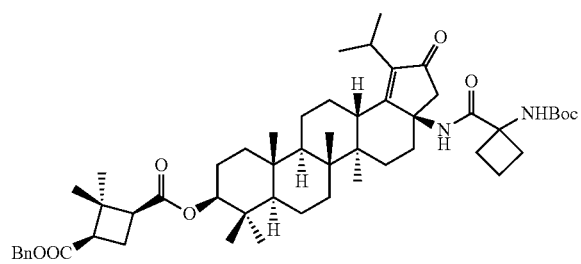

To a stirred solution of (1S,3R)-3-((benzyloxy)carbonyl)-2,2-dimethylcyclobutane-1-carboxylic acid (prepared as described in WO 2011/007230 A2, 11.08 g, 42.31 mmol, 1.5 eq) in DMF (120 ml) at 0° C. under nitrogen atmosphere was added EDCI (16.25 g, 84.63 mmol, 2 eq), HOBT (5.71 g, 42.31 mmol, 1.5 eq), DMAP (1.72 g, 14.10 mmol, 0.5 eq), and added triethylamine (11.77 ml, 84.63 mmol, 3 eq) and stirred it for about 30 minutes. Then added tert-butyl (1-(((3aR,5aR,5bR,7aR,9S,11aR,11bR,13aS)-9-hydroxy-1-isopropyl-5a,5b,8,8,11a-pentamethyl-2-oxo-2,3,4,5,5a,5b,6, 7,7a,8,9,10,11,11a,11b,12,13,13a-octadecahydro-3aH-cyclopenta[a]chrysen-3a-yl)carbamoyl)cyclobutyl) carbamate (step 3, 18 g, 28.21 mmol,1 eq). The reaction mixture was stirred at room temperature for about 14 hours. TLC indicated starting material was consumed and the desired product was observed. The reaction mixture was quenched with ice cold water then filtered through Buchner funnel then solid was separated, then that solid compound was dissolved in DCM and washed with sodium bicarbonate, water and brine solution then dried over sodium sulfate and concentrated under reduced pressure to give a crude compound. The crude compound was purified by flash silica column chromatography (100-200 silica gel) using 2% MeOH in DCM gradient. The fractions containing the product were combined and concentrated under reduced pressure to give the desired product (18 g, yield: 72.58%) as an off-white solid. $^1$H NMR (300 MHz, DMSO-$d_6$): δ ppm 7.37-7.35 (m, 5H), 7.31-7.22 (m, 2H), 5.15, 5.09 (ABq, $J_{AB}$=12.3 Hz, 2H), 4.34-4.30 (m, 1H), 3.77-3.70 (m, 2H), 3.14-2.87 (m, 5H), 2.47-2.38 (m, 2H), 2.32-2.16 (m, 4H), 1.99-1.95 (m, 3H), 1.75-1.60 (m, 8H), 1.38-1.30 (m, 14H), 1.20-1.11 (m, 14H), 0.90-0.83 (m, 16H); ESI-MS: m/z 905.43 (M+Na)$^+$.

Step 5: Synthesis of 1-((3aR,5aR,5bR,7aR,9S,11aR, 11bR,13aS)-3a-(1-aminocyclobutane-1-carboxamido)-1-isopropyl-5a,5b,8,8,11a-pentamethyl-2-oxo-3,3a,4,5,5a,5b,6,7,7a,8,9,10, 11, 11a,11b, 12,13, 13a-octadecahydro-2H-cyclopenta[a]chrysen-9-yl) 3-benzyl (1S,3R)-2,2-dimethylcyclobutane-1,3-dicarboxylate To a stirred solution of 1-benzyl 3-((3aR,5aR,5bR,7aR, 9S,11aR,11bR,13aS)-3a-(1-((tert-butoxy)carbonyl)amino) cyclobutane-1-carboxamido)-1-isopropyl-5a,5b,8,8,11a-penta methyl-2-oxo-3,3a,4,5,5a,5b,6,7,7a,8,9,10,11,11a, 11b,12,13,13a-octadecahydro-2H-cyclo penta[a]chrysen-9-yl) (1R,3S)-2,2-dimethylcyclobutane-1,3-dicarboxylate (step 4, 18 g, 22.95 mmol, 1.0 eq) in DCM (160 ml) was added trifluoroacetic acid (36 ml). The reaction mixture was stirred at room temperature for about 3 hours. TLC indicated starting material was consumed and the desired product was observed. The reaction mixture was slowly poured in to cold sodium bicarbonate solution, pH adjusted to 8.0 then filtered through celite pad, the filtrate was extracted with DCM (3×200 ml). The combined organic layer was washed with water (200 ml), dried over sodium sulfate, and evaporated under reduced pressure to give the desired product (14 g, yield: 87.77%) as an off-white solid. $^1$H NMR (300 MHz, DMSO-$d_6$): δ ppm 7.34-7.32 (m, 5H), 7.31-7.22 (m, 2H), 5.15, 5.09 (ABq, $J_{AB}$=12.3 Hz, 2H), 4.34-4.32 (m, 1H), 3.77-3.70 (m, 2H), 3.14-2.85 (m, 5H), 2.46-2.41 (m, 2H), 2.38-2.14 (m, 4H), 1.97-1.91 (m, 3H), 1.74-1.60 (m, 7H), 1.40-1.38 (m, 7H), 1.14-1.11 (m, 14H), 0.89-0.83 (m, 16H); ESI-MS: m/z 805.32 (M+Na)$^+$.

Intermediate 6: Preparation of 1-((3aR,5aR,5bR, 7aR,9S,11aR,11bR,13aS)-3a-(1-aminocyclo pentane-1-carboxamido)-1-isopropyl-5a,5b,8,8,11a-pentamethyl-2-oxo-3,3a,4,5,5a,5b,6,7,7a,8,9,10,11, 11a,11b,12,13,13a-octadecahydro-2H-cyclopenta[a]chrysen-9-yl) 3-benzyl (1S,3R)-2,2-dimethylcyclobutane-1,3-dicarboxylate

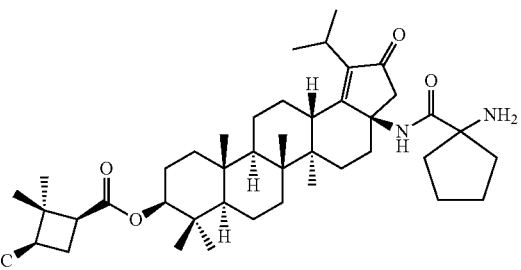

Step 1: Synthesis of 1-((tert-butoxy)carbonyl) amino)cyclopentane-1-carboxylic acid

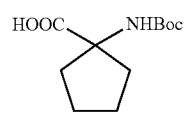

To a stirred solution of 1-aminocyclopentane-1-carboxylic acid (10 g, 77.51 mmol, 1.0 eq) in 1,4-dioxane (100 ml) at 0° C. was added 2N NaOH solution (100 ml) followed by (Boc)$_2$O (25.34 g, 116.27 mmol, 1.5 eq). The reaction mixture was allowed to stir at room temperature for overnight. TLC indicated starting material was consumed and the desired product was observed. The organic phase was evaporated under reduced pressure, the reaction mixture was diluted with water (50 ml), cooled to 0° C., pH adjusted to 5 with 1N HCl and then extracted with DCM (3×300 ml). The combined organic extracts were washed with water (300 ml), brine (100 ml) solution, dried over Na$_2$SO$_4$, filtered and evaporated under reduced pressure. The residue was stirred with n-hexane (300 ml) at room temperature for about 30 minutes, the obtained solid was filtered and dried under vacuum to obtain the desired product (10.0 g, yield: 56.33%) as a white solid. $^1$H NMR (300 MHz, DMSO-$d_6$): δ ppm 12.11 (s, 1H), 7.10-6.86 (m, 1H), 1.94-1.84 (m, 4H), 1.62-1.58 (m, 4H), 1.36 (s, 9H); ESI-MS: m/z 252.02 (M+Na)$^+$.

Step 2: Synthesis of (3aR,5aR,5bR,7aR,9S,11aR, 11bR,13aS)-3a-(1-((tert-butoxy)carbonyl) amino) cyclopentane-1-carboxamido)-1-isopropyl-5a,5b,8,8, 11a-pentamethyl-2-oxo-3,3a,4,5,5a,5b,6,7,7a,8,9,10, 11,11a,11b,12, 13,13a-octadecahydro-2H-cyclopenta [a]chrysen-9-yl acetate

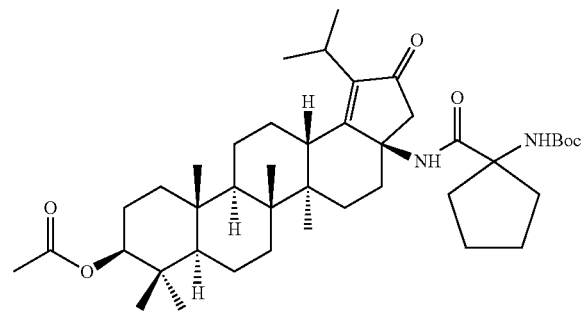

To a stirred solution of 1-((tert-butoxy)carbonyl)amino) cyclopentane-1-carboxylic acid (step 1, 8.5 g, 37.11 mmol, 1.5 eq) in DMF (100 ml) at 0° C. under nitrogen atmosphere was added EDCI (9.54 g, 49.68 mmol, 2 eq), HOBT (5.03 g, 37.26 mmol, 1.5 eq), DMAP (1.51 g, 12.42 mmol, 0.5 eq), and added Triethylamine (10.36 ml 74.53 mmol, 3 eq) and stirred it for about 30 minutes. Then added (3aR,5aR,5bR, 7aR,9S,11aR,11bR,13aS)-3a-amino-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl acetate (Intermediate 1-step 8, 12 g, 24.84 mmol,1 eq). The reaction mixture was stirred at room temperature for about 14 hours. TLC indicated starting material was consumed and the desired product was observed. The reaction mixture was quenched with ice cold water then filtered through Buchner funnel then solid was separated, then that solid compound was dissolved in DCM and washed with sodium bicarbonate, water and brine solution then dried over sodium sulfate and concentrated under reduced pressure to give a crude compound. The crude compound was purified by flash silica column chromatography (100-200 silica gel) using 2% MeOH in DCM gradient. The fractions containing the product were combined and concentrated under reduced pressure to give the desired product (10 g, yield: 58.00%) as an off-white solid. $^1$H NMR (300 MHz, DMSO-$d_6$): δ ppm 7.10 (brs, 1H), 6.89 (brs, 1H), 4.42-4.36 (m, 1H), 3.74-3.66 (m, 1H), 3.12-3.08 (m, 2H), 2.83-2.79 (m, 1H), 2.35-2.26 (m, 2H), 2.11-1.81 (m, 11H), 1.56-1.47 (m, 9H), 1.35-1.23 (m, 13H), 1.14-1.07 (m, 11H), 0.90-0.80 (m, 10H), 0.76 (brs, 3H); ESI-MS: m/z 717.52 (M+Na)$^+$.

Step 3: Synthesis of tert-butyl (1-(((3aR,5aR,5bR, 7aR,9S,11aR,11bR,13aS)-9-hydroxy-1-isopropyl-5a, 5b,8,8,11a-pentamethyl-2-oxo-2,3,4,5,5a,5b,6,7,7a,8, 9, 10,11,11a,11b,12, 13,13a-octadecahydro-3aH-cyclopenta[a]chrysen-3a-yl)carbamoyl)cyclopentyl) carbamate

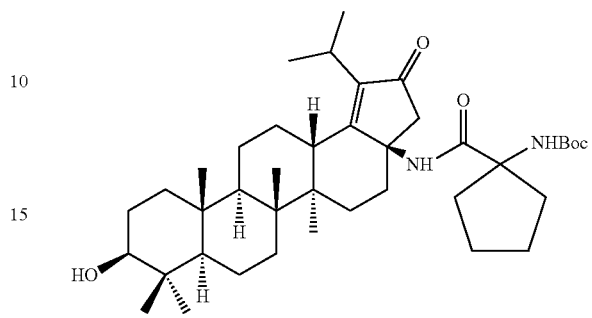

To a stirred solution of (3aR,5aR,5bR,7aR,9S,11aR,11bR, 13aS)-3a-(1-((tert-butoxy carbonyl)amino)cyclopentane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (step 2, 10 g, 14.40 mmol, 1.0 eq) in MeOH (60 ml), THF (30 ml) and water (15 ml) at 0° C. was added NaOH (5.76 g, 144.0 mmol, 10.0 eq). The mixture was removed from the ice bath and was stirred at room temperature for overnight. TLC indicated starting material was consumed and the desired product was observed. The organic phase was evaporated under reduced pressure, the reaction mixture was diluted with water (180 ml) and extracted with DCM (3×180 ml). The combined organic extracts were washed with water (100 ml), brine solution (50 ml), dried over sodium sulfate, filtered and evaporated under reduced pressure. The residue was purified by silicagel column chromatography by using 0-3% methanol in dichloromethane gradient. The fractions containing the product were combined and concentrated under reduced pressure to give the desired product (7 g, yield: 75.26%) as a white solid. $^1$H NMR (300 MHz, DMSO-$d_6$): δ ppm 7.09 (brs, 1H), 6.89 (brs, 1H), 4.31-4.29 (m, 1H), 3.17-3.15 (m, 1H), 3.11-2.98 (m, 2H), 2.82-2.79 (m, 1H), 2.35-2.27 (m, 2H), 2.11-1.81 (m, 9H), 1.57-1.47 (m, 9H), 1.35-1.23 (m, 12H), 1.19-1.06 (m, 11H), 0.94-0.82 (m, 11H), 0.66 (brs, 3H); ESI-MS: m/z 675.72 (M+Na)$^+$.

Step 4: Synthesis of 1-benzyl 3-((3aR,5aR,5bR, 7aR,9S,11aR,11bR,13aS)-3a-(1-((tert-butoxy carbonyl)amino)cyclopentane-1-carboxamido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate

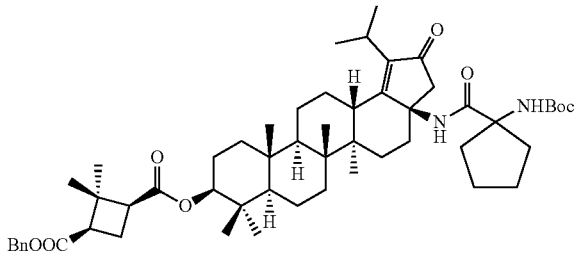

To a stirred solution of (1S,3R)-3-((benzyloxy)carbonyl)-2,2-dimethylcyclobutane-1-carboxylic acid (prepared as described in WO 2011/007230 A2, 4.2 g, 16.03 mmol, 1.5 eq) in DMF (60 ml) at 0° C. under nitrogen atmosphere was added EDCI (4.12 g, 21.47 mmol, 2 eq), HOBT (2.17 g, 16.10 mmol, 1.5 eq), DMAP (0.65 g, 5.36 mmol, 0.5 eq), and added Triethylamine (4.48 ml 32.20 mmol, 3 eq) and stirred it for about 30 minutes. Then added tert-butyl (1-(((3aR,5aR,5bR,7aR,9S,11aR,11bR,13aS)-9-hydroxy-1-isopropyl-5a,5b,8,8,11a-pentamethyl-2-oxo-2,3,4,5,5a,5b,6,7,7a,8,9,10,11,11a,11b,12,13,13a-octadecahydro-3aH-cyclopenta[a]chrysen-3a-yl)carbamoyl)cyclopentyl) carbamate (step 3, 7 g, 10.73 mmol, 1 eq). The reaction mixture was stirred at room temperature for about 14 hours. TLC indicated starting material was consumed and the desired product was observed. The reaction mixture was quenched with ice cold water then filtered through Buchner funnel then solid was separated, then that solid compound was dissolved in DCM and washed with sodium bicarbonate, water and brine solution then dried over sodium sulfate and concentrated under reduced pressure to give a crude compound. The crude compound was purified by flash silica column chromatography (100-200 silica gel) using 2% MeOH in DCM gradient. The fractions containing the product were combined and concentrated under reduced pressure to give the desired product (6 g, yield: 62.41%) as an off-white solid. $^1$H NMR (300 MHz, DMSO-d$_6$): δ ppm 7.37-7.32 (m, 5H), 7.10 (s, 1H), 6.89 (s, 1H), 5.14, 5.08 (ABq, J$_{AB}$=12.3 Hz, 2H), 4.38-4.32 (m, 1H), 3.61-3.59 (m, 1H), 3.12-3.07 (m, 1H), 2.97-2.80 (m, 3H), 2.38-2.31 (m, 4H), 2.22-1.88 (m, 6H), 1.81-1.77 (m, 5H), 1.69-1.57 (m, 8H), 1.35 (m, 10H), 1.26-1.23 (m, 7H), 1.14-1.03 (m, 11H), 0.89-0.78 (m, 14H); ESI-MS: m/z 919.45 (M+Na)$^+$.

Step 5: Synthesis of 1-((3aR,5aR,5bR,7aR,9S,11aR, 11bR,13aS)-3a-(1-aminocyclopentane-1-carboxamido)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) 3-benzyl (1S,3R)-2,2-di methylcyclobutane-1,3-dicarboxylate To a stirred solution of 1-benzyl 3-((3aR,5aR,5bR,7aR, 9S,11aR,11bR,13aS)-3a-(1-(((tert-butoxy)carbonyl)amino) cyclopentane-1-carboxamido)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl) (1R,3S)-2,2-dimethylcyclobutane-1,3-dicarboxylate (step 4, 6.0 g, 6.69 mmol, 1.0 eq) in DCM (60 ml) was added trifluoroacetic acid (12 ml). The reaction mixture was stirred at room temperature for about 3 hours. TLC indicated starting material was consumed and the desired product was observed. The reaction mixture was slowly poured in to cold sodium bicarbonate solution, pH adjusted to 8.0 then filtered through celite pad and the filtrate was extracted with DCM (3×200 ml). The combined organic layer was washed with water (200 ml), dried over sodium sulfate, and evaporated under reduced pressure to give the desired product (4.0 g, yield: 75.47%) as an off-white solid. $^1$H NMR (300 MHz, DMSO-d$_6$): δ ppm 7.36-7.35 (m, 5H), 7.10 (s, 1H), 5.14, 5.08 (ABq, J$_{AB}$=12.3 Hz, 2H), 4.38-4.32 (m, 1H), 3.61-3.59 (m, 1H), 3.12-3.07 (m, 1H), 2.97-2.80 (m, 3H), 2.38-2.31 (m, 4H), 2.22-1.88 (m, 6H), 1.81-1.77 (m, 5H), 1.69-1.35 (m, 11H), 1.26-1.23 (m, 7H), 1.14-1.03 (m, 11H), 0.89-0.78 (m, 14H); ESI-MS: m/z 819.32 (M+Na)$^+$.

Intermediate 7: Preparation of 1-((3aR,5aR,5bR, 7aR,9 S,11aR,11bR,13aS)-3a-(1-aminocyclohexane-1-carboxamido)-1-isopropyl-5a,5b,8,8,11a-pentamethyl-2-oxo-3,3a,4,5,5a,5b,6,7,7a, 8,9,10,11,11a,11b, 12,13,13a-octadecahydro-2H-cyclopenta[a]chrysen-9-yl) 3-benzyl (1S,3R)-2,2-dimethylcyclobutane-1, 3-dicarboxylate

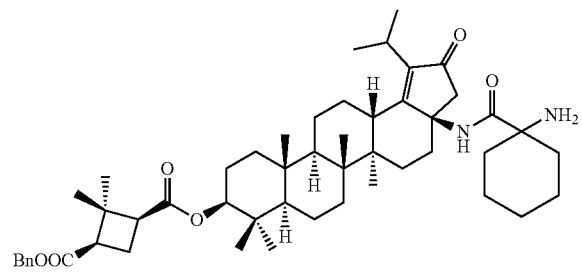

Step 1: Synthesis of 1-((tert-butoxy)carbonyl) amino)cyclohexane-1-carboxylic acid

To a stirred solution of 1-aminocyclohexane-1-carboxylic acid (10 g, 69.93 mmol, 1.0 eq) in 1,4-dioxane (300 ml) at 0° C. was added 2N NaOH solution (100 ml) followed by (Boc)$_2$O (22.86 g, 104.89 mmol, 1.5 eq). The reaction mixture was allowed to stir at room temperature for overnight. TLC indicated starting material was consumed and the desired product was observed. The organic phase was evaporated under reduced pressure, the reaction mixture was diluted with water (50 ml), cooled to 0° C., pH adjusted to 5 with 1N HCl and then extracted with DCM (3×300 ml). The combined organic extracts were washed with water (300 ml), brine (100 ml) solution, dried over Na$_2$SO$_4$, filtered and evaporated under reduced pressure. The residue was stirred with n-hexane (300 ml) at room temperature for about 30 minutes, the obtained solid was filtered and dried under vacuum to afford the desired product (11.0 g, yield: 64.74%) as a white solid. $^1$H NMR (300 MHz, DMSO-d$_6$): δ ppm 12.08 (s, 1H), 6.88 (s, 1H), 1.92-1.88 (m, 2H), 1.62-1.56 (m, 2H), 1.45-1.43 (m, 4H), 1.36 (s, 9H), 1.25-1.19 (m, 2H); ESI-MS: m/z 266.32 (M+Na)$^+$.

Step 2: Synthesis of (3aR,5aR,5bR,7aR,9S,11aR, 11bR,13aS)-3a-(1-((tert-butoxy)carbonyl)amino) cyclohexane-1-carboxamido)-1-isopropyl-5a,5b,8,8, 11a-pentamethyl-2-oxo-3,3a,4,5,5a,5b,6,7,7a,8,9,10, 11,11a,11b,12,13,13a-octadecahydro-2H-cyclopenta [a]chrysen-9-yl acetate

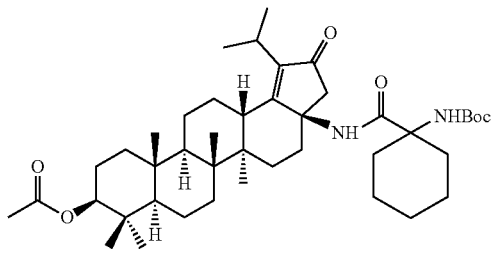

To a stirred solution of 1-((tert-butoxy)carbonyl)amino) cyclohexane-1-carboxylic acid (step 1, 9.05 g, 37.26 mmol, 1.5 eq) in DMF (120 ml) at 0° C. under nitrogen atmosphere was added HBTU (18.83 g, 49.68 mmol, 2 eq), DMAP (1.51 g, 12.42 mmol, 0.5 eq), and added Diisopropylethylamine (12.81 ml, 74.53 mmol, 3 eq) and stirred it for about 10 minutes. Then added (3aR,5aR,5bR,7aR,9S,11aR,11bR, 13aS)-3a-amino-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (Intermediate 1-step 8, 12 g, 24.84 mmol, 1 eq). The reaction mixture was stirred at room temperature for about 14 hours. TLC indicated starting material was consumed and the desired product was observed. The reaction mixture was evaporated under reduced pressure, the reaction mixture was diluted with water (200 ml), and extracted with DCM (3×200 ml). The combined organic extracts were washed with water (300 ml), sodium bicarbonate, and brine solution, then dried over sodium sulfate, filtered and concentrated under reduced pressure to give a crude compound, The crude compound was purified by flash silica column chromatography (100-200 silica gel) using 2% MeOH in DCM as an eluent. The fractions containing the product were combined and concentrated under reduced pressure to give the desired product (12 g, yield: 68.22%) as an off-white solid. $^1$H NMR (300 MHz, DMSO-d$_6$): δ ppm 7.04 (brs, 1H), 6.53 (brs, 1H), 4.41-4.37 (m, 1H), 3.69-3.58 (m, 1H), 3.12-3.07 (m, 1H), 2.89-2.82 (m, 1H), 2.73-2.68 (m, 2H), 2.37-2.27 (m, 3H), 2.11-2.05 (m, 2H), 2.02-1.95 (m, 3H), 1.88-1.80 (m, 3H), 1.74-1.71 (m, 6H), 1.60-1.55 (m, 3H), 1.47 (s, 8H), 1.42-1.41 (m, 7H), 1.35-1.23 (m, 3H), 1.39-1.11 (m, 10H), 1.09-1.07 (m, 7H), 1.04-0.80 (m, 5H); ESI-MS: m/z 731.44 (M+Na)$^+$.

Step 3: Synthesis of tert-butyl (1-(((3aR,5aR,5bR, 7aR,9S,11aR,11bR,13aS)-9-hydroxy-1-isopropyl-5a, 5b,8,8,11a-pentamethyl-2-oxo-2,3,4,5,5a,5b,6,7,7a,8, 9,10,11,11a,11b,12,13,13a-octadecahydro-3aH-cyclopenta[a]chrysen-3a-yl)carbamoyl)cyclohexyl) carbamate

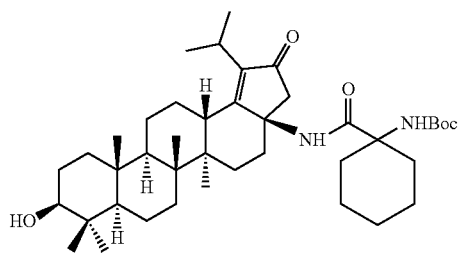

To a stirred solution of (3aR,5aR,5bR,7aR,9S,11aR,11bR, 13aS)-3a-(1-((tert-butoxy carbonyl)amino)cyclohexane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (step 2, 12 g, 16.94 mmol, 1.0 eq) in MeOH (120 ml), THF (60 ml) and water (30 ml) at 0° C. was added NaOH (6.77 g, 169.4 mmol, 10.0 eq). The mixture was removed from the ice bath and was stirred at room temperature for overnight. TLC indicated starting material was consumed and the desired product was observed. The organic phase was evaporated under reduced pressure, the reaction mixture was diluted with water (180 ml) and extracted with DCM (3×180 ml). The combined organic extracts were washed with water (100 ml), brine solution (50 ml), dried over sodium sulfate, filtered and evaporated under reduced pressure. The residue was purified by silicagel column chromatography by using 0-3% methanol in dichloromethane gradient. The fractions containing the product were combined and concentrated under reduced pressure to give the desired product (9 g, yield: 79.78%) as a white solid. $^1$H NMR (300 MHz, DMSO-d$_6$): δ ppm 7.04 (s, 1H), 6.53 (s, 1H), 4.31-4.30 (m, 1H), 3.11-2.99 (m, 3H), 2.86-2.82 (m, 1H), 2.32-2.28 (m, 2H), 2.11 (m, 1H), 1.89-1.85 (m, 4H), 1.65-1.56 (m, 5H), 1.45 (brs, 9H), 1.35-1.28 (brs, 12H), 1.13-0.99 (m, 14H), 0.94-0.82 (m, 9H), 0.66 (s, 3H); ESI-MS: m/z 689.50 (M+Na)$^+$.

Step 4: Synthesis of 1-benzyl 3-((3aR,5aR,5bR, 7aR,9S,11aR,11bR,13aS)-3a-(1-((tert-butoxy carbonyl)amino)cyclohexane-1-carboxamido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate

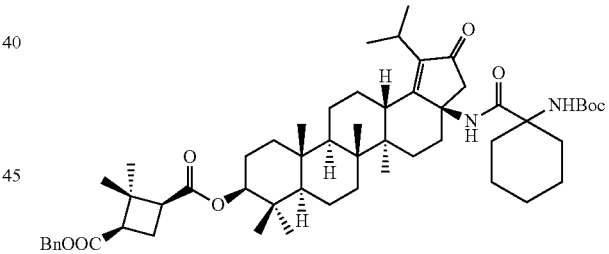

To a stirred solution of (1S,3R)-3-((benzyloxy)carbonyl)-2,2-dimethylcyclobutane-1-carboxylic acid (prepared as described in WO 2011/007230 A2, 5.31 g, 20.27 mmol, 1.5 eq) in DMF (100 ml) at 0° C. under nitrogen atmosphere was added EDCI (5.18 g, 27.02 mmol, 2 eq), HOBT (2.73 g, 20.27 mmol, 1.5 eq), DMAP (0.82 g, 6.75 mmol, 0.5 eq), and added Triethylamine (5.63 ml, 40.54 mmol, 3 eq) and stirred it for about 30 minutes. Then added tert-butyl (1-(((3aR,5aR,5bR,7aR,9S,11aR,11bR,13aS)-9-hydroxy-1-isopropyl-5a,5b,8,8,11a-pentamethyl-2-oxo-2,3,4,5,5a,5b,6, 7,7a,8,9,10,11,11a,11b,12,13,13a-octadecahydro-3aH-cyclopenta[a]chrysen-3a-yl)carbamoyl)cyclohexyl) carbamate (step 3, 9.0 g, 13.51 mmol, 1 eq). The reaction mixture was stirred at room temperature for about 14 hours. TLC indicated starting material was consumed and desired product was observed. The reaction mixture was quenched with ice cold water then filtered through Buchner funnel then solid was separated, then that solid compound was dissolved in DCM and washed with sodium bicarbonate, water and brine solution then dried over sodium sulfate and concentrated under reduced pressure to give a crude compound. The crude compound was purified by flash silica column chromatography (100-200 silica gel) using 2% MeOH in DCM as an eluent. The fractions containing the product were combined and concentrated under reduced pressure to give the desired product (8 g, yield: 65.09%) as an off-white solid. $^1$H NMR (300 MHz, DMSO-$d_6$): δ ppm 8.13 (s, 1H), 7.36-7.35 (m, 5H), 7.34 (s, 1H), 5.14, 5.08 (ABq, $J_{AB}$=12.3 Hz, 2H), 4.38-4.32 (m, 1H), 3.13-3.09 (m, 1H), 3.00-2.67 (m, 4H), 2.38-2.25 (m, 5H), 1.96-1.90 (m, 5H), 1.69-1.40 (m, 21H), 1.36 (brs, 9H), 1.15-1.03 (m, 14H), 0.92-0.81 (m, 13H); ESI-MS: m/z 933.63 (M+Na)$^+$.

Step 5: Synthesis of 14(3aR,5aR,5bR,7aR,9S,11aR, 11bR,13aS)-3a-(1-aminocyclohexane-1-carboxamido)-1-isopropyl-5a,5b,8,8,11a-pentamethyl-2-oxo-3,3a,4,5,5a,5b,6,7,7a,8,9,10, 11,11a,11b,12,13, 13a-octadecahydro-2H-cyclopenta[a]chrysen-9-yl) 3-benzyl (1S,3R)-2,2-dimethylcydobutane-1,3-dicarboxylate To a stirred solution of 1-benzyl 3-((3aR,5aR,5bR,7aR, 9S,11aR,11bR,13aS)-3a-(1-(((tert-butoxy)carbonyl)amino) cyclohexane-1-carboxamido)-1-isopropyl-5a,5b,8,8,11a-penta methyl-2-oxo-3,3a,4,5,5a,5b,6,7,7a,8,9,10,11,11a, 11b,12,13,13a-octadecahydro-2H-cyclo penta[a]chrysen-9-yl) (1R,3S)-2,2-dimethylcyclobutane-1,3-dicarboxylate (step 4, 8.0 g, 8.79 mmol, 1.0 eq) in DCM (80 ml) was added trifluoroacetic acid (16 ml). The reaction mixture was stirred at room temperature for about 3 hours. TLC indicated starting material was consumed and the desired product was observed. The reaction mixture was slowly poured in to cold sodium bicarbonate solution, pH adjusted to 8.0 then filtered through celite pad, the filtrate was extracted with DCM (3×200 ml). The combined organic layer was washed with water (200 ml), dried over sodium sulfate, and evaporated under reduced pressure to give the desired product (6.0 g, yield: 84.26%) as an off-white solid. $^1$H NMR (300 MHz, DMSO-$d_6$): δ ppm 8.13 (s, 1H), 7.36-7.35 (m, 5H), 5.14, 5.08 (ABq, $J_{AB}$=12.3 Hz, 2H), 4.38-4.32 (m, 1H), 3.13-3.09 (m, 1H), 3.00-2.67 (m, 4H), 2.38-2.25 (m, 5H), 1.96-1.90 (m, 5H), 1.69-1.23 (m, 23H), 1.15-1.03 (m, 14H), 0.92-0.81 (m, 13H); ESI-MS: m/z 833.55 (M+Na)$^+$.

Intermediate 8: Preparation of 1-(4-chlorophenyl)cyclopropane-1-carboxylic acid

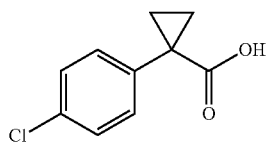 [SMILES: O=C(O)C1(c2ccc(Cl)cc2)CC1]

Step 1: Synthesis of 1-(4-chlorophenyl)cyclopropane-1-carbonitrile

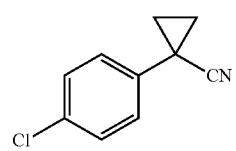 [SMILES: N#CC1(c2ccc(Cl)cc2)CC1]

A suspension of 55% sodium hydride (25.27 g, 1052.9 mmol, 5.3 eq) and THF (200 ml) under nitrogen atmosphere was heated to 40° C. and a solution of 2-(4-chlorophenyl) acetonitrile (30.0 g, 198.67 mmol, 1.0 eq) in THF (50 ml) was added dropwise over about 30 minutes. The mixture was stirred at 40° C. for about 30 minutes and a solution of 1,2-dibromoethane (74.3 g, 397.35 mmol, 2.0 eq) in THF (50 ml) was added dropwise over about 30 minutes. The reaction mixture was stirred at 40° C. for about 1 hour. TLC indicated starting material was consumed and the desired product was observed. The reaction mixture was cooled to 0° C., quenched with ice water (250 ml) and extracted with ethyl acetate (3×400 ml). The combined organic extracts were washed with brine solution (400 ml), dried over sodium sulfate, filtered and evaporated under reduced pressure to obtain the desired product (30.0 g) as a semi solid, which is used as such for next step without further purification. $^1$H NMR (300 MHz, CDCl$_3$): δ ppm 7.33 (d, J=8.7 Hz, 2H), 7.24 (d, J=8.7 Hz, 2H), 1.78-1.71 (m, 2H), 1.42-1.35 (m, 2H).

Step 2: Synthesis of 1-(4-chlorophenyl)cyclopropane-1-carboxylic acid

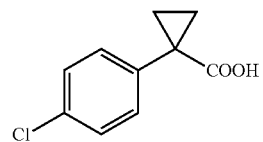 [SMILES: O=C(O)C1(c2ccc(Cl)cc2)CC1]

A stirred solution of 1-(4-chlorophenyl)cyclopropane-1-carbonitrile (step 1, 30.0 g, 169.49 mmol, 1.0 eq), sodium hydroxide (20.3 g, 508.47 mmol, 3.0 eq), diethylene glycol (120 ml) and water (35.4 ml) was refluxed for about 18 hours. TLC indicated starting material was consumed and the desired product was observed. The reaction mixture was poured into water (1800 ml) and acidified to pH 4.0 with concentrated HCl (54 ml). The generated crystals were collected by filtration and dried under vacuum to obtain the desired product (30.0 g, yield: 90.3%) as a pale-brown color solid. $^1$H NMR (300 MHz, DMSO-$d_6$): δ ppm 12.40 (brs, 1H), 7.34 (m, 4H), 1.48-1.42 (m, 2H), 1.16-1.10 (m, 2H).

Intermediate 9: Preparation of 2,2,2-trifluoroacetate salt of 2-(4-ethylpiperazin-1-yl)acetic acid

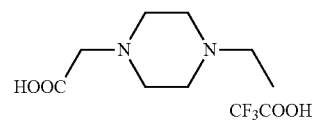

Step 1: Synthesis of tert-butyl 2-(4-ethylpiperazin-1-yl)acetate

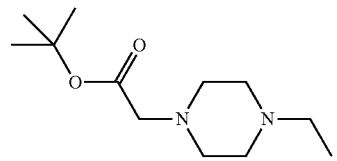 [SMILES: CCN1CCN(CC(=O)OC(C)(C)C)CC1]

To a stirred solution of 1-ethylpiperazine (5.0 g, 43.78 mmol, 1.0 eq) in DCM (100 ml) at 0° C. was added Et₃N (30.4 ml, 218.93 mmol, 5.0 eq) followed by tert-butyl 2-chloroacetate (9.41 ml, 65.68 mmol, 1.5 eq). The reaction mixture was stirred at room temperature for overnight. TLC indicated starting material was consumed and the desired product was observed. The reaction mixture was diluted with water (150 ml) and extracted with DCM (3×150 ml). The combined organic extracts were washed with water (100 ml), brine solution (50 ml), dried over Na₂SO₄, filtered and evaporated under reduced pressure to obtain the desired product (9.0 g, yield: 90.09%) as a solid, which is used as such for next step without further purification. ESI-MS: m/z 229.09 (M+H)⁺.

Step 2: Synthesis of 2,2,2-trifluoroacetate salt of 2-(4-ethylpiperazin-1-yl)acetic acid To a stirred solution of tert-butyl 2-(4-ethylpiperazin-1-yl) acetate (step 1, 9.0 g, 39.414 mmol, 1.0 eq) in DCM (72 ml) at 0° C. was added TFA (18 ml). The reaction mixture was allowed to stir at room temperature for overnight. TLC indicated starting material was consumed and the desired product was observed. The reaction mixture was evaporated under reduced pressure to obtain the desired product (11.2 g) as a solid, which is used as such for next step without further purification. ESI-MS: m/z 173.18 (M-TFA+H)⁺.

Intermediate 10: Preparation of 1-(carboxymethyl)piperidin-1-ium 2,2,2-trifluoroacetate

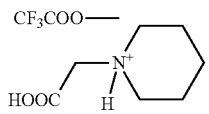

Step 1: Synthesis of tert-butyl 2-(piperidin-1-yl)acetate

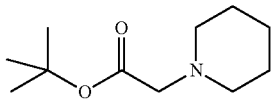

To a stirred solution of piperidine (5.0 g, 58.71 mmol, 1.0 eq) in DCM (75 ml) at 0° C. was added triethylamine (29.7 g, 293.55 mmol, 5.0 eq) followed by tert-butyl 2-chloroacetate (12.62 ml, 88.07 mmol, 1.5 eq). The reaction mixture was stirred at room temperature for overnight. TLC indicated starting material was consumed and the desired product was observed. The reaction mixture was diluted with water (200 ml) and extracted with DCM (3×100 ml). The combined organic extracts were washed with water (100 ml), brine solution (50 ml), dried over Na₂SO₄, filtered and concentrated under reduced pressure to obtain the desired product (10.0 g, yield: 85.47%) as a solid, which is used as such for next step without further purification.

Step 2: Synthesis of 1-(carboxymethyl)piperidin-1-itn 2,2,2-trifluoroacetate

To a stirred solution of tert-butyl 2-(piperidin-1-yl)acetate (step 1, 10.0 g, 50.17 mmol, 1.0 eq) in DCM (80 ml) at 0° C. was added trifluoroacetic acid (20 ml). The reaction mixture was allowed to stir at room temperature for overnight. TLC indicated starting material was consumed and the desired product was observed. The reaction mixture was evaporated under reduced pressure to obtain the desired product (12.9 g) as a solid, which is used as such for next step without further purification. ESI-MS: m/z 144.03 (M-TFA+H)⁺.

Intermediate 11: Preparation of 2-(6-methylpyridin-3-yl)-1H-benzo[d]imidazole-5-carboxylic acid

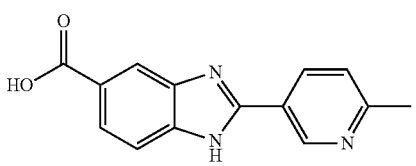 [SMILES: Cc1ccc(-c2nc3cc(C(=O)O)ccc3[nH]2)cn1]

Step 1: Synthesis of methyl 2-(6-methylpyridin-3-yl)-1H-benzo[d]imidazole-5-carboxylate

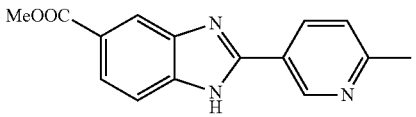 [SMILES: COC(=O)c1ccc2[nH]c(-c3ccc(C)nc3)nc2c1]

To a stirred solution of 6-methylnicotinic acid (1.23 g, 9.026 mmol, 1.5 eq) in DMF (10 ml) was added HBTU (3.47 g, 9.026 mmol, 1.5 eq), DIPEA (4.12 ml, 24.070 mmol, 4.0 eq) followed by methyl 3,4-diaminobenzoate (1.0 g, 6.017 mmol, 1.0 eq). The reaction mixture was stirred at room temperature for about 5 hours. TLC indicated starting material was consumed and the desired product was observed. The reaction mixture was diluted with water (50 ml) and extracted with Ethyl acetate (2×100 ml). The combined organic extracts were dried over Na₂SO₄, filtered and evaporated under reduced pressure. The residue was mixed with acetic acid (5 ml) and heated at 60° C. for overnight. Acetic acid was removed under reduced pressure and the residue was treated with 10 ml of 5N sodium hydroxide solution. The resulting solid was filtered and was washed with water and dried under vacuum to obtain the desired product (0.804 g, yield: 50%) as an off-white solid. NMR (300 MHz, DMSO-d₆): δ ppm 13.4 (brs, 1H), 9.24 (d, J=1.5 Hz, 1H), 8.41 (dd, J=8.1, 2.1 Hz, 1H), 8.21 (brs, 1H), 7.87 (dd, J=8.4, 1.2 Hz, 1H), 7.71 (d, J=8.4 Hz, 1H), 7.48 (d, J=8.1 Hz 1H), 3.88 (s, 3H), 2.56 (s, 3H); ESI-MS: m/z 267.93 (M+H)⁺.

Step 2: Synthesis of 2-(6-methylpyridin-3-yl)-1H-benzo[d]imidazole-5-carboxylic acid To a stirred solution of methyl 2-(6-methylpyridin-3-yl)-1H-benzo[d]imidazole-5-carboxylate (step 1, 0.8 g, 2.993 mmol, 1.0 eq) in MeOH (8 ml) and THF (8 ml) was added aqueous 2.5N KOH solution (8.98 ml, 22.447 mmol, 7.5 eq). The reaction mixture was stirred at room temperature for overnight. TLC indicated starting material was consumed and the desired product was observed. The organic phase was evaporated under reduced pressure and diluted with water (15 ml), cooled to 0° C., pH adjusted to 6.0 with 1N HCl and extracted with 20% MeOH: DCM (4×50 ml). The combined organic extracts were washed with water (2×50 ml), dried over sodium sulfate, filtered and evaporated under reduced pressure to obtain to obtain the desired product (0.5 g, yield: 65.9%) as an off white solid. $^1$H NMR (300 MHz, DMSO-$d_6$): δ ppm 13.38 (brs, 1H), 12.78 (brs, 1H), 9.24 (d, J=1.5 Hz, 1H), 8.41 (dd, J=8.1, 1.8 Hz, 1H), 8.25 (brs, 1H), 7.85 (m, 1H), 7.78-7.60 (m, 1H), 7.48 (d, J=8.1 Hz, 1H), 2.56 (s, 3H); ESI-MS: m/z 253.85 (M+H)$^+$.

Intermediate 12: Preparation of 2-(pyrazin-2-yl)-1H-benzo[d]imidazole-5-carboxylic acid

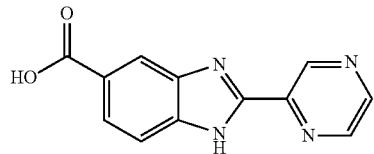 [SMILES: O=C(O)c1ccc2[nH]c(-c3cnccn3)nc2c1]

Step 1: Synthesis of methyl 2-(pyrazin-2-yl)-1H-benzo[d]imidazole-5-carboxylate

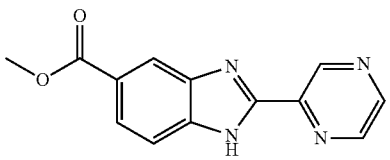 [SMILES: COC(=O)c1ccc2[nH]c(-c3cnccn3)nc2c1]

To a stirred solution of pyrazine-2-carboxylic acid (1.120 g, 9.026 mmol, 1.5 eq) in DMF (10 ml) was added HBTU (3.42 g, 9.026 mmol, 1.5 eq) followed by DIPEA (4.12 ml, 24.07 mmol, 4.0 eq). The reaction mixture was stirred at room temperature for about 30 minutes, then methyl 3,4-diaminobenzoate (1.0 g, 6.017 mmol, 1.0 eq) was added and stirred at room temperature for overnight. TLC indicated starting material was consumed and the desired product was observed. The reaction mixture was diluted with ice cooled water (50 ml) and stirred at room temperature for about 15 minutes. The precipitates formed were collected by filtration, washed with water (50 ml) and dried under vacuum to obtain the solid. The resulting solid was purified by silicagel column chromatography by using 0-7% methanol in dichloromethane gradient. The fractions containing the expected product were combined and concentrated under reduced pressure to obtain the desired product (0.400 g, yield: 26.3%) as an off-white solid. $^1$H NMR (300 MHz, DMSO-$d_6$): δ ppm 9.52 (d, J=1.2 Hz, 1H), 8.78-8.69 (m, 2H), 8.25 (d, J=0.9 Hz, 1H), 7.79 (dd, J=8.7, 1.2 Hz, 1H), 7.67 (d, J=8.4 Hz, 1H), 3.87 (s, 3H); ESI-MS: m/z 254.99 (M+H)$^+$.

Step 2: Synthesis of 2-(pyrazin-2-yl)-1H-benzo[d]imidazole-5-carboxylic acid

To a stirred solution of methyl 2-(pyrazin-2-yl)-1H-benzo[d]imidazole-5-carboxylate (step 1, 0.400 g, 1.573 mmol, 1.0 eq) in MeOH (4 ml) and THF (4 ml) was added aqueous 2.5N KOH solution (4.71 ml, 11.79 mmol, 7.5 eq). The reaction mixture was stirred at room temperature for overnight. TLC indicated starting material was consumed and the desired product was observed. The organic phase was evaporated under reduced pressure, diluted with water (5 ml), cooled to 0° C., pH adjusted to 6.0 with 1N HCl and extracted with 20% methanol in dichloromethane (4×50 ml). The combined organic extracts were washed with water (2×50 ml), dried over sodium sulfate, filtered and evaporated under reduced pressure to obtain the desired product (0.373 g, yield: 98%) as an off white solid. $^1$H NMR (300 MHz, DMSO-$d_6$): δ ppm 13.68 (brs, 1H), 12.72 (brs, 1H), 9.53 (d, J=1.2 Hz, 1H), 8.88-8.80 (m, 2H), 8.33-8.20 (m, 1H), 7.79-7.60 (m, 2H).

Intermediate 13: Preparation of 4(4-methyl-1H-imidazol-1-yl)benzoic acid

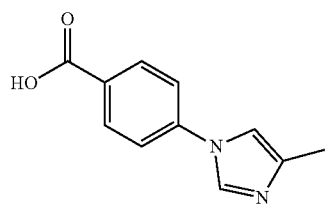

Step 1: Synthesis of methyl 4-(4-methyl-1H-imidazol-1-yl)benzoate

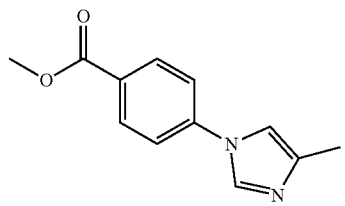

To a stirred solution of methyl 4-bromobenzoate (8.0 g, 37.20 mmol, 1.0 eq) in DMF (150 ml) was added $CS_2CO_3$ (24.24 g, 74.4 mmol, 2.0 eq) and 4-methyl-1H-imidazole (4.58 g, 55.8 mmol, 1.5 eq). The reaction mixture was bubbled through nitrogen for about 20 minutes, then CuI (3.542 g, 18.6 mmol, 0.5 eq) was added and the mixture was again bubbled through nitrogen for about 40 minutes. The reaction mixture was heated at 100° C. for about 72 hours. TLC indicated starting material was consumed and the desired product was observed. The reaction mixture was allowed cool to room temperature and filtered through celite. The filtrate was evaporated under reduced pressure and the residue was purified by silicagel column chromatography by using 40% EtOAc in hexane eluent. The fractions containing the expected product were combined and concentrated under reduced pressure to obtain the desired product (2.413 g, yield: 30%) as an off-white solid. $^1$H NMR (300 MHz, CDCl$_3$): δ ppm 8.14 (d, J=8.7 Hz, 2H), 7.85 (s, 1H), 7.44 (d, J=8.7 Hz, 2H), 7.07 (s, 1H), 3.94 (s, 3H), 2.30 (s, 3H); ESI-MS: m/z 217.09 (M+H)$^+$.

Step 2: Synthesis of 4-(4-methyl-1H-imidazol-1-yl)benzoic acid

To a stirred solution of methyl 4-(4-methyl-1H-imidazol-1-yl)benzoate (step 1, 2.0 g, 9.248 mmol, 1.0 eq) in methanol (20 ml) was added 1N NaOH (75 ml, 73.99 mmol, 8.0 eq). The reaction mixture was stirred at room temperature for overnight. TLC indicated starting material was consumed and the desired product was observed. The reaction mixture was cooled to 0° C., pH adjusted to 7.0 with 1N HCl and evaporated under reduced pressure to afford the desired product (1.5 g, yield: 80.2%) as a white solid. $^1$H NMR (300 MHz, CDCl$_3$): δ ppm 9.50 (d, J=1.5 Hz, 1H), 8.27 (d, J=8.7 Hz, 2H), 7.90 (s, 1H), 7.84 (d, J=8.7 Hz, 2H), 2.47 (s, 3H); ESI-MS: m/z 203.12 (M+H)$^+$.

Intermediate 14: Preparation of 2-aminothiazole-4-carboxylic acid

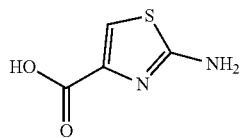

To a stirred solution of ethyl 2-aminothiazole-4-carboxylate (1.5 g, 8.71 mmol, 1.0 eq) in ethanol (15 ml) at 0° C. was added 1N NaOH solution (69.68 ml, 69.68 mmol, 8.0 eq). The reaction mixture was stirred at room temperature for overnight. TLC indicated starting material was consumed and the desired product was observed. The reaction mixture was evaporated under reduced pressure to obtain the desired compound (3.0 g) as an off-white solid.

Intermediate 15: Preparation of 4-(5-methyl-1,3,4-oxadiazol-2-yl)benzoic acid

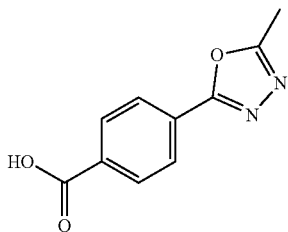

Step 1: Synthesis of methyl 4-(2-acetylhydrazine-1-carbonyl)benzoate

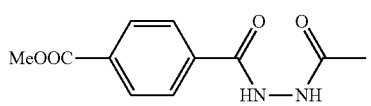 [SMILES: COC(=O)c1ccc(C(=O)NNC(C)=O)cc1]

To a stirred solution of 4-(methoxy)carbonyl)benzoic acid (5.0 g, 27.74 mmol, 1.0 eq) in DMF (50 ml) was added HBTU (15.7 g, 41.62 mmol, 1.5 eq), followed by triethyl amine (15.4 ml, 110.98 mmol, 4.0 eq). The reaction mixture was stirred at room temperature for about 30 minutes then acetic hydrazide (3.0 g, 41.62 mmol, 1.5 eq) was added and stirred at room temperature for overnight. TLC indicated starting material was consumed and the desired product was observed. The reaction mixture was diluted with water (500 ml) and extracted with EtOAc (2×200 ml). The combined organic extracts were dried over Na$_2$SO$_4$, filtered and evaporated under reduced pressure to obtain the desired compound (5.0 g, yield: 76%) as a colourless liquid. $^1$H NMR (300 MHz, DMSO-d$_6$): δ ppm 10.5 (s, 1H), 9.97 (s, 1H), 8.07 (d, J=8.1 Hz, 2H), 7.98 (d, J=8.4 Hz, 2H), 3.89 (s, 3H), 2.73 (s, 3H); Step 2: Synthesis of methyl 4-(5-methyl-1,3,4-oxadiazol-2-yl)benzoate

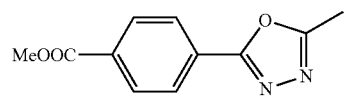

To a stirred solution of methyl 4-(2-acetylhydrazine-1-carbonyl)benzoate (step 1, 5.0 g, 21.186 mmol, 1.0 eq) in DCM (50 ml) at 0° C. was added triethyl amine (14.77 ml, 105.82 mmol, 5.0 eq) followed by para-toluenesulphonyl chloride (6.0 g, 31.779 mmol, 1.5 eq). The reaction mixture was allowed to stir at room temperature for overnight. TLC indicated starting material was consumed and the desired product was observed. The reaction mixture was diluted with DCM (200 ml) and washed with water (2×100 ml). The combined organic extracts were dried over Na$_2$SO$_4$, filtered and evaporated under reduced pressure. The crude compound (3.0 g) was used as such for next step without further purification. $^1$H NMR (300 MHz, CDCl$_3$): δ ppm 8.17 (d, J=8.7 Hz, 2H), 8.09 (d, J=8.7 Hz, 2H), 3.95 (s, 3H), 2.64 (s, 3H).

Step 3: Synthesis of 4-(5-methyl-1,3,4-oxadiazol-2-yl)benzoic acid

To a stirred solution of methyl 4-(5-methyl-1,3,4-oxadiazol-2-yl)benzoate (step 2, 3.0 g, 13.761 mmol, 1.0 eq) in MeOH (30 ml) was added aqueous 1N NaOH solution (110 ml, 110.097 mmol, 8.0 eq). The reaction mixture was stirred at room temperature for overnight. TLC indicated starting material was consumed and the desired product was observed. The reaction mixture was neutralized with 1N HCl and evaporated under reduced pressure. To this compound acetonitrile (100 ml) was added and concentrated under reduced pressure to obtain the crude desired product (3.0 g) as a white solid. $^1$H NMR (300 MHz, DMSO-d$_6$): δ ppm 13.34 (brs, 1H), 8.12-8.10 (m, 4H), 2.61 (s, 3H); ESI-MS: m/z 226.87 (M+Na)$^+$.

Intermediate 16: Preparation of 4-(1,1-dioxidothiomorpholino)benzoic acid

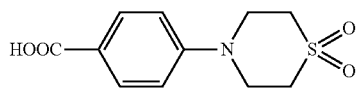

Step 1: Synthesis of Methyl 4-(1,1-dioxidothiomorpholino)benzoate

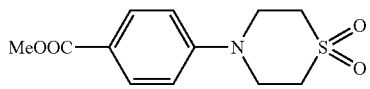 [SMILES: COC(=O)c1ccc(N2CCS(=O)(=O)CC2)cc1]

To a stirred solution of methyl 4-bromobenzoate (1.5 g, 6.975 mmol, 1.0 eq) in toluene (30 ml) was added thiomorpholine 1,1-dioxide (1.13 g, 8.37 mmol, 1.2 eq) and Cs$_2$CO$_3$ (6.817 g, 20.92 mmol, 3.0 eq). The reaction mixture was purged with nitrogen for about 10 minutes. Next, palladium acetate (0.015 g, 0.069 mmol, 0.01 eq) and BINAP (0.065 g, 0.104 mmol, 0.015 eq) were added and the reaction mixture was degassed for about 30 minutes and heated to 100° C. for overnight. TLC indicated starting material was consumed and the desired product was observed. The reaction mixture was allowed to cool to room temperature, filtered through celite pad and was washed with ethyl acetate (140 ml). The organic layer was separated and was washed with saturated sodium bicarbonate solution, dried over Na$_2$SO$_4$, filtered and evaporated under reduced pressure. The residue was purified by silicagel column chromatography by using 90% ethyl acetate in hexane as an eluent to obtain the desired product (1.2 g, yield: 63.8%) as an off-white solid. $^1$H NMR (300 MHz, DMSO-d$_6$): δ ppm 7.82 (d, J=9.0 Hz, 2H), 7.09 (d, J=9.0 Hz, 2H), 3.92 (t, J=4.5 Hz, 4H), 3.78 (s, 3H), 3.14 (t, J=4.5 Hz, 4H); ESI-MS: m/z 292.0 (M+Na)$^+$.

Step 2: Synthesis of 4-(1,1-dioxidothiomorpholino)benzoic acid

To a stirred solution of methyl 4-(1,1-dioxidothiomorpholino)benzoate (step 1, 1.6 g, 5.947 mmol, 1.0 eq) in MeOH (20 ml) was added aqueous 1N NaOH solution (47.5 ml, 47.5 mmol, 8.0 eq). The reaction mixture was stirred at room temperature for overnight. TLC indicated starting material was consumed and the desired product was observed. The reaction mixture was neutralized with 1N HCl (47.5 ml) and evaporated under reduced pressure. The crude solid was co-distilled with CH$_3$CN (10 ml) to obtain the desired product (2.0 g) as a white solid.

Intermediate 17: Preparation of 4-((1,1-dioxidothiomorpholino)methyl)benzoic acid

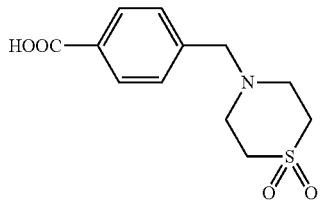 [SMILES: O=C(O)c1ccc(CN2CCS(=O)(=O)CC2)cc1]

Step 1: Synthesis of methyl 4-((1,1-dioxidothiomorpholino)methyl)benzoate

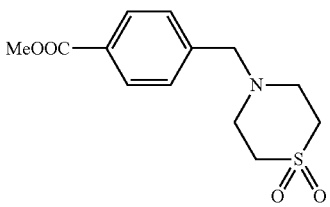 [SMILES: COC(=O)c1ccc(CN2CCS(=O)(=O)CC2)cc1]

To a stirred solution of methyl 4-(bromomethyl)benzoate (4.0 g, 17.46 mmol, 1.0 eq) in CH$_3$CN (100 ml) was added Cs$_2$CO$_3$ (17.0 g, 52.38 mmol, 3.0 eq). The reaction mixture was stirred at room temperature for about 1 hour then thiomorpholine 1,1-dioxide (2.36 g, 17.46 mmol, 1.0 eq) was added and heated to reflux for overnight. TLC indicated starting material was consumed and the desired product was observed. The reaction mixture was cooled to room temperature, filtered through celite pad and was washed with ethyl acetate (100 ml). The filtrate was washed with water (100 ml), dried over Na$_2$SO$_4$, filtered and evaporated under reduced pressure to obtain the desired product (4.0 g) as a yellow oil. NMR (300 MHz, DMSO-d$_6$): δ ppm 7.94 (d, J=8.1 Hz, 2H), 7.50 (d, J=8.4 Hz, 2H), 3.85 (s, 3H), 3.75 (s, 2H), 3.16-3.09 (m, 4H), 2.92-2.85 (m, 4H); ESI-MS: m/z 306.03 (M+Na)$^+$. Step 2: Synthesis of 4-((1,1-dioxidothiomorpholino)methyl)benzoic acid To a stirred solution of methyl 4-((1,1-dioxidothiomorpholino)methyl)benzoate (step 1, 1.0 g, 3.53 mmol, 1.0 eq) in MeOH (10 ml) and THF (10 ml) was added aqueous 1N NaOH solution (28.2 ml, 28.2 mmol, 8.0 eq). The reaction mixture was stirred at room temperature for overnight. TLC indicated starting material was consumed and the desired product was observed. The reaction mixture was neutralized with 1N HCl (28 ml) and evaporated under reduced pressure to obtain the desired product (1.5 g crude) as a white solid. $^1$H NMR (300 MHz, DMSO-d$_6$): δ ppm 7.86 (d, J=8.1 Hz, 2H), 7.31 (d, J=7.8 Hz, 2H), 3.68 (s, 2H), 3.12-3.08 (m, 4H), 2.88-2.84 (m, 4H); ESI-MS: m/z 268.06 (M−H)$^−$.

Intermediate 18: Preparation of 1-(4-chlorophenyl)cyclopropane-1-carbaldehyde

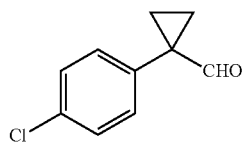 [SMILES: O=CC1(c2ccc(Cl)cc2)CC1]

Step 1: Synthesis of (1-(4-chlorophenyl)cyclopropyl)methanol

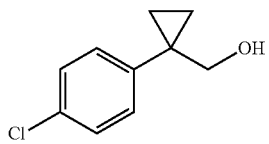 [SMILES: OCC1(c2ccc(Cl)cc2)CC1]

To a stirred solution of 1-(4-chlorophenyl)cyclopropane-1-carboxylic acid (Intermediate 8, 10 g, 51.02 mmol, 1.0 eq) in THF (150 ml) at 0° C. under nitrogen was added boranedimethyl sulphide (51 ml, 102.04 mmol, 2.0 eq, 2.0 M in THF). The reaction mixture was allowed to stir at room temperature for overnight. TLC indicated starting material was consumed and the desired product was observed. The reaction mixture was cooled to 0° C., quenched with saturated aqueous ammonium chloride solution (50 ml) then diluted with water (100 ml) and extracted with EtOAc (3×200 ml). The combined organic extracts were washed with water (100 ml), brine solution (50 ml), dried over Na$_2$SO$_4$, filtered and evaporated under reduced pressure to obtain the desired product (8.0 g) as colourless oil. NMR (300 MHz, CDCl$_3$): δ ppm 7.36-7.27 (m, 4H), 3.65 (s, 2H), 0.86 (m, 4H).

Step 2: Synthesis of 1-(4-chlorophenyl)cyclopropane-1-carbaldehyde

To a stirred solution of (1-(4-chlorophenyl)cyclopropyl) methanol (step 1, 6.0 g, 32.84 mmol, 1.0 eq) in DCM (60 ml) was added pyridinium chlorochromate (21.23 g, 98.54 mmol, 3.0 eq) and silicagel (21.23 g). The reaction mixture was stirred at room temperature for about 1 hour. TLC indicated starting material was consumed and the desired product was observed. The reaction mixture was filtered through celite, filtrate was diluted with water (150 ml) and extracted with DCM (3×50 ml). The combined organic extracts were washed with saturated sodium bicarbonate solution (2×30 ml), dried over Na$_2$SO$_4$, filtered and evaporated under reduced pressure to obtain the desired product (6.0 g) as an oil, which is used as such for next step without further purification.

Intermediate 19: Preparation of 5-isocyanato-2-methylpyridine

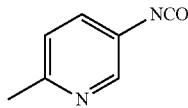

To a stirred solution of 6-methylnicotinic acid (1.0 g, 7.299 mmol, 1.0 eq) in toluene (15 ml) was added triethylamine (0.88 g, 8.759 mmol, 1.2 eq) and DPPA (2.4 g, 8.759 mmol, 1.2 eq). The reaction mixture was stirred at room temperature for about 4 hours. TLC indicated starting material was consumed and the desired product was observed. The reaction mixture was concentrated to dryness. The residue was purified by silicagel column chromatography by using 2% methanol in dichloromethane as an eluent to obtain the desired product (0.75 g, yield: 77%) as an off-white solid. $^1$H NMR (300 MHz, CDCl$_3$): δ ppm 9.09 (d, J=1.8 Hz, 1H), 8.16 (dd, J=8.1, 2.1 Hz, 1H), 7.27 (d, J=8.1 Hz, 1H), 2.64 (s, 3H).

Intermediate 20: Preparation of 2-isocyanato-6-methylpyridine

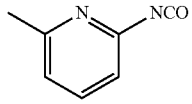

To a stirred solution of 6-methylpicolinic acid (1.5 g, 10.937 mmol, 1.0 eq) in toluene (20 ml) was added triethylamine (1.328 g, 13.12 mmol, 1.2 eq) and diphenylphosphonic azide (3.61 g, 13.12 mmol, 1.2 eq). The reaction mixture was stirred at room temperature for overnight. TLC indicated starting material was consumed and the desired product was observed. The reaction mixture was evaporated under reduced pressure to obtain the desired product (0.6 g) as a oil, which is used as such for next step without further purification.

Intermediate 21: Preparation of sodium 2-(dimethylamino)-1-hydroxyethane-1-sulfonate

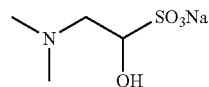

A stirred solution of 2,2-diethoxy-N,N-dimethylethan-1-amine (15 g, 93.16 mmol. 1.0 eq), conc. hydrochloric acid (15.5 ml) and water (7.5 ml) heated at 40° C. for about 3 hours. Then a solution of sodium pyro sulphite (15.93 g, 83.84 mmol, 0.9 eq) dissolved in water (27 ml) was added dropwise and the mixture was stirred for about 1 hour. Then 90 ml of ethanol was added to reaction mixture and stirred for about 2 hours at 0° C. The suspension was filtered and washed with ethanol (20 ml), then dried under vacuum at 40° C. for about 30 minutes to afford the desired product (15 g, yield: 84%) as a white solid.

Intermediate 22: Preparation of 4-(carboxymethyl)thiomorpholin-4-ium 1,1-dioxide 2,2,2-trifluoroacetate

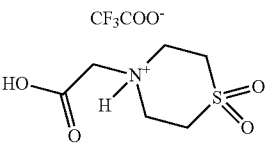 [SMILES: O=C(O)C[NH+]1CCS(=O)(=O)CC1 ; "CF3COO-"]

Step 1: Synthesis of tert-butyl 2-(1,1-dioxidothiomorpholino)acetate

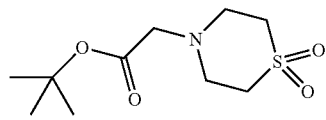 [SMILES: CC(C)(C)OC(=O)CN1CCS(=O)(=O)CC1]

To a stirred solution of thiomorpholine 1,1-dioxide (3.0 g, 17.48 mmol) in DCM (30 ml) at 0° C., were added TEA (17 ml, 122.37 mmol) and tert-butyl 2-chloroacetate (3.8 ml, 26.22 mmol). The reaction mixture was stirred for overnight at room temperature. After completion of the reaction (monitored by TLC), the reaction mixture was diluted with DCM and washed with water, saturated NH$_4$Cl solution, brine and dried over Na$_2$SO$_4$. The solvent was evaporated under reduced pressure and purified by silica gel column (elution 1% MeOH in DCM) to afford the title compound (3.0 g, yield: 68.96%) as a thick oil. H$^1$ NMR (DMSO-d$_6$, 300 MHz): δ 3.35 (s, 2H), 3.06 (m, 8H), 1.41 (s, 9H).

Step 2: Synthesis of 4-(carboxymethyl)thiomorpholin-4-ium 1,1-dioxide 2,2,2-trifluoroacetate To a stirred solution of tert-butyl 2-(1,1-dioxidothiomorpholino)acetate (step 1, 1.0 g, 4.01 mmol) in DCM (10 ml), was added TFA (3 ml) and stirred for about 2 hours. After completion of the reaction (monitored by TLC), the reaction mixture was concentrated under reduced pressure to afford the desired compound as a TFA salt (1.2 g, yield: 100%). Next reaction was carried out without any further purification.

EXAMPLES

Example 1: Preparation of (1R,3S)-3-((((3aR,5aR, 5bR,7aR,9S,11aR,11bR,13aS)-3a-(2-(4-chlorobenzamido)-2-methylpropanamido)-1-isopropyl-5a,5b,8, 8,11a-pentamethyl-2-oxo-3, 3a,4,5,5a,5b,6,7,7a,8,9, 10,11,11a,11b,12,13,13a-octadecahydro-2H-cyclopenta[a]chrysen-9-yl)oxy)carbonyl)-2,2-dimethylcyclobutane-1-carboxylic acid

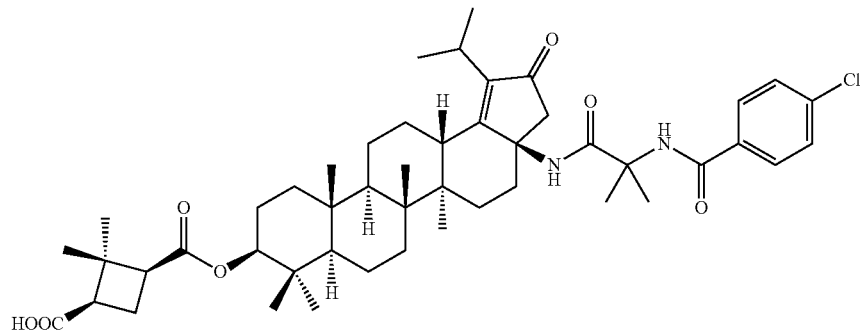

Step 1: Synthesis of 1-benzyl 3-((3aR,5aR,5bR, 7aR,9S,11aR,11bR,13aS)-3a-(2-(4-chlorobenzamido)-2-methylpropanamido)-1-isopropyl-5a,5b,8, 8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl) (1R,3S)-2,2-dimethylcyclobutane-1,3-dicarboxylate

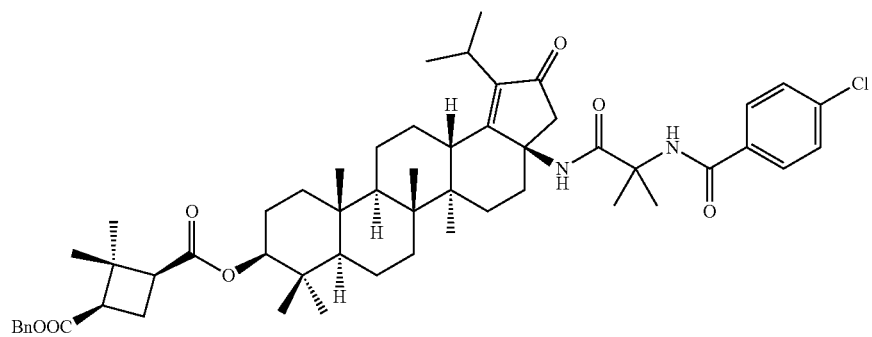

To a stirred solution of 4-chlorobenzoic acid (0.304 g, 1.945 mmol, 1.5 eq) in DMF (10 ml) was added HBTU (0.737 g, 1.945 mmol, 1.5 eq) followed by DIPEA (1.55 ml, 9.07 mmol, 7.0 eq). The reaction mixture was stirred at room temperature for about 30 minutes, then 1-((3aR,5aR,5bR, 7aR,9S,11aR,11bR,13aS)-3a-(2-amino-2-methylpropanamido)-1-iso propyl-5a,5b,8,8,11a-pentamethyl-2-oxo-3,3a, 4,5,5a,5b,6,7,7a,8,9,10,11,11a,11b,12,13,13a-octadecahydro-2H-cyclopenta[a]chrysen-9-yl) 3-benzyl (1S,3R)-2,2-dimethylcyclobutane-1,3-dicarboxylate (Intermediate 1, 1.0 g, 1.296 mmol, 1.0 eq) was added and stirred at same temperature for overnight. TLC indicated starting material was consumed and the desired product was observed. The reaction mixture was diluted with water (150 ml) and extracted with ethyl acetate (3×50 ml). The combined organic extracts were washed with water (50 ml), brine solution (50 ml), dried over $Na_2SO_4$, filtered and evaporated under reduced pressure. The residue was purified by silicagel column chromatography by using 0-5% methanol in dichloromethane gradient. The fractions containing the expected product were combined and concentrated under reduced pressure to obtain the desired product (0.700 g, yield: 59.3%) as a white solid. $^1$H NMR (300 MHz, $CDCl_3$): δ ppm 7.71 (d, J=8.7 Hz, 2H), 7.41 (d, J=8.4 Hz, 2H), 7.37-7.31 (m, 5H), 7.09 (brs, 1H), 6.82 (brs, 1H), 5.14, 5.08 (ABq, $J_{AB}$=12.3 Hz, 2H), 4.43 (dd, J=11.4, 4.8 Hz, 1H), 3.21-3.10 (m, 1H), 2.85-2.72 (m, 3H), 2.70-2.57 (m, 2H), 2.37-2.23 (m, 2H), 2.08-1.72 (m, 6H), 1.68 (s, 3H), 1.66 (s, 3H), 1.62-1.37 (m, 6H), 1.34 (s, 3H), 1.32-1.28 (m, 2H), 1.28-1.16 (m, 8H), 1.16-1.06 (m, 1H), 1.03 (s, 3H), 0.95 (s, 3H), 0.93 (s, 3H), 0.86 (s, 3H), 0.84 (s, 3H), 0.83 (s, 3H), 0.82-0.78 (m, 1H); ESI-MS: m/z 931.5 $(M+Na)^+$.

Step 2: Synthesis of (1R,3S)-3-((((3aR,5aR,5bR, 7aR,9S,11aR,11bR,13aS)-3a-(2-(4-chloro benzamido)-2-methylpropanamido)-1-isopropyl-5a,5b,8, 8,11a-pentamethyl-2-oxo-3,3a,4,5, 5a,5b,6,7,7a,8,9, 10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR, 9S,11aR,11bR,13aS)-3a-(2-(4-chlorobenzamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a- octadecahydro-2H-cyclopenta[a]chrysen-9-yl) (1R,3S)-2,2-dimethylcyclobutane-1,3-dicarboxylate (step 1, 0.700 g, 0.769 mmol, 1.0 eq) in MeOH (15 ml) and THF (15 ml) was added aqueous 2.5N KOH solution (2.15 ml, 5.383 mmol, 7.0 eq). The reaction mixture was stirred at room temperature for overnight. TLC indicated starting material was consumed and the desired product was observed. The organic phase was evaporated under reduced pressure, the reaction mixture was diluted with water (15 ml), cooled to 0° C., pH adjusted to 5.0 with 1N HCl and extracted with DCM (3×75 ml). The combined organic extracts were washed with water (50 ml), dried over sodium sulfate, filtered and evaporated under reduced pressure. The residue was purified by silicagel column chromatography by using 0-5% methanol in dichloromethane gradient. The fractions containing the product were combined and concentrated under reduced pressure to give a solid. To this solid, acetonitrile (10 ml) was added and heated to reflux for about 30 minutes. The mixture was cooled to 0° C., solid was filtered and was washed with n-hexane (10 ml) and dried under vacuum to obtain the desired product (0.4 g, yield: 63.43%) as a white solid. $^1$H NMR (300 MHz, CDCl$_3$): δ ppm 7.72 (d, J=8.4 Hz, 2H), 7.42 (d, J=8.4 Hz, 2H), 7.09 (s, 1H), 6.77 (s, 1H), 4.46 (dd, J=11.1, 4.5 Hz, 1H), 3.22-3.11 (m, 1H), 2.86-2.76 (m, 3H), 2.71-2.53 (m, 2H), 2.38-2.25 (m, 2H), 2.10-2.0 (m, 1H), 1.98-1.73 (m, 5H), 1.69 (s, 3H), 1.68 (s, 3H), 1.65-1.40 (m, 6H), 1.37 (s, 3H), 1.34-1.30 (m, 2H), 1.28-1.18 (m, 8H), 1.16-0.99 (m, 1H), 1.06 (s, 3H), 1.04 (s, 3H), 0.94 (s, 3H), 0.88 (s, 3H), 0.86 (s, 3H), 0.85 (s, 3H), 0.84-0.78 (m, 1H); ESI-MS: m/z 841.5 (M+Na)$^+$; HPLC: 97.93%.

The below examples 2-21 were prepared by the procedure similar (including reagents and reaction conditions) to the above described in the synthesis of example-1 using with their appropriate intermediates.

Example 2: Preparation of (1R,3S)-3-((((3aR,5aR,5bR,7aR,9S,11aR,11bR,13aS)-3a-(2-(1-(4-chlorophenyl)cyclopropane-1-carboxamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

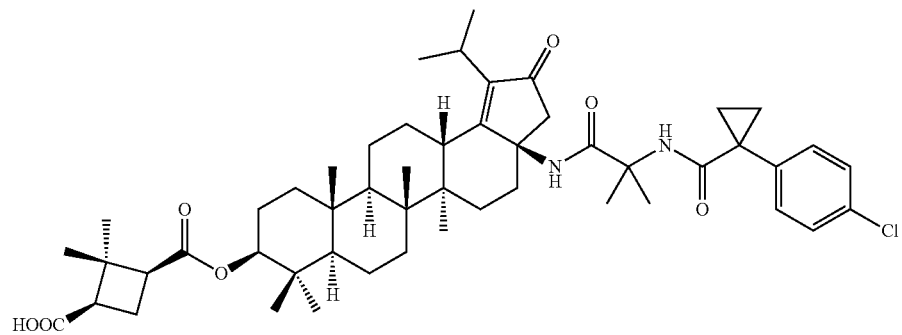

Intermediate 1 was coupled with 1-(4-chlorophenyl)cyclopropane-1-carboxylic acid (Intermediate 8) followed by hydrolysis gave the desired product as a white solid. $^1$H NMR (300 MHz, CDCl$_3$): δ ppm 7.59 (s, 1H), 7.37 (d, J=8.4 Hz, 2H), 7.31 (d, J=8.4 Hz, 2H), 5.46 (brs, 1H), 4.48 (dd, J=11.1, 4.5 Hz, 1H), 3.20-3.08 (m, 1H), 2.87-2.75 (m, 3H), 2.67-2.53 (m, 2H), 2.35-2.17 (m, 2H), 2.12-2.01 (m, 1H), 1.97-1.91 (m, 2H), 1.88-1.70 (m, 4H), 1.67-1.48 (m, 6H), 1.44-1.41 (m, 1H), 1.39 (s, 3H), 1.38 (s, 3H), 1.36 (s, 3H), 1.35-1.33 (m, 2H), 1.27-1.19 (m, 10H), 1.17 (s, 3H), 1.08 (s, 3H), 1.07-1.04 (m, 1H), 0.93 (s, 6H), 0.88 (s, 3H), 0.87 (s, 3H), 0.84-0.80 (m, 1H); ESI-MS: m/z 881.3 (M+Na)$^+$; HPLC: 97.2%.

Example 3: Preparation of (1R,3S)-3-((((3aR,5aR, 5bR,7aR,9S,11aR,11bR,13aS)-3a-(2-benzamido-2-methylpropanamido)-1-isopropyl-5a,5b,8,8,11a-pentamethyl-2-oxo-3,3a,4,5,5a, 5b,6,7,7a,8,9,10,11, 11a,11b,12,13,13a-octadecahydro-2H-cyclopenta[a]chrysen-9-yl)oxy) carbonyl)-2,2-dimethylcyclobutane-1-carboxylic acid

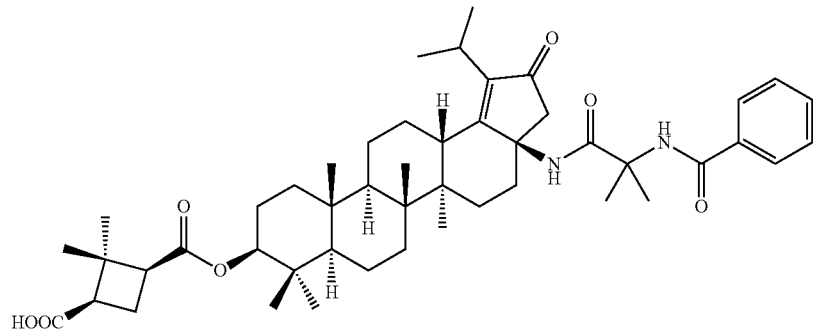

Intermediate 1 was coupled with benzoic acid followed by hydrolysis gave the desired product as a white solid. $^1$H NMR (300 MHz, CDCl$_3$): δ ppm 7.77 (d, J=7.2 Hz, 2H), 7.50-7.40 (m, 3H), 6.64 (brs, 1H), 4.46 (dd, J=11.1, 4.5 Hz, 1H), 3.22-3.11 (m, 1H), 2.88-2.53 (m, 5H), 2.39-2.24 (m, 2H), 2.10-2.0 (m, 1H), 2.0-1.85 (m, 3H), 1.81-1.72 (m, 2H), 1.69 (s, 3H), 1.67 (s, 3H), 1.65-1.42 (m, 7H), 1.37 (s, 3H), 1.36-1.30 (m, 2H), 1.27-1.21 (m, 7H), 1.20-1.15 (m, 1H), 1.07 (s, 3H), 1.02 (s, 3H), 0.94 (s, 3H), 0.86 (s, 6H), 0.84 (s, 3H), 0.82-0.78 (m, 1H); ESI-MS: m/z 807.53 (M+Na)$^+$; HPLC: 95.3%.

Example 4: Preparation of (1R,3S)-3-((((3aR,5aR, 5bR,7aR,9S,11aR,11bR,13aS)-3a-(2-(3,4-dichlorobenzamido)-2-methylpropanamido)-1-isopropyl-5a,5b,8,8,11a-pentamethyl-2-oxo-3,3a,4,5,5a,5b,6,7, 7a,8, 9,10,11,11a,11b,12,13,13a-octadecahydro-2H-cyclopenta[a]chrysen-9-yl)oxy)carbonyl)-2,2-dimethylcyclobutane-1-carboxylic acid

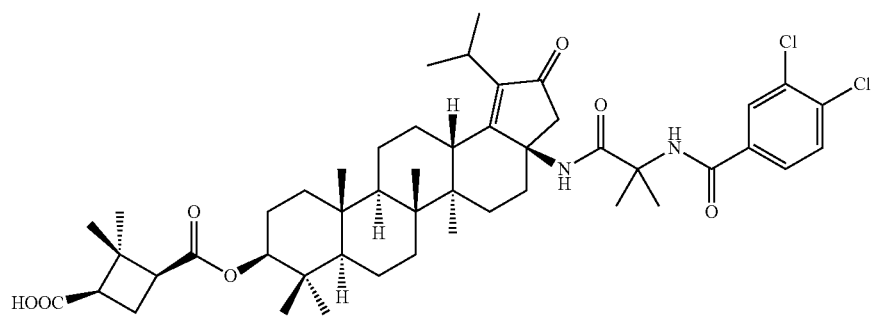

Intermediate 1 was coupled with 3,4-dichlorobenzoic acid followed by hydrolysis gave the desired product as a white solid. $^1$H NMR (300 MHz, CDCl$_3$): δ ppm 7.89 (d, J=2.1 Hz, 1H), 7.59 (dd, J=8.4, 1.8 Hz, 1H), 7.52 (d, J=8.4 Hz, 1H), 6.89 (brs, 1H), 6.85 (brs, 1H), 4.46 (dd, J=11.1, 4.5 Hz, 1H), 3.22-3.10 (m, 1H), 2.85-2.75 (m, 3H), 2.70-2.51 (m, 2H), 2.35-2.26 (m, 2H), 2.10-2.0 (m, 1H), 1.99-1.74 (m, 5H), 1.69 (s, 6H), 1.67-1.40 (m, 7H), 1.36 (s, 3H), 1.32 (m, 1H), 1.30-1.18 (m, 8H), 1.12-1.03 (m, 7H), 0.94 (s, 3H), 0.89 (s, 3H), 0.86 (s, 3H), 0.85 (s, 3H), 0.79 (m, 1H); ESI-MS: m/z 875.38 (M+Na)$^+$; HPLC: 98.06%.

Example 5: Preparation of (1R,3S)-3-((((3aR,5aR, 5bR,7aR,9S,11aR,11bR,13aS)-1-isopropyl-5a,5b,8, 8,11a-pentamethyl-3a-(2-methyl-2-(pyrazine-2-carboxamido)propanamido)-2-oxo-3, 3a,4,5,5a,5b,6,7, 7a,8,9,10,11,11a,11b,12,13,13a-octadecahydro-2H-cyclopenta[a]chrysen-9-yl)oxy)carbonyl)-2,2-dimethylcyclobutane-1-carboxylic acid

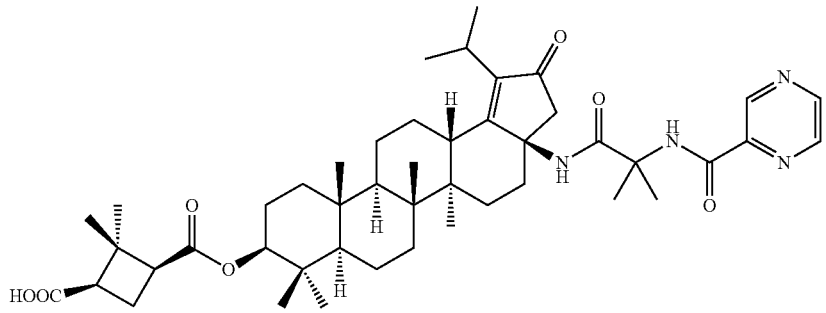

Intermediate 1 was coupled with pyrazine-2-carboxylic acid followed by hydrolysis gave the desired product as a white solid. $^1$H NMR (300 MHz, CDCl$_3$): δ ppm 9.39 (d, J=1.2 Hz, 1H), 8.80 (d, J=2.1 Hz, 1H), 8.56 (d, J=1.5 Hz, 1H), 8.19 (s, 1H), 7.46 (s, 1H), 4.45 (dd, J=11.1, 4.5 Hz, 1H), 3.21-3.10 (m, 1H), 2.87-2.53 (m, 5H), 2.38-2.25 (m, 2H), 2.11-1.80 (m, 5H), 1.80-1.62 (m, 3H), 1.70 (s, 3H), 1.68 (s, 3H), 1.60-1.42 (m, 5H), 1.41-1.28 (m, 3H), 1.37 (s, 3H), 1.28-1.12 (m, 8H), 1.07 (s, 3H), 0.94 (s, 3H), 0.93 (s, 3H), 0.90-0.75 (m, 10H); ESI-MS: m/z 809.39 (M+Na)$^+$; HPLC: 97.0%.

Example 6: Preparation of (1R,3S)-3-((((3aR,5aR, 5bR,7aR,9S,11aR,11bR,13aS)-3a-(2-(6-aminonicotinamido)-2-methylpropanamido)-1-isopropyl-5a,5b, 8,8,11a-pentamethyl-2-oxo-3, 3a,4,5,5a,5b,6,7,7a,8, 9,10,11,11a,11b,12,13,13a-octadecahydro-2H-cyclopenta[a]chrysen-9-yl)oxy)carbonyl)-2,2-dimethylcyclobutane-1-carboxylic acid

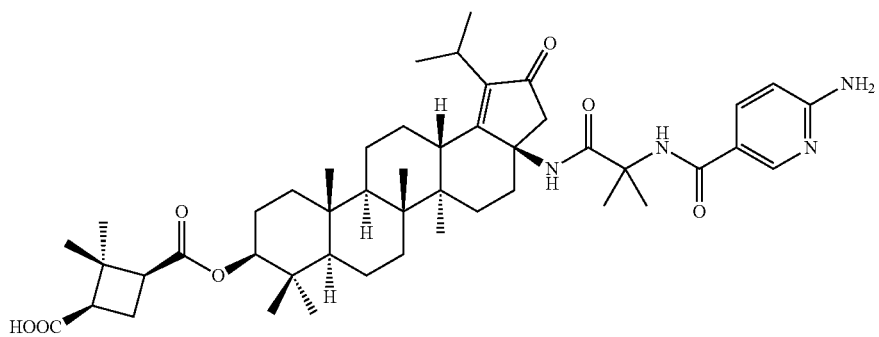

Intermediate 1 was coupled with 6-aminonicotinic acid followed by hydrolysis gave the desired product as a white solid. $^1$H NMR (300 MHz, DMSO-d$_6$): δ ppm 12.15 (brs, 1H), 8.48 (d, J=1.8 Hz, 1H), 7.81 (s, 1H), 7.79 (d, J=1.8 Hz, 1H), 7.30 (s, 1H), 6.47 (brs, 2H), 6.40 (d, J=6.6 Hz, 1H), 4.38-4.32 (m, 1H), 3.13-3.03 (m, 1H), 2.85-2.73 (m, 3H), 2.43-2.26 (m, 4H), 2.07-2.03 (m, 1H), 1.92-1.80 (m, 3H), 1.78-1.64 (m, 2H), 1.62-1.43 (m, 4H), 1.39 (s, 3H), 1.38 (s, 3H), 1.35-1.17 (m, 4H), 1.26 (s, 3H), 1.15-1.10 (m, 6H), 1.07-0.94 (m, 3H), 0.91 (s, 3H), 0.88 (s, 3H), 0.85 (s, 3H), 0.82 (s, 3H), 0.81 (s, 3H), 0.80 (s, 3H), 0.84-0.77 (m, 1H); ESI-MS: m/z 823.49 (M+Na)$^+$; HPLC: 97.38%.

Example 7: Preparation of (1R,3S)-3-((((3aR,5aR,5bR,7aR,9S,11aR,11bR,13aS)-1-isopropyl-5a,5b,8,8,11a-pentamethyl-3a-(2-methyl-2-(5-methylpyrazine-2-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

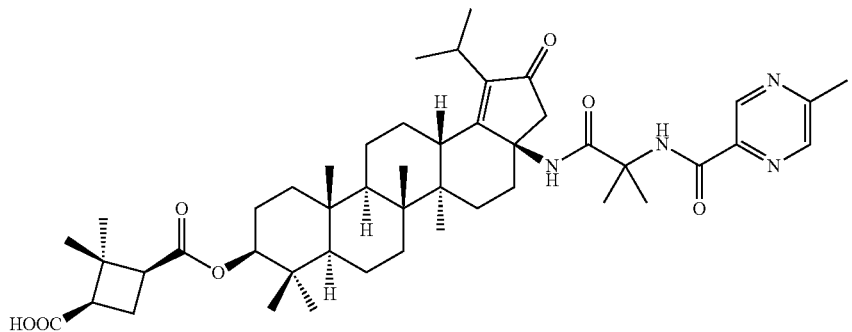

Intermediate 1 was coupled with 5-methylpyrazine-2-carboxylic acid followed by hydrolysis gave the desired product as a white solid. $^1$H NMR (300 MHz, CDCl$_3$): δ ppm 9.25 (d, J=0.9 Hz, 1H), 8.402 (d, J=0.6 Hz, 1H), 8.10 (s, 1H), 7.54 (s, 1H), 4.46 (dd, J=8.4, 3.3 Hz, 1H), 3.20-3.11 (m, 1H), 2.85-2.77 (m, 3H), 2.70-2.55 (m, 2H), 2.69 (s, 3H), 2.36-2.25 (m, 2H), 2.08-1.82 (m, 4H), 1.80-1.70 (m, 2H), 1.69 (s, 3H), 1.66 (s, 3H), 1.65-1.57 (m, 2H), 1.55-1.40 (m, 4H), 1.37 (s, 3H), 1.36-1.25 (m, 3H), 1.25-1.17 (m, 7H), 1.17-1.02 (m, 1H), 1.07 (s, 3H), 0.97 (s, 3H), 0.92 (s, 3H), 0.90-0.82 (m, 9H), 0.81-0.78 (m, 1H); ESI-MS: m/z 823.49 (M+Na)$^+$; HPLC: 96.29%.

Example 8: Preparation of (1R,3S)-3-((((3aR,5aR,5bR,7aR,9S,11aR,11bR,13aS)-3a-(2-((S)-1-(tert-butoxy)carbonyl)pyrrolidine-2-carboxamido)-2-methylpropanamido)-1-isopropyl-5a, 5b,8,8,11a-pentamethyl-2-oxo-3,3a,4,5,5a,5b,6,7,7a,8,9,10,11,11a,11b,12,13,13a-octadeca hydro-2H-cyclopenta[a]chrysen-9-yl)oxy)carbonyl)-2,2-dimethylcyclobutane-1-carboxylic acid

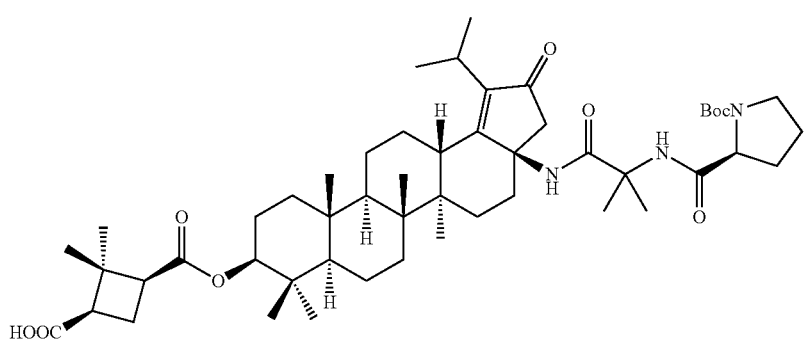

Intermediate 1 was coupled with (tert-butoxy)carbonyl)-L-proline followed by hydrolysis gave the desired product as a white solid. $^1$H NMR (300 MHz, DMSO-d$_6$): δ ppm 12.13 (brs, 1H), 8.18 (s, 1H), 6.75 (s, 1H), 4.39-4.33 (m, 1H), 4.05-3.99 (m, 1H), 3.36 (m, 1H), 3.26 (m, 1H), 3.13-3.06 (m, 1H), 2.84-2.64 (m, 3H), 2.42-2.15 (m, 4H), 2.10-1.83 (m, 5H), 1.80-1.63 (m, 5H), 1.62-1.48 (m, 4H), 1.45-1.23 (m, 22H), 1.22-1.02 (m, 13H), 0.93-0.80 (m, 15H); ESI-MS: m/z 900.53 (M+Na)$^+$; HPLC: 98.3%.

Example 9: Preparation of (1R,3S)-3-((((3aR,5aR,5bR,7aR,9S,11aR,11bR,13aS)-3a-(2-(2-(4-ethylpiperazin-1-yl)acetamido)-2-methylpropanamido)-1-isopropyl-5a,5b,8,8,11a-penta methyl-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid

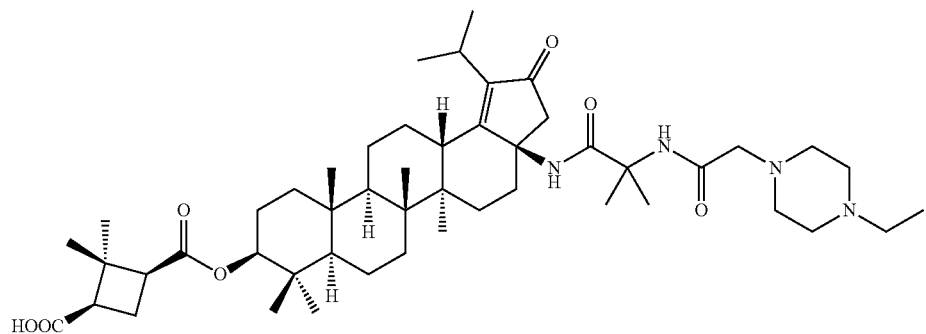

Intermediate 1 was coupled with 2,2,2-trifluoroacetate salt of 2-(4-ethylpiperazin-1-yl)acetic acid (Intermediate 9) followed by hydrolysis gave the desired product as a white solid. $^1$H NMR (300 MHz, CDCl$_3$+CD$_3$OD): δ ppm 7.17 (s, 1H), 4.50-4.42 (m, 1H), 3.26-3.22 (m, 2H), 3.20-3.08 (m, 10H), 3.0-2.90 (m, 2H), 2.86-2.75 (m, 2H), 2.66-2.53 (m, 2H), 2.36-2.20 (m, 2H), 2.10-1.86 (m, 3H), 1.85-1.66 (m, 2H), 1.57 (s, 3H), 1.54 (s, 3H), 1.50-1.34 (m, 16H), 1.28-1.18 (m, 11H), 1.13 (s, 3H), 1.05 (s, 3H), 1.0-0.80 (m, 10H); ESI-MS: m/z 835.6 (M+H)$^+$; HPLC: 95.03%.

Example 10: Preparation of (1R,3S)-3-((((3aR,5aR,5bR,7aR,9S,11aR,11bR,13aS)-1-isopropyl-5a,5b,8,8,11a-pentamethyl-3a-(2-methyl-2-(2-(piperidin-1-yl)acetamido)propan amido)-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid

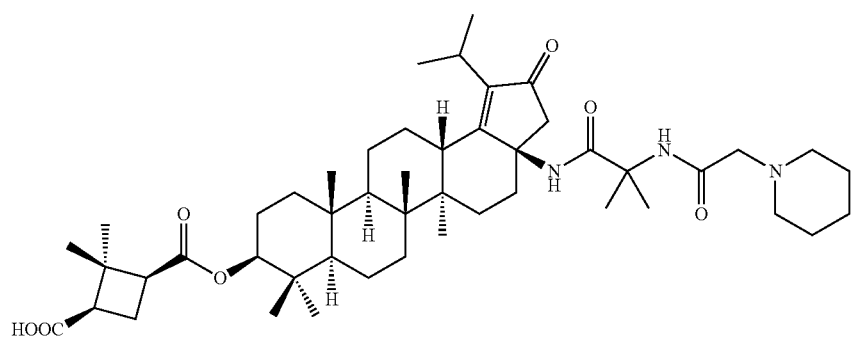

Intermediate 1 was coupled with 1-(carboxymethyl)piperidin-1-ium 2,2,2-trifluoroacetate (Intermediate 10) followed by hydrolysis gave the desired product as a white solid. $^1$H NMR (300 MHz, pyridine-d5): δ ppm 8.33 (s, 1H), 8.30 (s, 1H), 4.73 (dd, J=11.1, 4.5 Hz, 1H), 3.25-2.98 (m, 7H), 2.73-2.56 (m, 2H), 2.40-2.35 (m, 4H), 2.25-2.08 (m, 2H), 1.93-1.75 (m, 2H), 1.85 (s, 3H), 1.78 (s, 3H), 1.75-1.62 (m, 3H), 1.57 (s, 3H), 1.53-1.36 (m, 17H), 1.35-1.22 (m, 9H), 1.21-1.05 (m, 2H), 1.05-0.88 (m, 13H), 0.84-0.76 (m, 1H); ESI-MS: m/z 806.5 (M+H)$^+$; HPLC: 91.5%.

Example 11: Preparation of (1R,3S)-3-((((3aR,5aR,5bR,7aR,9S,11aR,11bR,13aS)-3a-(2-(2-amino-2-methylpropanamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid hydrochloride

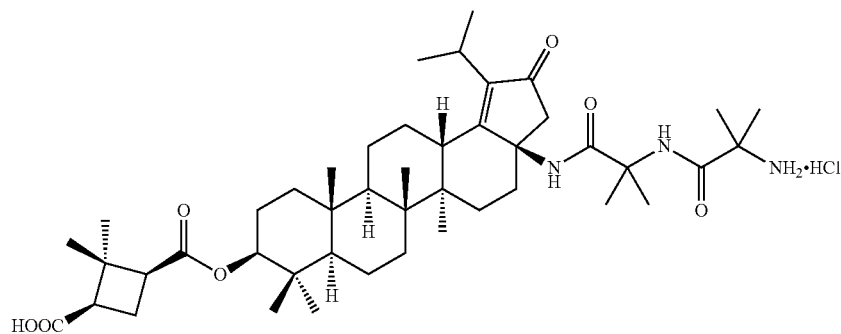

Step 1: Synthesis of (1R,3S)-3-((((3aR,5aR,5bR,7aR,9S,11aR,11bR,13aS)-3a-(2-(2-((tert-butoxy)carbonyl)amino)-2-methylpropanamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

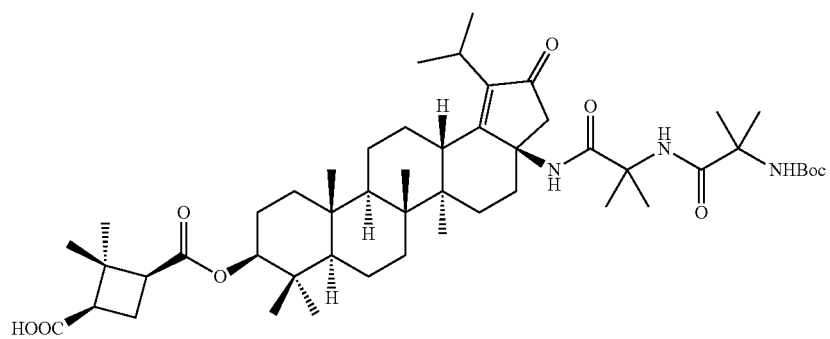

Intermediate 1 was coupled with 2-((tert-butoxy)carbonyl)amino)-2-methylpropanoic acid (Intermediate 1-step 9) followed by hydrolysis gave the desired product as an off-white solid. $^1$H NMR (300 MHz, CDCl$_3$): δ ppm 7.18 (s, 1H), 6.39 (s, 1H), 4.87 (s, 1H), 4.47 (dd, J=11.1, 4.5 Hz, 1H), 3.22-3.12 (m, 1H), 2.96-2.74 (m, 3H), 2.67-2.48 (m, 3H), 2.20 (d, J=18.6 Hz, 1H), 2.11-1.90 (m, 4H), 1.83-1.51 (m, 9H), 1.50-1.28 (m, 23H), 1.28-1.20 (m, 8H), 1.15 (s, 3H), 1.07 (s, 3H), 0.99-0.83 (m, 16H).

Step 2: Synthesis of (1R,3S)-3-((((3aR,5aR,5bR,7aR,9S,11aR,11bR,13aS)-3a-(2-(2-amino-2-methylpropanamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid hydrochloride To a stirred solution of (1R,3S)-3-((((3aR,5aR,5bR,7aR,9S,11aR,11bR,13aS)-3a-(2-(2-((tert-butoxy carbonyl)

amino)-2-methylpropanamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (step 1, 0.600 g, 0.692 mmol, 1.0 eq) in a round bottomed flask at 0° C. was added 3N HCl in 1,4-dioxane (5 ml). The reaction mixture was allowed to stir at room temperature for overnight. TLC indicated starting material was consumed and the desired product was observed. The reaction mixture was evaporated under reduced pressure, the residue was washed with n-hexane (10 ml) and dried under vacuum to obtain the solid. To this solid compound, MTBE (10 ml) was added and heated to reflux for 30 minutes. The mixture was cooled to 0° C., filtered, solid was washed with MTBE and dried under vacuum to obtain the desired product (0.360 g, yield: 64.75%) as a white solid. $^1$H NMR (300 MHz, CD$_3$OD): δ ppm 7.19 (s, 1H), 4.48-4.41 (m, 1H), 3.21 (m, 1H), 2.95-2.80 (m, 3H), 2.63 (d, J=18.6 Hz, 1H), 2.57-2.42 (m, 1H), 2.40-2.28 (m, 1H), 2.23-2.14 (m, 1H), 2.10-1.77 (m, 4H), 1.76-1.60 (m, 4H), 1.60-1.50 (m, 15H), 1.50-1.38 (m, 2H), 1.35 (s, 3H), 1.32-1.28 (m, 3H), 1.27-1.18 (m, 9H), 1.18-1.05 (m, 1H), 1.05-0.97 (m, 9H), 0.95-0.87 (m, 7H); ESI-MS: m/z 788.51 (M–HCl+Na)$^+$; HPLC: 93.5%, Cl$^-$ ion content by Ion chromatography: 5.2%.

Example 12: Preparation of (1R,3S)-3-((((3aR,5aR,5bR,7aR,9S,11aR,11bR,13aS)-3a-(2-(1H-benzo[d]imidazole-5-carboxamido)-2-methylpropanamido)-1-isopropyl-5a,5b,8,8,11a-penta methyl-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid

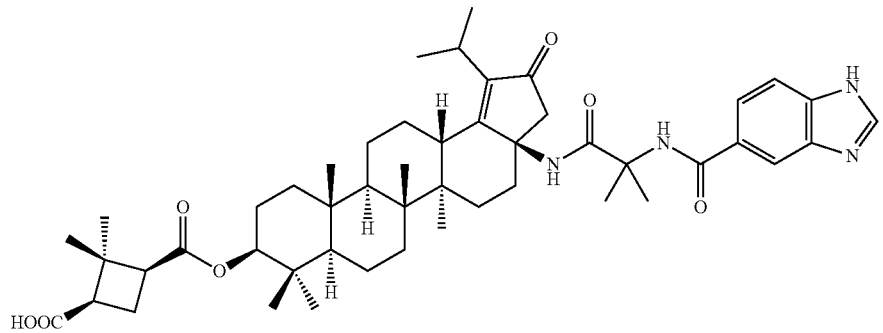

Intermediate 1 was coupled with 1H-benzo[d]imidazole-5-carboxylic acid followed by hydrolysis gave the desired product as a white solid. $^1$H NMR (300 MHz, CD$_3$OD): δ ppm 8.29 (d, J=8.4 Hz, 1H), 8.22 (brs, 1H), 7.84 (dd, J=8.4, 1.2 Hz, 1H), 7.67 (d, J=8.4 Hz, 1H), 7.50 (brs, 1H), 4.47-4.38 (m, 1H), 3.28-3.18 (m, 1H), 3.0-2.92 (m, 1H), 2.88-2.77 (m, 2H), 2.67 (d, J=18.6 Hz, 1H), 2.53-2.42 (m, 1H), 2.38-2.28 (m, 1H), 2.21 (d, J=18.6 Hz, 1H), 2.02-1.88 (m, 4H), 1.82-1.72 (m, 1H), 1.70-1.62 (m, 2H), 1.58 (brs, 6H), 1.56-1.40 (m, 4H), 1.38-1.27 (m, 8H), 1.27-1.10 (m, 7H), 1.01 (s, 3H), 0.96 (s, 3H), 0.92 (s, 3H), 0.90 (s, 3H), 0.90-0.78 (m, 7H); ESI-MS: m/z 823.62 (M–H)$^-$; HPLC: 96.3%.

Example 13: Preparation of (1R,3S)-3-((((3aR,5aR,5bR,7aR,9S,11aR,11bR,13aS)-1-iso propyl-5a,5b,8,8,11a-pentamethyl-3a-(2-methyl-2-(2-(6-methylpyridin-3-yl)-1H-benzo[d] imidazole-5-carboxamido) propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

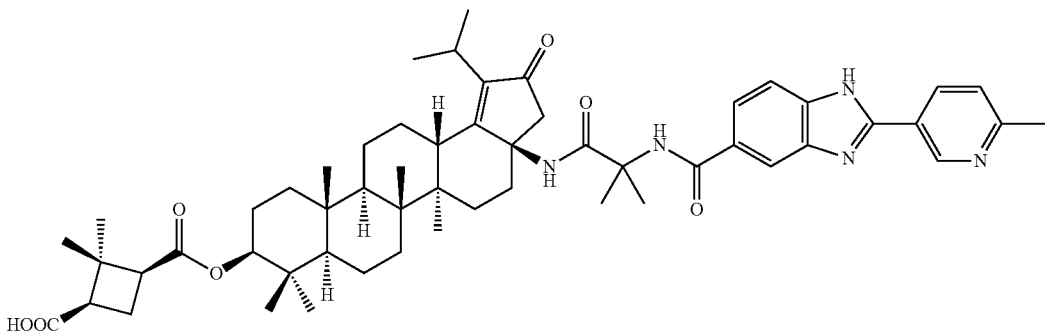

Intermediate 1 was coupled with 2-(6-methylpyridin-3-yl)-1H-benzo[d]imidazole-5-carboxylic acid (Intermediate 11) followed by hydrolysis gave the desired product as an off-white solid. $^1$H NMR (300 MHz, DMSO-d$_6$): δ ppm 13.2 (brs, 1H), 12.1 (brs, 1H), 9.23 (d, J=1.8 Hz, 1H), 8.40 (dd, J=8.1, 2.1 Hz, 1H), 8.14 (brs, 1H), 7.78 (d, J=7.8 Hz, 1H), 7.75-7.55 (m, 1H), 7.47 (d, J=8.1 Hz, 1H), 7.34 (brs, 1H), 4.38-4.30 (m, 1H), 3.15-3.05 (m, 1H), 2.88-2.70 (m, 4H), 2.56 (s, 3H), 2.35-2.22 (m, 3H), 2.14-2.05 (m, 1H), 1.95-1.80 (m, 4H), 1.80-1.60 (m, 2H), 1.60-1.50 (m, 2H), 1.48 (s, 3H), 1.47 (s, 3H), 1.42-1.20 (m, 5H), 1.32 (s, 3H), 1.20-1.10 (m, 8H), 1.08-0.93 (m, 2H), 0.90 (s, 3H), 0.87 (s, 3H), 0.86 (s, 3H), 0.79 (s, 3H), 0.77 (s, 3H), 0.76 (s, 3H); ESI-MS: m/z 939.03 (M+Na)$^+$; HPLC: 97.12%.

Example 14: Preparation of (1R,3S)-3-((((3aR,5aR, 5bR,7aR,9S,11aR,11bR,13aS)-3a-(2-(2,4-dimethyl-thiazole-5-carboxamido)-2-methylpropanamido)-1-isopropyl-5a,5b,8,8,11a-penta methyl-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid

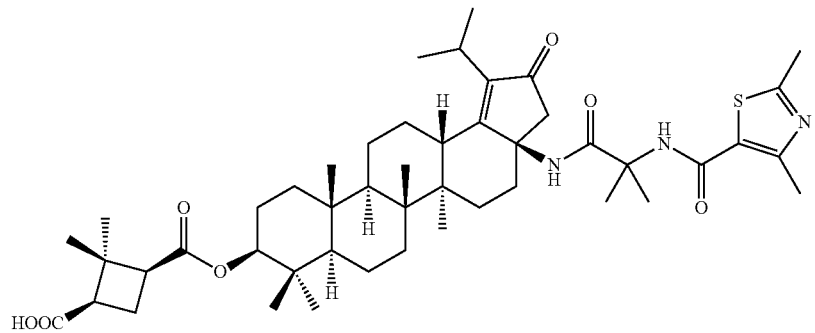

Intermediate 1 was coupled with 2,4-dimethylthiazole-5-carboxylic acid followed by hydrolysis gave the desired product as an off-white solid. $^1$H NMR (300 MHz, CDCl$_3$): δ ppm 7.01 (s, 1H), 6.26 (s, 1H), 4.46 (dd, J=11.4, 4.8 Hz, 1H), 3.19-3.10 (m, 1H), 2.88-2.75 (m, 3H), 2.67 (s, 3H), 2.64 (s, 3H), 2.63-2.56 (m, 2H), 2.40-2.26 (m, 2H), 2.12-1.82 (m, 5H), 1.82-1.50 (m, 8H), 1.65 (s, 3H), 1.64 (s, 3H), 1.49-1.30 (m, 2H), 1.37 (s, 3H), 1.28-1.18 (m, 7H), 1.07 (m, 7H), 0.94 (s, 3H), 0.89 (s, 3H), 0.86 (s, 3H), 0.85 (s, 3H), 0.99-0.78 (m, 1H); ESI-MS: m/z 842.51 (M+Na)$^+$; HPLC: 95.6%.

Example 15: Preparation of (1R,3S)-3-((((3aR,5aR, 5bR,7aR,9S,11aR,11bR,13aS)-1-iso propyl-5a,5b,8,8,11a-pentamethyl-3a-(2-methyl-2-(2-(pyrazin-2-yl)-1H-benzo[d]imidazole-5-carboxamido) propanamido)-2-oxo-3,3a,4,5,5a,5b,6,7,7a,8,9,10,11,11a,11b,12,13,13a-octa decahydro-2H-cyclopenta[a] chrysen-9-yl)oxy)carbonyl)-2,2-dimethylcyclobutane-1-carboxylic acid

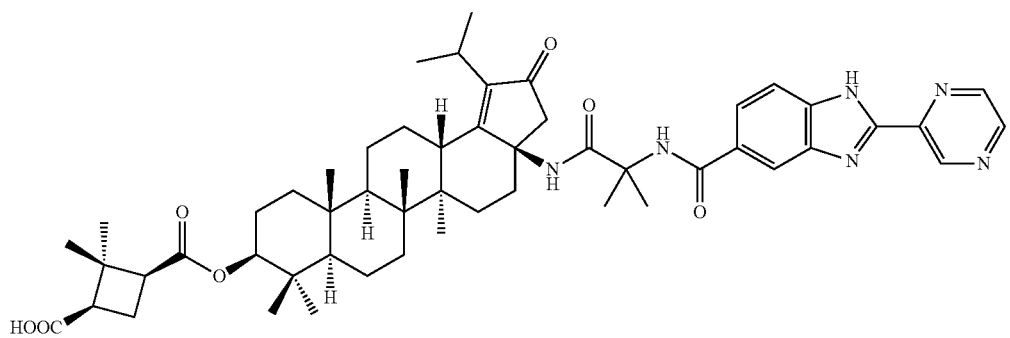

Intermediate 1 was coupled with 2-(pyrazin-2-yl)-1H-benzo[d]imidazole-5-carboxylic acid (Intermediate 12) followed by hydrolysis gave the desired product as an off-white solid. $^1$H NMR (300 MHz, DMSO-d$_6$): δ ppm 13.65 (s, 0.5H), 13.55 (s, 0.5H), 12.1 (s, 1H), 9.52 (s, 1H), 8.85-8.79 (m, 2H), 8.42 (s, 0.5H), 8.22-8.17 (m, 1H), 8.09 (s, 0.5H), 7.86-7.76 (m, 1H), 7.58 (d, J=8.4 Hz, 1H), 4.38-4.30 (m, 1H), 3.14-3.06 (m, 1H), 2.87-2.72 (m, 3H), 2.35-2.22 (m, 3H), 2.14-2.05 (m, 2H), 1.95-1.72 (m, 4H), 1.70-1.55 (m, 3H), 1.48 (s, 3H), 1.46 (s, 3H), 1.44-1.30 (m, 5H), 1.28-1.20 (m, 3H), 1.26 (s, 3H), 1.16-1.10 (m, 6H), 1.05-0.95 (m, 1H), 0.90 (s, 3H), 0.86 (m, 6H), 0.82-0.75 (m, 10H); ESI-MS: m/z 903.5 (M+H)$^+$; HPLC: 96.6%.

Example 16: Preparation of (1R,3S)-3-((((3aR,5aR,5bR,7aR,9S,11aR,11bR,13aS)-1-iso propyl-5a,5b,8,8,11a-pentamethyl-3a-(2-methyl-2-(1-methyl-1H-imidazole-2-carboxamido) propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

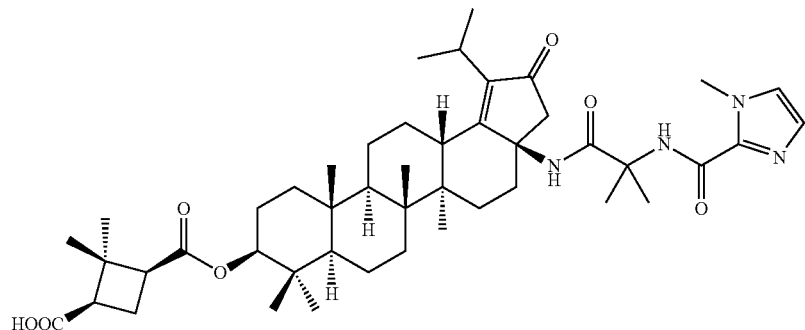

Intermediate 1 was coupled with 1-methyl-1H-imidazole-2-carboxylic acid followed by hydrolysis gave the desired product as an off-white solid. $^1$H NMR (300 MHz, CDCl$_3$): δ ppm 7.61 (m, 1H), 7.04 (s, 1H), 7.0 (d, J=6.6 Hz, 1H), 4.46 (dd, J=11.1, 4.5 Hz, 1H), 4.02 (s, 3H), 3.20-3.08 (m, 1H), 2.88-2.52 (m, 5H), 2.43-2.22 (m, 2H), 2.10-2.0 (m, 1H), 1.98-1.82 (m, 4H), 1.82-1.40 (m, 14H), 1.37 (s, 3H), 1.36-1.18 (m, 9H), 1.07 (s, 3H), 1.05-1.0 (m, 1H), 0.95 (s, 3H), 0.92 (s, 3H), 0.89-0.83 (m, 9H), 0.78 (m, 1H); ESI-MS: m/z 789.7 (M+H)$^+$; HPLC: 93.5%.

Example 17: Preparation of (1R,3S)-3-((((3aR,5aR,5bR,7aR,9S,11aR,11bR,13aS)-1-iso propyl-3a-(2-(3-isopropyl-1H-pyrazole-5-carboxamido)-2-methyl-propanamido)-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

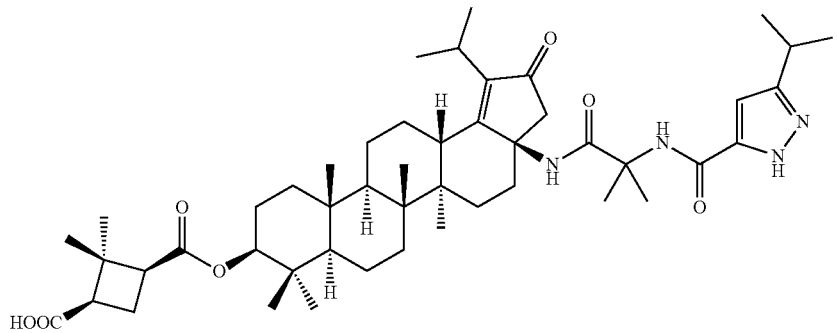

Intermediate 1 was coupled with 3-isopropyl-1H-pyrazole-5-carboxylic acid followed by hydrolysis gave the desired product as an off-white solid. $^1$H NMR (300 MHz, CDCl$_3$): δ ppm 7.79 (s, 1H), 7.14 (s, 1H), 6.58 (s, 1H), 4.46 (dd, J=11.1, 4.5 Hz, 1H), 3.18-3.10 (m, 1H), 3.10-2.90 (m, 1H), 2.90-2.75 (m, 3H), 2.75-2.52 (m, 2H), 2.40-2.20 (m, 2H), 2.10-2.0 (m, 1H), 2.0-1.85 (m, 4H), 1.78-1.69 (m, 2H), 1.65 (s, 3H), 1.60 (s, 3H), 1.58-1.40 (m, 6H), 1.37 (s, 3H), 1.32 (s, 3H), 1.29 (s, 3H), 1.27-1.20 (m, 9H), 1.17-1.10 (m, 1H), 1.07 (s, 3H), 0.99 (s, 3H), 0.92 (s, 3H), 0.88-0.77 (m, 10H); ESI-MS: m/z 817.7 (M+H)$^+$; HPLC: 96.5%.

Example 18: Preparation of (1R,3S)-3-((((3aR,5aR,5bR,7aR,9S,11aR,11bR,13aS)-1-iso propyl-5a,5b,8,8,11a-pentamethyl-3a-(2-methyl-2-(4-morpholinobenzamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

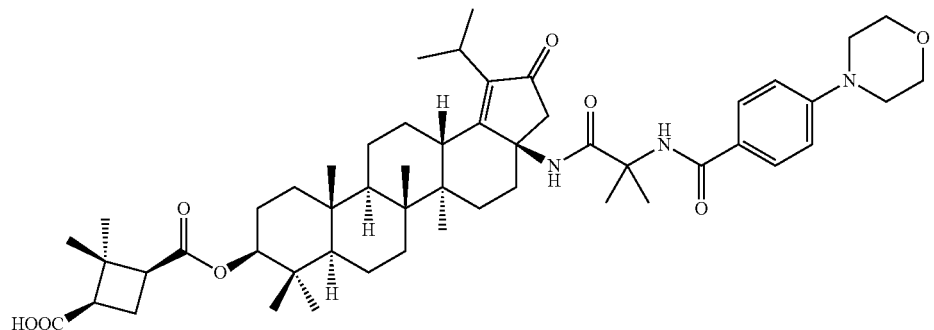

Intermediate 1 was coupled with 4-morpholinobenzoic acid followed by hydrolysis gave the desired product as an off-white solid. $^1$H NMR (300 MHz, CDCl$_3$): δ ppm 7.69 (d, J=8.4 Hz, 2H), 6.89 (d, J=9.0 Hz, 2H), 6.43 (s, 1H), 4.46 (dd, J=11.1, 4.5 Hz, 1H), 3.90-3.83 (m, 4H), 3.30-3.23 (m, 4H), 3.20-3.09 (m, 1H), 2.90-2.75 (m, 3H), 2.70-2.52 (m, 2H), 2.38-2.23 (m, 2H), 2.10-2.0 (m, 1H), 2.0-1.82 (m, 3H), 1.82-1.70 (m, 2H), 1.67 (s, 3H), 1.63 (s, 3H), 1.61-1.54 (m, 2H), 1.54-1.40 (m, 3H), 1.39-1.29 (m, 3H), 1.37 (s, 3H), 1.28-1.17 (m, 9H), 1.06 (s, 3H), 1.02 (s, 3H), 0.93 (s, 3H), 0.89-0.82 (m, 9H), 0.78 (m, 1H); ESI-MS: m/z 892.76 (M+Na)$^+$; HPLC: 98.1%.

Example 19: Preparation of (1R,3S)-3-((((3aR,5aR,5bR,7aR,9S,11aR,11bR,13aS)-3a-(2-(3,5-dimethylisoxazole-4-carboxamido)-2-methylpropanamido)-1-isopropyl-5a,5b,8,8,11a-penta methyl-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid

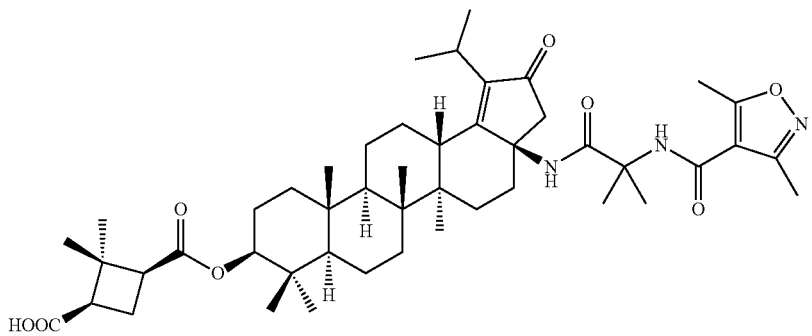

Intermediate 1 was coupled with 3,5-dimethylisoxazole-4-carboxylic acid followed by hydrolysis gave the desired product as an off-white solid. $^1$H NMR (300 MHz, CDCl$_3$): δ ppm 6.75 (s, 1H), 6.48 (s, 1H), 4.46 (dd, J=11.1, 4.5 Hz, 1H), 3.20-3.10 (m, 1H), 2.89-2.51 (m, 5H), 2.60 (s, 3H), 2.42 (s, 3H), 2.40-2.27 (m, 2H), 2.10-2.0 (m, 1H), 1.98-1.80 (m, 3H), 1.78-1.72 (m, 2H), 1.69 (s, 3H), 1.66 (s, 3H), 1.63-1.51 (m, 3H), 1.50-1.39 (m, 3H), 1.36 (s, 3H), 1.35-1.31 (m, 2H), 1.29-1.18 (m, 8H), 1.12 (s, 3H), 1.05 (s, 3H), 1.01 (m, 1H), 0.95 (s, 3H), 0.90 (s, 3H), 0.87 (s, 3H), 0.85 (s, 3H), 0.80 (m, 1H); ESI-MS: m/z 804.52 (M+H)$^+$; HPLC: 97.6%.

Example 20: Preparation of (1R,3S)-3-((((3aR,5aR,5bR,7aR,9S,11aR,11bR,13aS)-1-iso propyl-5a,5b,8,8,11a-pentamethyl-3a-(2-methyl-2-(4-(4-methyl-1H-imidazol-1-yl)benzamido)propanamido)-2-oxo-3,3a,4,5,5a,5b,6,7,7a,8,9,10,11,11a,11b,12,13,13a-octadeca hydro-2H-cyclopenta[a]chrysen-9-yl)oxy)carbonyl)-2,2-dimethylcyclobutane-1-carboxylic acid

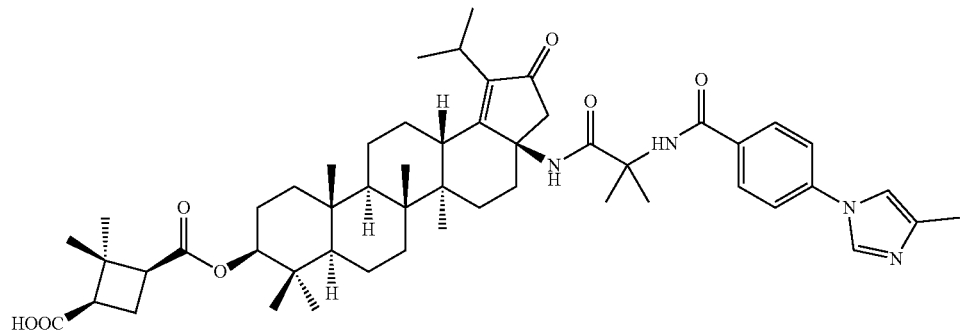

Intermediate 1 was coupled with 4-(4-methyl-1H-imidazol-1-yl)benzoic acid (Intermediate 13) followed by hydrolysis gave the desired product as an off-white solid. $^1$H NMR (300 MHz, CDCl$_3$): δ ppm 7.89 (d, J=8.4 Hz, 2H), 7.43 (d, J=8.4 Hz, 2H), 7.08-6.97 (m, 2H), 4.46 (dd, J=11.1, 4.5 Hz, 1H), 3.22-3.11 (m, 1H), 2.90-2.53 (m, 5H), 2.35-2.27 (m, 2H), 2.30 (s, 3H), 2.10-1.84 (m, 4H), 1.78-1.68 (m, 7H), 1.67-1.18 (m, 17H), 1.37 (s, 3H), 1.12-1.05 (m, 7H), 0.95 (s, 3H), 0.87 (s, 3H), 0.85 (s, 3H), 0.84 (s, 3H), 0.79 (m, 1H); ESI-MS: m/z 865.72 (M+H)$^+$; HPLC: 96.8%.

Example 21: Preparation of (1S,3R)-3-((((3aR,5aR,5bR,7aR,9S,11aR,11bR,13aS)-3a-(2-(4-chlorobenzamido)-2-methylpropanamido)-1-isopropyl-5a,5b,8,8,11a-pentamethyl-2-oxo-3, 3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

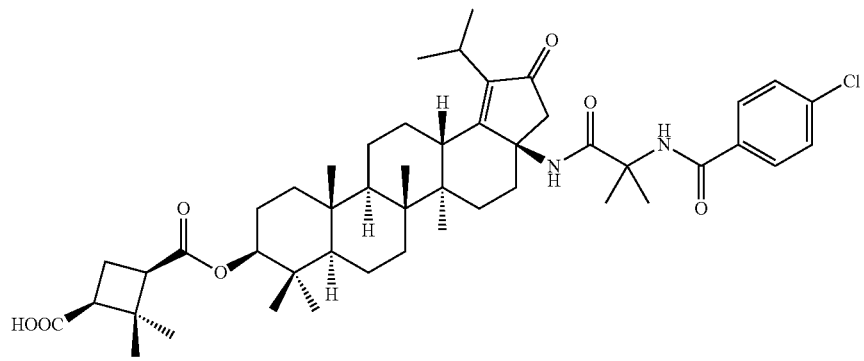

Intermediate 2 was coupled with 4-chlorobenzoic acid followed by hydrolysis gave the desired product as a white solid. ¹H NMR (300 MHz, CDCl₃): δ ppm 7.72 (d, J=8.1 Hz, 2H), 7.42 (d, J=7.8 Hz, 2H), 7.07 (s, 1H), 6.78 (s, 1H), 4.47 (dd, J=11.4, 4.5 Hz, 1H), 3.23-3.10 (m, 1H), 2.86-2.76 (m, 3H), 2.72-2.50 (m, 2H), 2.40-2.25 (m, 2H), 2.13-2.04 (m, 1H), 2.04-1.82 (m, 4H), 1.80-1.66 (m, 7H), 1.64-1.45 (m, 6H), 1.44-1.41 (m, 1H), 1.40-1.31 (m, 2H), 1.36 (s, 3H), 1.30-1.20 (m, 7H), 1.20-1.09 (m, 1H), 1.04 (s, 6H), 0.95 (s, 3H), 0.88 (s, 3H), 0.857 (s, 3H), 0.851 (s, 3H), 0.79 (m, 1H); ESI-MS: m/z 841.52 (M+Na)⁺; HPLC: 94.19%.

Example 22: Preparation of (1R,3S)-3-((((3aR,5aR, 5bR,7aR,9S,11aR,11bR,13aS)-3a-(2-(4-fluorobenzamido)-2-methylpropanamido)-1-isopropyl-5a,5b,8, 8,11a-pentamethyl-2-oxo-3,3a, 4,5,5a,5b,6,7,7a,8,9, 10,11,11a,11b,12,13,13a-octadecahydro-2H-cyclopenta[a]chrysen-9-yl) oxy)carbonyl)-2,2-dimethylcyclobutane-1-carboxylic acid

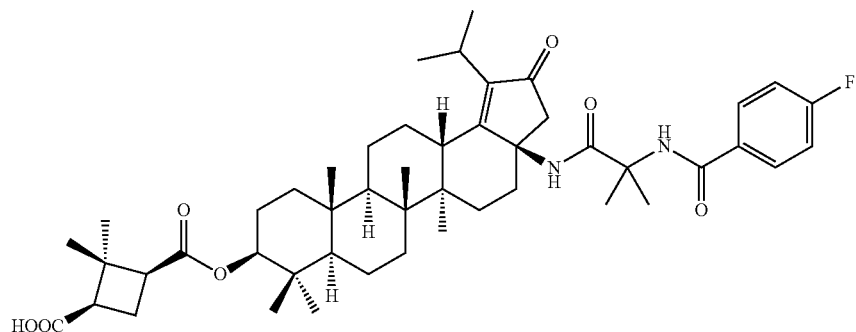

Step 1: Synthesis of 1-benzyl 34(3aR,5aR,5bR,7aR, 9S,11aR,11bR,13aS)-3a-(2-(4-fluorobenzamido)-2-methylpropanamido)-1-isopropyl-5a,5b,8,8,11a-pentamethyl-2-oxo-3,3a,4,5,5a,5b,6,7,7a,8,9,10,11, 11a,11b,12,13,13a-octadecahydro-2H-cyclopenta[a] chrysen-9-yl) (1R,3S)-2,2-dimethylcyclobutane-1,3-dicarboxylate

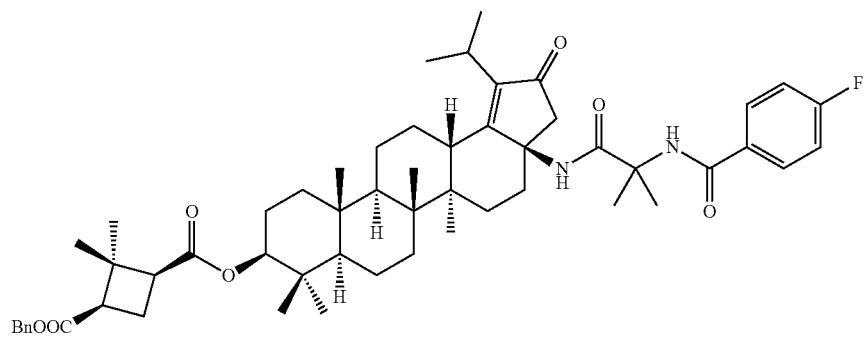

To a stirred solution of 4-fluorobenzoic acid (0.54 g, 3.89 mmol, 1.5 eq) in DMF (20 ml) at 0° C. under nitrogen atmosphere was added EDCI (0.99 g, 5.18 mmol, 2 eq), HOBT (0.52 g, 3.89 mmol, 1.5 eq), DMAP (0.15 g, 1.29 mmol, 0.5 eq) and added Triethylamine (1.08 ml, 7.78 mmol, 3 eq) and stirred it for about 30 minutes. Then added 1-((3aR,5aR,5bR,7aR,9S,11aR,11bR,13aS)-3a-(2-amino-2-methylpropanamido)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) 3-benzyl (1S,3R)-2,2-dimethylcyclobutane-1,3-dicarboxylate (Intermediate 1, 2.0 g, 2.59 mmol, 1 eq). The reaction mixture was stirred at room temperature for about 14 hours. TLC indicated starting material was consumed and the desired product was observed. The reaction mixture was quenched with ice cold water, filtered through Buchner funnel. The solid was separated, was dissolved in DCM, washed with sodium bicarbonate, water, brine solution then dried over sodium sulfate and concentrated under reduced pressure to give a crude compound. The crude compound was purified by flash silica column chromatography (100-200 silica gel) using 2% MeOH in DCM as an eluent gave the desired product (1.5 g, yield: 65.21%) as an off-white solid. $^1$H NMR (300 MHz, CDCl$_3$): δ ppm 8.16 (s, 1H), 7.94-7.98 (m, 2H), 7.35 (m, 5H), 7.27-7.34 (m, 3H), 5.15, 5.10 (ABq, J$_{AB}$=12.3 Hz, 2H), 4.32-4.36 (t, 1H), 3.07-3.10 (t, 1H), 2.75-2.88 (m, 4H), 2.39-2.43 (m, 1H), 2.27-2.30 (m, 2H), 2.04-2.09 (m, 1H), 1.84-1.90 (m, 3H), 1.48-1.75 (m, 6H), 1.41-1.42 (m, 6H), 1.23-1.32 (m, 9H), 1.11-1.13 (m, 5H), 0.90-1.05 (m, 3H), 0.87 (s, 3H), 0.85 (s, 3H), 0.83 (s, 3H), 0.79-0.80 (m, 9H); ESI-MS: m/z 915.54 (M+Na)$^+$.

Step 2: Synthesis of (1R,3S)-3-((((3aR,5aR,5bR, 7aR,9S,11aR,11bR,13aS)-3a-(2-(4-fluorobenz amido)-2-methylpropanamido)-1-isopropyl-5a,5b,8, 8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR, 9S,11aR,11bR,13aS)-3a-(2-(4-fluorobenzamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 1, 1.5 g, 0.541 mmol, 1.0 eq) in MeOH (15 ml) and THF (15 ml) was added aqueous 2.5 N KOH solution (3.35 ml, 8.39 mmol, 5 eq). The reaction mixture was stirred at room temperature for overnight. TLC indicated starting material was consumed and the desired product was observed. The organic phase was evaporated under reduced pressure, the reaction mixture was diluted with water (10 ml), cooled to 0° C., pH adjusted to 5.0 with 1N HCl and extracted with DCM (2×75 ml). The combined organic extracts were washed with water (50 ml), dried over sodium sulfate, filtered and evaporated under reduced pressure. The residue was purified by silicagel column chromatography by using 0-5% methanol in dichloromethane gradient. The fractions containing the expected product were combined and concentrated under reduced pressure to obtain the solid. The solid compound was dissolved in MTBE (10 ml) and added Hexane (30 ml) then precipitate was formed, and filtered through Buchner funnel. The solid was washed with MTBE:Hexane (1:3, 10 ml) and dried under vacuum to obtain the desired product (200 mg, yield: 15.38%) as a white solid. $^1$H NMR (400 MHz, DMSO-d$_6$): δ ppm 12.14 (s, 1H), 8.16 (s, 1H), 7.94-7.98 (m, 2H), 7.27-7.34 (m, 3H), 4.32-4.36 (t, 1H), 3.07-3.10 (t, 1H), 2.75-2.88 (m, 4H), 2.39-2.43 (m, 1H), 2.27-2.30 (m, 2H), 2.04-2.09 (m, 1H), 1.84-1.90 (m, 3H), 1.48-1.75 (m, 6H), 1.41-1.42 (m, 6H), 1.23-1.32 (m, 9H), 1.11-1.13 (m, 5H), 0.90-1.05 (m, 3H), 0.87 (s, 3H), 0.85 (s, 3H), 0.83 (s, 3H), 0.79-0.80 (m, 9H); ESI-MS: m/z 803.47 (M+H)$^+$; HPLC: 92.89%.

The below examples 23-50 were prepared by the procedure similar (including reagents and reaction conditions) to the above described in the synthesis of example-22 using with their appropriate intermediates.

Example 23: Preparation of (1R,3S)-3-((((3aR,5aR, 5bR,7aR,9S,11aR,11bR,13aS)-1-iso propyl-5a,5b,8, 8,11a-pentamethyl-3a-(2-methyl-2-(4-methylbenzamido)propanamido)-2-oxo-3,3a,4, 5,5a,5b,6,7,7a, 8,9,10,11,11a,11b,12,13,13a-octadecahydro-2H-cyclopenta[a]chrysen-9-yl) oxy)carbonyl)-2,2-dimethylcyclobutane-1-carboxylic acid

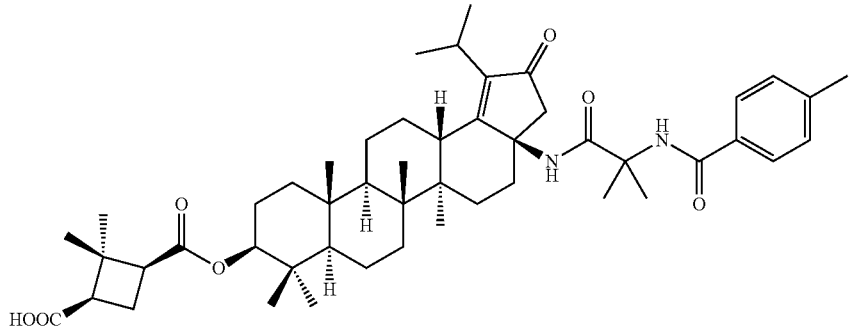

Intermediate 1 was coupled with 4-methylbenzoic acid followed by hydrolysis gave the desired product as a white solid. $^1$H NMR (400 MHz, DMSO-d$_6$): δ ppm 12.13 (s, 1H), 8.03 (s, 1H), 7.78 (d, J=8.0 Hz, 2H), 7.31 (s, 1H), 7.25 (d, J=8.0 Hz, 2H), 4.32-4.36 (m, 1H), 3.07-3.10 (m, 1H), 2.73-2.81 (m, 3H), 2.39-2.44 (m, 1H), 2.35 (s, 3H), 2.25-2.30 (m, 2H), 2.04-2.08 (m, 1H), 1.86-1.95 (m, 3H), 1.51-1.75 (m, 6H), 1.425 (d, J=8.0 Hz, 6H), 1.23-1.29 (m, 8H), 1.11-1.13 (m, 7H), 0.95-1.02 (m, 3H), 0.91 (s, 3H), 0.865 (d, J=8.0 Hz, 6H), 0.80-0.81 (m, 9H); ESI-MS: m/z 799.42 (M+H)$^+$; HPLC: 91.77%.

Example 24: Preparation of (1R,3S)-3-((((3aR,5aR,5bR,7aR,9S,11aR,11bR,13aS)-3a-(2-(furan-3-carboxamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) oxy)carbonyl)-2,2-dimethylcyclobutane-1-carboxylic acid

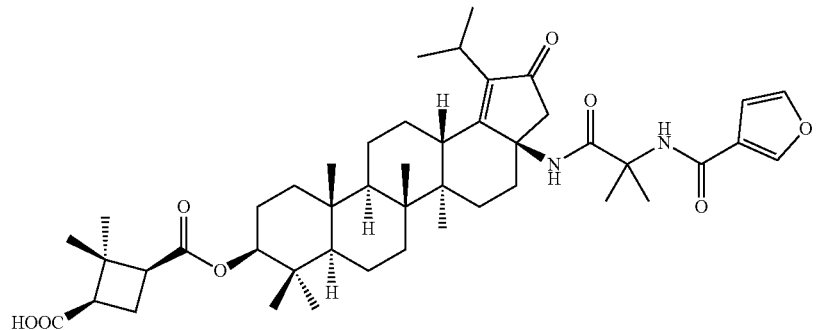

Intermediate 1 was coupled with furan-3-carboxylic acid followed by hydrolysis gave the desired product as a white solid. $^1$H NMR (300 MHz, DMSO-$d_6$): δ ppm 12.15 (s, 1H), 8.215 (d, J=3 Hz, 1H), 7.83 (s, 1H), 7.715 (d, J=3 Hz, 1H), 7.35 (s, 1H), 6.835 (d, J=3 Hz, 1H), 4.33-4.38 (m, 1H), 3.07-3.11 (m, 1H), 2.73-2.83 (m, 3H), 2.28-2.43 (m, 3H), 2.03-2.10 (m, 1H), 1.86-1.90 (m, 3H), 1.40-1.76 (m, 6H), 1.34-1.38 (m, 6H), 1.23-1.30 (m, 8H), 1.11-1.19 (m, 9H), 1.01 (m, 2H), 0.95 (s, 3H), 0.87-0.91 (s, 3H), 0.81-0.85 (m, 11H); ESI-MS: m/z 797.42 (M+Na)$^+$; HPLC: 92.55%.

Example 25: Preparation of (1R,3S)-3-((((3aR,5aR,5bR,7aR,9S,11aR,11bR,13aS)-1-iso propyl-5a,5b,8,8,11a-pentamethyl-3a-(2-methyl-2-(4-(trifluoromethyl)benzamido)propan amido)-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid

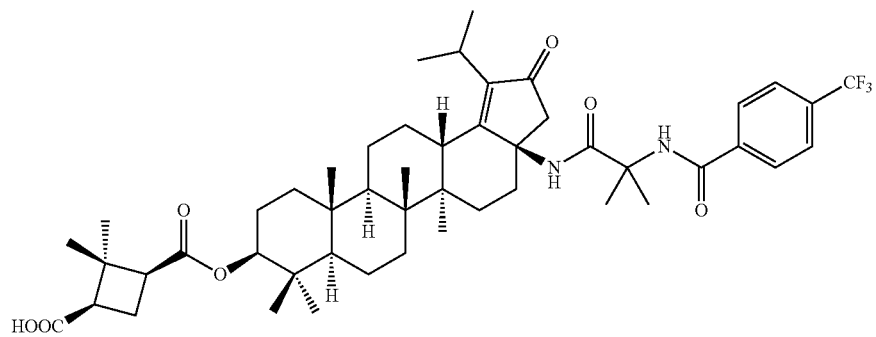

Intermediate 1 was coupled with 4-(trifluoromethyl)benzoic acid followed by hydrolysis gave the desired product as an off white solid. $^1$H NMR (300 MHz, DMSO): δ ppm 12.13 (s, 1H), 8.39 (s, 1H), 8.10 (d, J=8.4 Hz, 2H), 7.85 (d, J=8.4 Hz, 2H), 7.39 (s, 1H), 4.31-4.36 (t, 1H), 3.07-3.11 (t, 1H), 2.72-2.82 (m, 3H), 2.27-2.31 (m, 3H), 2.05-2.11 (m, 2H), 1.76-1.89 (m, 5H), 1.56-1.63 (m, 4H), 1.43-1.44 (m, 9H), 1.26-1.30 (m, 8H), 1.11-1.13 (m, 6H), 0.98-1.03 (m, 3H), 0.85-0.90 (m, 6H), 0.76-0.80 (m, 9H); ESI-MS: m/z 853.43 (M+H)$^+$. HPLC: 97.60%.

Example 26: Preparation of (1R,3S)-3-((((3aR,5aR, 5bR,7aR,9S,11aR,11bR,13aS)-3a-(2-(furan-2-car- boxamido)-2-methylpropanamido)-1-isopropyl-5a, 5b,8,8,11a-pentamethyl-2-oxo-3,3a,4,5,5a,5b,6,7,7a, 8,9,10,11,11a,11b,12,13,13a-octadecahydro-2H- cyclopenta[a]chrysen-9-yl) oxy)carbonyl)-2,2- dimethylcyclobutane-1-carboxylic acid

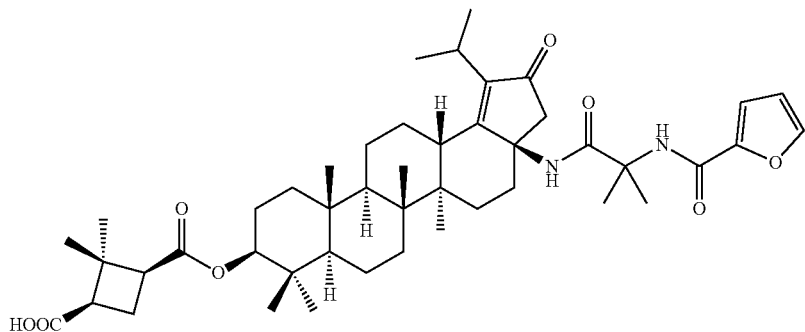

Intermediate 1 was coupled with furan-2-carboxylic acid followed by hydrolysis gave the desired product as a white solid. $^1$H NMR (300 MHz, DMSO-$d_6$): δ ppm 12.13 (s, 1H), 7.83-7.91 (m, 2H), 7.45 (s, 1H), 7.08-7.10 (m, 1H), 6.61-6.63 (m, 1H), 4.33-4.38 (m, 1H), 3.07-3.11 (m, 1H), 2.73-2.83 (m, 3H), 2.28-2.43 (m, 3H), 2.03-2.10 (m, 1H), 1.86-1.90 (m, 3H), 1.40-1.76 (m, 6H), 1.34-1.38 (m, 6H), 1.23-1.30 (m, 8H), 1.11-1.19 (m, 9H), 1.01 (m, 2H), 0.95 (s, 3H), 0.87-0.91 (s, 3H), 0.81-0.85 (m, 11H); ESI-MS: m/z 797.42 (M+Na)$^+$; HPLC: 92.65%.

Example 27: Preparation of (1R,3S)-3-((((3aR,5aR, 5bR,7aR,9S,11aR,11bR,13aS)-1-iso propyl-5a,5b,8, 8,11a-pentamethyl-3a-(2-methyl-2-(1-phenylcyclo- pentane-1-carboxamido) propanamido)-2-oxo-3,3a, 4,5,5a,5b,6,7,7a,8,9,10,11,11a,11b,12,13,13a- octadecahydro-2H-cyclo penta[a]chrysen-9-yl)oxy) carbonyl)-2,2-dimethylcyclobutane-1-carboxylic acid

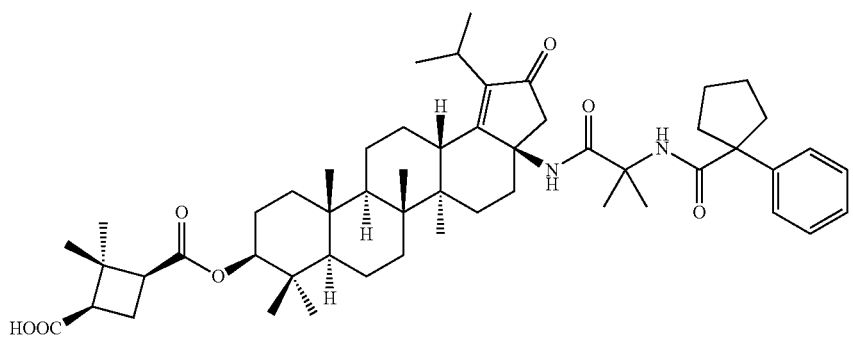

Intermediate 1 was coupled with 1-phenylcyclopentane-1-carboxylic acid followed by hydrolysis gave the desired product as a white solid. $^1$H NMR (300 MHz, DMSO-$d_6$): δ ppm 12.03 (brs, 1H), 7.20-7.36 (m, 6H), 6.48 (s, 1H), 4.33-4.38 (m, 1H), 3.07-3.09 (m, 1H), 2.70-2.82 (m, 3H), 2.28-2.31 (m, 2H), 1.50-2.03 (m, 16H), 1.27-1.36 (m, 15H), 1.03-1.10 (m, 14H), 0.81-0.96 (m, 16H); ESI-MS: m/z 853.56 (M+H)$^+$; HPLC: 98.50%.

Example 28: Preparation of (1R,3S)-3-((((3aR,5aR,5bR,7aR,9S,11aR,11bR,13aS)-1-iso propyl-5a,5b,8,8,11a-pentamethyl-3a-(2-methyl-2-(quinoline-2-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

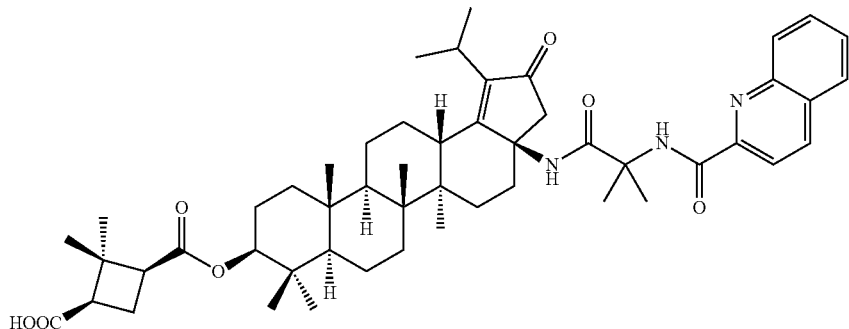

Intermediate 1 was coupled with quinoline-2-carboxylic acid followed by hydrolysis gave the desired product as a white solid. $^1$H NMR (300 MHz, DMSO-$d_6$): δ ppm 12.13 (s, 1H), 8.98 (s, 1H), 8.59 (d, J=8.7 Hz, 1H), 8.16 (d, J=8.7 Hz, 1H), 8.119-8.092 (m, 2H), 7.90-7.85 (m, 1H), 7.75-7.70 (m, 2H), 4.37-4.32 (t, 1H), 3.12-3.07 (m, 2H), 2.85-2.73 (m, 3H), 2.40-2.12 (m, 5H), 1.92-1.79 (m, 5H), 1.60 (m, 9H), 1.31-1.26 (m, 6H), 1.17-1.10 (m, 8H), 0.91-0.88 (m, 11H), 0.81-0.79 (m, 10H); ESI-MS: m/z 858.55 (M+Na)$^+$. HPLC: 97.06%.

Example 29: Preparation of (1R,3S)-3-((((3aR,5aR,5bR,7aR,9S,11aR,11bR,13aS)-1-iso propyl-5a,5b,8,8,11a-pentamethyl-3a-(2-methyl-2-(3-methylpicolinamido)propanamido)-2-oxo-3,3a,4,5,5a,5b,6,7,7a,8,9,10,11,11a,11b,12,13,13a-octadecahydro-2H-cyclopenta[a]chrysen-9-yl) oxy)carbonyl)-2,2-dimethylcyclobutane-1-carboxylic acid

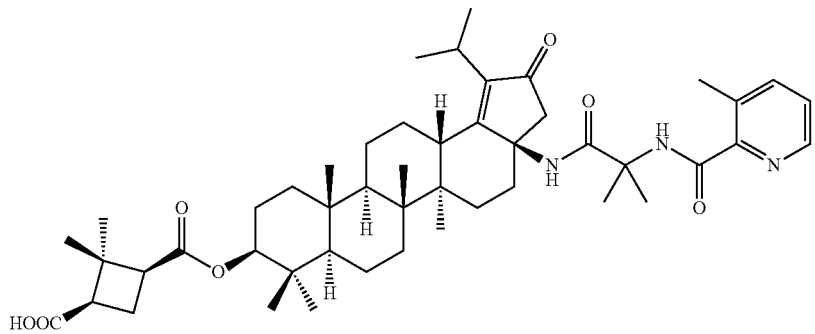

Intermediate 1 was coupled with 3-methylpicolinic acid followed by hydrolysis gave the desired product as a white solid. $^1$H NMR (300 MHz, DMSO-$d_6$): δ ppm 12.18 (brs, 1H), 8.66 (s, 1H), 8.47-8.45 (m, 1H), 7.76-7.73 (m, 1H), 7.51-7.45 (m, 2H), 4.37-4.32 (m, 1H), 3.12-3.07 (m, 2H), 2.84-2.73 (m, 4H), 2.53 (brs, 3H), 2.42 (brs, 1H), 2.34-2.23 (m, 2H), 2.15 (brs, 1H), 2.09 (brs, 1H), 1.92-1.83 (m, 3H), 1.52-1.49 (m, 8H), 1.36 (m, 4H), 1.26-1.23 (m, 3H), 1.14-1.10 (m, 9H), 1.03-1.00 (m, 2H), 0.90-0.89 (m, 9H), 0.81-0.79 (m, 10H); ESI-MS: m/z 799.73 (M+H)$^+$; HPLC: 99.31%.

Example 30: Preparation of (1R,3S)-3-((((3aR,5aR,5bR,7aR,9S,11aR,11bR,13aS)-1-iso propyl-5a,5b,8,8,11a-pentamethyl-3a-(2-methyl-2-(2-methylfuran-3-carboxamido)propan amido)-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid

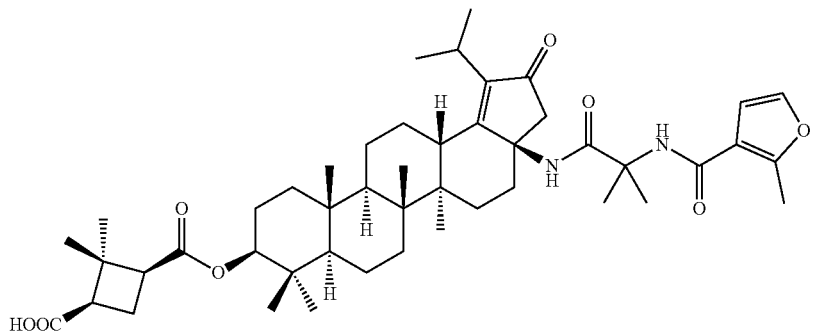

Intermediate 1 was coupled with 2-methylfuran-3-carboxylic acid followed by hydrolysis gave the desired product as a white solid. $^1$H NMR (300 MHz, DMSO-$d_6$): δ ppm 12.14 (brs, 1H), 7.64 (s, 1H), 7.519 (d, $J_{AB}$=1.5 Hz, 1H), 7.29 (s, 1H), 6.915 (d, $J_{AB}$=1.5 Hz, 1H), 4.38-4.33 (m, 1H), 3.11-3.07 (m, 1H), 2.88-2.67 (m, 5H), 2.48-2.46 (m, 4H), 2.40-2.15 (m, 4H), 2.09-2.03 (m, 1H), 1.92-1.58 (m, 10H), 1.40-1.36 (m, 6H), 1.28-1.17 (m, 5H), 1.16-1.10 (m, 8H), 1.06-0.97 (m, 3H), 0.95-0.80 (m, 15H); ESI-MS: m/z 788.73 (M+H)$^+$; HPLC: 99.08%.

Example 31: Preparation of (1R,3S)-3-((((3aR,5aR,5bR,7aR,9S,11aR,11bR,13aS)-1-iso propyl-5a,5b,8,8,11a-pentamethyl-3a-(2-methyl-2-(2-morpholinonicotinamido)propan amido)-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid

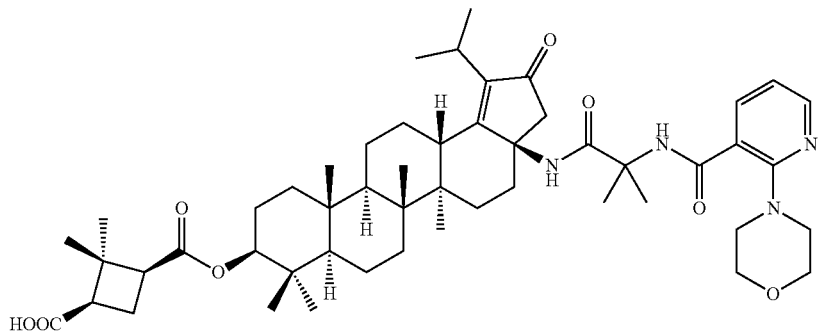

Intermediate 1 was coupled with 2-morpholinonicotinic acid followed by hydrolysis gave the desired product as a white solid. $^1$H NMR (300 MHz, DMSO-$d_6$): δ ppm 12.09-12.06 (brs, 1H), 9.06 (s, 1H), 8.31-8.29 (m, 1H), 7.96-7.93 (m, 1H), 7.63 (s, 1H), 7.05-7.01 (m, 1H), 4.36 (m, 1H), 3.69 (brs, 4H), 3.13-3.07 (m, 6H), 2.79-2.72 (m, 4H), 2.40-2.12 (m, 6H), 1.96-1.78 (m, 5H), 1.61-1.55 (m, 11H), 1.39-1.26 (m, 10H), 1.15-1.04 (m, 12H), 0.91-0.81 (m, 9H); ESI-MS: m/z 871.78 (M+H)$^+$; HPLC: 93.74%.

Example 32: Preparation of (1R,3S)-3-((((3aR,5aR,5bR,7aR,9S,11aR,11bR,13aS)-1-iso propyl-5a,5b,8,8,11a-pentamethyl-3a-(2-methyl-2-(pyrimidine-2-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

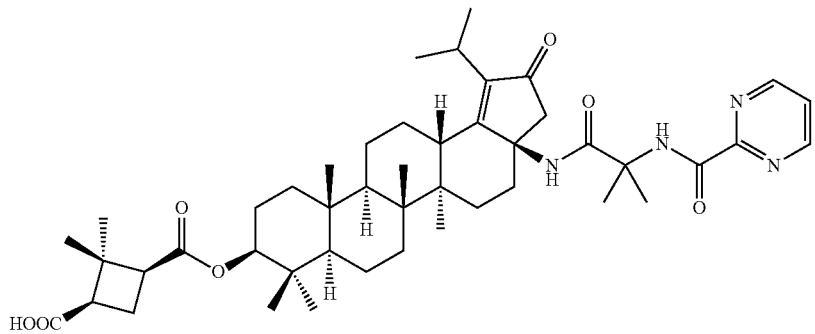

Intermediate 1 was coupled with pyrimidine-2-carboxylic acid followed by hydrolysis gave the desired product as a white solid. $^1$H NMR (300 MHz, DMSO-d$_6$): δ ppm 12.12 (brs, 1H) 8.98-8.97 (m, 3H), 7.72-7.67 (m, 2H), 4.35 (m, 1H), 3.13-3.07 (m, 1H), 2.82-2.73 (m, 4H), 2.44-2.12 (m, 4H), 1.92-1.85 (m, 3H), 1.83-1.63 (m, 3H), 1.48 (m, 3H), 1.35-1.26 (m, 9H), 1.15-1.10 (m, 8H), 1.03-0.99 (m, 2H), 0.902-0.88 (m, 10H), 0.81-0.80 (m, 12H); ESI-MS: m/z 787.62 (M+H)$^+$; HPLC: 92.90%.

Example 33: Preparation of (1R,3S)-3-((((3aR,5aR,5bR,7aR,9S,11aR,11bR,13aS)-3a-(2-(2,5-dimethyl-furan-3-carboxamido)-2-methylpropanamido)-1-isopropyl-5a,5b,8,8,11a-penta methyl-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid

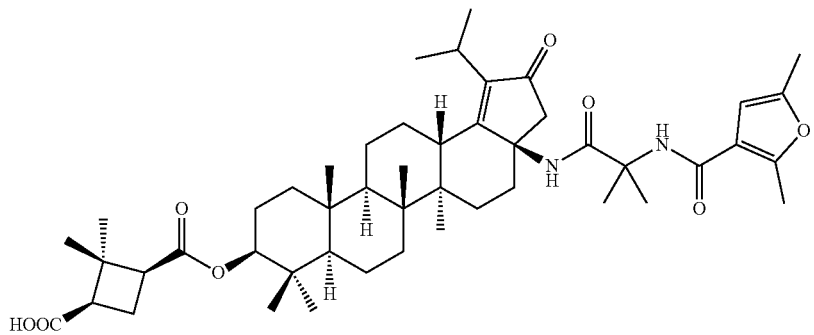

Intermediate 1 was coupled with 2,5-dimethylfuran-3-carboxylic acid followed by hydrolysis gave the desired product as a white solid. $^1$H NMR (300 MHz, DMSO-d$_6$): δ ppm 12.17 (brs, 1H), 7.51 (s, 1H), 7.27 (s, 1H), 6.49 (s, 1H), 4.38-4.32 (m, 1H), 3.11-3.07 (m, 1H), 2.87-2.73 (m, 3H), 2.44-2.38 (m, 4H), 2.31-2.22 (m, 5H), 2.09-2.03 (m, 1H), 1.92-1.83 (m, 3H), 1.75-1.58 (m, 5H), 1.38-1.37 (m, 9H), 1.30-1.26 (m, 5H), 1.13-1.10 (m, 9H), 1.02 (m, 2H), 0.95-0.81 (m, 18H); ESI-MS: m/z 803.59 (M+H)$^+$; HPLC: 95.83%.

Example 34: Preparation of (1R,3S)-3-((((3aR,5aR, 5bR,7aR,9S,11aR,11bR,13aS)-3a-(2-(2-(1,1-dioxi-dothiomorpholino)acetamido)-2-methylpropana-mido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid

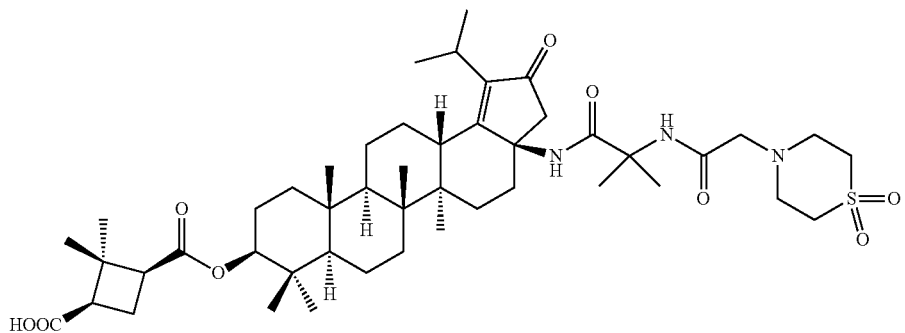

Intermediate 1 was coupled with 4-(carboxymethyl)thiomorpholin-4-ium 1,1-dioxide 2,2,2-trifluoroacetate (Intermediate 22) followed by hydrolysis gave the desired product as a white solid. $^1$H NMR (300 MHz, DMSO-$d_6$): δ ppm 12.19 (brs, 1H), 7.15 (s, 1H), 6.73 (brs, 1H), 4.38-4.33 (m, 1H), 3.11-3.07 (m, 1H), 2.86-2.73 (m, 3H), 2.39-2.27 (m, 3H), 2.17-1.99 (m, 2H), 1.92-1.87 (m, 3H), 1.69-1.56 (m, 8H), 1.39-1.27 (m, 21H), 1.14-1.09 (m, 12H), 0.91-0.81 (m, 16H); HPLC: 94.66%.

Example 35: Preparation of (1R,3S)-3-((((3aR,5aR, 5bR,7aR,9S,11aR,11bR,13aS)-1-iso propyl-5a,5b,8, 8,11a-pentamethyl-3a-(2-methyl-2-(piperidine-4-carboxamido)propanamido)-2-oxo-3,3a,4,5,5a,5b,6, 7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid hydrochloride

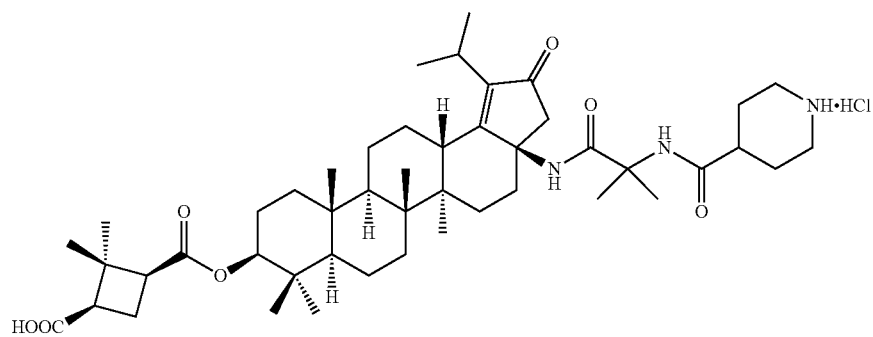

Step 1: Synthesis of (1R,3S)-3-((((3aR,5aR,5bR, 7aR,9S,11aR,11bR,13aS)-3a-(2-(1-(tert-butoxy)carbonyl)piperidine-4-carboxamido)-2-methylpropanamido)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl)oxy)carbonyl)-2,2-dimethylcyclobutane-1-carboxylic acid

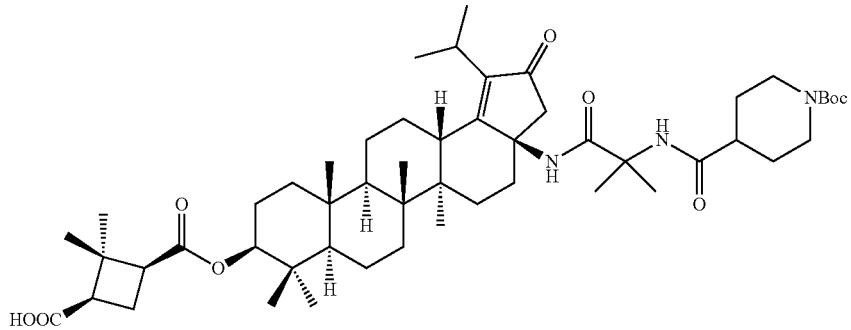

Intermediate 1 was coupled with 1-(tert-butoxy)carbonyl piperidine-4-carboxylic acid followed by hydrolysis gave the desired product as a white solid. $^1$H NMR (300 MHz, DMSO-$d_6$): δ ppm 12.16 (brs, 1H), 7.14 (s, 1H), 6.09 (s, 1H), 4.47-4.42 (m, 1H), 4.11 (brs, 2H), 3.15 (m, 1H), 3.02-2.57 (m, 8H), 2.28-2.22 (m, 3H), 2.05-1.83 (m, 3H), 1.67-1.62 (m, 4H), 1.56-1.54 (m, 7H), 1.45-1.40 (m, 13H), 1.36-1.34 (s, 6H), 1.28-1.20 (m, 9H), 1.13 (s, 3H), 0.96-0.91 (m, 11H), 0.85 (m, 7H); ESI-MS: m/z 892.53 (M+H)$^+$.

Step 2: Synthesis of (1R,3S)-3-((((3aR,5aR,5bR, 7aR,9S,11aR,11bR,13aS)-1-isopropyl-5a,5b,8,8,11a-pentamethyl-3a-(2-methyl-2-(piperidine-4-carboxamido)propanamido)-2-oxo-3,3a,4, 5, 5a, 5b,6,7,7a, 8,9,10,11,11a,11b, 12,13,13a-octadecahydro-2H-cyclopenta[a]chrysen-9-yl) oxy)carbonyl)-2,2-dimethylcyclobutane-1-carboxylic acid hydrochloride To a stirred solution of (1R,3S)-3-((((3aR,5aR,5bR,7aR, 9S,11aR,11bR,13aS)-3a-(2-(1-(tert-butoxy)carbonyl)piperidine-4-carboxamido)-2-methylpropanamido)-1-isopropyl-5a,5b,8,8,11a-pentamethyl-2-oxo-3,3a,4,5,5a,5b,6,7,7a,8,9, 10,11,11a,11b,12,13,13a-octadeca hydro-2H-cyclopenta[a] chrysen-9-yl)oxy)carbonyl)-2,2-dimethylcyclobutane-1-carboxylic acid (step 1, 0.52 g, 0.58 mmol, 1.0 eq) in DCM (15 ml) then cooled to 0° C. and added 1,4-Dioxane.Hcl (10 ml) then the reaction mixture was stirred at room temperature for about 14 hours. TLC indicated starting material was consumed and the desired product was observed. The organic phase was evaporated under reduced pressure to get the solid compound, that solid compound was stirred in MTBE for about 1 hour and filtered through Buchner funnel then the solid was washed with n-pentane then the solid compound was filtered through the Buchner funnel to obtain the desired product (210 mg, yield: 43.75%) as a white solid. $^1$H NMR (300 MHz, DMSO-$d_6$): δ ppm 12.16 (brs, 1H), 8.91-8.88 (m, 1H), 8.43-8.37 (m, 1H), 7.88 (s, 1H), 7.24 (s, 1H), 4.38-4.33 (m, 1H), 3.26-3.22 (m, 2H), 3.07 (s, 2H), 2.85-2.83 (m, 3H), 2.39-2.31 (m, 2H), 2.06-1.58 (m, 14H), 1.48-1.32 (m, 14H), 1.27-1.10 (m, 16H), 1.07-0.81 (m, 15H); ESI-MS: m/z 792.57 (M+H)$^+$; HPLC: 91.08%, Chloride content is 4.2%.

Example 36: Preparation of (1R,3S)-3-((((3aR,5aR, 5bR,7aR,9S,11aR,11bR,13aS)-3a-(2-((S)-2-amino-3-methylbutanamido)-2-methylpropanamido)-1-isopropyl-5a,5b,8,8,11a-penta methyl-2-oxo-3,3a,4,5, 5a,5b,6,7,7a,8,9,10,11,11a,11b,12,13,13a-octadecahydro-2H-cyclo penta[a]chrysen-9-yl)oxy) carbonyl)-2,2-dimethylcyclobutane-1-carboxylic acid hydrochloride

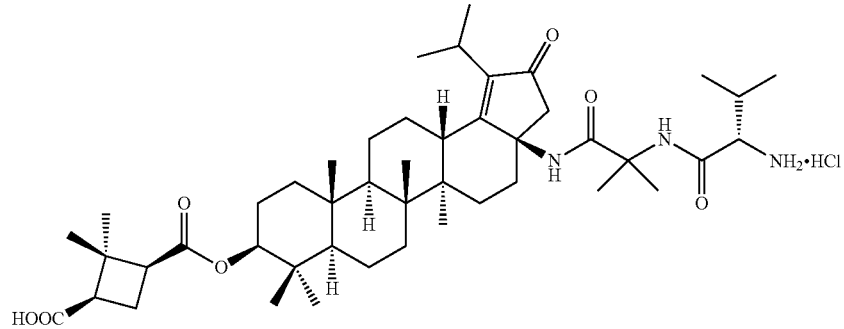

Step 1: Synthesis of (1R,3S)-3-((((3aR,5aR,5bR, 7aR,9S,11aR,11bR,13aS)-3a-(2-((S)-2-((tert-butoxy)carbonyl)amino)-3-methylbutanamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

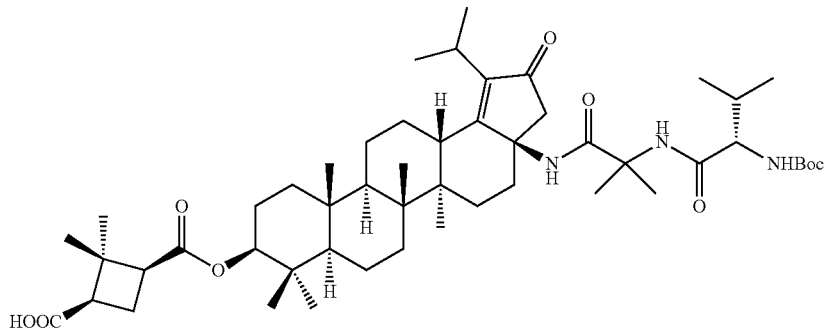

Intermediate 1 was coupled with (tert-butoxy)carbonyl)-L-valine followed by hydrolysis gave the desired product as a white solid. $^1$H NMR (300 MHz, DMSO-$d_6$): δ ppm 12.09 (brs, 1H), 7.98-6.91 (m, 3H), 4.38-4.33 (m, 1H), 3.67-3.54 (m, 1H), 3.11-3.07 (m, 2H), 2.83-2.79 (m, 2H), 2.39-2.09 (m, 2H), 2.01-1.86 (m, 6H), 1.75-1.49 (m, 7H), 1.38-1.26 (m, 24H), 1.13-1.107 (m, 12H), 0.91-0.82 (m, 20H); ESI-MS: m/z 880.48 (M+H)$^+$.

Step 2: Synthesis of (1R,3S)-3-((((3aR,5aR,5bR, 7aR,9S,11aR,11bR,13aS)-3a-(2-((S)-2-amino-3-methylbutanamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid hydrochloride To a stirred solution of (1R,3S)-3-((((3aR,5aR,5bR,7aR,9S,11aR,11bR,13aS)-3a-(2-((S)-2-((tert-butoxy)carbonyl)amino)-3-methylbutanamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (step 1, 0.52 g, 0.58 mmol, 1.0 eq) in DCM (15 ml) then cool to 0° C. and added 1,4-Dioxane.Hcl (10 ml) then the reaction was stirred at room temperature for about 14 hours. TLC indicated starting material was consumed and the desired product was observed. The organic phase was evaporated under reduced pressure to get the solid compound, that solid compound was stirred in MTBE for about 1 hour and filtered through Buchner funnel then the solid was washed with n-pentane then the solid compound was filtered through the Buchner funnel to obtain the desired product (55 mg, yield: 14.86%) as a white solid. $^1$H NMR (300 MHz, DMSO-$d_6$): δ ppm 12.08 (brs, 1H), 8.56-8.40 (m, 3H), 7.32-7.26 (m, 1H), 4.38-4.36 (m, 1H), 3.62 (brs, 1H), 3.17-3.07 (m, 2H), 2.82-2.73 (m, 3H), 2.39-2.03 (m, 5H), 1.92-1.86 (m, 3H), 1.77-1.65 (m, 7H), 1.46-1.34 (m, 12H), 1.26 (s, 4H), 1.13-1.06 (m, 12H), 0.90-0.81 (m, 19H); ESI-MS: m/z 802.68 (M+Na)$^+$; HPLC: 95.54%, Chloride content 4.65%.

Example 37: Preparation of (1R,3S)-3-((((3aR,5aR,5bR,7aR,9S,11aR,11bR,13aS)-3a-(1-(4-chlorobenzamido)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

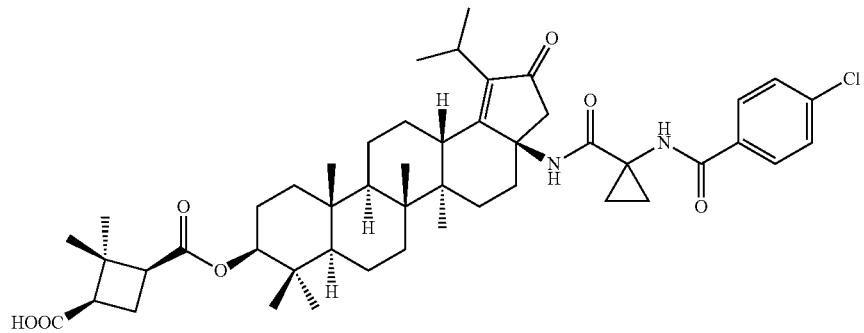

Intermediate 3 was coupled with 4-chlorobenzoic acid followed by hydrolysis gave the desired product as a white solid. $^1$H NMR (300 MHz, DMSO-d$_6$): δ ppm 12.14 (s, 1H), 8.85 (s, 1H), 7.93 (d, J=6.0 Hz, 2H), 7.57 (d, J=6.0 Hz, 2H), 7.48 (s, 1H), 4.36-4.31 (m, 1H), 3.11-3.07 (m, 2H), 2.83-2.67 (m, 5H), 2.38-2.12 (m, 6H), 1.89-1.83 (m, 3H), 1.71-1.63 (m, 4H), 1.57-1.47 (m, 8H), 1.43-1.39 (m, 11H), 1.29-1.26 (m, 6H), 1.12-0.80 (m, 12H); ESI-MS: m/z 817.45 (M+H)$^+$; HPLC: 97.69%.

Example 38: Preparation of (1R,3S)-3-((((3aR,5aR, 5bR,7aR,9S,11aR,11bR,13aS)-1-isopropyl-5a,5b,8, 8,11a-pentamethyl-3a-(1-(6-methylnicotinamido) cyclopropane-1-carbox amido)-2-oxo-3,3a,4,5,5a,5b, 6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid

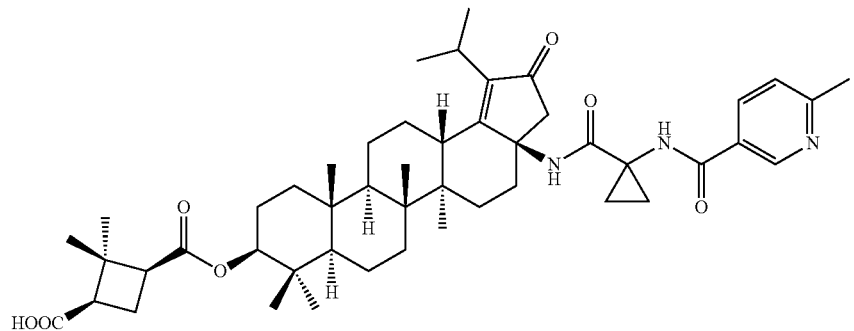

Intermediate 3 was coupled with 6-methylnicotinic acid followed by hydrolysis gave the desired product as a white solid. $^1$H NMR (300 MHz, DMSO-d$_6$): δ ppm 12.16 (brs, 1H), 8.95-8.86 (m, 2H), 8.14-8.11 (m, 1H), 7.50-7.36 (m, 2H), 4.37-4.31 (m, 1H), 3.11-3.07 (m, 1H), 2.83-2.76 (m, 2H), 2.45-2.07 (m, 6H), 1.89-1.83 (m, 2H), 1.71-1.47 (m, 9H), 1.44-1.26 (m, 20H), 1.29-1.07 (m, 4H), 1.03.-0.80 (m, 16H); ESI-MS: m/z 820.44 (M+H)$^+$ HPLC: 96.39%.

Example 39: Preparation of (1R,3S)-3-((((3aR,5aR, 5bR,7aR,9S,11aR,11bR,13aS)-3a-(1-(4-fluorobenzamido)cyclopropane-1-carboxamido)-1-isopropyl-5a,5b,8,8,11a-pentamethyl-2-oxo-3,3a,4,5,5a,5b,6,7, 7a,8,9,10,11,11a,11b,12,13,13a-octadecahydro-2H-cyclopenta[a]chrysen-9-yl)oxy)carbonyl)-2,2-dimethylcyclobutane-1-carboxylic acid

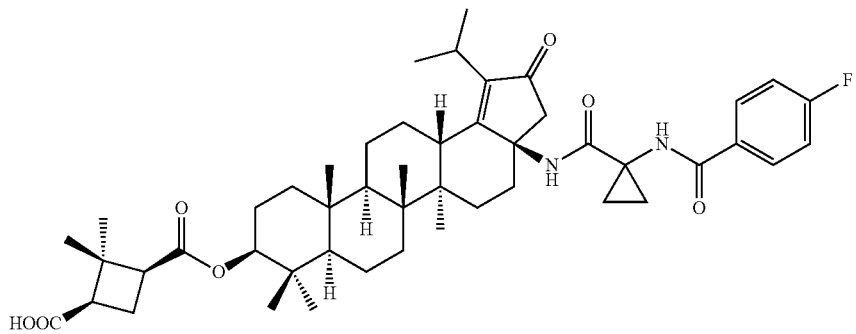

Intermediate 3 was coupled with 4-fluorobenzoic acid followed by hydrolysis gave the desired product as a white solid. $^1$H NMR (300 MHz, DMSO-d$_6$): δ ppm 12.14 (s, 1H), 8.81-8.00 (s, 1H), 7.98-7.96 (m, 2H), 7.49 (s, 1H), 7.36-7.30 (m, 2H), 4.36-4.31 (m, 1H), 3.17-3.07 (m, 2H), 2.83-2.76 (m, 2H), 2.45-2.12 (m, 5H), 1.89-1.83 (m, 2H), 1.73-1.57 (m, 9H), 1.47-1.43 (m, 11H), 1.26-1.12 (m, 9H), 1.10-1.03 (m, 5H), 1.00-0.90 (m, 12H); ESI-MS: m/z 823.35 (M+Na)$^+$; HPLC: 99.10%.

Example 40: Preparation of (1R,3S)-3-((((3aR,5aR,5bR,7aR,9S,11aR,11bR,13aS)-1-isopropyl-5a,5b,8,8,11a-pentamethyl-3a-(1-(4-methylbenzamido)cyclopropane-1-carb oxamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

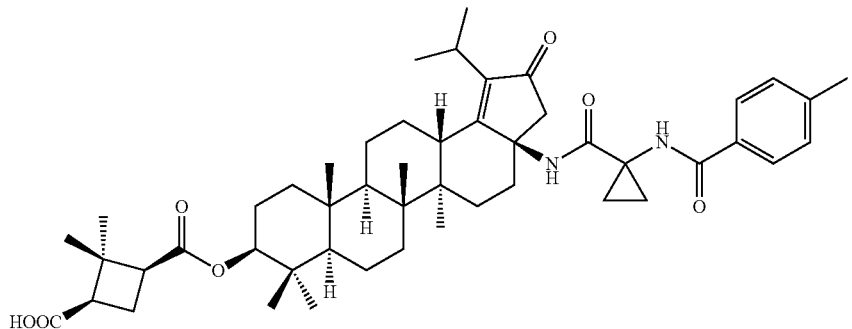

Intermediate 3 was coupled with 4-methylbenzoic acid followed by hydrolysis gave the desired product as a white solid. $^1$H NMR (300 MHz, DMSO-d$_6$): δ ppm 12.03 (brs, 1H), 8.74 (s, 1H), 7.80 (d, J=6.0 Hz, 2H), 7.43 (s, 1H), 7.28 (d, J=6.0 Hz, 2H), 4.36-4.31 (m, 1H), 3.11-3.07 (m, 1H), 2.82-2.73 (m, 3H), 2.45 (m, 1H), 2.39-2.12 (m, 8H), 1.92-1.83 (m, 2H), 1.71-1.40 (m, 9H), 1.26 (m, 8H), 1.12-1.10 (m, 9H), 1.02-1.00 (m, 4H), 0.90-0.87 (m, 5H), 0.84-0.80 (m, 10H); ESI-MS: m/z 819.16 (M+Na)$^+$; HPLC: 98.11%.

Example 41: Preparation of (1S,3R)-3-((((3aR,5aR,5bR,7aR,9S,11aR,11bR,13aS)-3a-(1-(4-chlorobenzamido)cyclopropane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

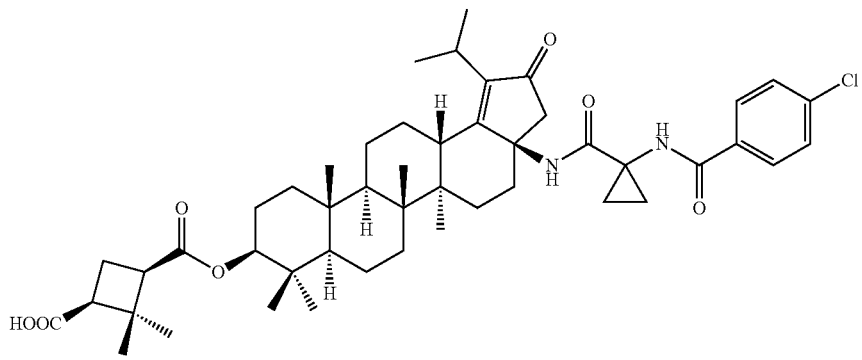

Intermediate 4 was coupled with 4-chlorobenzoic acid followed by hydrolysis gave the desired product as a white solid. $^1$H NMR (300 MHz, DMSO-d$_6$): δ ppm 12.14 (s, 1H), 8.85 (s, 1H), 7.93 (d, J=6.0 Hz, 2H), 7.57 (d, J=6.0 Hz, 2H), 7.48 (s, 1H), 4.36-4.31 (m, 1H), 3.11-3.07 (m, 1H), 2.87-2.73 (m, 3H), 2.45-2.38 (m, 1H), 2.33-2.22 (m, 2H), 2.18-2.12 (m, 1H), 1.98-1.82 (m, 2H), 1.73-1.40 (m, 8H), 1.29-1.26 (m, 10H), 1.17-1.10 (m, 7H), 1.01-0.93 (m, 4H), 0.89 (s, 3H) 0.84 (s, 3H) 0.79 (s, 12H); ESI-MS: m/z 817.50 (M+H)$^+$; HPLC: 93.55%.

Example 42: Preparation of (1R,3S)-3-((((3aR,5aR,5bR,7aR,9S,11aR,11bR,13aS)-3a-(1-(4-chlorobenzamido)cyclobutane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

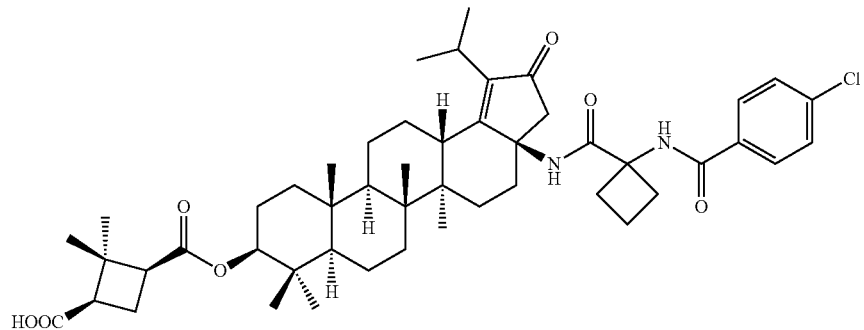

Intermediate 5 was coupled with 4-chlorobenzoic acid followed by hydrolysis gave the desired product as a white solid. $^1$H NMR (300 MHz, DMSO-d$_6$): δ ppm 12.14 (brs, 1H), 8.79 (s, 1H), 7.955 (d, J=9.0 Hz, 2H), 7.565 (d, J=9.0 Hz, 2H), 7.44 (s, 1H), 4.35-4.30 (m, 1H), 3.11-3.04 (m, 1H), 2.82-2.66 (m, 3H), 2.44-2.38 (m, 1H), 2.30-2.19 (m, 6H), 1.92-1.38 (m, 12H), 1.26 (brs, 8H), 1.15-1.10 (m, 7H), 0.98 (s, 3H), 0.90 (s, 3H), 0.83 (s, 3H), 0.79-0.77 (m, 6H), 0.72 (s, 3H), 0.58 (s, 3H); ESI-MS: m/z 853.62 (M+Na)$^+$; HPLC: 98.95%.

Example 43: Preparation of (1R,3S)-3-((((3aR,5aR,5bR,7aR,9S,11aR,11bR,13aS)-1-isopropyl-5a,5b,8,8,11a-pentamethyl-3a-(1-(6-methylnicotinamido)cyclobutane-1-carboxamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

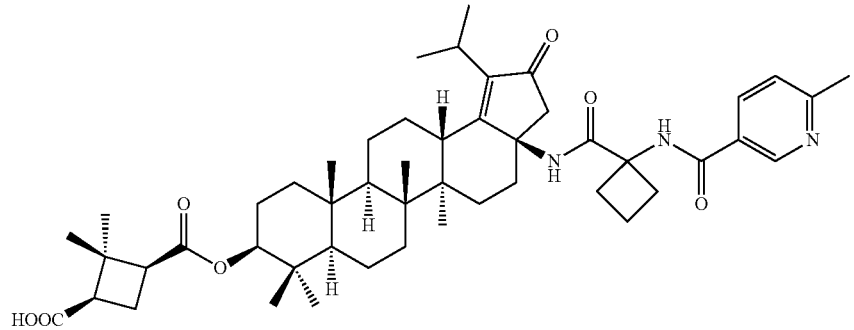

Intermediate 5 was coupled with 6-methylnicotinic acid followed by hydrolysis gave the desired product as a white solid. $^1$H NMR (300 MHz, DMSO-$d_6$): δ ppm 12.09 (brs, 1H), 8.98-8.83 (m, 2H), 8.17-8.13 (m, 1H), 7.46-7.36 (m, 2H), 4.35-4.30 (m, 1H), 3.11-3.07 (m, 1H), 2.94-2.68 (m, 4H), 2.59-2.56 (m, 2H), 2.44-2.13 (m, 6H), 1.89-1.76 (m, 13H), 1.26-1.23 (m, 8H), 1.15-1.11 (m, 7H), 0.97 (m, 3H), 0.90-0.71 (m, 15H), 0.58 (s, 3H); ESI-MS: m/z 812.52 (M+H)$^+$; HPLC: 94.64%.

Example 44: Preparation of (1R,3S)-3-((((3aR,5aR, 5bR,7aR,9S,11aR,11bR,13aS)-1-isopropyl-5a,5b,8, 8,11a-pentamethyl-2-oxo-3a-(1-(pyrimidine-2-carboxamido)cyclobutane-1-carboxamido)-3,3a,4,5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid

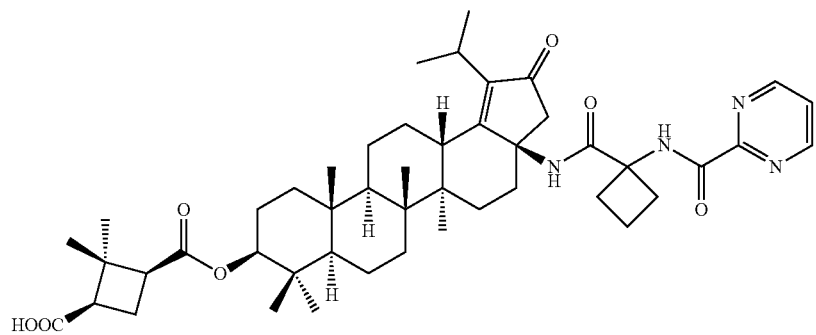

Intermediate 5 was coupled with pyrimidine-2-carboxylic acid followed by hydrolysis gave the desired product as a white solid. $^1$H NMR (300 MHz, DMSO-$d_6$): δ ppm 12.12 (brs, 1H), 9.31 (s, 1H), 9.00-8.99 (m, 2H), 7.74-7.70 (m, 1H), 7.51 (s, 1H), 4.35-4.29 (m, 1H), 3.10-3.06 (m, 1H), 2.82-2.75 (m, 2H), 2.72-2.63 (m, 3H), 2.34-2.18 (m, 6H), 1.92-1.36 (m, 12H), 1.26-1.11 (m, 15H), 1.01-0.97 (m, 2H), 0.90 (brs, 3H), 0.82-0.68 (m, 12H), 0.42 (brs, 3H); ESI-MS: m/z 799.79 (M+H)$^+$; HPLC: 98.35%.

Example 45: Preparation of (1R,3S)-3-((((3aR,5aR, 5bR,7aR,9S,11aR,11bR,13aS)-1-isopropyl-5a,5b,8, 8,11a-pentamethyl-3a-(1-(2-morpholinonicotinamido)cyclobutane-1-carboxamido)-2-oxo-3,3a,4,5, 5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid

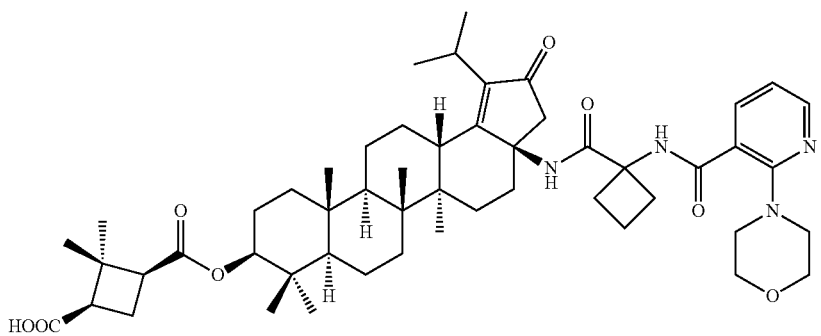

Intermediate 5 was coupled with 2-morpholinonicotinic acid followed by hydrolysis gave the desired product as a white solid. $^1$H NMR (300 MHz, DMSO-d$_6$): δ ppm 12.15 (brs, 1H), 8.94 (s, 1H), 8.27-8.25 (m, 1H), 7.86-7.83 (m, 1H), 7.48 (s, 1H), 6.95-6.91 (m, 1H), 4.37-4.32 (m, 1H), 3.67 (brs, 4H), 3.25 (bs, 2H), 3.11-3.07 (m, 2H), 2.79-2.73 (m, 3H), 2.50 (m, 2H), 2.41-2.14 (m, 6H), 1.91-1.78 (m, 7H), 1.57-1.46 (m, 6H), 1.31-1.26 (m, 6H), 1.14-1.10 (m, 9H), 0.90-0.88 (m, 10H), 0.81-0.80 (m, 10H); ESI-MS: m/z 905.84 (M+Na)$^+$; HPLC: 97.06%.

Example 46: Preparation of (1R,3S)-3-((((3aR,5aR,5bR,7aR,9S,11aR,11bR,13aS)-3a-(1-(4-chlorobenzamido) cyclopentane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

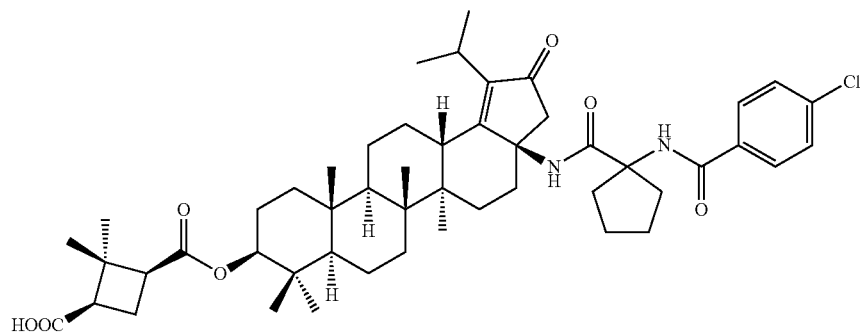

Intermediate 6 was coupled with 4-chlorobenzoic acid followed by hydrolysis gave the desired product as a white solid. $^1$H NMR (300 MHz, DMSO-d$_6$): δ ppm 12.08 (brs, 1H), 8.31 (s, 1H), 7.93 (d, J=9.0 Hz, 2H), 7.54 (d, J=9.0 Hz, 2H), 7.43 (s, 1H), 4.36-4.30 (m, 1H), 3.10-3.07 (m, 1H), 2.79 (m, 3H), 2.38-2.23 (m, 3H), 2.16-2.08 (m, 3H), 1.95-1.82 (m, 4H), 1.76-1.57 (m, 8H), 1.43-1.39 (m, 2H), 1.26 (brs, 8H), 1.03-1.10 (m, 8H), 1.04-0.96 (m, 2H), 0.90 (brs, 3H), 0.83-0.76 (m, 12H), 0.69 (brs, 3H); ESI-MS: m/z 845.21 (M+H)$^+$; HPLC: 95.88%.

Example 47: Preparation of (1R,3S)-3-((((3aR,5aR,5bR,7aR,9S,11aR,11bR,13aS)-1-isopropyl-5a,5b,8,8,11a-pentamethyl-3a-(1-(6-methylnicotinamido) cyclopentane-1-carboxamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

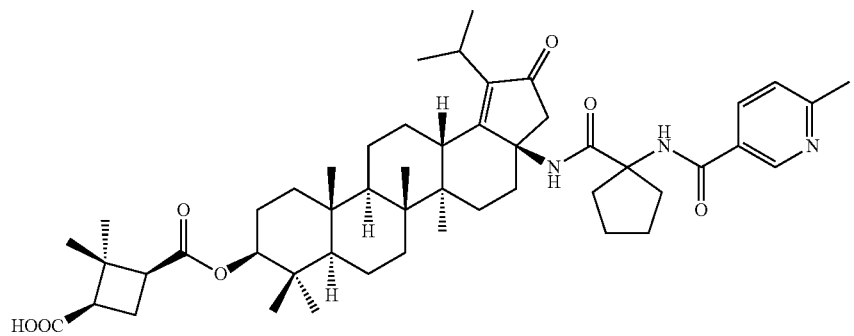

Intermediate 6 was coupled with 6-methylnicotinic acid followed by hydrolysis gave the desired product as a white solid. $^1$H NMR (300 MHz, DMSO-d$_6$): δ ppm 12.16 (brs, 1H), 8.95 (s, 1H), 8.34 (s, 1H), 8.15-8.11 (m, 1H), 7.43 (s, 1H), 7.37-7.34 (m, 1H), 4.36-4.31 (m, 1H), 3.11-3.06 (m, 1H), 2.79-2.76 (m, 1H), 2.39 (m, 1H), 2.16-2.07 (m, 4H), 1.95-1.43 (m, 16H), 1.39-1.25 (m, 11H), 1.14-1.12 (m, 7H), 1.04-0.99 (m, 2H), 0.96-0.86 (m, 18H), 0.84 (brs, 3H); ESI-MS: m/z 848.44 (M+Na)$^+$; HPLC: 99.78%.

Example 48: Preparation of (1R,3S)-3-((((3aR,5aR, 5bR,7aR,9S,11aR,11bR,13aS)-3a-(1-(4-chlorobenzamido) cyclohexane-1-carboxamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

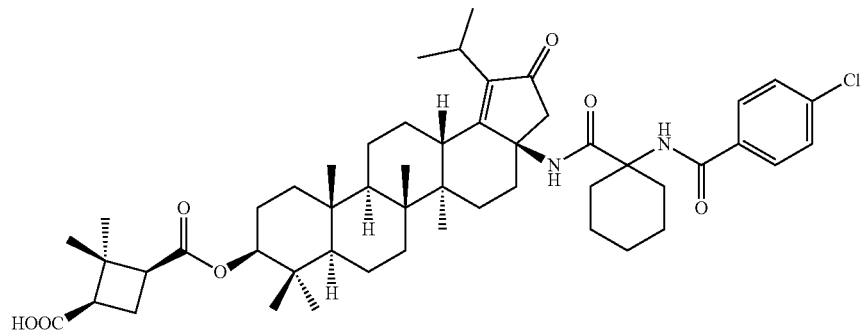

Intermediate 7 was coupled with 4-chlorobenzoic acid followed by hydrolysis gave the desired product as a white solid. $^1$H NMR (300 MHz, DMSO-d$_6$): δ ppm 12.17 (brs, 1H), 7.90 (d, J=8.4 Hz, 2H), 7.87 (s, 1H), 7.55 (d, J=8.4 Hz, 2H), 7.30 (s, 1H), 4.37-4.31 (m, 1H), 3.11-3.07 (m, 1H), 2.82-2.76 (m, 3H), 2.31-2.06 (m, 6H), 1.89-1.71 (m, 8H), 1.63-1.39 (s, 10H), 1.31 (m, 10H), 1.26-1.10 (m, 9H), 1.01-0.90 (m, 2H), 0.85-0.80 (m, 14H); ESI-MS: m/z 859.30 (M+H)$^+$; HPLC: 98.57%.

Example 49: Preparation of (1R,3S)-3-((((3aR,5aR, 5bR,7aR,9S,11aR,11bR,13aS)-1-isopropyl-5a,5b,8,8,11a-pentamethyl-3a-(1-(6-methylnicotinamido) cyclohexane-1-carboxamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

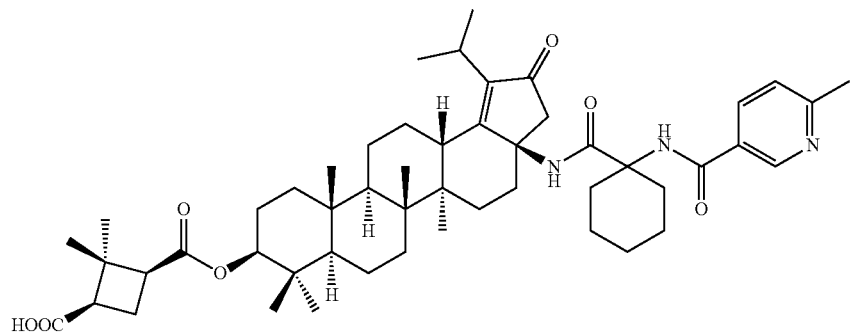

Intermediate 7 was coupled with 6-methylnicotinic acid followed by hydrolysis gave the desired product as a white solid. $^1$H NMR (300 MHz, DMSO-$d_6$): δ ppm 12.16 (brs, 1H), 8.926-8.920 (m, 1H), 8.12-8.09 (m, 1H), 7.93 (s, 1H), 7.37-7.31 (m, 2H), 4.37-4.31 (m, 1H), 3.07-2.75 (brs, 3H), 2.41-2.35 (m, 2H), 2.21-2.06 (m, 2H), 1.89-1.75 (m, 5H), 1.52 (brs, 10H), 1.42-1.26 (m, 8H), 1.13-1.10 (m, 10H), 1.06-0.96 (m, 4H), 0.90-0.79 (m, 22H); ESI-MS: m/z 840.52 (M+H)$^+$; HPLC: 99.89%.

Example 50: Preparation of (1R,3S)-3-((((3aR,5aR, 5bR,7aR,9S,11aR,11bR,13aS)-1-isopropyl-5a,5b,8, 8,11a-pentamethyl-3a-(1-(4-methylbenzamido)cyclohexane-1-carboxamido)-2-oxo-3,3a,4,5,5a,5b,6,7, 7a,8,9,10,11,11a,11b,12,13,13a-octadecahydro-2H-cyclopenta[a]chrysen 9-yl)oxy)carbonyl)-2,2-dimethylcyclobutane-1-carboxylic acid

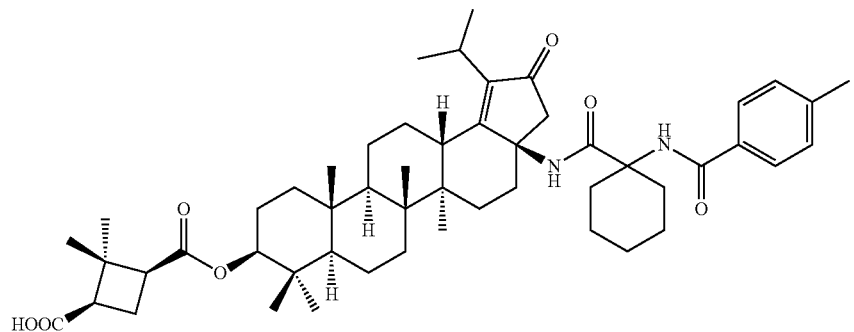

Intermediate 7 was coupled with 4-methylbenzoic acid followed by hydrolysis gave the desired product as a white solid. $^1$H NMR (300 MHz, DMSO-$d_6$): δ ppm 12.18 (brs, 1H), 8.74 (s, 1H), 7.757 (d, J=13.2 Hz, 2H), 7.34 (s, 1H), 7.291 (d, J=13.2, Hz, 2H), 4.37-4.32 (m, 1H), 3.11-3.06 (m, 1H), 2.82-2.76 (m, 1H), 2.43-2.36 (m, 6H), 2.16-2.06 (m, 6H), 1.89-1.64 (m, 7H), 1.51 (brs, 9H), 1.32-1.26 (m, 10H), 1.13-1.11 (m, 8H), 1.06-1.02 (m, 4H), 0.90-0.86 (m, 14H); ESI-MS: m/z 839.46 (M+H)$^+$; HPLC: 92.98%.

Example 51: Preparation of (1R,3S)-3-((((3aR,5aR, 5bR,7aR,9S,11aR,11bR,13aS)-1-isopropyl-5a,5b,8, 8,11a-pentamethyl-3a-(2-methyl-2-(4-(methylsulfonyl)benzamido) propanamido)-2-oxo-3,3a,4,5,5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

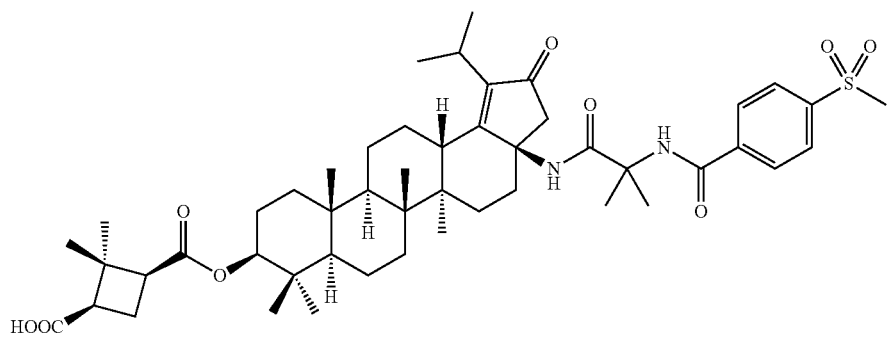

Step 1: Synthesis of 1-benzyl 3-((3aR,5aR,5bR,
7aR,9S,11aR,11bR,13aS)-1-isopropyl-5a,5b,8,8,11a-
pentamethyl-3a-(2-methyl-2-(4-(methylsulfonyl)
benzamido)propanamido)-2-oxo-3,3a, 4,5,5a,5b,6,7,
7a,8,9,10,11,11a,11b,12,13,13a-octadecahydro-2H-
cyclopenta[a]chrysen-9-yl) (1R,3S)-2,2-
dimethylcyclobutane-1,3-dicarboxylate

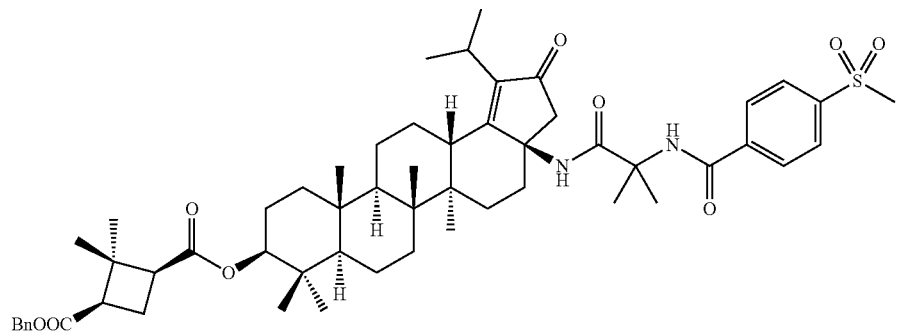

To a stirred solution of 4-(methylsulfonyl)benzoic acid (0.778 g, 3.889 mmol, 3.0 eq) in DMF (10 ml) was added HBTU (1.475 g, 3.889 mmol, 3.0 eq) followed by triethylamine (1.08 ml, 7.776 mmol, 6.0 eq). The reaction mixture was stirred at room temperature for about 30 minutes then 1-((3aR,5aR,5bR,7aR,9S,11aR,11bR,13aS)-3a-(2-amino-2-methyl propanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 3-benzyl (1S,3R)-2,2-di methylcyclobutane-1,3-dicarboxylate (Intermediate 1, 1.0 g, 1.296 mmol, 1.0 eq) was added and stirred at room temperature for overnight. TLC indicated starting material was consumed and the desired product was observed. The reaction mixture was diluted with water (120 ml) and extracted with ethyl acetate (2×50 ml). The combined organic extracts were washed with water (70 ml), dried over $Na_2SO_4$, filtered and evaporated under reduced pressure. The residue was purified by silicagel column chromatography by using 0-2% methanol in dichloromethane gradient. The fractions containing the expected product were combined and concentrated under reduced pressure to obtain the desired product (0.75 g, yield: 60.97%) as a white solid. $^1$H NMR (300 MHz, $CDCl_3$): δ ppm 8.0 (d, J=6.9 Hz, 2H), 7.96 (d, J=6.9 Hz, 2H), 7.34 (m, 5H), 7.18 (s, 1H), 6.70 (s, 1H), 5.15, 5.09 (ABq, $J_{AB}$=12.3 Hz, 2H), 4.45 (dd, J=11.1, 4.5 Hz, 1H), 3.22-3.11 (m, 1H), 3.06 (s, 3H), 2.84-2.72 (m, 3H), 2.70-2.60 (m, 2H), 2.38-2.26 (m, 2H), 2.09-1.98 (m, 1H), 1.97-1.83 (m, 3H), 1.72 (brs, 6H), 1.71-1.40 (m, 9H), 1.40-1.29 (m, 2H), 1.34 (s, 3H), 1.27-1.17 (m, 8H), 1.08 (s, 3H), 0.96 (s, 3H), 0.95 (s, 3H), 0.89 (s, 3H), 0.85 (s, 3H), 0.84 (s, 3H), 0.79 (m, 1H); ESI-MS: m/z 976.15 (M+Na)$^+$.

Step 2: Synthesis of (1R,3S)-3-((((3aR,5aR,5bR,
7aR,9S,11aR,11bR,13aS)-1-isopropyl-5a,5b,8,8,11a-
pentamethyl-3a-(2-methyl-2-(4-(methylsulfonyl)
benzamido)propanamido)-2-oxo-3, 3a,4,5,5a,5b,6,7,
7a,8,9,10,11,11a,11b,12,13,13a-octadecahydro-2H-
cyclopenta[a]chrysen-9-yl)oxy)carbonyl)-2,2-
dimethylcyclobutane-1-carboxylic acid To a stirred solution of 1-benzyl 3-((3aR,5aR,5bR,7aR,9S,11aR,11bR,13aS)-1-isopropyl-5a,5b,8,8,11a-pentamethyl-3a-(2-methyl-2-(4-(methylsulfonyl)benzamido)propan amido)-2-oxo-3,3a,4,5,5a,5b,6,7,7a,8,9,10,11,11a,11b,12,13,13a-octadecahydro-2H-cyclo penta[a]chrysen-9-yl) (1R,3S)-2,2-dimethylcyclobutane-1,3-dicarboxylate (step 1, 0.750 g, 0.786 mmol, 1.0 eq) in MeOH (7.5 ml) and THF (7.5 ml) was added aqueous 2.5N KOH solution (2.36 ml, 5.89 mmol, 7.5 eq). The reaction mixture was stirred at room temperature for overnight. TLC indicated starting material was consumed and the desired product was observed. The organic phase was evaporated under reduced pressure, the reaction mixture was diluted with water (10 ml), cooled to 0° C., pH adjusted to 5.0 with 1N HCl and extracted with DCM (2×50 ml). The combined organic extracts were washed with water (30 ml), dried over sodium sulfate, filtered and evaporated under reduced pressure. The residue was purified by silicagel column chromatography by using 0-5% methanol in dichloromethane gradient. The fractions containing the expected product were combined and concentrated under reduced pressure to obtain the solid. To this solid compound, $CH_3CN$:EtOAc (4:1, 10 ml) was added and heated to reflux for about 30 minutes. The mixture was cooled to 0° C., solid was filtered and dried under vacuum to obtain the desired product (0.275 g, yield: 40.48%) as a white solid. $^1$H NMR (300 MHz, $CDCl_3$): δ ppm 8.02 (d, J=8.4 Hz, 2H), 7.96 (d, J=8.4 Hz, 2H), 7.10 (s, 1H), 6.63 (s, 1H), 4.46 (dd, J=11.1, 4.5 Hz, 1H), 3.22-3.11 (m, 1H), 3.06 (s, 3H), 2.86-2.75 (m, 3H), 2.71-2.52 (m, 2H), 2.40-2.26 (m, 2H), 2.10-2.01 (m, 1H), 2.0-1.78 (m, 3H), 1.72 (brs, 6H), 1.69-1.40 (m, 9H), 1.40-1.32 (m, 2H), 1.37 (s, 3H), 1.26-1.20 (m, 8H), 1.08 (s, 3H), 1.06 (s, 3H), 0.96 (s, 3H), 0.89 (s, 3H), 0.86 (s, 3H), 0.85 (s, 3H), 0.79 (m, 1H); ESI-MS: m/z 863.6 (M+H)$^+$; HPLC: 97.9%.

The below examples 52-58 were prepared by the procedure similar (including reagents and reaction conditions) to the above described in the synthesis of example-51 using with their appropriate intermediates.

Example 52: Preparation of (1R,3S)-3-((((3aR,5aR, 5bR,7aR,9S,11aR,11bR,13aS)-1-isopropyl-5a,5b,8, 8,11a-pentamethyl-3a-(2-methyl-2-((S)-piperidine-3-carboxamido)propan amido)-2-oxo-3,3a,4,5,5a,5b,6, 7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid hydrochloride

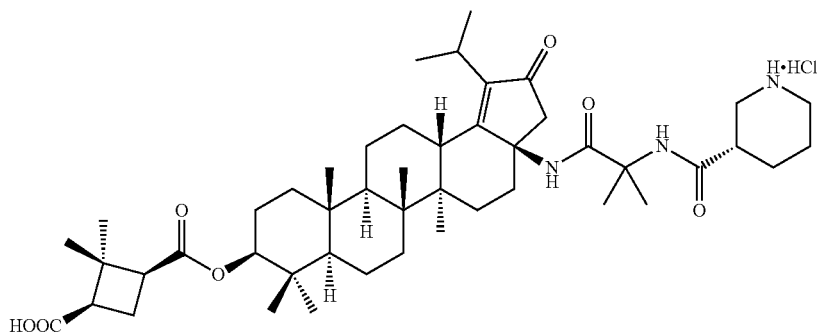

Step 1: Synthesis of (1R,3S)-3-((((3aR,5aR,5bR, 7aR,9S,11aR,11bR,13aS)-3a-(2-((S)-1-(tert-butoxy) carbonyl)piperidine-3-carboxamido)-2-methylpropanamido)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) oxy)carbonyl)-2,2-dimethylcyclobutane-1-carboxylic acid

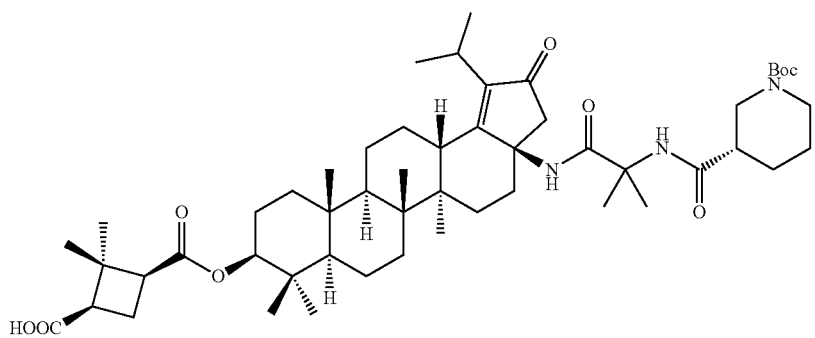

Intermediate 1 was coupled with (S)-1-(tert-butoxy)carbonyl)piperidine-3-carboxylic acid followed by hydrolysis gave the desired product as a white solid. $^1$H NMR (300 MHz, CDCl$_3$): δ ppm 4.47 (dd, J=11.1, 4.5 Hz, 1H), 3.83-3.50 (m, 2H), 3.40-3.02 (m, 3H), 3.0-2.73 (m, 4H), 2.68-2.53 (m, 2H), 2.38-2.20 (m, 4H), 2.10-1.65 (m, 15H), 1.58-1.53 (m, 4H), 1.53 (s, 3H), 1.46 (s, 9H), 1.37 (m, 4H), 1.35-1.32 (m, 2H), 1.25-1.18 (m, 7H), 1.14 (s, 3H), 1.07 (s, 3H), 0.93 (s, 3H), 0.92 (s, 3H), 0.87 (s, 3H), 0.85 (s, 3H), 0.83 (m, 1H); ESI-MS: m/z 914.71 (M+Na)$^+$.

Step 2: Synthesis of (1R,3S)-3-((((3aR,5aR,5bR, 7aR,9S,11aR,11bR,13aS)-1-isopropyl-5a,5b,8,8,11a-pentamethyl-3a-(2-methyl-2-((S)-piperidine-3-carboxamido)propanamido)-2-oxo-3, 3a,4,5,5a,5b,6,7, 7a,8,9, 10,11,11a,11b,12,13,13a-octadecahydro-2H-cyclopenta[a]chrysen-9-yl)oxy)carbonyl)-2,2-dimethylcyclobutane-1-carboxylic acid hydrochloride A solution of (1R,3S)-3-((((3aR,5aR,5bR,7aR,9S,11aR, 11bR,13aS)-3a-(2-((S)-1-(tert-butoxy)carbonyl)piperidine-3-carboxamido)-2-methylpropanamido)-1-isopropyl-5a,5b, 8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (step 1, 0.500 g, 0.560 mmol, 1.0 eq) and 3N HCl in 1,4-dioxane (10 ml) was stirred at room temperature for overnight. TLC indicated starting material was consumed and the desired product was observed. The reaction mixture was evaporated under reduced pressure, MTBE (10 ml) was added and heated to reflux for about 30 minutes. The reaction mixture was cooled to 0° C., filtered, solid was washed with MTBE (10 ml) and dried under vacuum to obtain the desired product (0.220 g, yield: 47.4%) as a white solid. $^1$H NMR (300 MHz, CD$_3$OD): δ ppm 8.02 (s, 1H), 7.15 (s, 1H), 4.32-4.23 (m, 1H), 3.07-2.85 (m, 6H), 2.80-2.55 (m, 4H), 2.50-2.21 (m, 3H), 2.21-1.93 (m, 2H), 1.93-1.76 (m, 4H), 1.76-1.58 (m, 5H), 1.58-1.40 (m, 4H), 1.40-1.36 (m, 2H), 1.36-1.21 (m, 11H), 1.17 (s, 3H), 1.15-1.10 (m, 1H), 1.08-1.0 (m, 9H), 0.96-0.89 (m, 1H), 0.87-0.78 (m, 7H), 0.72 (brs, 6H); ESI-MS: m/z 792.58 (M−HCl+H)$^+$; HPLC: 90.7%; chloride content by Ion chromatography: 6.8%.

Example 53: Preparation of (1R,3S)-3-((((3aR,5aR,5bR,7aR,9S,11aR,11bR,13aS)-3a-(2-(2-(4-chlorophenyl)acetamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

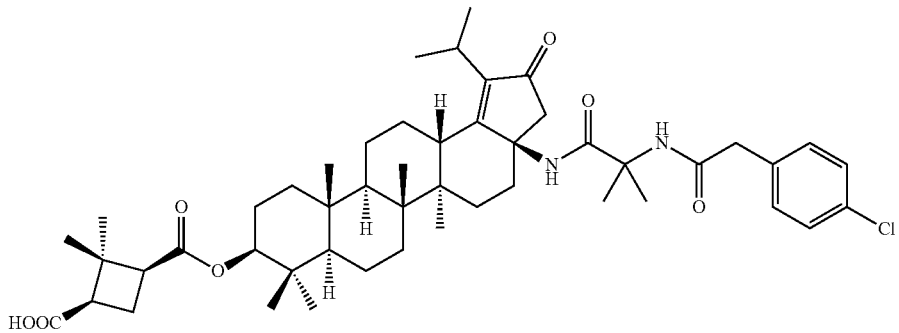

Intermediate 1 was coupled with 2-(4-chlorophenyl)acetic acid followed by hydrolysis gave the desired product as a white solid. $^1$H NMR (300 MHz, CDCl$_3$): δ ppm 7.33 (d, J=8.1 Hz, 2H), 7.19 (d, J=8.4 Hz, 2H), 7.11 (brs, 1H), 5.84 (brs, 1H), 4.47 (dd, J=11.1, 4.5 Hz, 1H), 3.50 (s, 2H), 3.20-3.08 (m, 1H), 2.87-2.70 (m, 3H), 2.67-2.53 (m, 2H), 2.29-2.02 (m, 3H), 1.98-1.65 (m, 6H), 1.55-1.47 (m, 4H), 1.51 (s, 3H), 1.49 (s, 3H), 1.42-1.35 (m, 2H), 1.37 (s, 3H), 1.28-1.18 (m, 9H), 1.13-1.03 (m, 1H), 1.10 (s, 3H), 1.07 (s, 3H), 0.93 (s, 3H), 0.91 (s, 3H), 0.89-0.78 (m, 7H); ESI-MS: m/z 855.6 (M+Na)$^+$; HPLC: 89.2%+9% isomer.

Example 54: Preparation of (1R,3S)-3-((((3aR,5aR,5bR,7aR,9S,11aR,11bR,13aS)-1-isopropyl-5a,5b,8,8,11a-pentamethyl-3a-(2-methyl-2-(pyrazolo[1,5-a]pyrimidine-3-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

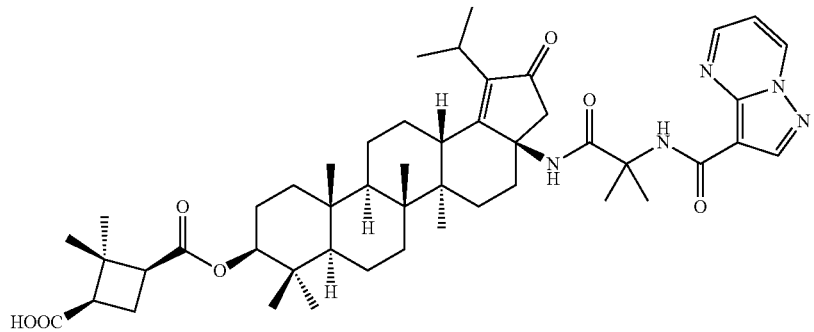

Intermediate 1 was coupled with pyrazolo[1,5-a]pyrimidine-3-carboxylic acid followed by hydrolysis gave the desired product as an off-white solid. ¹H NMR (300 MHz, CDCl₃): δ ppm 11.74 (brs, 1H), 9.02 (dd, J=7.2, 1.5 Hz, 1H), 8.75 (dd, J=4.2, 1.5 Hz, 1H), 8.57 (s, 1H), 8.27 (s, 1H), 7.66 (m, 1H), 7.16 (dd, J=6.9, 4.2 Hz, 1H), 4.40 (dd, J=10.5, 4.5 Hz, 1H), 3.20-3.10 (m, 1H), 2.97-2.83 (m, 1H), 2.81-2.70 (m, 2H), 2.62-2.58 (m, 2H), 2.42-2.12 (m, 2H), 2.07-1.87 (m, 4H), 1.80-1.50 (m, 6H), 1.66 (s, 3H), 1.62 (s, 3H), 1.47-1.31 (m, 4H), 1.34 (s, 3H), 1.23-1.15 (m, 8H), 1.05-0.97 (m, 1H), 1.02 (s, 3H), 0.99 (s, 3H), 0.92 (s, 3H), 0.88-0.78 (m, 10H); ESI-MS: m/z 826.7 (M+H)⁺; HPLC: 91%.

Example 55: Preparation of (1R,3S)-3-((((3aR,5aR, 5bR,7aR,9S,11aR,11bR,13aS)-3a-(2-(2-aminothiazole-4-carboxamido)-2-methylpropanamido)-1-isopropyl-5a,5b,8,8,11a-penta methyl-2-oxo-3,3a,4,5, 5a,5b,6,7,7a,8,9,10,11,11a,11b,12,13,13a-octadecahydro-2H-cyclo penta[a]chrysen-9-yl)oxy) carbonyl)-2,2-dimethylcyclobutane-1-carboxylic acid

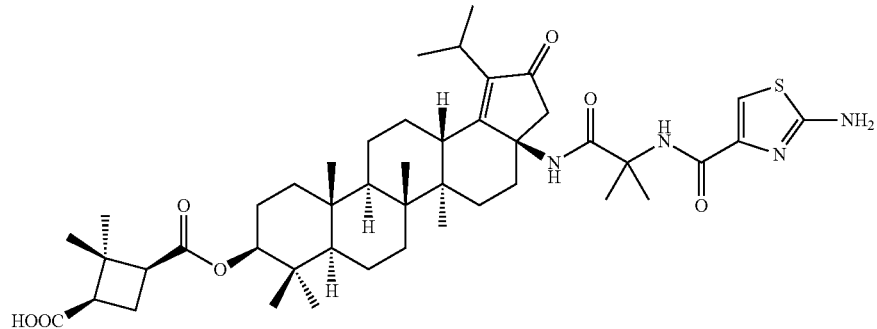

Intermediate 1 was coupled with 2-aminothiazole-4-carboxylic acid (Intermediate 14) followed by hydrolysis gave the desired product as an off-white solid. ¹H NMR (300 MHz, DMSO-d₆): δ ppm 12.18 (brs, 1H), 7.95 (s, 1H), 7.66 (s, 1H), 7.20 (brs, 2H), 7.13 (s, 1H), 4.40-4.32 (m, 1H), 3.18-3.07 (m, 1H), 2.85-2.72 (m, 3H), 2.40-2.22 (m, 3H), 2.13 (d, J=18.3 Hz, 1H), 2.0-1.82 (m, 3H), 1.80-1.61 (m, 3H), 1.60-1.44 (m, 2H), 1.52 (brs, 6H), 1.43-1.30 (m, 5H), 1.30-1.23 (m, 2H), 1.26 (s, 3H), 1.18-1.10 (m, 7H), 1.08-0.98 (m, 1H), 1.0 (s, 3H), 0.91 (s, 3H), 0.89 (s, 3H), 0.88-0.72 (m, 10H); ESI-MS: m/z 829.54 (M+Na)⁺; HPLC: 91.3%.

Example 56: Preparation of (1R,3S)-3-((((3aR,5aR, 5bR,7aR,9S,11aR,11bR,13aS)-1-isopropyl-5a,5b,8, 8,11a-pentamethyl-3a-(2-methyl-2-(4-(5-methyl-1,3, 4-oxadiazol-2-yl) benzamido)propanamido)-2-oxo-3,3a,4,5,5a,5b,6,7,7a,8,9,10,11,11a,11b,12,13,13a-octa decahydro-2H-cyclopenta[a]chrysen-9-yl)oxy) carbonyl)-2,2-dimethylcyclobutane-1-carboxylic acid

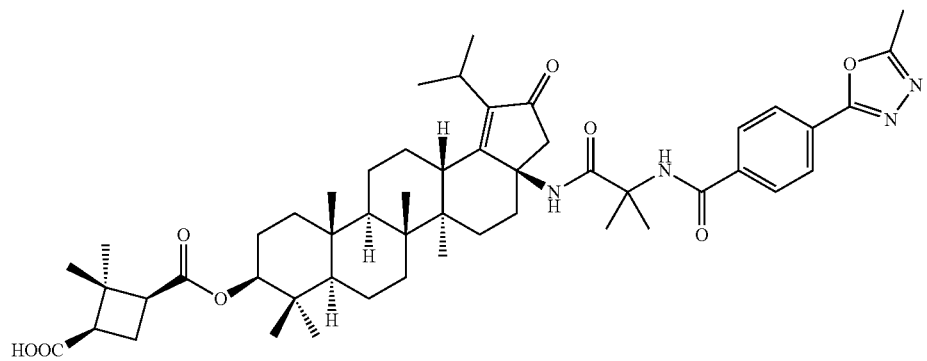

Intermediate 1 was coupled with 4-(5-methyl-1,3,4-oxadiazol-2-yl)benzoic acid (Intermediate 15) followed by hydrolysis gave the desired product as a white solid. $^1$H NMR (300 MHz, CDCl$_3$): δ ppm 8.11 (d, J=8.4 Hz, 2H), 7.91 (d, J=8.4 Hz, 2H), 6.98 (s, 1H), 6.92 (s, 1H), 4.46 (dd, J=11.1, 4.5 Hz, 1H), 3.22-3.10 (m, 1H), 2.88-2.70 (m, 4H), 2.65 (s, 3H), 2.61-2.52 (m, 1H), 2.38-2.27 (m, 2H), 2.10-1.83 (m, 5H), 1.80-1.67 (m, 1H), 1.72 (s, 3H), 1.71 (s, 3H), 1.65-1.42 (m, 7H), 1.40-1.31 (m, 2H), 1.36 (s, 3H), 1.28-1.20 (m, 7H), 1.08-1.04 (m, 7H), 0.95 (s, 3H), 0.90-0.78 (m, 10H); ESI-MS: m/z 889.67 (M+Na)$^+$; HPLC: 93.3%.

Example 57: Preparation of (1R,3S)-3-((((3aR,5aR,5bR,7aR,9S,11aR,11bR,13aS)-3a-(2-(4-(1,1-dioxidothiomorpholino)benzamido)-2-methylpropanamido)-1-isopropyl-5a,5b,8,8,11a-penta methyl-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid

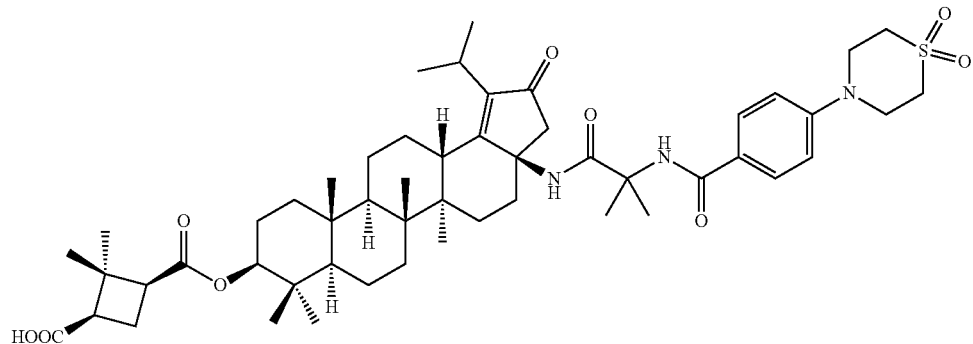

Intermediate 1 was coupled with 4-(1,1-dioxidothiomorpholino)benzoic acid (Intermediate 16) followed by hydrolysis gave the desired product as an off-white solid. $^1$H NMR (300 MHz, DMSO-d$_6$): δ ppm 12.10 (s, 1H), 7.92 (s, 1H), 7.80 (d, J=8.4 Hz, 2H), 7.31 (s, 1H), 7.07 (d, J=8.7 Hz, 2H), 4.40-4.30 (m, 1H), 3.90 (m, 4H), 3.09 (m, 5H), 2.87-2.70 (m, 3H), 2.48-2.18 (m, 4H), 2.06 (d, J=18.3 Hz, 1H), 1.98-1.80 (m, 3H), 1.80-1.48 (m, 6H), 1.42 (s, 3H), 1.40 (s, 3H), 1.38-1.20 (m, 6H), 1.26 (s, 3H), 1.18-1.10 (m, 6H), 0.93-0.75 (m, 20H); ESI-MS: m/z 940.72 (M+Na)$^+$; HPLC: 92.4%.

Example 58: Preparation of (1R,3S)-3-((((3aR,5aR,5bR,7aR,9S,11aR,11bR,13aS)-3a-(2-(4-((1,1-dioxidothiomorpholino)methyl)benzamido)-2-methylpropanamido)-1-isopropyl-5a,5b, 8,8,11a-pentamethyl-2-oxo-3,3a,4,5,5a,5b,6,7,7a,8,9,10,11,11a,11b,12,13,13a-octalecahydro-2H-cyclopenta[a]chrysen-9-yl)oxy)carbonyl)-2,2-dimethylcyclobutane-1-carboxylic acid

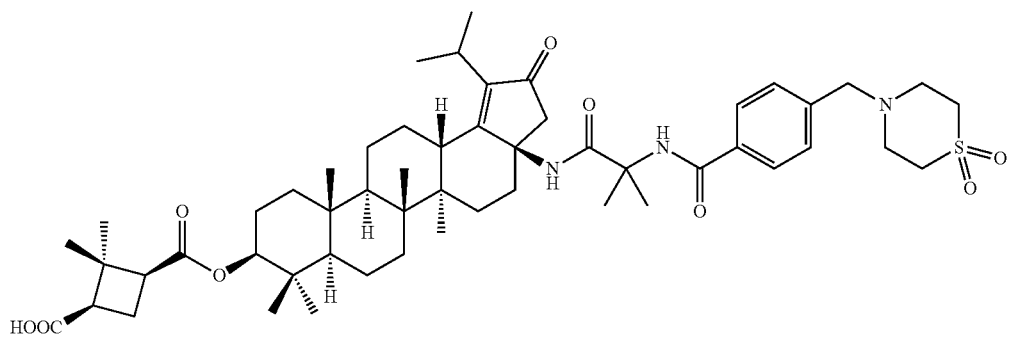

Intermediate 1 was coupled with 4-((1,1-dioxidothiomorpholino)methyl)benzoic acid (Intermediate 17) followed by hydrolysis gave the desired product as a white solid. $^1$H NMR (300 MHz, DMSO-d$_6$): δ ppm 11.8 (brs, 1H), 8.13 (s, 1H), 7.86 (d, J=7.8 Hz, 2H), 7.42 (d, J=7.8 Hz, 2H), 7.36 (s, 1H), 4.38-4.31 (m, 1H), 3.73 (s, 2H), 3.11 (m, 5H), 2.92-2.70 (m, 7H), 2.48-2.18 (m, 3H), 2.12-1.98 (m, 2H), 1.96-1.80 (m, 3H), 1.80-1.51 (m, 5H), 1.50-1.38 (m, 1H), 1.43 (s, 3H), 1.41 (s, 3H), 1.38-1.24 (m, 4H), 1.26 (s, 3H), 1.20-1.06 (m, 8H), 1.05-0.96 (m, 2H), 0.90 (s, 3H), 0.86 (m, 6H), 0.79 (m, 9H); ESI-MS: m/z 954.75 (M+Na)$^+$; HPLC: 92.9%.

Example 59: Preparation of (1R,3S)-3-((((3aR,5aR,5bR,7aR,9S,11aR,11bR,13aS)-3a-(2-(2-(dimethylamino)acetamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

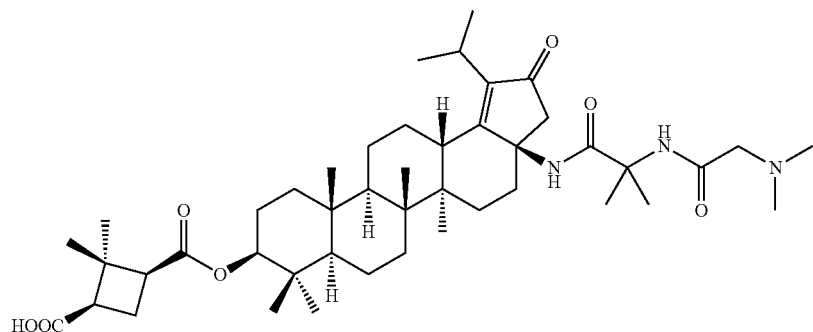

Step 1: Synthesis of 1-benzyl 3-((3aR,5aR,5bR,7aR,9S,11aR,11bR,13aS)-3a-(2-(2-(dimethyl amino)acetamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate

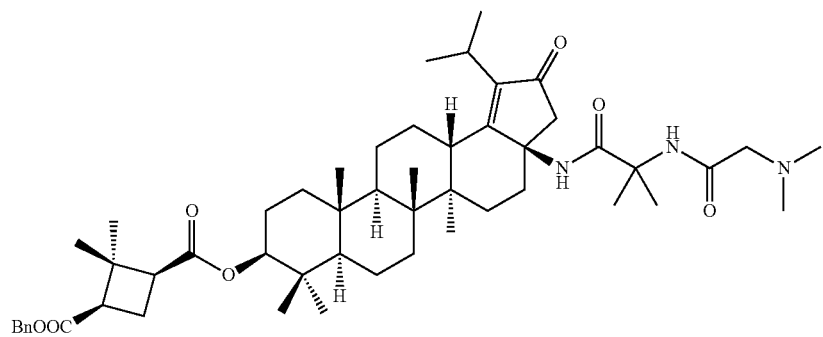

To a stirred solution of dimethyl glycine hydrochloride (0.543 g, 3.893 mmol, 3.0 eq) in DMF (10 ml) was added HATU (0.980 g, 2.59 mmol, 2.0 eq) followed by DIPEA (1.34 ml, 7.78 mmol, 6.0 eq). The reaction mixture was stirred at room temperature for about 30 minutes then 1-((3aR,5aR,5bR,7aR,9S,11aR,11bR,13aS)-3a-(2-amino-2-methylpropan amido)-1-isopropyl-5a,5b,8,8,11a-pentamethyl-2-oxo-3,3a,4,5,5a,5b,6,7,7a,8,9,10,11,11a, 11b,12,13, 13a-octadecahydro-2H-cyclopenta[a]chrysen-9-yl) 3-benzyl (1S,3R)-2,2-dimethyl cyclobutane-1,3-dicarboxylate (Intermediate 1, 1.0 g, 1.297 mmol, 1.0 eq) was added and stirred at the same temperature for overnight. TLC indicated starting material was consumed and the desired product was observed. The reaction mixture was diluted with water (150 ml) and extracted with DCM (3×20 ml). The combined organic extracts were washed with water (20 ml), dried over Na$_2$SO$_4$, filtered and evaporated under reduced pressure. The residue was purified by silicagel column chromatography by using 0-3% MeOH in DCM gradient. The fractions containing the product were combined and concentrated under reduced pressure to give the desired product (0.5 g, yield: 45.4%) as a white solid. $^1$H NMR (300 MHz, CDCl$_3$): δ ppm 7.99 (s, 1H), 7.46 (s, 1H), 7.35 (m, 5H), 5.15, 5.09 (ABq, J$_{AB}$=12.3 Hz, 2H), 4.45 (dd, J=11.4, 4.8 Hz, 1H), 3.20-3.10 (m, 1H), 2.97 (s, 2H), 2.87-2.73 (m, 3H), 2.70-2.60 (m, 2H), 2.33 (s, 6H), 2.30-2.22 (m, 2H), 2.08-1.99 (m, 2H), 1.98-1.83 (m, 2H), 1.80-1.72 (m, 2H), 1.60-1.53 (m, 2H), 1.56 (s, 3H), 1.51 (s, 3H), 1.49-1.38 (m, 4H), 1.38-1.30 (m, 2H), 1.34 (s, 3H), 1.27-1.18 (m, 8H), 1.13 (s, 3H), 1.10-0.98 (m, 1H), 0.96 (s, 3H), 0.93 (s, 3H), 0.92 (s, 3H), 0.85 (s, 3H), 0.84 (s, 3H), 0.78 (m, 1H); ESI-MS: m/z 856.4 (M+H)$^+$.

Step 2: Synthesis of (1R,3S)-3-((((3aR,5aR,5bR, 7aR,9S,11aR,11bR,13aS)-3a-(2-(2-(dimethyl amino) acetamido)-2-methylpropanamido)-1-isopropyl-5a, 5b,8,8,11a-pentamethyl-2-oxo-3,3a,4,5,5a,5b,6,7,7a, 8,9,10,11,11a,11b,12,13,13a-octadecahydro-2H-cyclopenta[a]chrysen-9-yl)oxy)carbonyl)-2,2-dimethylcydobutane-1-carboxylic acid To a stirred solution of 1-benzyl 3-((3aR,5aR,5bR,7aR, 9S,11aR,11bR,13aS)-3a-(2-(2-(dimethylamino)acetamido)-2-methylpropanamido)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) (1R,3S)-2,2-dimethylcyclobutane-1,3-dicarboxylate (step 1, 0.5 g, 0.584 mmol, 1.0 eq) in MeOH (10 ml) and THF (10 ml) was added aqueous 2.5N KOH solution (1.85 ml). The reaction mixture was stirred at room temperature for overnight. TLC indicated starting material was consumed and the desired product was observed. The organic phase was evaporated under reduced pressure, the reaction mixture was diluted with water (15 ml), cooled to 0° C., acidified with IN HCl to pH 5.0 and extracted with DCM (3×25 ml). The combined organic extracts were washed with water (10 ml), dried over sodium sulfate, filtered and evaporated under reduced pressure. The residue was purified by silicagel column chromatography by using 0-10% MeOH in DCM gradient. The fractions containing the product were combined and concentrated under reduced pressure to give a solid. To this solid compound, acetonitrile (15 ml) was added and heated to reflux for about 30 minutes. The mixture was cooled to 0° C., the solids formed were collected by filtration and were washed with n-hexane (10 ml) and dried under vacuum to obtain the desired product (0.266 g, yield: 59.5%) as a white solid. $^1$H NMR (300 MHz, CDCl$_3$): δ ppm 8.01 (s, 1H), 7.53 (s, 1H), 4.47 (dd, J=11.1, 4.5 Hz, 1H), 3.20-3.10 (m, 1H), 2.96 (s, 2H), 2.86-2.75 (m, 3H), 2.68-2.40 (m, 2H), 2.32 (s, 6H), 2.30-2.22 (m, 2H), 2.12-2.0 (m, 1H), 1.99-1.83 (m, 3H), 1.82-1.67 (m, 2H), 1.65-1.58 (m, 2H), 1.56 (s, 3H), 1.51 (s, 3H), 1.49-1.40 (m, 3H), 1.40-1.30 (m, 3H), 1.37 (s, 3H), 1.30-1.15 (m, 8H), 1.13 (s, 3H), 1.07 (s, 3H), 1.01 (m, 1H), 0.93 (s, 3H), 0.91 (s, 3H), 0.86 (s, 3H), 0.85 (s, 3H), 0.80 (m, 1H); ESI-MS: m/z 766.49 (M+H)$^+$; HPLC: 97.5%.

The below examples 60-61 were prepared by the procedure similar (including reagents and reaction conditions) to the above described in the synthesis of example-59 using with their appropriate intermediates.

Example 60: Preparation of (1R,3S)-3-((((3aR,5aR, 5bR,7aR,9S,11aR,11bR,13aS)-1-isopropyl-5a,5b,8, 8,11a-pentamethyl-3a-(2-methyl-2-(6-methylpicolinamido)propanamido)-2-oxo-3,3a,4,5,5a,5b,6,7, 7a,8,9,10,11,11a,11b,12,13,13a-octadecahydro-2H-cyclopenta[a]chrysen-9-yl)oxy)carbonyl)-2,2-dimethylcyclobutane-1-carboxylic acid

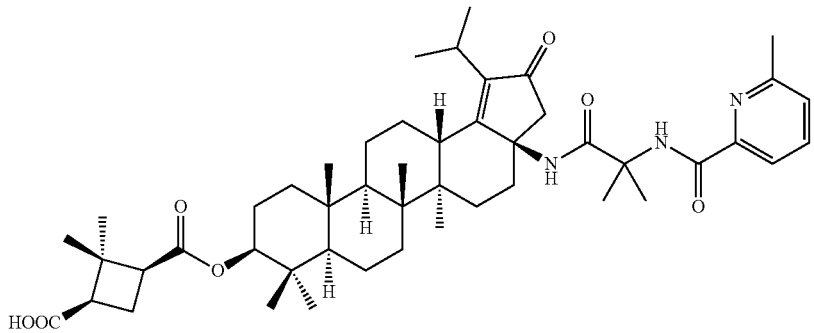

Intermediate 1 was coupled with 6-methylpicolinic acid followed by hydrolysis gave the desired product as a white solid. $^1$H NMR (300 MHz, DMSO-d$_6$): δ ppm 12.13 (brs, 1H), 8.76 (s, 1H), 7.90-7.80 (m, 2H), 7.62 (s, 1H), 7.47 (d, J=6.9 Hz, 1H), 4.39-4.31 (m, 1H), 3.18-3.06 (m, 1H), 2.88-2.70 (m, 3H), 2.55 (s, 3H), 2.48-2.38 (m, 2H), 2.27-2.22 (m, 2H), 2.14 (d, J=18.3 Hz, 1H), 2.0-1.62 (m, 6H), 1.55 (brs, 6H), 1.62-1.50 (m, 3H), 1.50-1.38 (m, 2H), 1.38-1.20 (m, 2H), 1.33 (s, 3H), 1.20-0.99 (m, 9H), 0.98-0.80 (m, 19H); ESI-MS: m/z 800.79 (M+H)$^+$; HPLC: 96.27%.

Example 61: Preparation of (1R,3S)-3-((((3aR,5aR,5bR,7aR,9S,11aR,11bR,13aS)-1-isopropyl-5a,5b,8,8,11a-pentamethyl-3a-(2-methyl-2-(6-methylnicotinamido)propanamido)-2-oxo-3,3a,4,5,5a,5b,6,7,7a,8,9,10,11,11a,11b,12,13,13a-octadecahydro-2H-cyclopenta[a]chrysen-9-yl) oxy)carbonyl)-2,2-dimethylcyclobutane-1-carboxylic acid

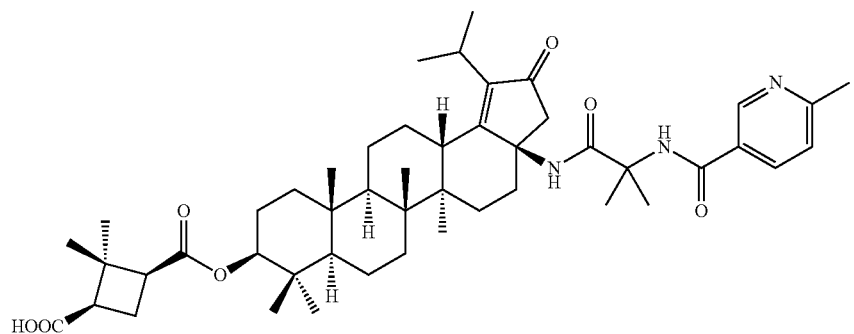

Intermediate 1 was coupled with 6-methylnicotinic acid followed by hydrolysis gave the desired product as a white solid. $^1$H NMR (300 MHz, CDCl$_3$): δ ppm 8.90 (d, J=1.8 Hz, 1H), 7.99 (dd, J=8.1, 2.4 Hz, 1H), 7.26 (d, 1H), 6.98 (brs, 1H), 6.80 (brs, 1H), 4.48 (dd, J=11.1, 4.5 Hz, 1H), 3.23-3.12 (m, 1H), 2.88-2.70 (m, 4H), 2.64 (s, 3H), 2.63-2.57 (m, 1H), 2.38-2.27 (m, 2H), 2.13-2.02 (m, 1H), 2.01-1.76 (m, 5H), 1.71 (brs, 6H), 1.66-1.43 (m, 8H), 1.39 (s, 3H), 1.37-1.20 (m, 8H), 1.20-1.15 (m, 1H), 1.08 (s, 3H), 1.07 (s, 3H), 0.96 (s, 3H), 0.90 (s, 3H), 0.88 (s, 3H), 0.86 (s, 3H), 0.80 (m, 1H); ESI-MS: m/z 800.6 (M+H)$^+$; HPLC: 95.4%.

Example 62: Preparation of (1R,3S)-3-((((3aR,5aR,5bR,7aR,9S,11aR,11bR,13aS)-1-isopropyl-5a,5b,8,8,11a-pentamethyl-3a-(2-methyl-2-pivalamidopropanamido)-2-oxo-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid

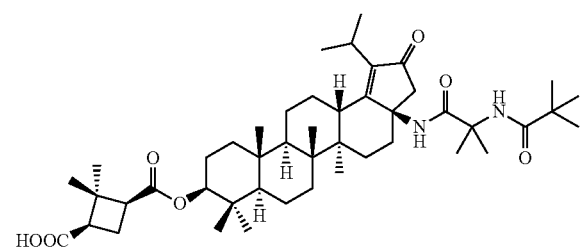

Step 1: Synthesis of 1-benzyl 3-((3aR,5aR,5bR,7aR,9S,11aR,11bR,13aS)-1-isopropyl-5a,5b,8,8,11a-pentamethyl-3a-(2-methyl-2-pivalamidopropanamido)-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate

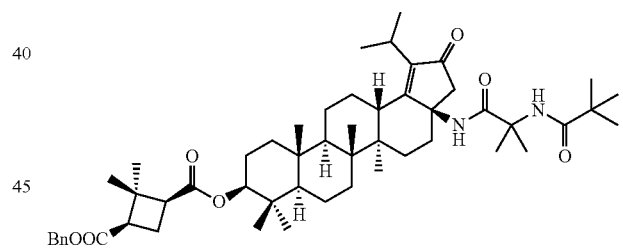

To a stirred solution of 1-((3aR,5aR,5bR,7aR,9S,11aR,11bR,13aS)-3a-(2-amino-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 3-benzyl (1S,3R)-2,2-dimethylcyclobutane-1,3-dicarboxylate (Intermediate 1, 0.800 g, 1.037 mmol, 1.0 eq) in DCM (10 ml) at 0° C. was added triethyl amine (0.72 ml, 5.187 mmol, 5.0 eq) followed by pivaloyl chloride (0.192 ml, 1.556 mmol, 1.5 eq). The reaction mixture was allowed to stir at room temperature for overnight. TLC indicated starting material was consumed and the desired product was observed. The reaction mixture was diluted with water (50 ml) and extracted with DCM (3×30 ml). The combined organic extracts were washed with 0.5N HCl (10 ml), water (20 ml), dried over sodium sulfate, filtered and evaporated under reduced pressure. The residue was purified by silicagel column chromatography by using 0-3% methanol in dichloromethane gradient. The fractions containing the expected product were combined and concentrated under reduced pressure to obtain the desired product (0.800 g, yield: 90.19%) as a white solid. $^1$H NMR (300 MHz, CDCl$_3$): δ ppm 7.35 (m, 5H), 5.97 (s, 1H), 5.15, 5.09 (ABq, J$_{AB}$=12.3 Hz, 2H), 4.45 (dd, J=11.4, 4.8 Hz, 1H), 3.20-3.10 (m, 1H), 2.87-2.73 (m, 3H), 2.71-2.57 (m, 2H), 2.36-2.22 (m, 2H), 2.09-2.0 (m, 1H), 1.98-1.82 (m, 3H), 1.78-1.60 (m, 5H), 1.55 (s, 3H), 1.53 (s, 3H), 1.50-1.38 (m, 4H), 1.37-1.30 (m, 3H), 1.34 (s, 3H), 1.26-1.20 (m, 6H), 1.18 (s, 9H), 1.14 (s, 3H), 1.10-1.0 (m, 1H), 0.96 (s, 3H), 0.95-0.89 (m, 1H), 0.93 (s, 3H), 0.91 (s, 3H), 0.85 (s, 3H), 0.84 (s, 3H), 0.81-0.77 (m, 1H); ESI-MS: m/z 855.56 (M+H)$^+$.

Step 2: Synthesis of (1R,3S)-3-((((3aR,5aR,5bR, 7aR,9S,11aR,11bR,13aS)-1-isopropyl-5a,5b,8,8,11a-pentamethyl-3a-(2-methyl-2-pivalamidopropanamido)-2-oxo-3,3a,4,5,5a,5b,6,7,7a,8,9,10,11,11a,11b, 12,13,13a-octadecahydro-2H-cyclopenta[a]chrysen-9-yl)oxy)carbonyl)-2,2-dimethylcydobutane-1-carboxylic acid To a stirred solution of 1-benzyl 3-((3aR,5aR,5bR,7aR, 9S,11aR,11bR,13aS)-1-isopropyl-5a,5b,8,8,11a-pentamethyl-3a-(2-methyl-2-pivalamidopropanamido)-2-oxo-3,3a, 4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 1, 0.800 g, 0.935 mmol, 1.0 eq) in MeOH (8 ml) and THF (8 ml) was added aqueous 2.5N KOH solution (2.8 ml, 7.015 mmol, 7.5 eq). The reaction mixture was stirred at room temperature for overnight. TLC indicated starting material was consumed and the desired product was observed. The organic phase was evaporated under reduced pressure, the reaction mixture was diluted with water (10 ml), cooled to 0° C., pH adjusted to 5.0 with 1N HCl and extracted with DCM (3×40 ml). The combined organic extracts were washed with water (40 ml), dried over sodium sulfate, filtered and evaporated under reduced pressure. The residue was purified by silica-gel column chromatography by using 0-4% methanol in dichloromethane gradient. The fractions containing the expected product were combined and concentrated under reduced pressure to obtain the desired product (0.320 g, yield: 44.71%) as a white solid. $^1$H NMR (300 MHz, CDCl$_3$): δ ppm 7.36 (s, 1H), 5.97 (s, 1H), 4.47 (dd, J=8.7, 3.3 Hz, 1H), 3.20-3.11 (m, 1H), 2.87-2.76 (m, 3H), 2.65-2.57 (m, 2H), 2.34-2.23 (m, 2H), 2.10-2.02 (m, 1H), 1.97-1.82 (m, 3H), 1.80-1.68 (m, 2H), 1.64-1.47 (m, 6H), 1.56 (s, 3H), 1.53 (s, 3H), 1.46-1.30 (m, 4H), 1.37 (s, 3H), 1.22 (s, 3H), 1.21 (s, 3H), 1.18 (s, 9H), 1.15 (s, 3H), 1.07 (s, 3H), 1.06-1.0 (m, 1H), 0.93 (s, 3H), 0.92 (s, 3H), 0.87 (s, 3H), 0.86 (s, 3H), 0.84-0.79 (m, 1H); ESI-MS: m/z 765.63 (M+H)$^+$; HPLC: 95.2%.

The below examples 63-66 were prepared by the procedure similar (including reagents and reaction conditions) to the above described in the synthesis of example-62 using with their appropriate intermediates.

Example 63: Preparation of sodium (1R,3S)-3-((((3aR,5aR,5bR,7aR,9S,11aR,11bR,13aS)-1-iso propyl-5a,5b,8,8,11a-pentamethyl-3a-(2-methyl-2-(methylsulfonamido)propanamido)-2-oxo-3,3a,4,5, 5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylate

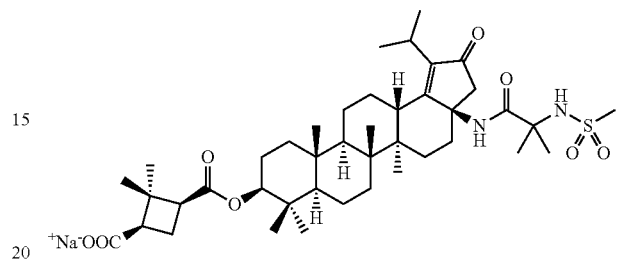

Step 1: Synthesis of (1R,3S)-3-((((3aR,5aR,5bR, 7aR,9S,11aR,11bR,13aS)-1-isopropyl-5a,5b,8,8,11a-pentamethyl-3a-(2-methyl-2-(methylsulfonamido) propanamido)-2-oxo-3,3a,4,5,5a, 5b,6,7,7a,8,9,10, 11,11a,11b,12,13,13a-octadecahydro-2H-cyclopenta [a]chrysen-9-yl)oxy) carbonyl)-2,2-dimethylcyclobutane-1-carboxylic acid

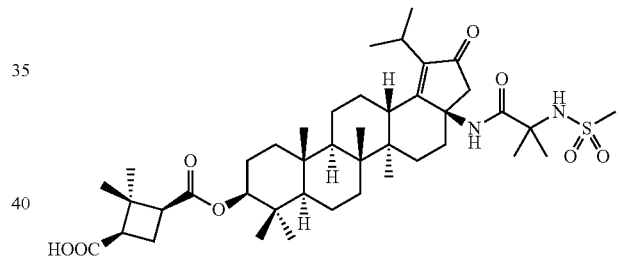

Intermediate 1 was coupled with methanesulfonyl chloride followed by hydrolysis gave the desired product as an off-white solid. $^1$H NMR (300 MHz, CDCl$_3$): δ ppm 6.50 (s, 1H), 4.96 (s, 1H), 4.46 (dd, J=11.1, 4.5 Hz, 1H), 3.22-3.10 (m, 1H), 3.07 (s, 3H), 2.87-2.75 (m, 3H), 2.69-2.53 (m, 2H), 2.35-2.24 (m, 2H), 2.11-2.0 (m, 1H), 1.97-1.82 (m, 3H), 1.79-1.65 (m, 2H), 1.65-1.53 (m, 2H), 1.60 (s, 3H), 1.58 (s, 3H), 1.52-1.43 (m, 3H), 1.42-1.30 (m, 3H), 1.37 (s, 3H), 1.29-1.18 (m, 8H), 1.14 (s, 3H), 1.07 (s, 3H), 1.03-0.97 (m, 1H), 0.94 (s, 3H), 0.92 (s, 3H), 0.86 (s, 3H), 0.85 (s, 3H), 0.79 (m, 1H); ESI-MS: m/z 759.51 (M+H)$^+$.

Step 2: Synthesis of sodium (1R,3S)-3-((((3aR,5aR, 5bR,7aR,9S,11aR,11bR,13aS)-1-isopropyl-5a,5b,8, 8,11a-pentamethyl-3a-(2-methyl-2-(methylsulfona-mido)propanamido)-2-oxo-3,3a,4, 5,5a,5b,6,7,7a,8, 9, 10,11,11a,11b,12,13,13a-octadecahydro-2H-cyclopenta[a]chrysen-9-yl) oxy)carbonyl)-2,2-dimethylcyclobutane-1-carboxylate To a stirred solution of (1R,3S)-3-((((3aR,5aR,5bR,7aR, 9S,11aR,11bR,13aS)-1-isopropyl-5a,5b,8,8,11a-pentamethyl-3a-(2-methyl-2-(methylsulfonamido)propanamido)-2-oxo-3,3a,4,5,5a,5b,6,7,7a,8,9,10,11,11a,11b,12,13,13a- octadecahydro-2H-cyclopenta[a]chrysen-9-yl)oxy)carbonyl)-2,2-dimethylcyclobutane-1-carboxylic acid (step 1, 0.320 g, 0.421 mmol, 1.0 eq) in MeOH (3.2 ml) and water (0.15 ml) was added sodium hydroxide (0.0168 g, 0.421 mmol, 1.0 eq). The reaction mixture was stirred at room temperature for about 2 hours and then distilled out 90% of methanol under reduced pressure. Ethyl acetate (5 ml) was added and the reaction mixture was stirred at room temperature for overnight. The reaction mixture was filtered, solid was washed ethyl acetate (5 ml) and then dried under vacuum to obtain the desired product (0.185 g, yield: 56.19%) as an off-white solid. $^1$H NMR (300 MHz, CD$_3$OD): δ ppm 4.47-4.40 (m, 1H), 3.28-3.20 (m, 1H), 3.03 (s, 3H), 2.98-2.92 (m, 1H), 2.72-2.43 (m, 4H), 2.36-2.17 (m, 2H), 2.12-1.85 (m, 5H), 1.83-1.76 (m, 1H), 1.73-1.55 (m, 4H), 1.51 (s, 3H), 1.55-1.38 (m, 3H), 1.49 (s, 3H), 1.38-1.26 (m, 2H), 1.33 (s, 3H), 1.24-1.05 (m, 8H), 1.03 (s, 3H), 1.0 (s, 3H), 0.96 (s, 3H), 0.95-0.85 (m, 10H); ESI-MS: m/z 781.46 (M+H)$^+$; HPLC: 97.84%; sodium content by Ion chromatography: 3.7%.

Example 64: Preparation of (1R,3S)-3-((((3aR,5aR,5bR,7aR,9S,11aR,11bR,13aS)-3a-(2-((ethoxy)carbonyl)amino)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

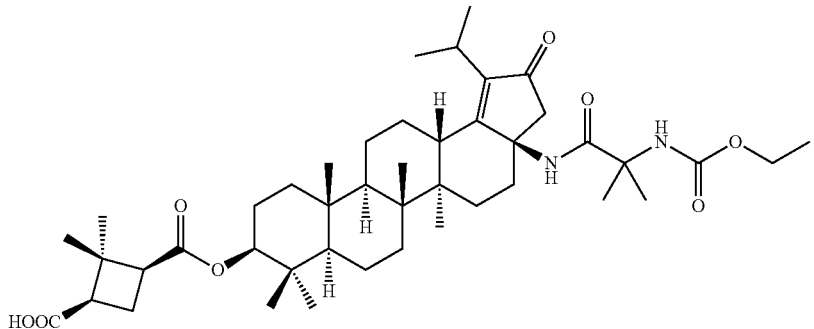

Intermediate 1 was coupled with ethyl carbonochloridate followed by hydrolysis gave the desired product as a white solid. $^1$H NMR (300 MHz, CDCl$_3$): δ ppm 5.48 (s, 1H), 4.50-4.40 (m, 1H), 3.23-3.12 (m, 1H), 2.88-2.76 (m, 2H), 2.67-2.32 (m, 4H), 2.11-1.92 (m, 3H), 1.80-1.50 (m, 11H), 1.50-1.31 (m, 15H), 1.30-1.18 (m, 8H), 1.12-0.98 (m, 1H), 1.07 (s, 3H), 1.03 (s, 3H), 0.99 (s, 3H), 0.89 (s, 3H), 0.86 (s, 3H), 0.85 (s, 3H), 0.79 (m, 1H); ESI-MS: m/z 775.47 (M+Na)$^+$; HPLC: 93.5%.

Example 65: Preparation of (1R,3S)-3-((((3aR,5aR,5bR,7aR,9S,11aR,11bR,13aS)-3a-(2-((4-chlorophenyl)sulfonamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

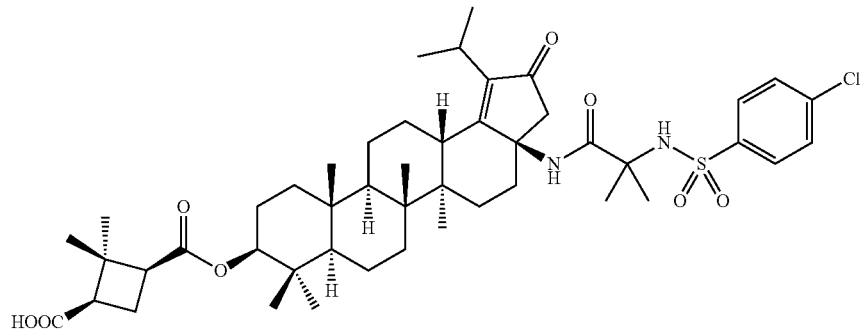

Intermediate 1 was coupled with 4-chlorobenzenesulfonyl chloride followed by hydrolysis gave the desired product as an off-white solid. $^1$H NMR (300 MHz, CDCl$_3$): δ ppm 7.81 (d, J=8.7 Hz, 2H), 7.49 (d, J=8.7 Hz, 2H), 6.58 (brs, 1H), 5.40 (s, 1H), 4.47 (dd, J=11.1, 4.5 Hz, 1H), 3.22-3.10 (m, 1H), 2.88-2.75 (m, 3H), 2.67-2.53 (m, 2H), 2.40-2.26 (m, 2H), 2.11-2.0 (m, 1H), 2.0-1.82 (m, 3H), 1.80-1.68 (m, 3H), 1.68-1.48 (m, 6H), 1.47-1.30 (m, 11H), 1.27-1.20 (m, 7H), 1.15 (s, 3H), 1.07 (s, 3H), 0.97 (s, 3H), 1.05-0.98 (m, 1H), 0.97 (s, 3H), 0.95 (s, 3H), 0.87 (s, 3H), 0.86 (s, 3H), 0.83-0.80 (m, 1H); ESI-MS: m/z 855.6 (M+H)$^+$; HPLC: 99.6%.

Example 66: Preparation of (1R,3S)-3-((((3aR,5aR, 5bR,7aR,9S,11aR,11bR,13aS)-3a-(2-(cyclo hexanecarboxamido)-2-methylpropanamido)-1-isopropyl-5a,5b,8,8,11a-pentamethyl-2-oxo-3,3a,4,5,5a,5b,6,7, 7a,8,9,10,11,11a,11b,12,13,13a-octadecahydro-2H-cyclopenta[a]chrysen-9-yl)oxy)carbonyl)-2,2-dimethylcyclobutane-1-carboxylic acid

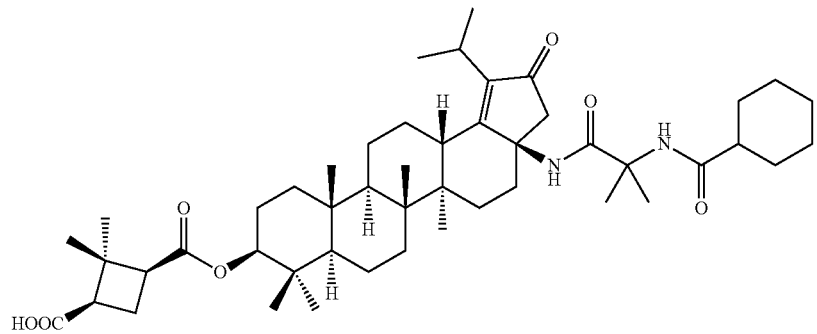

Intermediate 1 was coupled with cyclohexane carbonyl chloride followed by hydrolysis gave the desired product as a white solid. $^1$H NMR (300 MHz, CDCl$_3$): δ ppm 7.51 (s, 1H), 5.78 (s, 1H), 4.47 (dd, J=11.1, 4.8 Hz, 1H), 3.20-3.09 (m, 1H), 2.87-2.77 (m, 3H), 2.65-2.53 (m, 2H), 2.32-2.20 (m, 2H), 2.12-2.0 (m, 2H), 2.0-1.90 (m, 2H), 1.88-1.75 (m, 5H), 1.75-1.65 (m, 4H), 1.56 (s, 3H), 1.52 (s, 3H), 1.55-1.50 (m, 1H), 1.50-1.40 (m, 4H), 1.40-1.37 (m, 2H), 1.37 (s, 3H), 1.36-1.28 (m, 4H), 1.27-1.18 (m, 9H), 1.14 (s, 3H), 1.07 (m, 4H), 0.93 (s, 3H), 0.91 (s, 3H), 0.87 (s, 3H), 0.85 (s, 3H), 0.80 (m, 1H); ESI-MS: m/z 813.48 (M+Na)$^+$; HPLC: 96.4%.

Example 67: Preparation of (1R,3S)-3-((((3aR,5aR, 5bR,7aR,9S,11aR,11bR,13aS)-1-isopropyl-5a,5b,8, 8,11a-pentamethyl-3a-(2-methyl-2-((pyridin-2-ylmethyl)amino)propan amido)-2-oxo-3,3a,4,5,5a,5b,6, 7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid

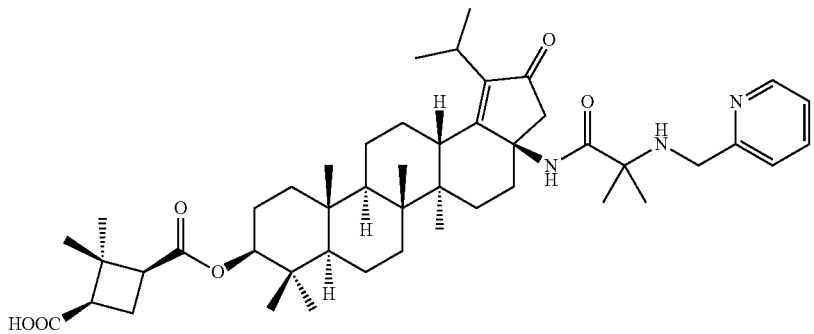

Step 1: Synthesis of 1-benzyl 3-((3aR,5aR,5bR, 7aR,9S,11aR,11bR,13aS)-1-isopropyl-5a,5b, 8,8, 11a-pentamethyl-3a-(2-methyl-2-((pyridin-2-ylmethyl)amino)propanamido)-2-oxo-3,3a,4,5,5a,5b,6,7, 7a,8,9,10,11,11a,11b,12,13,13a-octadecahydro-2H-cyclopenta[a]chrysen-9-yl) (1R,3S)-2,2-dimethylcyclobutane-1,3-dicarboxylate

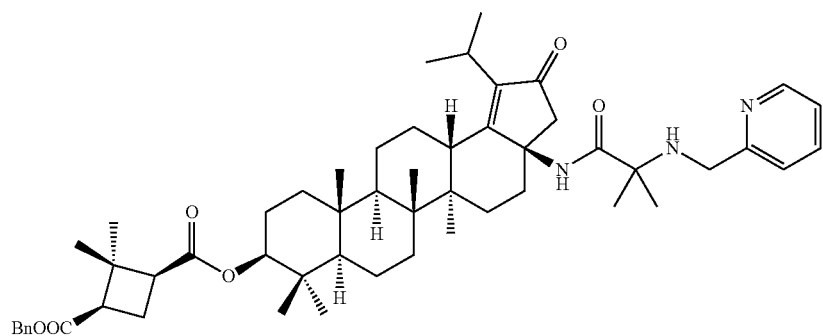

To a stirred solution of 1-((3aR,5aR,5bR,7aR,9S,11aR, 11bR,13aS)-3a-(2-amino-2-methylpropanamido)-1-isopropyl-5a,5b,8,8,11a-pentamethyl-2-oxo-3,3a,4,5,5a,5b,6,7,7a, 8,9,10,11,11a,11b,12,13,13a-octadecahydro-2H-cyclopenta [a]chrysen-9-yl) 3-benzyl (1S,3R)-2,2-dimethylcyclobutane-1,3-dicarboxylate (Intermediate 1, 1.0 g, 1.29 mmol, 1.0 eq) in THF (10 ml) was added picolinaldehyde (0.153 g, 1.42 mmol, 1.1 eq). The reaction mixture was stirred at room temperature for about 30 minutes, then sodiumtriacetoxyborohydride (0.60 g, 2.83 mmol, 2.2 eq) was added and stirred at same temperature for overnight. TLC indicated starting material was consumed and the desired product was observed. The reaction mixture was cooled to 0° C., pH adjusted to 7.0 with 1N HCl, diluted with water (20 ml) and extracted with CH$_2$Cl$_2$ (3×50 ml). The combined organic extracts were dried over Na$_2$SO$_4$, filtered and evaporated under reduced pressure. The residue was purified by silicagel column chromatography by using 5% MeOH in DCM as an eluent to obtain the desired product (0.5 g, yield: 44.7%) as a white solid. $^1$H NMR (300 MHz, DMSO-d$_6$): δ ppm 8.49 (d, J=4.2 Hz, 1H), 8.20 (brs, 1H), 7.75 (td, J=7.5, 1.5 Hz, 1H), 7.43-7.31 (m, 6H), 7.25 (dd, J=6.9, 5.1 Hz, 1H), 5.12, 5.05 (ABq, J$_{AB}$=12.6 Hz, 2H), 4.38-4.31 (m, 1H), 3.76-3.61 (m, 2H), 3.18-3.05 (m, 1H), 2.98-2.72 (m, 3H), 2.43-2.25 (m, 3H), 2.18 (d, J=18.3 Hz, 1H), 2.0-1.72 (m, 5H), 1.70-1.42 (m, 5H), 1.40-1.20 (m, 13H), 1.18-1.0 (m, 9H), 0.90 (s, 3H), 0.89 (s, 3H), 0.86-0.77 (m, 13H); ESI-MS: m/z 862.7 (M+H)$^+$.

Step 2: Synthesis of (1R,3S)-3-(((((3aR,5aR,5bR, 7aR,9S,11aR,11bR,13aS)-1-isopropyl-5a,5b, 8,8, 11a-pentamethyl-3a-(2-methyl-2-((pyridin-2-ylmethyl)amino)propanamido)-2-oxo-3,3a,4,5,5a,5b,6,7, 7a,8,9,10,11,11a,11b, 12,13,13a-octadecahydro-2H-cyclopenta[a]chrysen-9-yl) oxy)carbonyl)-2,2-dimethylcyclobutane-1-carboxylic acid To a stirred solution of 1-benzyl 3-((3aR,5aR,5bR,7aR, 9S,11aR,11bR,13aS)-1-isopropyl-5a,5b,8,8,11a-pentam ethyl-3a-(2-methyl-2-((pyridin-2-ylmethyl)amino)propan amido)-2-oxo-3,3a,4,5,5a,5b,6,7,7a,8,9,10,11,11a,11b,12, 13,13a-octadecahydro-2H-cyclo penta[a]chrysen-9-yl) (1R, 3S)-2,2-dimethylcyclobutane-1,3-dicarboxylate (step 1, 0.5 g, 0.58 mmol, 1.0 eq) in MeOH (10 ml), THF (10 ml) and water (1.6 ml) was added KOH (0.227 g, 4.06 mmol, 7.0 eq). The reaction mixture was stirred at room temperature for about 16 hours. TLC indicated starting material was consumed and the desired product was observed. The organic phase was evaporated under reduced pressure, the reaction mixture was diluted with water (20 ml), cooled to 0° C., pH adjusted to 7.0 with 1N HCl and extracted with DCM (2×25 ml). The combined organic extracts were dried over sodium sulfate, filtered and evaporated under reduced pressure. The residue was purified by silicagel column chromatography by using 8% MeOH in DCM as an eluent to obtain the desired product (350 mg, yield: 78.1%) as a white solid. $^1$H NMR (300 MHz, DMSO-d$_6$): δ ppm 8.49 (d, J=4.2 Hz, 1H), 8.20 (brs, 1H), 7.79-7.71 (m, 1H), 7.41 (d, J=7.5 Hz, 1H), 7.29-7.22 (m, 1H), 4.38-4.31 (m, 1H), 3.75-3.62 (m, 2H), 3.16-3.06 (m, 1H), 2.83-2.72 (m, 3H), 2.42-2.14 (m, 5H), 1.95-1.70 (m, 5H), 1.69-1.31 (m, 8H), 1.29-1.21 (m, 9H), 1.17-1.02 (m, 9H), 0.94-0.88 (m, 9H), 0.86-0.76 (m, 10H); ESI-MS: m/z 772.6 (M+H)$^+$; HPLC: 94.9%.

The below example 68 was prepared by the procedure similar (including reagents and reaction conditions) to the above described in the synthesis of example-67 using with their appropriate intermediates.

Example 68: Preparation of (1R,3S)-3-((((3aR,5aR,5bR,7aR,9S,11aR,11bR,13aS)-3a-(2-((4-chlorobenzypamino)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

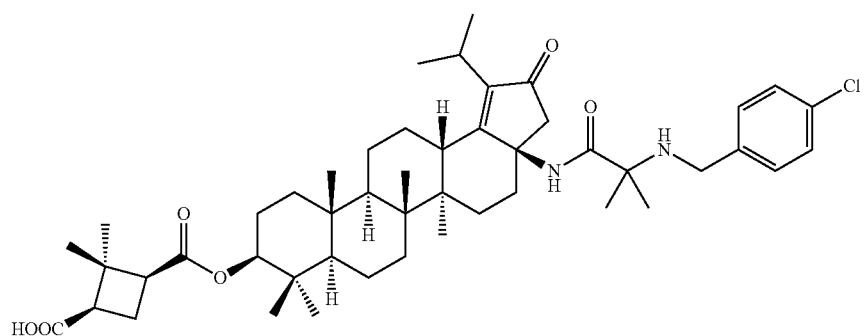

Intermediate 1 was coupled with 4-chlorobenzaldehyde followed by hydrolysis gave the desired product as a white solid. $^1$H NMR (300 MHz, CDCl$_3$): δ ppm 7.62 (s, 1H), 7.25 (d, J=8.4 Hz, 2H), 7.17 (d, J=8.7 Hz, 2H), 4.38 (dd, J=11.1, 4.5 Hz, 1H), 4.17-4.12 (m, 1H), 3.65, 3.58 (ABq, J$_{AB}$=13.5 Hz, 2H), 3.12-3.02 (m, 1H), 2.92-2.68 (m, 2H), 2.63-2.45 (m, 3H), 2.41-2.23 (m, 2H), 2.04-1.92 (m, 2H), 1.75-1.59 (m, 4H), 1.58-1.40 (m, 4H), 1.40-1.23 (m, 14H), 1.23-1.10 (m, 7H), 1.09-0.93 (m, 1H), 1.0 (s, 3H), 0.93-0.75 (m, 15H), 0.75-0.68 (m, 1H); ESI-MS: m/z 805.4 (M+H)$^+$; HPLC: 92.56%.

Example 69: Preparation of (1R,3S)-3-((((3aR,5aR,5bR,7aR,9S,11aR,11bR,13aS)-3a-(2-(((1-(4-chlorophenyl)cyclopropyl)methyl)amino)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

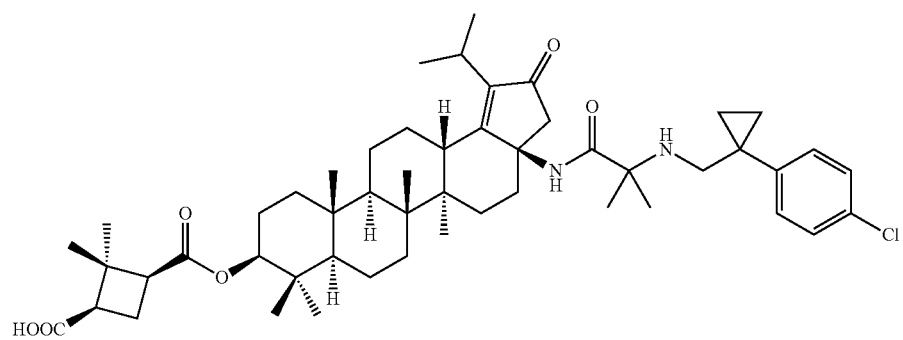

Step 1: Synthesis of 1-benzyl 3-((3aR,5aR,5bR, 7aR,9S,11aR,11bR,13aS)-3a-(2-(((1-(4-chloro phenyl)cyclopropyl)methyl)amino)-2-methylpropanamido)-1-isopropyl-5a,5b,8,8,11a-penta methyl-2-oxo-3,3a,4,5,5a,5b,6,7,7a,8,9,10,11,11a,11b,12,13, 13a-octadecahydro-2H-cyclo penta[a]chrysen-9-yl) (1R,3S)-2,2-dimethylcyclobutane-1,3-dicarbaxylate

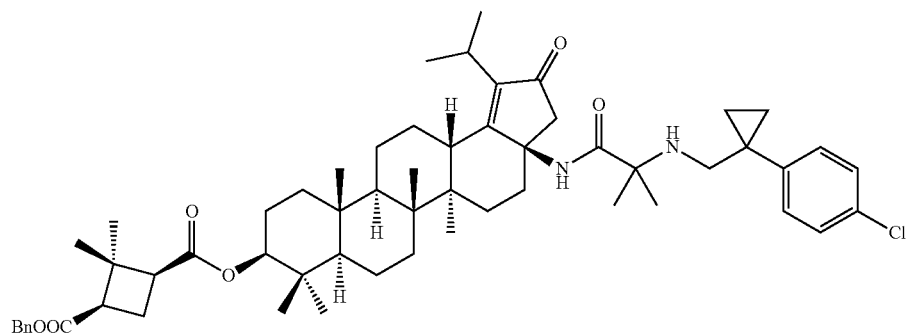

To a stirred solution of 1-((3aR,5aR,5bR,7aR,9S,11aR, 11bR,13aS)-3a-(2-amino-2-methylpropanamido)-1-isopropyl-5a,5b,8,8,11a-pentamethyl-2-oxo-3,3a,4,5,5a,5b,6,7,7a, 8,9,10,11,11a,11b,12,13,13a-octadecahydro-2H-cyclopenta [a]chrysen-9-yl) 3-benzyl (1S,3R)-2,2-dimethylcyclobutane-1,3-dicarboxylate (Intermediate 1, 1.0 g, 1.297 mmol, 1.0 eq) in 1,2-DCE (10 ml) at 0° C. was added 1-(4-chlorophenyl)cyclopropane-1-carbaldehyde (Intermediate 18, 0.468 g, 2.595 mmol, 2.0 eq), followed by acetic acid (0.116 g, 1.945 mmol, 1.5 eq). The reaction mixture was stirred at 0° C. for about 30 minutes then sodiumtriacetoxy borohydride (1.09 g, 5.18 mmol, 4.0 eq) was added and allowed to stir at room temperature for overnight. TLC indicated starting material was consumed and the desired product was observed. The reaction mixture was cooled to 0° C., quenched with saturated ammonium chloride solution (10 ml), diluted with water (30 ml) and extracted with DCM (3×30 ml). The combined organic extracts were washed with water (30 ml), dried over sodium sulfate, filtered and evaporated under reduced pressure. The residue was purified by silicagel column chromatography by using 0-5% methanol in dichloromethane gradient. The fractions containing the expected product were combined and concentrated under reduced pressure to obtain the desired product (600 mg, yield: 49.4%) as a white solid. $^1$H NMR (300 MHz, CDCl$_3$): δ ppm 7.37-7.23 (m, 9H), 5.15, 5.09 (ABq, J$_{AB}$=12.3 Hz, 2H), 4.45 (dd, J=11.1, 4.5 Hz, 1H), 3.16-3.05 (m, 1H), 2.86-2.73 (m, 2H), 2.70-2.44 (m, 5H), 2.12-1.99 (m, 2H), 1.96-1.82 (m, 2H), 1.80-1.65 (m, 3H), 1.57-1.44 (m, 4H), 1.44-1.37 (m, 2H), 1.37-1.32 (m, 2H), 1.34 (s, 3H), 1.31-1.16 (m, 14H), 1.16-1.03 (m, 2H), 0.99 (s, 3H), 0.96 (s, 3H), 0.93-0.84 (m, 12H), 0.83-0.64 (m, 5H); ESI-MS: m/z 935.52 (M+H)$^+$.

Step 2: Synthesis of (1R,3S)-3-((((3aR,5aR,5bR, 7aR,9S,11aR,11bR,13aS)-3a-(2-(((1-(4-chlorophenyl)cyclopropyl)methyl)amino)-2-methylpropanamido)-1-isopropyl-5a,5b,8,8,11a-pentamethyl-2-oxo-3,3a,4,5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid To a stirred solution of 1-benzyl 3-((3aR,5aR,5bR,7aR, 9S,11aR,11bR,13aS)-3a-(2-(((1-(4-chlorophenyl)cyclopropyl)methyl)amino)-2-methylpropanamido)-1-isopropyl-5a, 5b, 8,8,11a-pentamethyl-2-oxo-3,3a,4,5,5a,5b,6,7,7a,8,9,10, 11,11a,11b,12,13,13a-octadecahydro-2H-cyclopenta[a] chrysen-9-yl) (1R,3S)-2,2-dimethylcyclobutane-1,3-dicarboxylate (step 1, 0.6 g, 0.641 mmol, 1.0 eq) in MeOH (10 ml) and THF (10 ml) was added aqueous 2.5N KOH solution (1.78 ml, 4.49 mmol, 7.0 eq). The reaction mixture was stirred at room temperature for overnight. TLC indicated starting material was consumed and the desired product was observed. The organic phase was evaporated under reduced pressure, the reaction mixture was diluted with water (30 ml), cooled to 0° C., pH adjusted to 5.0 with 1N HCl and extracted with DCM (3×30 ml). The combined organic extracts were washed with water (20 ml), dried over sodium sulfate, filtered and evaporated under reduced pressure. The residue was purified by silicagel column chromatography by using 0-10% methanol in dichloromethane gradient. The fractions containing the expected product were combined and concentrated under reduced pressure to obtain the solid. To this solid compound, MTBE (5 ml) and hexane (5 ml) was added and heated to reflux for about 20 minutes. The mixture was filtered and dried under vacuum to obtain the desired product (90 mg, yield: 16.6%) as a white solid. $^1$H NMR (300 MHz, CDCl$_3$): δ ppm 7.36-7.20 (m, 4H), 4.47 (dd, J=11.1, 4.5 Hz, 1H), 3.18-3.05 (m, 1H), 2.88-2.76 (m, 2H), 2.68-2.60 (m, 1H), 2.60-2.52 (m, 2H), 2.50-2.44 (m, 2H), 2.13-2.0 (m, 2H), 1.92-1.83 (m, 2H), 1.77-1.63 (m, 3H), 1.63-1.41 (m, 6H), 1.38 (s, 3H), 1.37-1.29 (m, 3H), 1.26-1.10 (m, 14H), 1.08 (s, 3H), 1.05 (m, 1H), 1.0 (s, 3H), 0.93-0.84 (m, 12H), 0.83-0.73 (m, 4H), 0.72-0.65 (m, 1H); ESI-MS: m/z 845.44 (M+H)+; HPLC: 91.5%.

Example 70: Preparation of (1R,3S)-3-((((3aR,5aR, 5bR,7aR,9S,11aR,11bR,13aS)-3a-(2-(5-chloropicolinamido)-2-methylpropanamido)-1-isopropyl-5a, 5b,8,8,11a-pentamethyl-2-oxo-3,3a,4,5,5a,5b,6,7,7a, 8,9,10,11,11a,11b,12,13,13a-octadecahydro-2H-cyclopenta[a]chrysen-9-yl)oxy)carbonyl)-2,2-dimethylcyclobutane-1-carboxylic acid

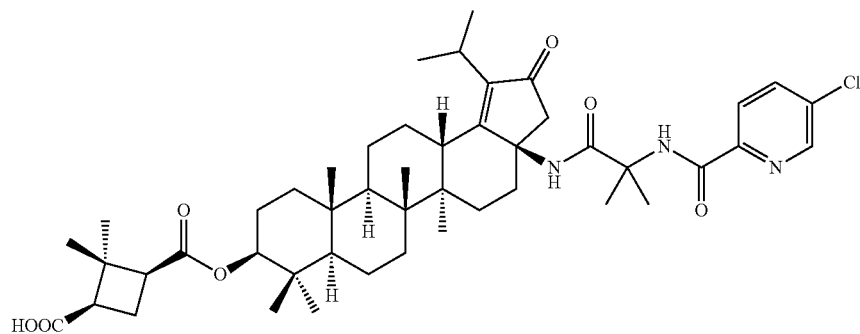

Step 1: Synthesis of 1-benzyl 3-((3aR,5aR,5bR, 7aR,9S,11aR,11bR,13aS)-3a-(2-(5-chloro picolinamido)-2-methylpropanamido)-1-isopropyl-5a,5b,8,8, 11a-pentamethyl-2-oxo-3,3a,4,5,5a,5b,6,7,7a,8,9,10, 11,11a,11b,12,13,13a-octadecahydro-2H-cyclopenta [a]chrysen-9-yl) (1R,3S)-2,2-dimethylcyclobutane-1,3-dicarboxylate

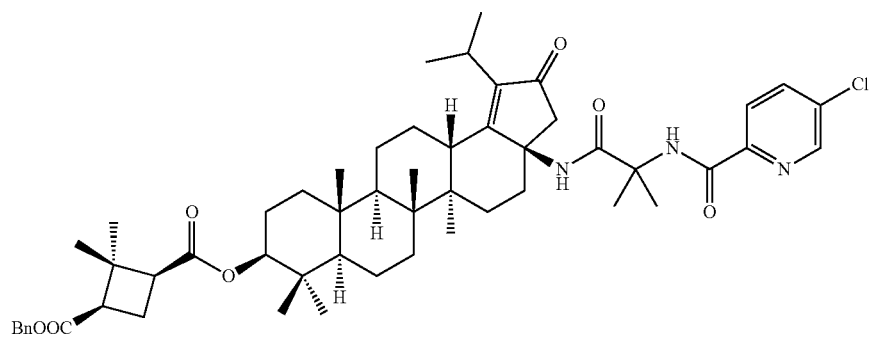

To a stirred solution of 5-chloropicolinic acid (0.286 g, 1.815 mmol, 2.0 eq) in DMF (7 ml) was added HATU (1.034 g, 2.721 mmol, 3.0 eq) followed by triethylamine (0.89 ml, 6.35 mmol, 7.0 eq). The reaction mixture was stirred at room temperature for about 30 minutes then 1-((3aR,5aR,5bR, 7aR,9S,11aR,11bR,13aS)-3a-(2-amino-2-methylpropan amido)-1-isopropyl-5a,5b,8,8,11a-pentamethyl-2-oxo-3,3a, 4,5,5a,5b,6,7,7a,8,9,10,11,11a, 11b,12,13,13a-octadecahydro-2H-cyclopenta[a]chrysen-9-yl) 3-benzyl (1S,3R)-2,2-dimethyl cyclobutane-1,3-dicarboxylate (Intermediate 1, 0.700 g, 0.907 mmol, 1.0 eq) was added and heated at 60° C. for overnight. TLC indicated starting material was consumed and the desired product was observed. The reaction mixture was diluted with water (100 ml) and stirred at room temperature for about 30 minutes. The precipitates formed were collected by filtration, washed with water (100 ml), and dried under vacuum to obtain the solid. The resulting solid was purified by silicagel column chromatography by using 0-2% methanol in dichloromethane gradient. The fractions containing the expected product were combined and concentrated under reduced pressure to obtain the desired product (0.800 g, yield: 96.85%) as a white solid. $^1$H NMR (300 MHz, CDCl$_3$): δ ppm 8.52 (d, J=2.1 Hz, 1H), 8.25 (brs, 1H), 8.13 (d, J=8.4 Hz, 1H), 7.85 (dd, J=8.4, 2.4 Hz, 1H), 7.56 (brs, 1H), 7.35 (m, 5H), 5.15, 5.09 (ABq, J$_{AB}$=12.3 Hz, 2H), 4.44 (dd, J=11.1, 4.5 Hz, 1H), 3.22-3.10 (m, 1H), 2.87-2.57 (m, 5H), 2.40-2.22 (m, 2H), 2.09-2.0 (m, 1H), 1.98-1.80 (m, 3H), 1.78-1.70 (m, 2H), 1.68 (s, 3H), 1.65 (s, 3H), 1.53-1.40 (m, 4H), 1.37-1.33 (m, 4H), 1.31-1.0 (m, 12H), 0.96 (s, 3H), 0.93 (s, 3H), 0.92 (s, 3H), 0.87-0.76 (m, 10H).

Step 2: Synthesis of (1R,3S)-3-((((3aR,5aR,5bR, 7aR,9S,11aR,11bR,13aS)-3a-(2-(5-chloro picolinamido)-2-methylpropanamido)-1-isopropyl-5a,5b,8,8, 11a-pentamethyl-2-oxo-3,3a,4,5,5a,5b,6,7,7a,8,9,10, 11,11a,11b,12,13,13a-octadecahydro-2H-cyclopenta [a]chrysen-9-yl)oxy) carbonyl)-2,2-dimethylcyclobutane-1-carboxylic acid To a stirred solution of 1-benzyl 3-((3aR,5aR,5bR,7aR, 9S,11aR,11bR,13aS)-3a-(2-(5-chloropicolinamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 1, 0.800 g, 0.878 mmol, 1.0 eq) in MeOH (8 ml) and THF (8 ml) was added aqueous 2.5N KOH solution (2.63 ml, 6.585 mmol, 7.5 eq). The reaction mixture was stirred at room temperature for overnight. TLC indicated starting material was consumed and the desired product was observed. The organic phase was evaporated under reduced pressure, the reaction mixture was diluted with water (10 ml), cooled to 0° C., pH adjusted to 5.0 with 1N HCl and extracted with DCM (2×50 ml). The combined organic extracts were washed with water (30 ml), dried over sodium sulfate, filtered and evaporated under reduced pressure. The residue was purified by silicagel column chromatography by using 0-5% methanol in dichloromethane gradient. The fractions containing the expected product were combined and concentrated under reduced pressure to obtain the solid. To this solid compound, MTBE (10 ml) was added and heated to reflux for about 30 minutes. The mixture was cooled to 0° C., solid was filtered and dried under vacuum to obtain the desired product (0.048 g, yield: 6.6%) as an off-white solid. $^1$H NMR (300 MHz, CDCl$_3$): δ ppm 8.52 (d, J=2.1 Hz, 1H), 8.24 (brs, 1H), 8.13 (d, J=8.4 Hz, 1H), 7.85 (dd, J=8.4, 2.1 Hz, 1H), 7.56 (s, 1H), 4.46 (dd, J=11.4, 4.8 Hz, 1H), 3.20-3.07 (m, 1H), 2.87-2.75 (m, 3H), 2.72-2.53 (m, 2H), 2.37-2.24 (m, 2H), 2.11-2.0 (m, 1H), 1.98-1.80 (m, 5H), 1.70-1.63 (m, 4H), 1.68 (s, 3H), 1.64 (s, 3H), 1.44-1.36 (m, 5H), 1.37 (s, 3H), 1.25-1.18 (m, 7H), 1.07 (m, 4H), 0.94 (s, 3H), 0.92 (s, 3H), 0.89-0.82 (m, 10H); ESI-MS: m/z 820.78 (M+H)$^+$; HPLC: 90.8%.

Example 71: Preparation of (1R,3S)-3-((((3aR,5aR,5bR,7aR,9S,11aR,11bR,13aS)-1-isopropyl-5a,5b,8,8,11a-pentamethyl-3a-(2-methyl-2-(3-(6-methylpyridin-3-yl)ureido) propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

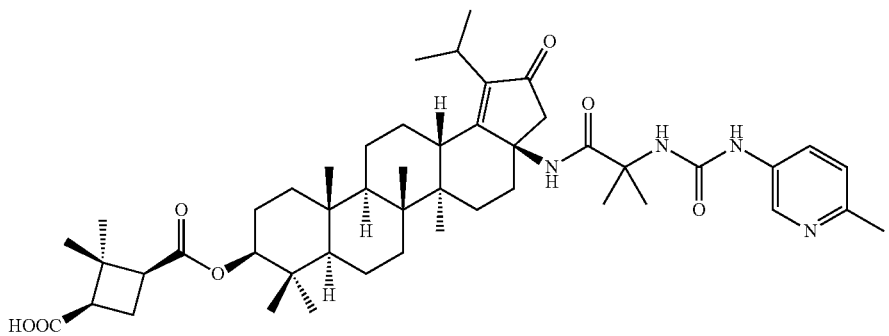

Step 1: Synthesis of 1-benzyl 3-((3aR,5aR,5bR,7aR,9S,11aR,11bR,13aS)-1-isopropyl-5a,5b, 8,8,11a-pentamethyl-3a-(2-methyl-2-(3-(6-methylpyridin-3-yl)ureido)propanamido)-2-oxo-3, 3a,4,5,5a,5b,6,7,7a,8,9, 10,11,11a,11b,12,13,13a-octadecahydro-2H-cyclopenta[a]chrysen-9-yl) (1R,3S)-2,2-dimethylcyclobutane-1,3-dicarboxylate

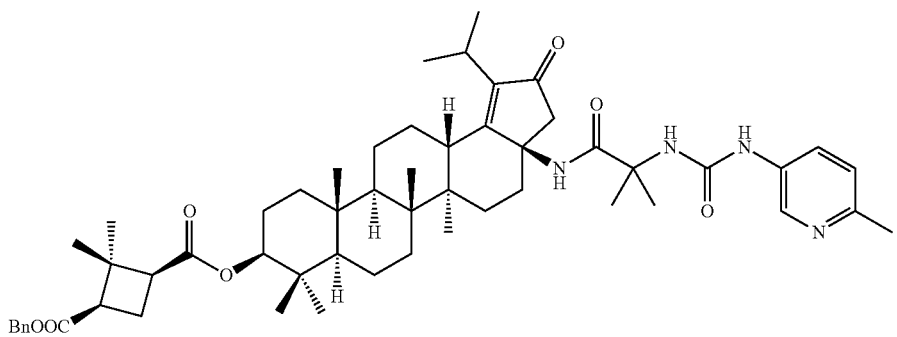

To a stirred solution of 1-((3aR,5aR,5bR,7aR,9S,11aR,11bR,13aS)-3a-(2-amino-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 3-benzyl (1S,3R)-2,2-dimethylcyclobutane-1,3-dicarboxylate (Intermediate 1, 0.800 g, 1.037 mmol, 1.0 eq) in THF (20 ml) was added DIPEA (0.73 ml, 4.148 mmol, 4.0 eq) and 5-isocyanato-2-methylpyridine (Intermediate 19, 0.139 g, 1.037 mmol, 1.0 eq). The reaction mixture was heated at 60° C. for about 16 hours. TLC indicated starting material was consumed and the desired product was observed. The reaction mixture was diluted with water (15 ml) and extracted with ethyl acetate (3×25 ml). The combined organic extracts were washed with water (25 ml), dried over sodium sulfate, filtered and evaporated under reduced pressure. The residue was purified by silicagel column chromatography by using 3% methanol in dichloromethane as an eluent to obtain the desired product (560 mg, yield: 59.7%) as a white solid. $^1$H NMR (300 MHz, CDCl$_3$): δ ppm 8.30 (d, J=1.8 Hz, 1H), 7.94 (brs, 1H), 7.86 (dd, J=8.4, 2.1 Hz, 1H), 7.54 (s, 1H), 7.35 (m, 5H), 7.03 (d, J=8.4 Hz, 1H), 5.96 (s, 1H), 5.15, 5.09 (ABq, J$_{AB}$=12.3 Hz, 2H), 4.43 (dd, J=10.8, 4.2 Hz, 1H), 3.20-3.08 (m, 1H), 2.98-2.90 (m, 1H), 2.88-2.72 (m, 2H), 2.70-2.58 (m, 2H), 2.49 (s, 3H), 2.35-2.20 (m, 2H), 2.20-1.83 (m, 8H), 1.63-1.40 (m, 2H), 1.49 (s, 3H), 1.47 (s, 3H), 1.40-1.10 (m, 12H), 1.34 (s, 3H), 1.10-0.75 (m, 20H); ESI MS: m/z 905.58 (M+H)$^+$.

Step 2: Synthesis of (1R,3S)-3-((((3aR,5aR,5bR,7aR,9S,11aR,11bR,13aS)-1-isopropyl-5a,5b, 8,8,11a-pentamethyl-3a-(2-methyl-2-(3-(6-methylpyridin-3-yl)ureido)propanamido)-2-oxo-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid To a stirred solution of 1-benzyl 3-((3aR,5aR,5bR,7aR,9S,11aR,11bR,13aS)-1-isopropyl-5a,5b,8,8,11a-pentamethyl-3a-(2-methyl-2-(3-(6-methylpyridin-3-yl)ureido)propanamido)-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 1, 0.700 g, 0.773 mmol, 1.0 eq) in MeOH (14 ml) and THF (14 ml) was added aqueous 2.5 N KOH solution (2.32 ml, 5.80 mmol, 7.5 eq). The reaction mixture was stirred at room temperature for overnight. TLC indicated starting material was consumed and the desired product was observed. The organic phase was evaporated under reduced pressure, the reaction mixture was diluted with water (20 ml), cooled to 0° C., pH adjusted to 5.0 with 1N HCl and extracted with DCM (3×40 ml). The combined organic extracts were washed with water (40 ml), dried over sodium sulfate, filtered and evaporated under reduced pressure. The residue was purified by silicagel column chromatography by using 0-6% methanol in dichloromethane gradient. The fractions containing the expected product were combined and concentrated under reduced pressure to give a solid. To this solid compound, acetonitrile (15 ml) was added and heated to reflux for about 30 minutes. The mixture was cooled to 0° C., filtered and dried under vacuum to obtain the desired product (310 mg, yield: 49.1%) as a white solid. $^1$H NMR (300 MHz, DMSO-d$_6$): δ ppm 12.1 (brs, 1H), 8.72 (s, 1H), 8.35 (d, J=2.4 Hz, 1H), 7.74 (dd, J=8.4, 2.4 Hz, 1H), 7.50 (s, 1H), 7.08 (d, J=8.7 Hz, 1H), 6.48 (s, 1H), 4.34 (m, 1H), 3.09 (m, 1H), 2.88-2.72 (m, 3H), 2.45-2.20 (m, 4H), 2.43 (s, 3H), 2.10 (d, J=17.7 Hz, 1H), 2.0-1.80 (m, 3H), 1.80-1.50 (m, 4H), 1.50-1.40 (m, 2H), 1.42 (s, 3H), 1.40 (s, 3H), 1.38-1.18 (m, 5H), 1.26 (s, 3H), 1.18-0.98 (m, 8H), 0.91 (s, 3H), 0.87 (s, 3H), 0.84 (s, 3H), 0.80 (s, 3H), 0.78 (s, 3H), 0.75-0.63 (m, 1H), 0.72 (s, 3H); ESI MS: m/z 815.45 (M+H)$^+$; HPLC: 95.0%.

Example 72: Preparation of (1R,3S)-3-((((3aR,5aR,5bR,7aR,9S,11aR,11bR,13aS)-1-isopropyl-5a,5b,8,8,11a-pentamethyl-3a-(2-methyl-2-(3-(6-methylpyridin-2-yl)ureido) propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

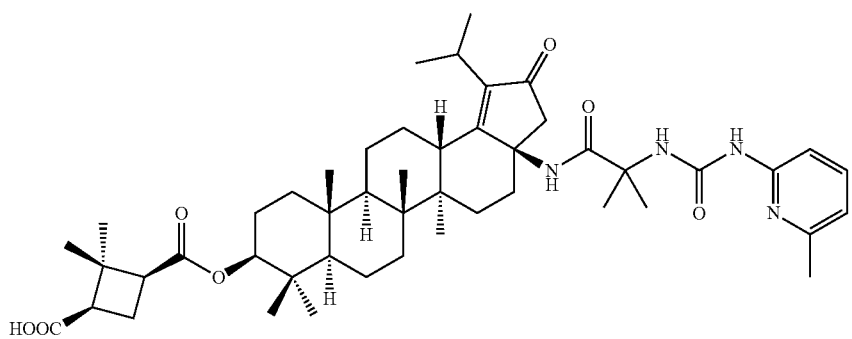

Step 1: Synthesis of 1-benzyl 3-((3aR,5aR,5bR,
7aR,9S,11aR,11bR,13aS)-1-isopropyl-5a,5b,8,8,11a-
pentamethyl-3a-(2-methyl-2-(3-(6-methylpyridin-2-
yl)ureido)propanamido)-2-oxo-3, 3a,4,5,5a,5b,6,7,
7a,8,9, 10,11,11a,11b,12,13,13a-octadecahydro-2H-
cyclopenta[a]chrysen-9-yl) (1R,3S)-2,2-
dimethylcyclobutane-1,3-dicarboxylate

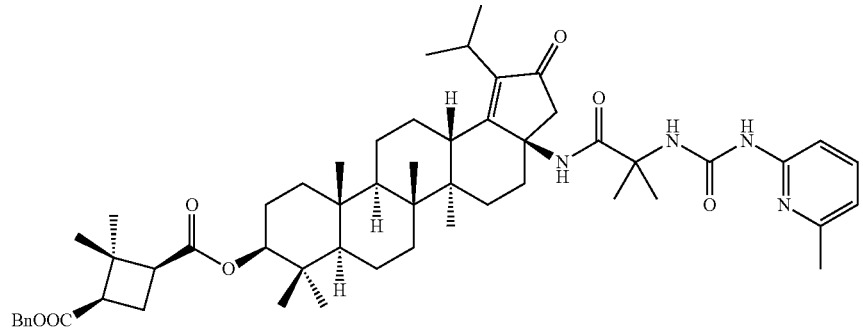

To a stirred solution of 1-((3aR,5aR,5bR,7aR,9S,11aR, 11bR,13aS)-3a-(2-amino-2-methylpropanamido)-1-isopropyl-5a,5b,8,8,11a-pentamethyl-2-oxo-3,3a,4,5,5a,5b,6,7,7a, 8,9, 10,11,11a,11b,12,13,13a-octadecahydro-2H-cyclopenta[a]chrysen-9-yl) 3-benzyl (1S,3R)-2,2-dimethylcyclobutane-1,3-dicarboxylate (Intermediate 1, 0.6 g, 0.778 mmol, 1.0 eq) in THF (6 ml) was added triethylamine (0.54 ml, 3.89 mmol, 5.0 eq) and 2-isocyanato-6-methylpyridine (Intermediate 20, 0.208 g, 1.556 mmol, 2.0 eq). The reaction mixture was stirred at room temperature for overnight. TLC indicated starting material was consumed and the desired product was observed. The reaction mixture was evaporated under reduced pressure, diluted with water (15 ml) and extracted with DCM (2×25 ml). The combined organic extracts were washed with water (25 ml), dried over sodium sulfate, filtered and evaporated under reduced pressure. The residue was purified by silicagel column chromatography by using 0-5% MeOH in DCM gradient. The fractions containing the expected product were combined and concentrated under reduced pressure to obtain the desired product (0.400 g, yield: 57.14%) as a white solid. $^1$H NMR (300 MHz, CDCl$_3$): δ ppm 10.39 (s, 1H), 7.94 (s, 1H), 7.56-7.48 (m, 1H), 7.35 (m, 5H), 6.79 (d, J=7.5 Hz, 1H), 6.48 (d, J=8.1 Hz, 1H), 5.15, 5.09 (ABq, J$_{AB}$=12.3 Hz, 2H), 4.44 (dd, J=11.4, 4.5 Hz, 1H), 3.20-3.08 (m, 1H), 2.90-2.58 (m, 5H), 2.46 (s, 3H), 2.35-2.23 (m, 2H), 2.09-1.98 (m, 1H), 1.97-1.86 (m, 3H), 1.80-1.67 (m, 2H), 1.64 (s, 3H), 1.61 (s, 3H), 1.55-1.10 (m, 17H), 1.34 (s, 3H), 1.08 (s, 3H), 0.96 (s, 3H), 0.92 (s, 3H), 0.86-0.80 (m, 10H); ESI-MS: m/z 905.76 (M+H)$^+$.

Step 2: Synthesis of (1R,3S)-3-((((3aR,5aR,5bR,
7aR,9S,11aR,11bR,13aS)-1-isopropyl-5a,5b, 8,8,
11a-pentamethyl-3a-(2-methyl-2-(3-(6-methylpyri-
din-2-yl)ureido)propanamido)-2-oxo-3,3a,4,5,5a,5b,
6,7,7a,8,9, 10,11,11a,11b, 12,13,13a-octadecahydro-
2H-cyclopenta[a]chrysen-9-yl)oxy)carbonyl)-2,
2-dimethylcyclobutane-1-carboxylic acid To a stirred solution of 1-benzyl 3-((3aR,5aR,5bR,7aR, 9S,11aR,11bR,13aS)-1-isopropyl-5a,5b,8,8,11a-pentamethyl-3a-(2-methyl-2-(3-(6-methylpyridin-2-yl)ureido)propan amido)-2-oxo-3,3a,4,5,5a,5b,6,7,7a,8,9,10,11,11a,11b, 12,13,13a-octadecahydro-2H-cyclo penta[a]chrysen-9-yl) (1R,3S)-2,2-dimethylcyclobutane-1,3-dicarboxylate (step 1, 0.4 g, 0.441 mmol, 1.0 eq) in MeOH (4 ml) and THF (4 ml) was added aqueous 2.5N KOH solution (1.23 ml, 3.093 mmol, 7.0 eq). The reaction mixture was stirred at room temperature for overnight. TLC indicated starting material was consumed and the desired product was observed. The organic phase was evaporated under reduced pressure, the reaction mixture was diluted with water (10 ml), cooled to 0° C., pH adjusted to 5.0 with 1N HCl and extracted with DCM (2×30 ml). The combined organic extracts were washed with water, dried over sodium sulfate, filtered and evaporated under reduced pressure. The residue was purified by silicagel column chromatography by using 0-6% methanol in dichloromethane gradient. The fractions containing the expected product were combined and concentrated under reduced pressure to obtain the solid. To this solid compound, acetonitrile (20 ml) was added and heated to reflux for about 30 minutes. The mixture was cooled to 0° C., filtered, was washed with acetonitrile (10 ml) and dried under vacuum to obtain the desired product (0.060 g, yield: 16%) as an off-white solid. $^1$H NMR (300 MHz, CDCl$_3$): δ ppm 10.5 (brs, 1H), 9.12 (s, 1H), 8.06 (s, 1H), 7.53 (t, J=7.8 Hz, 1H), 6.80 (d, J=7.2 Hz, 1H), 6.62 (d, J=7.8 Hz, 1H), 4.54-4.47 (m, 1H), 3.21-3.09 (m, 1H), 2.97-2.88 (m, 1H), 2.87-2.77 (m, 2H), 2.73-2.50 (m, 2H), 2.47 (s, 3H), 2.40-2.30 (m, 2H), 2.17-2.05 (m, 1H), 2.0-1.80 (m, 3H), 1.72-1.57 (m, 4H), 1.64 (s, 3H), 1.60 (s, 3H), 1.57-1.48 (m, 3H), 1.45-1.35 (m, 2H), 1.39 (s, 3H), 1.34-1.10 (m, 10H), 1.12 (s, 3H), 1.06 (s, 3H), 0.92 (s, 3H), 0.88 (s, 3H), 0.87-0.80 (m, 7H); ESI-MS: m/z 815.70 (M+H)$^+$; HPLC: 93.1%.

Example 73: Preparation of (1R,3S)-3-((((3aR,5aR, 5bR,7aR,9S,11aR,11bR,13aS)-3a-(2-((2-(dimethyl-amino)ethyl)amino)-2-methylpropanamido)-1-iso-propyl-5a,5b,8,8,11a-pentamethyl-2-oxo-3,3a,4,5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid

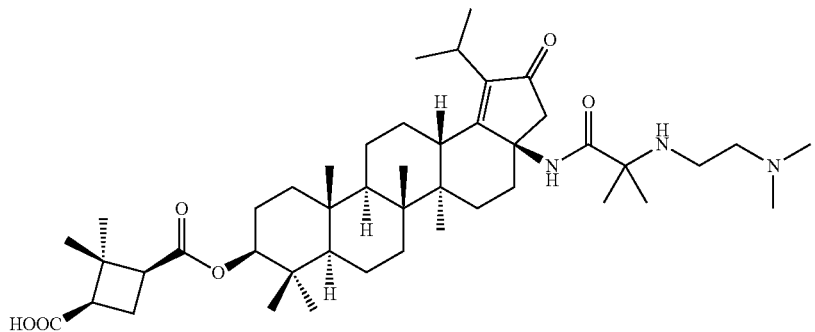

Step 1: Synthesis of 1-benzyl 3-((3aR,5aR,5bR, 7aR,9S,11aR,11bR,13aS)-3a-(2-((2-(dimethyl amino)ethyl)amino)-2-methylpropanamido)-1-iso-propyl-5a,5b,8,8,11a-pentamethyl-2-oxo-3, 3a,4,5, 5a,5b,6,7,7a,8,9,10,11,11a,11b,12,13,13a-octadeca-hydro-2H-cyclopenta[a]chrysen-9-yl) (1R,3S)-2, 2-dimethylcyclobutane-1, 3-dicarboxylate

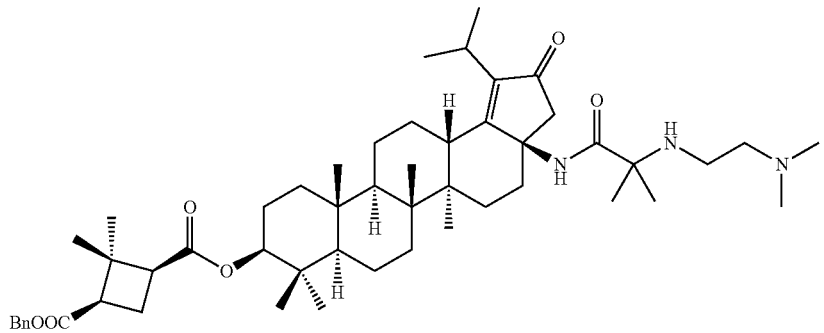

To a stirred solution of 1-((3aR,5aR,5bR,7aR,9S,11aR, 11bR,13aS)-3a-(2-amino-2-methylpropanamido)-1-isopropyl-5a,5b,8,8,11a-pentamethyl-2-oxo-3,3a,4,5,5a,5b,6,7,7a, 8,9, 10,11,11a,11b,12,13,13a-octadecahydro-2H-cyclopenta [a]chrysen-9-yl) 3-benzyl (1S,3R)-2,2-dimethylcyclobutane-1,3-dicarboxylate (Intermediate 1, 1.0 g, 1.298 mmol, 1.0 eq) and sodium 2-(dimethylamino)-1-hydroxyethane-1-sulfonate (Intermediate 21, 1.241 g, 6.49 mmol, 5.0 eq) in methanol (10 ml) at 0° C. under nitrogen was added TEA (1 ml, 7.139 mmol, 5.5 eq). The reaction mixture was stirred at 0° C. for about 30 minutes then sodium cyanoborohydride (0.163 g, 2.596 mmol, 2.0 eq) was added and stirred at room temperature for overnight. TLC indicated starting material was consumed and the desired product was observed. The reaction mixture cooled to 0° C., pH adjusted to 7.0 with 1N HCl, and evaporated under reduced pressure. The reaction mixture was diluted with DCM (75 ml), washed with water (30 ml) and brine solution (20 ml). The combined organic extracts were dried over $Na_2SO_4$, filtered and evaporated under reduced pressure. The residue was purified by silicagel column chromatography by using 0-10% methanol in dichloromethane gradient. The fractions containing the expected product were combined and concentrated under reduced pressure to obtain the desired product (0.3 g, yield: 27.7%) as a white solid. $^1H$ NMR (300 MHz, $CDCl_3$): δ ppm 7.65 (brs, 1H), 7.38-7.33 (m, 5H), 5.15, 5.09 (ABq, $J_{AB}$=12.3 Hz, 2H), 4.45 (dd, J=11.1, 4.5 Hz, 1H), 3.23-3.08 (m, 1H), 2.89-2.58 (m, 8H), 2.56-2.41 (m, 7H), 2.36-2.28 (m, 2H), 2.09-1.83 (m, 5H), 1.80-1.44 (m, 7H), 1.42-1.29 (m, 12H), 1.27-1.18 (m, 8H), 1.12 (s, 3H), 1.1-1.0 (m, 1H), 0.96 (s, 3H), 0.94 (s, 3H), 0.91 (s, 3H), 0.85 (s, 3H), 0.84 (s, 3H), 0.79 (m, 1H); ESI-MS: m/z 862.7 (M+H)$^+$ (100%).

Step 2: Synthesis of (1R,3S)-3-((((3aR,5aR,5bR, 7aR,9S,11aR,11bR,13aS)-3a-(2-((2-(dimethyl amino)ethyl)amino)-2-methylpropanamido)-1-iso-propyl-5a,5b,8,8,11a-pentamethyl-2-oxo-3, 3a,4,5, 5a,5b,6,7,7a,8,9,10,11,11a,11b,12,13,13a-octadeca-hydro-2H-cyclopenta[a]chrysen-9-yl)oxy)carbonyl)-2,2-dimethylcydobutane-1-carboxylic acid To a stirred solution of 1-benzyl 3-((3aR,5aR,5bR,7aR, 9S,11aR,11bR,13aS)-3a-(2-((2-(dimethylamino)ethyl) amino)-2-methylpropanamido)-1-isopropyl-5a,5b,8,8,11a-penta methyl-2-oxo-3,3a,4,5,5a,5b,6,7,7a,8,9,10,11,11a, 11b,12,13,13a-octadecahydro-2H-cyclo penta[a]chrysen-9-yl) (1R,3S)-2,2-dimethylcyclobutane-1,3-dicarboxylate (step 1, 0.3 g, 0.356 mmol, 1.0 eq) in MeOH (5 ml) and THF (5 ml) was added aqueous 2.5N KOH solution (1.0 ml, 2.492 mmol, 7.0 eq). The reaction mixture was stirred at room temperature for overnight. TLC indicated starting material was consumed and the desired product was observed. The organic phase was evaporated under reduced pressure, the reaction mixture was diluted with water (15 ml), cooled to 0° C., pH adjusted to 5.0 with 1N HCl and extracted with DCM (3×15 ml). The combined organic extracts were washed with water (10 ml), dried over sodium sulfate, filtered and evaporated under reduced pressure. The residue was purified by silicagel column chromatography by using 0-10% methanol in dichloromethane gradient. The fractions containing the expected product were combined and concentrated under reduced pressure to give a solid. To this solid, acetonitrile (15 ml) was added and heated to reflux for about 30 minutes. The mixture was filtered through a Buchner funnel and was washed with acetonitrile (10 ml) and dried under vacuum to obtain the desired product (60 mg, yield: 22.3%) as a white solid. $^1$H NMR (300 MHz, Pyridine-d$^5$): δ ppm 8.43 (s, 1H), 4.82 (dd, J=11.1, 4.2 Hz, 1H), 3.44-3.33 (m, 1H), 3.22-3.04 (m, 5H), 2.80-2.68 (m, 2H), 2.66-2.57 (m, 2H), 2.57-2.47 (m, 3H), 2.29 (s, 6H), 2.22-1.90 (m, 5H), 1.90-1.70 (m, 3H), 1.65 (s, 3H), 1.61-1.50 (m, 18H), 1.48-1.39 (m, 5H), 1.30 (s, 3H), 1.27-1.18 (m, 1H), 1.09 (s, 3H), 1.06 (s, 3H), 1.03 (s, 3H), 0.98 (s, 3H), 0.94-0.88 (m, 1H); ESI-MS: m/z 752.66 (M+H)$^+$; HPLC: 95.77%.

Example 74: Preparation of (1R,3S)-3-((((3aR,5aR, 5bR,7aR,9S,11aR,11bR,13aS)-3a-(2-amino-2-methylpropanamido)-1-isopropyl-5a,5b,8,8,11a-pentamethyl-2-oxo-3,3a,4,5,5a,5b, 6,7,7a,8,9,10,11,11a,11b, 12,13,13a-octadecahydro-2H-cyclopenta[a]chrysen-9-yl)oxy) carbonyl)-2,2-dimethylcyclobutane-1-carboxylic acid hydrochloride

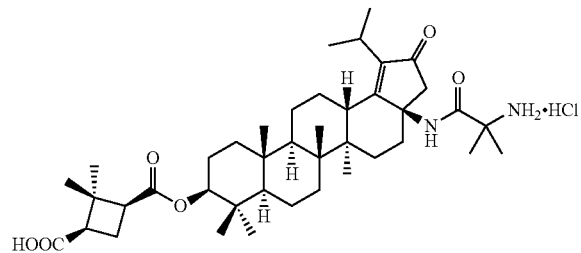

To a stirred solution of 1-((3aR,5aR,5bR,7aR,9S,11aR, 11bR,13aS)-3a-(2-amino-2-methylpropanamido)-1-isopropyl-5a,5b,8,8,11a-pentamethyl-2-oxo-3,3a,4,5,5a,5b,6,7,7a, 8,9, 10,11,11a,11b,12,13,13a-octadecahydro-2H-cyclopenta[a]chrysen-9-yl) 3-benzyl (1S,3R)-2,2-dimethylcyclobutane-1,3-dicarboxylate (Intermediate 1, 0.6 g, 0.778 mmol, 1.0 eq) in MeOH (10 ml) and THF (10 ml) was added aqueous 2.5N KOH solution (2.18 ml, 5.44 mmol, 7.0 eq). The reaction mixture was stirred at room temperature for overnight. TLC indicated starting material was consumed and the desired product was observed. The organic phase was evaporated under reduced pressure, the reaction mixture was diluted with water (20 ml), cooled to 0° C., pH adjusted to 5 with 1N HCl and extracted with DCM (3×15 ml). The combined organic extracts were washed with water (15 ml), dried over sodium sulfate, filtered and evaporated under reduced pressure. The residue was purified by silicagel column chromatography by using 0-10% methanol in dichloromethane gradient, followed by recrystallization over acetonitrile provided the solid. To this solid, 2N HCl in dioxane (5 ml) was added and stirred at room temperature for overnight. The mixture was evaporated under reduced pressure and recrystallization over MTBE gave the desired product (0.44 g, yield: 80%) as a white solid. $^1$H NMR (300 MHz, DMSO-d$_6$): δ ppm 12.16 (s, 1H), 8.17-8.08 (m, 4H), 4.40-4.32 (m, 1H), 3.16-3.06 (m, 1H), 2.84-2.67 (m, 3H), 2.32-2.22 (m, 4H), 2.02-1.83 (m, 3H), 1.80-1.55 (m, 5H), 1.53 (s, 3H), 1.49 (s, 3H), 1.47-1.32 (m, 6H), 1.27 (s, 3H), 1.31-1.23 (m, 1H), 1.22-1.10 (m, 9H), 1.06 (s, 3H), 0.92 (s, 3H), 0.91 (s, 3H), 0.87 (s, 3H), 0.83 (s, 3H), 0.82 (s, 3H); ESI-MS: m/z 681.5 (M−HCl+H)$^+$; HPLC: 97.9%; chloride content by Ion chromatography: 4.4%.

Example 75: Preparation of (1R,3S)-3-((((3aR,5aR, 5bR,7aR,9S,11aR,11bR,13aS)-3a-(2-((tert-butoxy) carbonyl)amino)-2-methylpropanamido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

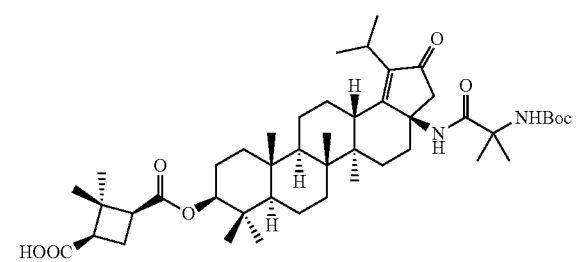

To a stirred solution of 1-benzyl 3-((3aR,5aR,5bR,7aR, 9S,11aR,11bR,13aS)-3a-(2-((tert-butoxy)carbonyl)amino)-2-methylpropanamido)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) (1R,3S)-2,2-dimethylcyclobutane-1,3-dicarboxylate (Intermediate 1-step 12, 0.700 g, 0.803 mmol, 1.0 eq) in MeOH (7 ml) and THF (7 ml) was added aqueous 2.5N KOH solution (2.41 ml, 6.026 mmol, 7.5 eq). The reaction mixture was stirred at room temperature for overnight. TLC indicated starting material was consumed and the desired product was observed. The organic phase was evaporated under reduced pressure, the reaction mixture was diluted with water (10 ml), cooled to 0° C., pH adjusted to 5.0 with 1N HCl and extracted with DCM (3×40 ml). The combined organic extracts were washed with water (40 ml), dried over sodium sulfate, filtered and evaporated under reduced pressure. The residue was purified by silicagel column chromatography by using 0-4% methanol in dichloromethane gradient. The fractions containing the expected product were combined and concentrated under reduced pressure to obtain the desired product (0.245 g, yield: 39%) as a white solid. $^1$H NMR (300 MHz, CDCl$_3$): δ ppm 4.88 (s, 1H), 4.47 (dd, J=11.1, 4.8 Hz, 1H), 3.20-3.09 (m, 1H), 2.90-2.70 (m, 3H), 2.67-2.50 (m, 2H), 2.40-2.22 (m, 2H), 2.10-2.0 (m, 1H), 1.98-1.85 (m, 3H), 1.80-1.66 (m, 4H), 1.65-1.55 (m, 3H), 1.49 (s, 3H), 1.47 (s, 3H), 1.42 (s, 9H), 1.40-1.35 (m, 4H), 1.35-1.27 (m, 3H), 1.26-1.18 (m, 7H), 1.14 (s, 3H), 1.07 (s, 3H), 1.0-0.98 (m, 1H), 0.93 (s, 3H), 0.92 (s, 3H), 0.87 (s, 3H), 0.86 (s, 3H), 0.83-0.78 (m, 1H); ESI-MS: m/z 803.51 (M+Na)$^+$.

Example 76: Preparation of (1R,3S)-3-((((3aR,5aR, 5bR,7aR,9S,11aR,11bR,13aS)-1-isopropyl-5a,5b,8, 8,11a-pentamethyl-3a-(2-methyl-2-((S)-pyrrolidine-2-carboxamido) propanamido)-2-oxo-3,3a,4,5,5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid hydrochloride

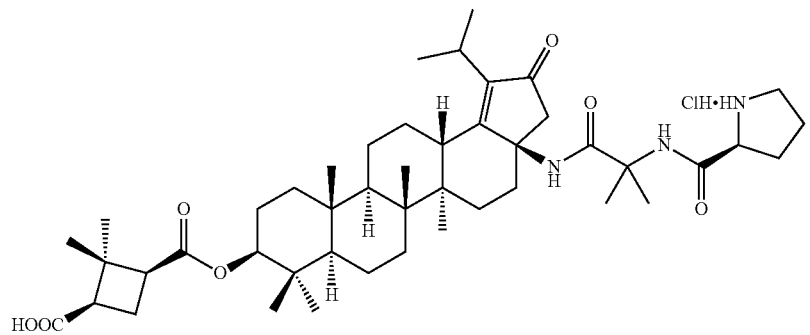

A solution of (1R,3S)-3-(4(3aR,5aR,5bR,7aR,9S,11aR, 11bR,13aS)-3a-(2-((S)-1-(tert-butoxy)carbonyl)pyrrolidine-2-carboxamido)-2-methylpropanamido)-1-isopropyl-5a,5b, 8,8,11a-pentamethyl-2-oxo-3,3a,4,5,5a,5b,6,7,7a,8,9,10,11, 11a,11b,12,13,13a-octadecahydro-2H-cyclopenta[a] chrysen-9-yl)oxy)carbonyl)-2,2-dimethylcyclobutane-1-carboxylic acid (Example 8, 0.400 g, 0.455 mmol, 1.0 eq) and 3N HCl in 1,4-dioxane (5 ml) was stirred at room temperature for overnight. TLC indicated starting material was consumed and the desired product was observed. The mixture was evaporated under reduced pressure, the residue was washed with n-hexane (10 ml), MTBE (10 ml) was added and heated to reflux for about 30 minutes. The reaction mixture was cooled to 0° C., filtered, solid was washed with MTBE (10 ml) and dried under vacuum to obtain the desired product (0.340 g, yield: 91.64%) as a white solid. $^1$H NMR (300 MHz, DMSO-$d_6$): δ ppm 12.16 (brs, 1H), 9.65 (brs, 1H), 8.52 (s, 1H), 8.46 (brs, 1H), 7.32 (s, 1H), 4.39-4.33 (m, 1H), 4.24-4.17 (m, 1H), 3.22-3.06 (m, 3H), 2.82-2.73 (m, 3H), 2.45-2.23 (m, 4H), 2.10 (d, J=13.8 Hz, 1H), 1.98-1.64 (m, 9H), 1.62-1.47 (m, 4H), 1.46-1.41 (m, 1H), 1.43 (s, 3H), 1.40-1.32 (m, 3H), 1.37 (s, 3H), 1.26 (s, 3H), 1.25-1.17 (m, 2H), 1.15-1.10 (m, 6H), 1.09-1.01 (m, 2H), 1.03 (s, 3H), 0.91 (s, 3H), 0.90 (s, 3H), 0.87 (s, 3H), 0.82 (s, 3H), 0.81 (s, 3H); ESI-MS: m/z 778.46 (M−HCl+ H)$^+$; HPLC: 99.6%; chloride content by Ion chromatography: 4.46%.

BIOLOGICAL ACTIVITY

The compounds described herein can be tested for their antiviral activity following procedures known to a person of ordinary skill in the art. For example, the following protocols can be employed for testing the compounds. These protocols are illustrative and do not limit the scope of the invention.

Example 77: Evaluation of Compounds Antiviral Activity Against HIV-1 Strain 92HT599 in MT2 Cells MT2 cells were infected with HIV-1 strain 92HT599 (10 TCID 50/30000 cells). The infected cells were plated at the concentration of 30,000 cells per well in 96 well plate. Test compound was added to the micro plate in defined format with the final concentration of DMSO (vehicle) is not more than 1%. Incubation was carried out in $CO_2$ incubator for ~96 hours for viral infection. At the end of incubation period an aliquot from each well was taken for p24 estimation. The quantitation of p24 is an index for antiviral activity of the compound. Percent inhibition was calculated with reference to control values (vehicle controls). p24 estimation was carried out using Advance biosciences kit as per the procedure detailed by supplier.

For 0% serum binding assay, wherein "A" refers to an $IC_{50}$ value of less than 3 nM, "B" refers to $IC_{50}$ value in range of 3.01-10 nM, and "C" refers to $IC_{50}$ values greater than 10 nM.

For 40% serum binding assay, wherein "A" refers to an $IC_{50}$ value of less than 50 nM, "B" refers to $IC_{50}$ value in range of 50.01-200 nM, and "C" refers to $IC_{50}$ values greater than 200 nM. The $IC_{50}$ (nM) values are set forth in Table-1.

TABLE 1

| Example no | $IC_{50}$ 0% serum | $IC_{50}$ 40% serum |
| --- | --- | --- |
| 1 | A | A |
| 2 | B | A |
| 3 | A | A |
| 4 | A | A |
| 5 | A | B |
| 6 | A | B |
| 7 | A | A |
| 8 | A | A |
| 9 | A | C |
| 10 | A | A |
| 11 | A | B |
| 12 | A | B |
| 13 | A | A |
| 14 | A | A |
| 15 | A | A |
| 16 | A | B |
| 17 | A | A |
| 18 | A | A |
| 19 | A | A |
| 20 | A | A |
| 21 | B | A |
| 22 | A | A |
| 23 | A | A |
| 24 | A | B |
| 25 | A | A |
| 26 | A | B |
| 27 | B | B |
| 28 | A | A |
| 30 | A | A |
| 31 | A | A |

TABLE 1-continued

| Example no | IC$_{50}$ 0% serum | IC$_{50}$ 40% serum |
|---|---|---|
| 32 | B | C |
| 33 | A | A |
| 34 | A | A |
| 35 | C | C |
| 36 | A | B |
| 37 | A | A |
| 38 | A | A |
| 39 | A | A |
| 40 | A | A |
| 41 | A | A |
| 42 | A | A |
| 43 | A | A |
| 44 | A | B |
| 45 | B | A |
| 46 | A | A |
| 47 | A | A |
| 48 | A | A |
| 49 | A | A |
| 50 | A | A |
| 51 | A | A |
| 53 | A | A |
| 54 | A | A |
| 55 | B | B |
| 56 | A | A |
| 57 | A | A |
| 58 | A | A |
| 59 | A | B |
| 60 | A | A |
| 61 | A | A |
| 63 | A | A |
| 64 | A | A |
| 65 | A | A |
| 67 | A | A |
| 68 | B | A |
| 69 | C | B |
| 70 | A | A |
| 71 | A | B |
| 72 | A | A |
| 73 | A | A |
| 74 | A | A |
| 75 | A | A |
| 76 | A | B |
| — | — | — |
| — | — | — |
| — | — | — |

TABLE 2

| Example no | pNL4-3 WT IC$_{50}$ | pNL4-3 V7A IC$_{50}$ |
|---|---|---|
| 1 | A | A |
| 5 | A | A |
| 7 | A | A |
| 14 | A | B |
| 15 | A | C |
| 16 | B | C |
| 17 | A | A |
| 18 | A | A |
| 19 | A | A |
| 20 | C | C |
| 25 | A | A |
| 28 | B | B |
| 29 | A | B |
| 30 | B | C |
| 31 | A | C |
| 32 | C | C |
| 33 | A | A |
| 34 | A | B |
| 37 | A | A |
| 38 | A | A |
| 39 | B | B |
| 40 | A | A |
| 41 | C | B |
| 42 | B | A |
| 44 | C | C |
| 45 | A | B |
| 47 | A | A |
| 51 | B | C |
| 53 | A | A |
| 54 | A | B |
| 55 | C | C |
| 56 | B | B |
| 57 | B | B |
| 58 | B | C |
| 61 | A | B |
| 63 | C | C |
| 64 | B | C |
| 65 | C | C |
| 70 | A | A |
| 72 | A | C |

Example 78: Evaluation of Compounds Antiviral Activity Against pNL4-3/WT & V7A Strains in MT4 Cells MT4 cells were Transfected with HIV-1 Plasmid (pNL4-3-WT & V7A) (Cells were incubating with required number of TCID50 of HIV-1 for 1.5 h at 37° C.). After infection, the infected cells were plated at the concentration of 3×10$^4$ cells per well in 96 well plate. Test compound was added to the test plate in defined format with the final concentration of DMSO is not more than 1%. Incubation was carried out in CO$_2$ incubator for 4 days for viral infection. At the end of incubation period an aliquot from each well was taken for p24 estimation. p24 estimation was carried out using Advance biosciences kit as per the procedure detailed by supplier.

For pNL4-3 WT assay, IC$_{50}$ wherein "A" refers to an IC$_{50}$ value of less than 5 nM, "B" refers to IC$_{50}$ value in range of 5.01-10 nM, and "C" refers to IC$_{50}$ values greater than 10 nM;

For pNL4-3 V7A assay, wherein "A" refers to an IC$_{50}$ value of less than 10 nM, "B" refers to IC$_{50}$ value in range of 10.01-50 nM, and "C" refers to IC$_{50}$ values greater than 50 nM. The IC$_{50}$ (nM) values are set forth in Table-2.

Example 79: Evaluation of Compounds Cyto-Toxicity (MTT Assay)

On day 1 calculate the number of cells required for the assay and seed 3×104 cells in 200 µl per well. Weigh the compound and dissolve it in DMSO to get 10 mM stock which is further diluted to 3 mM and 1 mM. The drugs from these stocks were added to plate to get final concentration of 100 µM, 30 µM and 10 µM. Add DMSO to controls in a way to obtain final concentration of solvent that is not greater than 1%. Incubate for 4 days in 5% CO$_2$ incubator at 37° C. On day 4, 100 µl of medium was removed from each well without disturbing the cells. Add 10 µl of MTT reagent and incubate for 4 hours at 5% CO$_2$ incubator at 37° C. for formation of crystals. Add 200 µl of 0.1N acidic isopropanol to dissolve the crystals and read the plate at 590 nm. The values are mentioned in below Table-3 and Table-3A.

TABLE 3

| | Cytotoxicity % viability | | |
|---|---|---|---|
| Example No. | 1 µM | 0.1 µM | 0.01 µM |
| 1 | 4 | 10 | 57 |
| 2 | 8 | 9 | 42 |
| 3 | 7 | 13 | 32 |

TABLE 3-continued

| Example No. | Cytotoxicity % viability | | |
|---|---|---|---|
| | 1 μM | 0.1 μM | 0.01 μM |
| 4 | 9 | 12 | 20 |
| 5 | 4 | 35 | 74 |
| 6 | 4 | 19 | 60 |
| 7 | 0 | 9 | 28 |
| 8 | 3 | 5 | 28 |
| 9 | 14 | 53 | 100 |
| 10 | 0 | 1 | 67 |
| 11 | 1 | 3 | 41 |
| 12 | 3 | 7 | 42 |
| 13 | 4 | 10 | 45 |
| 14 | 2 | 8 | 44 |
| 15 | 2 | 8 | 44 |
| 16 | 2 | 11 | 37 |
| 21 | 6 | 7 | 36 |
| 22 | 3 | 3 | 21 |
| 23 | 4 | 8 | 34 |
| 24 | 6 | 21 | 69 |
| 25 | 2 | 6 | 31 |
| 26 | 0 | 20 | 55 |
| 27 | 0 | 2 | 52 |
| 28 | 6 | 10 | 21 |
| 29 | 2 | 3 | 29 |
| 30 | 2 | 3 | 30 |
| 34 | 1 | 10 | 26 |
| 35 | 77 | 92 | 84 |
| 36 | 8 | 15 | 56 |
| 37 | 1 | 4 | 26 |
| 38 | 2 | 9 | 20 |
| 39 | 0 | 2 | 29 |
| 40 | 1 | 2 | 26 |
| 42 | 4 | 5 | 27 |
| 43 | 3 | 26 | 76 |
| 46 | 4 | 12 | 52 |
| 47 | 4 | 14 | 75 |
| 48 | 4 | 12 | 44 |
| 49 | 4 | 12 | 56 |
| 50 | 0 | 0 | 21 |
| 59 | 8 | 15 | 94 |
| 60 | 2 | 27 | 77 |
| 61 | 2 | 42 | 88 |
| 63 | 0 | 16 | 51 |
| 64 | 1 | 2 | 26 |
| 65 | 2 | 3 | 27 |
| 67 | 3 | 21 | 59 |
| 69 | 8 | 8 | 42 |
| 71 | 3 | 5 | 41 |
| 73 | 9 | 11 | 52 |
| 74 | 19 | 14 | 61 |
| 75 | 2 | 17 | 63 |
| 76 | 6 | 6 | 59 |

TABLE 3A

| Example No. | Cytotoxicity % viability | | |
|---|---|---|---|
| | 0.01 μM | 0.003 μM | 0.001 μM |
| 17 | 26 | 62 | 81 |
| 18 | 29 | 61 | 78 |
| 19 | 40 | 65 | 79 |
| 20 | 40 | 85 | 91 |
| 31 | 54 | 86 | 81 |
| 44 | 58 | 80 | 84 |
| 51 | 37 | 85 | 86 |
| 52 | 59 | 89 | 83 |
| 72 | 27 | 84 | 98 |

Example 80: Evaluation of Compounds Single Dose Oral Pharmacokinetic Study

The test item was administered through oral route to animals (rat/mice) at 30 mg/kg dose in a suitable vehicle (10% Solutol+20% PEG) at 10 ml/kg dose volume. Blood samples (~50 μL at each time point) were collected from retro-orbital plexus using K3 EDTA as anticoagulant in eppendorf tubes at defined time intervals 30 minutes, 1 hour, 2 hour, 4 hour, 8 hour, 24 hour & 48 hour under light ether anaesthesia. The samples were centrifuged at 3500×g to separate plasma and stored at −80° C. until analysis. Plasma 25 μl for Mice were processed as per described in sample preparation.

Standard solutions of the test compound 1 mg/mL solutions were prepared in DMSO and further dilutions were made in methanol. The calibration curve samples for LCMSMS analysis were prepared by spiking 25 μl of Mice plasma with 2.5 μl and of the appropriate working standard solution to obtain final concentrations 0.078, 0.156, 0.312, 0.625, 1.25, 2.5, 5, 10, 20 & 40 μg/ml. To the test compound plasma extraction was carried out using Acetonitrile precipitation. After reconstitution with solvent (50% Acetonitrile in Buffer) samples were analyzed by LCMSMS to get the concentrations to calculate PK Parameters. The values are set forth in Table-4.

TABLE 4

| | Mice oral PK @30 mg/kg | |
|---|---|---|
| Example no | $C_{max}$ (μg/ml) | $AUC_{0-t}$ (μg · hr/ml) |
| 2 | 13.153 | 165.708 |
| 3 | 29.61 | 544.857 |
| 4 | 8.845 | 184.919 |
| 5 | 26.008 | 289.239 |
| 6 | 11.099 | 100.412 |
| 7 | 41.921 | 517.02 |
| 10 | 9.794 | 69.762 |
| 12 | 8.54 | 61.312 |
| 13 | 2.716 | 18.218 |
| 14 | 26.752 | 377.338 |
| 15 | 12.843 | 141.167 |
| 17 | 28.565 | 332.923 |
| 18 | 15.925 | 235.704 |
| 19 | 13.875 | 93.04 |
| 20 | 18.992 | 236.062 |
| 21 | 16.034 | 191.391 |
| 22 | 23.6 | 489.844 |
| 23 | 29.736 | 589.886 |
| 24 | 29.618 | 427.527 |
| 25 | 23.997 | 336.08 |
| 28 | 16.239 | 344.768 |
| 30 | 22.971 | 477.469 |
| 31 | 18.68 | 254.609 |
| 33 | 11.391 | 231.111 |
| 37 | 38.844 | 874.12 |
| 38 | 10.069 | 113.719 |
| 40 | 20.255 | 343.317 |
| 42 | 22.873 | 480.991 |
| 43 | 31.344 | 320.392 |
| 44 | 19.807 | 153.713 |
| 45 | 21.17 | 214.252 |
| 46 | 29.49 | 835.997 |
| 47 | 23.578 | 537.72 |
| 48 | 20.301 | 477.13 |
| 50 | 23.295 | 454.291 |
| 51 | 32.327 | 277.12 |
| 53 | 9.746 | 57.84 |
| 54 | 29.226 | 402.064 |
| 59 | 13.92 | 185.948 |
| 60 | 20.228 | 216.625 |
| 61 | 45.721 | 615.349 |

TABLE 4-continued

| | Mice oral PK @30 mg/kg | |
|---|---|---|
| Example no | $C_{max}$ (μg/ml) | $AUC_{0-t}$ (μg · hr/ml) |
| 64 | 27.378 | 335.569 |
| 65 | 7.383 | 145.21 |
| 67 | 24.254 | 86.58 |
| 68 | 20.045 | 271.842 |
| 70 | 36.636 | 880.717 |
| 71 | 19.304 | 129.737 |
| 72 | 15.266 | 191.83 |

REFERENCES

1. Antiviral methods and protocols (Eds: D Kinchington and R. F. Schinazi) Humana Press Inc., 2000.
2. HIV protocols (Eds: N. L. Michael and J. H. Kim) Humana Press Inc, 1999.
3. DAIDS Virology manual from HIV laboratories, Publication NIH-97-3838, 1997.
4. HIV-1 p24 antigen capture assay, enzyme immunoassay for detection of Human immunodeficiency Virus Type 1 (HIV-1) p24 in tissue culture media—Advanced bio science laboratories, Inc kit procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent applications cited in this application are herein incorporated by reference to the same extent as if each individual publication or patent application was specifically and individually indicated to be incorporated herein by reference.

The invention claimed is:

1. A method for ameliorating or treating HIV infection in a subject in need thereof which comprises the administration of therapeutically effective amount of a compound of the formula (1)

Formula (1)

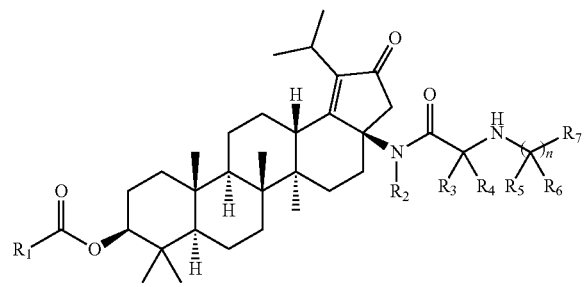

wherein, $R_1$ is substituted or unsubstituted $C_1$-$C_6$alkyl,

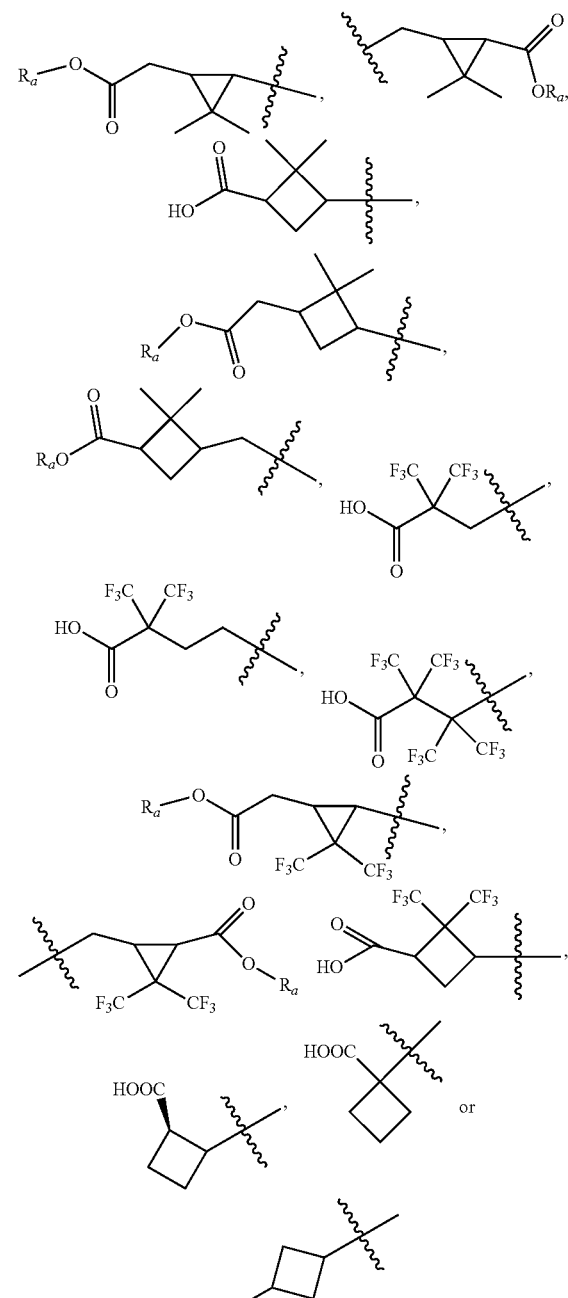

(wherein $R_a$ is selected from hydrogen, substituted or unsubstituted $C_1$-$C_6$ alkyl, or substituted or unsubstituted $C_3$-$C_8$ cycloalkyl);

$R_2$ is selected from hydrogen, substituted or unsubstituted $C_1$-$C_6$ alkyl;

$R_3$ and $R_4$ are independently selected from substituted or unsubstituted $C_1$-$C_6$ alkyl, substituted or unsubstituted amine, substituted or unsubstituted $C_3$-$C_8$ cycloalkyl and $R_3$ and $R_4$ are taken together with the carbon atom to which they are attached to form substituted or unsubstituted $C_3$-$C_8$ cycloalkyl, epoxide, oxetane or azetidine;

$R_5$ and $R_6$ are independently selected from hydrogen, substituted or unsubstituted $C_1$-$C_6$ alkyl and $R_5$ and $R_6$ are taken together with the carbon atom to which they are attached form substituted or unsubstituted $C_3$-$C_8$ cycloalkyl or $R_5$ and $R_6$ together represent oxo;

$R_7$ is selected from hydrogen, substituted or unsubstituted $C_1$-$C_6$ alkyl, substituted or unsubstituted $C_1$-$C_6$ alkoxy, substituted or unsubstituted amino, substituted or unsubstituted $C_1$-$C_6$ amino alkyl, substituted or unsubstituted $C_3$-$C_8$ cycloalkyl, substituted or unsubstituted $C_6$-$C_{12}$ aryl, substituted or unsubstituted heterocyclyl, substituted or unsubstituted heteroaryl, or —S(O)$_2$R$_b$; wherein the substituents are independently selected from one or more $R_m$;

$R_m$ is selected from halo, $C_1$-$C_6$ alkyl, haloalkyl, amino, —C(O)OR$_c$, substituted or unsubstituted heterocyclyl, substituted or unsubstituted heterocyclylalkyl, substituted or unsubstituted heteroaryl or —S(O)$_2$R$_b$;

$R_b$ and $R_c$ are independently selected from substituted or unsubstituted $C_1$-$C_6$ alkyl or substituted or unsubstituted $C_6$-$C_{12}$ aryl; and 'n' is an integer selected from 0, 1 or 2; or pharmaceutically acceptable salts, pharmaceutically acceptable solvates, pharmaceutically acceptable hydrates, tautomers, stereoisomers, ester prodrugs, or combination thereof.

2. The method according to claim 1, wherein $R_1$ is

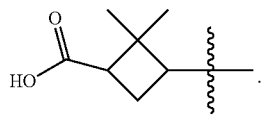 [SMILES: *C1CC(C(=O)O)C1(C)C]

3. A method for ameliorating or treating HIV infection in a subject in need thereof which comprises the administration of therapeutically effective amount of a compound of the formula (1A)

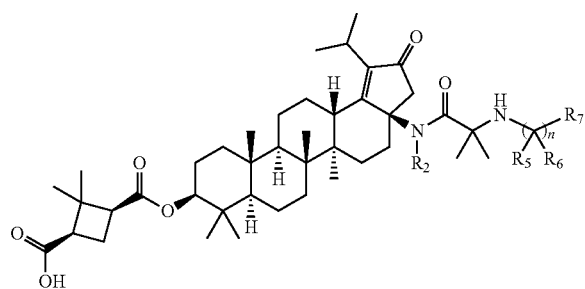

Formula (1A)

wherein, $R_2$, $R_5$, $R_6$, $R_7$ and 'n' are same as defined in formula (1).

4. A method for ameliorating or treating HIV infection in a subject in need thereof which comprises the administration of therapeutically effective amount of a compound of the formula (1B)

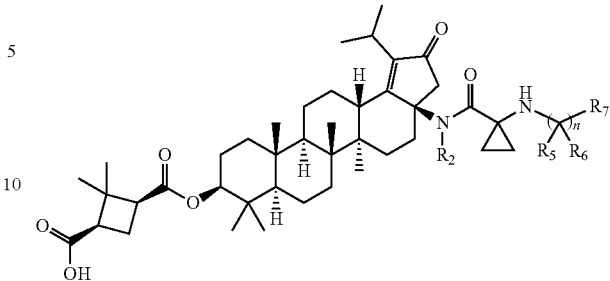

Formula (1B)

wherein, $R_2$, $R_5$, $R_6$, $R_7$ and 'n' are same as defined in formula (1);

X is selected from —O—, —CH$_2$O—, —CH$_2$N—, -or (—CH$_2$—)$_m$;

'm' is an integer selected from 1, 2, 3 or 4.

5. A method for ameliorating or treating HIV infection in a subject in need thereof which comprises the administration of therapeutically effective amount of a compound selected from the group consisting of:

(1R,3 S)-3-((((3aR,5aR,5bR,7aR,9S,11aR,11bR,13aS)-3a-(2-(4-chlorobenzamido)-2-methylpropanamido)-1-isopropyl-5a,5b,8,8,11a-pentamethyl-2-oxo-3,3a,4,5, 5a,5b,6,7,7a,8, 9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-3a-(2-(1-(4-chlorophenyl) cyclopropane-1-carboxamido)-2-methylpropanamido)-1-isopropyl-5a,5b,8,8, 11a-pentamethyl-2-oxo-3,3a,4,5,5a,5b,6,7,7a,8,9,10, 11,11a,11b,12,13,13a-octadecahydro-2H-cyclopenta [a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-3a-(2-benzamido-2-methyl propanamido)-1-isopropyl-5a,5b,8,8,11a-pentamethyl-2-oxo-3,3a,4,5,5a,5b,6,7, 7a,8,9,10,11, 11a,11b,12,13,13a-octadecahydro-2H-cyclopenta[a]chrysen-9-yl)oxy)carbonyl)-2,2-dimethyl cyclobutane-1-carboxylic acid, (1R,3S)-3-((((3aR,5aR,5bR,7aR,9S,11aR,11bR,13aS)-3a-(2-(3,4-dichlorobenzamido)-2-methylpropanamido)-1-isopropyl-5a,5b,8,8,11a-pentamethyl-2-oxo-3,3a,4,5,5a,5b,6,7,7a, 8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(pyrazine-2-carboxamido)propanamido)-2-oxo-3,3a,4, 5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-3a-(2-(6-aminonicotinamido)-2-methylpropanamido)-1-isopropyl-5a,5b,8,8,11a-pentamethyl-2-oxo-3,3a,4, 5,5a,5b,6,7,7a, 8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(5-methylpyrazine-2-carboxamido)propanamido)-2-oxo-3,3a, 4,5,5a,5b,6,7,7a,8,9,10,11,11a,11b,12,13, 13a-octadecahydro-2H-cyclopenta[a]chrysen-9-yl) oxy)carbonyl)-2,2-dimethylcyclobutane-1-carboxylic acid, (1R,3 S)-3-((((3aR,5aR,5bR,7aR,9S,11aR,11bR,13aS)-3a-(2-((S)-1-(tert-butoxy carbonyl)pyrrolidine-2-carboxamido)-2-methylpropanamido)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-3a-(2-(2-(4-ethylpiperazin-1-yl)acetamido)-2-methylpropanamido)-1-isopropyl-5a,5b,8,8,11a-pentamethyl-2-oxo-3,3a,4,5, 5a,5b,6,7,7a,8,9,10,11,11a,11b,12,13,13a-octadecahydro-2H-cyclopenta[a]chrysen-9-yl) oxy) carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(2-(piperidin-1-yl)acetamido)propanamido)-2-oxo-3,3a,4,5,5a, 5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-3a-(2-(2-amino-2-methyl propanamido)-2-methylpropanamido)-1-isopropyl-5a,5b,8,8,11a-pentamethyl-2-oxo-3,3a,4,5, 5a,5b,6,7,7a,8,9,10,11,11a,11b,12,13,13a-octadecahydro-2H-cyclopenta[a]chrysen-9-yl) oxy) carbonyl)-2,2-dimethylcyclobutane-1-carboxylic acid hydrochloride, (1R,3 S)-3-((((3aR,5aR,5bR,7aR,9S,11aR,11bR,13aS)-3a-(2-(1H-benzo[d]imidazole-5-carboxamido)-2-methylpropanamido)-1-isopropyl-5a,5b,8,8,11a-pentamethyl-2-oxo-3,3a,4, 5,5a,5b,6,7,7a,8,9,10,11,11a,11b,12,13,13a-octadecahydro-2H-cyclopenta[a]chrysen-9-yl) oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-3a-(2-methyl-2-(2-(6-methylpyridin-3-yl)-1H-benzo[d]imidazole-5-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-3a-(2-(2,4-dimethylthiazole-5-carboxamido)-2-methylpropanamido)-1-isopropyl-5a,5b,8,8,11a-pentamethyl-2-oxo-3,3a,4, 5,5a,5b,6,7,7a,8,9,10,11,11a,11b,12,13,13a-octadecahydro-2H-cyclopenta[a]chrysen-9-yl) oxy)carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(2-(pyrazin-2-yl)-1H-benzo[d]imidazole-5-carboxamido)propan amido)-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(1-methyl-1H-imidazole-2-carboxamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-1-isopropyl-3a-(2-(3-isopropyl-1H-pyrazole-5-carboxamido)-2-methylpropanamido)-5a,5b,8,8,11a-pentamethyl-2-oxo-3,3a, 4,5,5a,5b,6,7,7a,8,9,10,11,11a,11b,12,13,13a-octadecahydro-2H-cyclopenta[a]chrysen-9-yl) oxy)carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(4-morpholinobenzamido)propanamido)-2-oxo-3,3a,4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-3a-(2-(3,5-dimethylisoxazole-4-carboxamido)-2-methylpropanamido)-1-isopropyl-5a,5b,8,8,11a-pentamethyl-2-oxo-3,3a, 4,5,5a,5b,6,7,7a,8,9,10,11,11a,11b,12,13,13a-octadecahydro-2H-cyclopenta[a]chrysen-9-yl) oxy)carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(4-(4-methyl-1H-imidazol-1-yl)benzamido)propanamido)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1S,3R)-3-((((3aR,5aR,5bR,7aR,9S,11aR,11bR,13aS)-3a-(2-(4-chlorobenzamido)-2-methylpropanamido)-1-isopropyl-5a,5b,8,8,11a-pentamethyl-2-oxo-3,3a,4,5, 5a,5b,6,7,7a,8, 9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-3a-(2-(4-fluorobenzamido)-2-methylpropanamido)-1-isopropyl-5a,5b,8,8,11a-pentamethyl-2-oxo-3,3a,4,5, 5a,5b,6,7,7a,8, 9,10,11,11a,11b,12,13,13a-octadecahydro-2H-cyclopenta[a]chrysen-9-yl) oxy) carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(4-methylbenzamido)propanamido)-2-oxo-3,3a,4,5,5a, 5b,6,7, 7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-3a-(2-(furan-3-carboxamido)-2-methylpropanamido)-1-isopropyl-5a,5b,8,8,11a-pentamethyl-2-oxo-3,3a,4, 5,5a,5b,6,7,7a,8, 9,10,11,11a,11b,12,13,13a-octadecahydro-2H-cyclopenta[a]chrysen-9-yl) oxy) carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(4-(trifluoromethyl)benzamido)propanamido)-2-oxo-3,3a,4,5, 5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-3a-(2-(furan-2-carboxamido)-2-methylpropanamido)-1-isopropyl-5a,5b,8,8,11a-pentamethyl-2-oxo-3,3a,4, 5,5a,5b,6,7,7a, 8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(1-phenylcyclopentane-1-carboxamido)propanamido)-2-oxo-3,3a,4,5,5a,5b,6,7,7a,8,9,10,11,11a,11b,12,13, 13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(quinoline-2-carboxamido)propanamido)-2-oxo-3,3a, 4,5,5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(3-methylpicolinamido)propanamido)-2-oxo-3,3a,4,5, 5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(2-methylfuran-3-carboxamido)propanamido)-2-oxo-3,3a,4,5, 5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(2-morpholinonicotinamido)propanamido)-2-oxo-3,3a, 4,5,5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(pyrimidine-2-carboxamido)propanamido)-2-oxo-3,3a, 4,5,5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-3a-(2-(2,5-dimethylfuran-3-carboxamido)-2-methylpropanamido)-1-isopropyl-5a,5b,8,8,11a-pentamethyl-2-oxo-3,3a,4,5, 5a,5b,6,7,7a,8,9,10,11,11a,11b,12,13, 13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-3a-(2-(2-(1,1-dioxidothio morpholino)acetamido)-2-methylpropanamido)-1-isopropyl-5a,5b,8,8,11a-pentamethyl-2-oxo-3,3a,4,5,5a,5b,6,7,7a,8,9,10,11,11a, 11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(piperidine-4-carboxamido)propanamido)-2-oxo-3,3a, 4,5,5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid hydrochloride, (1R,3 S)-3-((((3aR,5aR,5bR,7aR,9S,11aR,11bR,13aS)-3a-(2-((S)-2-amino-3-methyl butanamido)-2-methylpropanamido)-1-isopropyl-5a,5b,8,8,11a-pentamethyl-2-oxo-3,3a,4,5, 5a,5b,6,7,7a,8,9,10,11,11a,11b,12,13, 13a-octadecahydro-2H-cyclopenta[a]chrysen-9-yl)oxy) carbonyl)-2,2-dimethylcyclobutane-1-carboxylic acid hydrochloride, (1R,3 S)-3-((((3aR,5aR,5bR,7aR,9S,11aR,11bR,13aS)-1-isopropyl-5a,5b,8,8,11a -pentamethyl-3a-(2-methyl-2-(4-(methylsulfonyl)benzamido)propanamido)-2-oxo-3, 3a,4,5,5a, 5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-((S)-piperidine-3-carboxamido)propanamido)-2-oxo-3,3a,4,5,5a, 5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid hydrochloride, (1R,3 S)-3-((((3aR,5aR,5bR,7aR,9S,11aR,11bR,13aS)-3a-(2-(2-(4-chlorophenyl) acetamido)-2-methylpropanamido)-1-isopropyl-5a,5b,8,8,11a-pentamethyl-2-oxo-3,3a,4,5, 5a,5b,6,7,7a,8,9,10,11,11a,11b,12,13, 13a-octadecahydro-2H-cyclopenta[a]chrysen-9-yl) oxy) carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(pyrazolo[1,5-a]pyrimidine-3-carboxamido)propanamido)-2-oxo-3,3a,4,5,5a,5b,6,7,7a,8,9,10,11,11a,11b, 12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-3a-(2-(2-aminothiazole-4-carboxamido)-2-methylpropanamido)-1-isopropyl-5a,5b,8,8,11a-pentamethyl-2-oxo-3,3a,4,5, 5a,5b,6,7,7a,8,9,10,11,11a,11b,12,13, 13a-octadecahydro-2H-cyclopenta[a]chrysen-9-yl) oxy) carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(4-(5-methyl-1,3,4-oxadiazol-2-yl)benzamido)propanamido)-2-oxo-3,3a,4,5,5a,5b,6,7,7a,8,9,10,11,11a, 11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-3a-(2-(4-(1,1-dioxidothio morpholino)benzamido)-2-methylpropanamido)-1-isopropyl-5a,5b,8,8,11a-pentamethyl-2-oxo-3,3a,4,5,5a,5b,6,7,7a,8,9,10,11,11a, 11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-3a-(2-(4-((1,1-dioxidothio morpholino)methyl)benzamido)-2-methylpropanamido)-1-isopropyl-5a,5b,8, 8,11a-penta methyl-2-oxo-3,3a,4,5,5a,5b,6,7,7a,8,9,10, 11,11a,11b,12,13,13a-octadecahydro-2H-cyclo penta [a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-(2-(2-(dimethylamino) acetamido)-2-methylpropanamido)-1-isopropyl-5a,5b,8,8,11a-pentamethyl-2-oxo-3,3a,4,5,5a, 5b,6,7,7a,8,9,10,11,11a,11b,12,13, 13a-octadecahydro-2H-cyclopenta[a]chrysen-9-yl) oxy) carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-3a-(2-methyl-2-(6-methylpicolinamido)propanamido)-2-oxo-3,3a,4,5, 5a,5b, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(2-methyl-2-(6-methylnicotinamido)propanamido)-2-oxo-3,3a,4,5, 5a,5b, 6,7,7a,8,9,10,11,11a,11b,12,13,13a- octadecahydro-2H-cyclopenta[a]chrysen-9-yl)oxy) carbonyl)-2,2-dimethylcyclobutane-1-carboxylic acid, (1R,3 S)-3-(((((3aR,5aR,5bR,7aR,9S,11aR,11bR,13aS)-1-isopropyl-5a,5b,8,8,11a-pentamethyl-3a-(2-methyl-2-pivalamidopropanamido)-2-oxo-3,3a,4,5,5a,5b,6,7,7a, 8,9,10,11, 11a,11b,12,13,13a-octadecahydro-2H-cyclopenta[a]chrysen-9-yl)oxy)carbonyl)-2,2-dimethyl cyclobutane-1-carboxylic acid, sodium (1R,3S)-3-(((((3aR,5aR,5bR,7aR,9S,11aR,11bR, 13aS)-1-isopropyl-5a,5b,8,8, 11a -pentamethyl-3a-(2-methyl-2-(methylsulfonamido)propanamido)-2-oxo-3, 3a,4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylate, (1R,3S)-3-(((((3aR,5aR,5bR,7aR,9S,11aR,11bR,13aS)-3a-(2-((ethoxycarbonyl)amino)-2-methylpropanamido)-1-isopropyl-5a,5b,8,8,11a-pentamethyl-2-oxo-3,3a,4,5,5a,5b,6,7,7a, 8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-(((((3aR,5aR,5bR,7aR,9S,11aR,11bR,13aS)-3a-(2-((4-chlorophenyl) sulfonamido)-2-methylpropanamido)-1-isopropyl-5a,5b,8,8,11a-pentamethyl-2-oxo-3,3a,4,5, 5a,5b,6,7,7a,8,9,10,11,11a,11b,12,13, 13a-octadecahydro-2H-cyclopenta[a]chrysen-9-yl) oxy) carbonyl)-2,2-dimethylcyclobutane-1-carboxylic acid, (1R,3 S)-3-(((((3aR,5aR,5bR,7aR,9S,11aR,11bR,13aS)-3a-(2-(cyclohexanecarboxamido)-2-methylpropanamido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-(((((3aR,5aR,5bR,7aR,9S,11aR,11bR,13aS)-1-isopropyl-5a,5b,8,8,11a-pentamethyl-3a-(2-methyl-2-((pyridin-2-ylmethyl)amino)propanamido)-2-oxo-3,3a, 4,5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-(((((3aR,5aR,5bR,7aR,9S,11aR,11bR,13aS)-3a-(2-((4-chlorobenzyl)amino)-2-methylpropanamido)-1-isopropyl-5a,5b,8,8,11a-pentamethyl-2-oxo-3,3a,4,5,5a,5b,6,7,7a, 8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-(((((3aR,5aR,5bR,7aR,9S,11aR,11bR,13aS)-3a-(2-(((1-(4-chlorophenyl) cyclopropyl)methyl) amino)-2-methylpropanamido)-1-isopropyl-5a,5b,8,8, 11a-pentamethyl-2-oxo-3,3a,4,5,5a,5b,6,7,7a,8,9,10, 11,11a,1b,12,13,13a-octadecahydro-2H-cyclopenta[a] chrysen-9-yl)oxy)carbonyl)-2,2-dimethylcyclobutane-1-carboxylic acid, (1R,3 S)-3-(((((3aR,5aR,5bR,7aR,9S,11aR,11bR,13aS)-3a-(2-(5-chloropicolinamido)-2-methylpropanamido)-1-isopropyl-5a,5b,8,8,11a-pentamethyl-2-oxo-3,3a,4, 5,5a,5b,6,7,7a, 8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-(((((3aR,5aR,5bR,7aR,9S,11aR,11bR,13aS)-1-isopropyl-5a,5b,8,8,11a-pentamethyl-3a-(2-methyl-2-(3-(6-methylpyridin-3-yl)ureido)propanamido)-2-oxo-3,3a,4,5, 5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-(((((3aR,5aR,5bR,7aR,9S,11aR,11bR,13aS)-1-isopropyl-5a,5b,8,8,11a-pentamethyl-3a-(2-methyl-2-(3-(6-methylpyridin-2-yl)ureido)propanamido)-2-oxo-3,3a,4,5, 5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-(((((3aR,5aR,5bR,7aR,9S,11aR,11bR,13aS)-3a-(2-((2-(dimethylamino) ethyl)amino)-2-methylpropanamido)-1-isopropyl-5a,5b,8,8,11a-pentamethyl-2-oxo-3,3a,4,5, 5a,5b,6,7,7a,8,9,10,11,11a,11b,12,13, 13a-octadecahydro-2H-cyclopenta[a]chrysen-9-yl) oxy) carbonyl)-2,2-dimethylcyclobutane-1-carboxylic acid, (1R,3 S)-3-(((((3aR,5aR,5bR,7aR,9S,11aR,11bR,13aS)-3a-(2-amino-2-methylpropan amido)-1-isopropyl-5a, 5b,8,8,11a-pentamethyl-2-oxo-3,3a,4,5,5a,5b,6,7,7a,8, 9,10,11,11a, 11b,12,13,13a-octadecahydro-2H-cyclopenta[a]chrysen-9-yl)oxy)carbonyl)-2,2-dimethyl cyclobutane-1-carboxylic acid hydrochloride, (1R,3 S)-3-(((((3aR,5aR,5bR,7aR,9S,11aR,11bR,13aS)-3a-(2-((tert-butoxycarbonyl) amino)-2-methylpropanamido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, and (1R,3 S)-3-(((((3aR,5aR,5bR,7aR,9S,11aR,11bR,13aS)-1-isopropyl-5a,5b,8,8,11a-pentamethyl-3a-(2-methyl-2-((S)-pyrrolidine-2-carboxamido)propanamido)-2-oxo-3,3a,4,5, 5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid hydrochloride, or pharmaceutically acceptable salts, solvates, hydrates and prodrugs thereof.

6. A method for ameliorating or treating HIV infection in a subject in need thereof which comprises the administration of therapeutically effective amount of a compound selected from the group consisting of:

(1R,3 S)-3-(((((3aR,5aR,5bR,7aR,9S,11aR,11bR,13aS)-3a-(1-(4-chlorobenzamido) cyclobutane-1-carboxamido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-(((((3aR,5aR,5bR,7aR,9S,11aR,11bR,13aS)-1-isopropyl-5a,5b,8,8,11a-pentamethyl-3a-(1-(6-methylnicotinamido)cyclobutane-1-carboxamido)-2-oxo-3, 3a,4,5,5a, 5b,6,7,7a,8,9,10,11,11a,1b,12,13,13a-octadecahydro-2H-cyclopenta[a]chrysen-9-yl)oxy) carbonyl)-2,2-dimethylcyclobutane-1-carboxylic acid, (1R,3 S)-3-(((((3aR,5aR,5bR,7aR,9S,11aR,11bR,13aS)-3a-(1-(4-chlorobenzamido) cyclohexane-1-carboxamido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-(((((3aR,5aR,5bR,7aR,9S,11aR,11bR,13aS)-3a-(1-(4-chlorobenzamido) cyclopentane-1-carboxamido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-(((((3aR,5aR,5bR,7aR,9S,11aR,11bR,13aS)-1-isopropyl-5a,5b,8,8,11a-pentamethyl-3a-(1-(6-methylnicotinamido)cyclohexane-1-carboxamido)-2-oxo-3, 3a,4,5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-(((((3aR,5aR,5bR,7aR,9S,11aR,11bR,13aS)-1-isopropyl-5a,5b,8,8,11a-pentamethyl-3a-(1-(6-methylnicotinamido)cyclopentane-1-carboxamido)-2-oxo-3, 3a,4,5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(1-(4-methyl-benzamido)cyclohexane-1-carboxamido)-2-oxo-3,3a, 4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-3a-(1-(4-chlorobenzamido) cyclopropane-1-carbox-amido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(1-(6-methyl-nicotinamido)cyclopropane-1-carboxamido)-2-oxo-3, 3a,4,5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-3a-(1-(4-fluorobenzamido) cyclopropane-1-carbox-amido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(1-(4-methyl-benzamido)cyclopropane-1-carboxamido)-2-oxo-3,3a, 4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-2-oxo-3a-(1-(py-rimidine-2-carboxamido)cyclobutane-1-carboxamido)-3,3a,4,5, 5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3 S)-3-((((3aR,5aR,5bR,7aR,9S,11aR,11bR,13aS)-1-isopropyl-5a,5b,8,8,11a-pentamethyl-3a-(1-(2-mor-pholinonicotinamido)cyclobutane-1-carboxamido)-2-oxo-3,3a,4,5, 5a,5b,6,7,7a,8,9,10,11,11a,11b,12,13, 13a-octadecahydro-2H-cyclopenta[a]chrysen-9-yl) oxy) carbonyl)-2,2-dimethylcyclobutane-1-carboxylic acid, and (1S,3R)-3-((((3aR,5aR,5bR,7aR,9S,11aR,11bR,13aS)-3a-(1-(4-chlorobenzamido) cyclopropane-1-carbox-amido)-1-isopropyl-5a,5b,8,8,11a-pentamethyl-2-oxo-3,3a,4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, or pharmaceutically acceptable salts, solvates, hydrates and prodrugs thereof.

7. The method for ameliorating or treating HIV infection in a subject in need thereof which comprises the administration of a pharmaceutical composition comprising a therapeutically effective amount of a compound according to any one of claims 1-6 and at least one pharmaceutically acceptable excipient.

8. The method according to claim 7, wherein the pharmaceutically acceptable excipient is a carrier or diluent.

9. The method according to any one of claims 1-6, wherein the subject is human.

10. The method according to claim 7, wherein the subject is human.

* * * * *